US012239126B2

(12) United States Patent
Yarmush et al.

(10) Patent No.: US 12,239,126 B2
(45) Date of Patent: Mar. 4, 2025

(54) METHODS AND COMPOSITIONS FOR PRESERVING TISSUES AND ORGANS

(71) Applicant: THE GENERAL HOSPITAL CORPORATION, Boston, MA (US)

(72) Inventors: Martin L. Yarmush, Newton, MA (US); Mehmet Toner, Wellesley, MA (US); Maria-Louisa Izamis, Boston, MA (US); Timothy Antonie Berendsen, Melrose, MA (US); Robert Marius Bieganski, Cambridge, MA (US); Osman Berk Usta, Watertown, MA (US); Basak Elif Uygun, Newton, MA (US); Mustafa Korkut Uygun, Newton, MA (US); Sinem Perk, Chicago, IL (US)

(73) Assignee: The General Hospital Corporation, Boston, MA (US)

( * ) Notice: Subject to any disclaimer, the term of this patent is extended or adjusted under 35 U.S.C. 154(b) by 504 days.

(21) Appl. No.: 16/705,966

(22) Filed: Dec. 6, 2019

(65) Prior Publication Data
US 2020/0236924 A1    Jul. 30, 2020

Related U.S. Application Data

(62) Division of application No. 13/695,459, filed as application No. PCT/US2011/035223 on May 4, 2011, now Pat. No. 10,575,515.
(Continued)

(51) Int. Cl.
*A01N 1/02* (2006.01)
*G01N 33/50* (2006.01)
*G01N 1/42* (2006.01)

(52) U.S. Cl.
CPC ....... *A01N 1/0226* (2013.01); *G01N 33/5091* (2013.01); *G01N 1/42* (2013.01)

(58) Field of Classification Search
CPC ..... A01N 1/0226; G01N 1/42; G01N 33/5091
See application file for complete search history.

(56) References Cited

U.S. PATENT DOCUMENTS 1,682,344 A    8/1928  Lesieur
1,916,658 A    7/1933  Davidson
(Continued)

FOREIGN PATENT DOCUMENTS

CN    103827302 A    5/2014
EP    1246903 B1    10/2002
(Continued)

OTHER PUBLICATIONS

Gary Lee et al., T0070907, a Selective Ligand for Peroxisome Proliferator-activated Receptor γ, Functions as an Antagonist of Biochemical and Cellular Activities, 2002, J.B.C., vol. 277, No. 22, pp. 19649-19657 (Year: 2002).*
(Continued)

*Primary Examiner* — David W Berke-Schlessel
*Assistant Examiner* — Trent R Clarke
(74) *Attorney, Agent, or Firm* — Fish & Richardson P.C.

(57) ABSTRACT

The present invention generally relates to methods and compositions to determine viability of an organ for transplantation and other medical purposes. One aspect of the invention relates to a method for assessing the viability of an organ by measuring the energy parameters to determine the energy level of the organ by determining the stored cellular energy (e.g., ATP levels), and/or energy consumption over a particular time period of viability. The energy parameters can be compared to reference energy parameters as a highly accurate and reliable prediction of viable cell yield, and
(Continued)

organ viability. Another aspect of the invention relates methods to preserve or extend the time period of viability of an organ any combination of (i) preservation perfusion of the organ to prevent ischemic damage, (ii) chemical metabolic suppression of the organ e.g., using metabolic suppressants, (iii) metabolic suppression by physical or environmental conditions, e.g., sub-zero non-freezing storage.

10 Claims, 80 Drawing Sheets

Specification includes a Sequence Listing.

Related U.S. Application Data

(60) Provisional application No. 61/447,905, filed on Mar. 1, 2011, provisional application No. 61/364,186, filed on Jul. 14, 2010, provisional application No. 61/330,959, filed on May 4, 2010.

(56) References Cited

U.S. PATENT DOCUMENTS

| | | | |
|---|---|---|---|
| 3,183,961 A | 5/1965 | Brandt | |
| 3,406,531 A | 10/1968 | Swenson et al. | |
| 3,468,136 A | 9/1969 | Swenson et al. | |
| 3,545,221 A | 12/1970 | Swenson et al. | |
| 3,607,646 A | 12/1971 | De Roissart | |
| 3,660,241 A | 5/1972 | Michielsen | |
| 3,738,914 A | 6/1973 | Knudson et al. | |
| 3,772,153 A | 11/1973 | De Roissart | |
| 3,810,367 A | 5/1974 | Peterson | |
| 3,843,455 A | 10/1974 | Bier | |
| 3,877,843 A | 4/1975 | Fischel | |
| 3,881,990 A | 5/1975 | Burton et al. | |
| 3,914,954 A | 10/1975 | Doerig | |
| 3,995,444 A | 12/1976 | Clark et al. | |
| 4,186,565 A | 2/1980 | Toledo-Pereyra | |
| 4,242,883 A | 1/1981 | Toledo-Pereyra | |
| 4,745,759 A | 5/1988 | Bauer et al. | |
| 4,798,824 A | 1/1989 | Belzer et al. | |
| 5,356,771 A | 10/1994 | O'Dell | |
| 6,020,120 A | 2/2000 | Sharvata | |
| 6,046,046 A | 4/2000 | Hassanein | |
| 6,524,785 B1 | 2/2003 | Cozzone et al. | |
| 6,642,045 B1 | 11/2003 | Brasile | |
| 6,942,859 B2 | 9/2005 | Fisher et al. | |
| 7,410,474 B1 | 8/2008 | Friend et al. | |
| 7,504,201 B2 | 3/2009 | Taylor et al. | |
| 7,572,622 B2 | 8/2009 | Hassanein et al. | |
| 7,651,835 B2 | 1/2010 | Hassanein et al. | |
| 7,691,622 B2 | 4/2010 | Garland et al. | |
| 7,749,693 B2 | 7/2010 | Brassil et al. | |
| 7,811,558 B2 | 10/2010 | Ho et al. | |
| 7,811,808 B2 | 10/2010 | Van Der Plaats et al. | |
| 7,824,848 B2 | 11/2010 | Owen et al. | |
| 8,268,612 B2 | 9/2012 | Owen et al. | |
| 8,287,580 B2 | 10/2012 | Rakhorst et al. | |
| 8,323,954 B2 | 12/2012 | Kravitz et al. | |
| 8,440,390 B2 | 5/2013 | Brockbank | |
| 8,765,364 B2 | 7/2014 | Curtis et al. | |
| 8,771,930 B2 | 7/2014 | Curtis et al. | |
| 8,927,257 B2 | 1/2015 | Hutzenlaub et al. | |
| 8,986,978 B2 | 3/2015 | Brassil | |
| 9,078,428 B2 | 7/2015 | Hassanein et al. | |
| 9,215,867 B2 | 12/2015 | Hassanein et al. | |
| 9,247,728 B2 | 2/2016 | Fishman et al. | |
| 10,750,739 B2 | 8/2020 | Sandlin et al. | |
| 2002/0039786 A1 | 4/2002 | Reid et al. | |
| 2003/0216455 A1* | 11/2003 | Bril | A61K 31/4439 514/342 |
| 2004/0038997 A1 | 2/2004 | Macey | |
| 2004/0058432 A1 | 3/2004 | Owen et al. | |
| 2005/0147958 A1 | 7/2005 | Hassanein et al. | |
| 2005/0214877 A1 | 9/2005 | Wyant et al. | |
| 2005/0221269 A1 | 10/2005 | Taylor et al. | |
| 2006/0011633 A1 | 1/2006 | Cook et al. | |
| 2007/0009881 A1 | 1/2007 | Arzt et al. | |
| 2007/0042339 A1 | 2/2007 | Toner et al. | |
| 2007/0202485 A1* | 8/2007 | Nees | A01N 1/0226 435/284.1 |
| 2008/0096184 A1 | 4/2008 | Brasile | |
| 2008/0234768 A1 | 9/2008 | Hassanein et al. | |
| 2008/0288399 A1 | 11/2008 | Curtis et al. | |
| 2009/0123437 A1 | 5/2009 | Takebe | |
| 2010/0069326 A1 | 3/2010 | Haque et al. | |
| 2011/0027771 A1 | 2/2011 | Deng | |
| 2012/0201906 A1 | 8/2012 | Reynolds et al. | |
| 2012/0251999 A1 | 10/2012 | Demirci et al. | |
| 2014/0004046 A1 | 1/2014 | Raghunath et al. | |
| 2015/0322404 A1 | 11/2015 | Yarmush et al. | |
| 2017/0202211 A1 | 7/2017 | Muller et al. | |
| 2018/0094232 A1 | 4/2018 | Toner et al. | |
| 2019/0335745 A1 | 11/2019 | Fekete et al. | |
| 2021/0007348 A1 | 1/2021 | Sandlin et al. | |
| 2021/0100827 A1 | 4/2021 | Audia et al. | |
| 2022/0104482 A1 | 4/2022 | Toner et al. | |
| 2022/0330543 A1 | 10/2022 | Toner et al. | |

FOREIGN PATENT DOCUMENTS

| | | |
|---|---|---|
| JP | 2004-513369 | 4/2004 |
| JP | 2008-509924 | 4/2008 |
| JP | 2009221128 A * | 10/2009 |
| JP | 2012-526849 | 11/2012 |
| KR | 20010002227 A | 1/2001 |
| WO | WO 1998/041087 | 9/1998 |
| WO | WO 2002/039124 | 5/2002 |
| WO | WO 2002/049653 | 6/2002 |
| WO | WO 2006/076401 | 7/2006 |
| WO | 2007025233 A1 | 3/2007 |
| WO | WO 2007/120829 | 10/2007 |
| WO | 2008024195 A2 | 2/2008 |
| WO | WO 2011/014741 | 2/2011 |
| WO | WO 2012/024693 | 2/2012 |
| WO | WO 2013/045458 | 4/2013 |
| WO | WO 2014/059316 | 4/2014 |
| WO | WO 2017/123759 | 7/2017 |
| WO | WO 2018/232110 | 12/2018 |
| WO | WO 2020/163500 | 8/2020 |
| WO | WO 2020/229761 | 11/2020 |
| WO | WO 2022/241417 | 11/2022 |

OTHER PUBLICATIONS

Jill M. Seargent, Elisabeth A. Yates, Jason H. Gill, GW9662, a potent antagonist of PPARγ, inhibits growth of breast tumour cells and promotes the anticancer effects of the PPARγ agonist rosiglitazone, independently of PPARγ activation, 2004, British Journal of Pharmacology, vol. 143, pp. 933-937 (Year: 2004).*

Jen-Hwey Chiu, Juo-Chi Wang, Wing-Yiu Lui, Chew-Wun Wu, and Chuang-Ye Hong, Effect of Magnolol on in Vitro Mitochondrial Lipid Peroxidation and Isolated Cold-Preserved Warm-Reperfused Rat Livers, 1999, Journal of Surgical Research, vol. 82, pp. 11-16 (Year: 1999).*

Sugimachi, K., Roach, K.L., Rhoads, D.B., Tompkins, R.G. & Toner, M. Nonmetabolizable glucose compounds impart cryotolerance to primary rat hepatocytes. Tissue Eng. 12, 579-588 (2006). (Year: 2006).*

Tolboom et al., "Subnormothermic Machine Perfusion at Both 20° C. and 30° C. Recovers Ischemic Rat Livers for Successful Transplantation", Journal of Surgical Research 175(1): 149-156 (2012).

Vairetti et al., "Correlation Between the Liver Temperature Employed During Machine Perfusion and Reperfusion Damage: Role of Ca2+", Liver Transplantation 14:494-503 (2008).

Vajdova et al., "ATP-Supplies in the Cold-Preserved Liver: A Long-Neglected Factor of Organ Viability", Hepatology 36(6):1543-1552 (2002).

Vajdova et al., "Cold-Preservation-Induced Sensitivity of Rat Hepatocyte Function to Rewarming Injury and Its Prevention by Short-Term Reperfusion", Hepatology 32(2):289-296 (2000).

(56) References Cited

OTHER PUBLICATIONS

Van Der Plaats et al., "The Groningen Hypothermic Liver Perfusion Pump: Functional Evaluation of a New Machine Perfusion System", Annals of Biomedical Engineering 34(12):1924-1934 (2006).
Vollmar et al., "In vivo quantification of ageing changes in the rat liver from early juvenile to senescent life", Liver 2:330-341 (2002).
Wojcicki et al., "Biliary Tract Complications after Liver Transplantation: A Review", Digestive Surgery 25:245-257 (2008).
Xu et al., "Excorporeal Normothermic Machine Perfusion Resuscitates Pig DCD Livers with Extended Warm Ischemia", Journal of Surgical Research 173(2):e83-e88 (2012).
Zhao et al., "Cell-permeable Peptide Antioxidants Targeted to Inner Mitochondrial Membrane inhibit Mitochondrial Swelling, Oxidative Cell Death, and Reperfusion Injury", The Journal of Biological Chemistry 279(33):34682-34690 (2004).
Berendsen et al., "Hepatocyte viability and ATP content decrease linearly over time during conventional cold storage of rat liver grafts", Transplantation Proceedings 43(5):1484-1488 (2011).
Bessems et al., "Improved Machine Perfusion Preservation of the Non-Heart-Beating Donor Rat Liver Using Polysol: A New Machine Perfusion Preservation Solution", Liver Transplantation 11(11):1379-1388 (2005).
Bessems et al., "Machine Perfusion Preservation of the Pig Liver Using a New Preservation Solution, Polysol", Transplantation Proceedings 38:1238-1242 (2006).
Brockmann et al., "Normothermic Perfusion: A New Paradigm for Organ Preservation", Annals of Surgery 250(1):1-6 (2009).
Buis et al., "Altered bile composition after liver transplantation is associated with the development of nonanastomotic biliary strictures", Journal of Hepatology 50:69-79 (2009).
Butler et al., "Successful Extracorporeal Porcine Liver Perfusion for 72 HR", Transplantation 73(8):1212-1218 (2002).
Chen et al., "Effective Application of ET-Kyoto Solution for Clinical Lung Transplantation", Transplantation Proceedings 36:2812-2815 (2004).
Cypel et al., "Normothermic Ex Vivo Perfusion Prevents Lung Injury Compared to Extended Cold Preservation for Transplantation", American Journal of Transplantation 9:2262-2269 (2009).
De Rougemont et al., "One Hour Hypothermic Oxygenated Perfusion (HOPE) Protects Nonviable Liver Allografts Donated After Cardiac Death", Annals of Surgery 250(5):674-683 (2009).
De Vera et al., "Liver Transplantation Using Donation After Cardiac Death Donors: Long-Term Follow-Up from a Single Center", American Journal of Transplantation 9:773-781 (2009).
Donato et al., "Liver Grafts Preserved in Celsior Solution as Source of Hepatocytes for Drug Metabolism Studies: Comparison With Surgical Liver Biopsies", Drug Metabolism and Disposition 33(1):108-114 (2005).
Fahy et al., "Cryopreservation of Complex Systems: The Missing Link in the Regenerative Medicine Supply Chain", Rejuvenation Research 9(2):279-291 (2006).
Ferrigno et al., "Machine perfusion at 20° C. reduces preservation damage to livers from non-heart beating donors", Cryobiology 62:152-158 (2011).
Friend et al., "Normothermic Perfusion of the Isolated Liver", Transplantation Proceedings 33:3436-3438 (2001).
Geuken et al., "Rapid increase of bile salt secretion is associated with bile duct injury after human liver transplantation", Journal of Hepatology 41:1017-1025 (2004).
Giknis et al., "Clinical Laboratory Parameters for the Crl:CD(SD) Rat", Charles River Laboratories 1-14 (2006).
Guarrera et al., "Hypothermic Machine Preservation in Human Liver Transplantation: The First Clinical Series", American Journal of Transplantation 10:372-381 (2010).
Guibert et al., "Organ Preservation: Current Concepts and New Strategies for the Next Decade", Transfusion Medicine and Hemotherapy 38:125-142 (2011).
Hertl et al., "Evidence of Preservation Injury to Bile Ducts by Bile Salts in the Pig and Its Prevention by Infusions of Hydrophilic Bile Salts", Hepatology 21(4): 1130-1137 (1995).

Hoekstra et al., "Bile Salt Toxicity Aggravates Cold Ischemic Injury of Bile Ducts After Liver Transplantation in Mdr2 +/− Mice", Hepatolgy 43(5):1022-1031 (2006).
Hughes et al., "Isolation of Hepatocytes from Livers from Non-Heart-Beating Donors for Cell Transplantation", Liver Transplantation 12:713-717 (2006).
Imber et al., "Optimisation of Bile Production during Normothermic Preservation of Porcine Livers", American Journal of Transplantation 2:593-599 (2002).
Izamis M., "Ex vivo perfusion optimization of donor liver grafts for transplantation and cell isolation", Doctoral dissertation, Massachusetts Institute of Technology 193-222 (2010).
Jain et al., "Long-Term Survival After Liver Transplantation in 4,000 Consecutive Patients at a Single Center", Annals of Surgery 232(4):490-500 (2000).
Kamiike et al., "Adenine Nucleotide Metabolism and Its Relation to Organ Viability in Human Liver Transplantation", Transplantation 45(1):138-143 (1988).
Koetting et al., "Donation After Cardiac Death: Dynamic Graft Reconditioning During or After Ischemic Preservation?", Artificial Organs 35(6):565-571 (2011).
Lanir et al., "Hepatic Transplantation Survival: Correlation with Adenine Nucleotide Level in Donor Liver", Hepatology 8(3):471-475 (1988).
Lee et al., "Metabolic Flux Analysis of Postburn Hepatic Hypermetabolism", Metabolic Engineering 2:312-327 (2000).
Luer et al., "Role of oxygen during hypothermic machine perfusion preservation of the liver", Transplant International 23:944-950 (2010).
McCord, "Oxygen-Derived Free Radicals in Postischemic Tissue Injury", The New England Journal of Medicine 312(3):159-163 (1985).
McCormack et al., "Use of Severely Steatotic Grafts in Liver Transplantation: A Matched Case-Control Study", Annals of Surgery 246(6):940-948 (2007).
Minor et al., "Fibrinolysis in organ procurement for transplantation after cardiocirculatory compromise", Thrombosis and Haemostasis 90:361-362 (2003).
Mitchell et al., "Energy Metabolism Following Prolonged Hepatic Cold Preservation: Benefits of Interrupted Hypoxia on the Adenine Nucleotide Pool in Rat Liver", Cryobiology 39:130-137 (1999).
Miyagi et al., "The Significance of Preserving the Energy Status and Microcirculation in Liver Grafts From Non-Heart-Beating Donor", Cell Transplantation 17:173-178 (2008).
Moore et al., "Impact of Donor, Technical, and Recipient Risk Factors on Survival and Quality of Life After Liver Transplantation", Archives of Surgery 140(3):273-277 (2005).
Nelson et al., "An improved ex vivo method of primary porcine hepatocyte isolation for use in bioartificial liver systems", European Journal of Gastroenterology & Hepatology 12(8):923-930 (2000). http://cat.inist.fr/?aModele=afficheN&cpsidt=1451795 accessed Aug. 21, 2008.
Okamoto et al., "Successful Sub-zero Non-freezing Preservation of Rat Lungs at -2° C. Utilizing a New Supercooling Technology", Journal of Heart and Lung Transplantation 27(10):1150-1157 (2008).
Perk et al., "A Metabolic Index of Ischemic Injury for Perfusion-Recovery of Cadaveric Rat Livers", PLoS ONE 6(12):e28518 (2011). (11 pages).
Peter et al., "Hepatic Control of Perfusate Homeostasis During Normothermic Extrocorporeal Preservation", Transplantation Proceedings 35:1587-1590 (2003).
Reddy et al., "Non-Heart-Beating Donor Porcine Livers: the Adverse Effect of Cooling", Liver Transplantation 11(1):35-38 (2005).
Reddy et al., "Preservation of Porcine Non-Heart-Beating Donor Livers By Sequential Cold Storage and Warm Perfusion", Transplantation 77(9):1328-1332 (2004).
Sakaguchi et al., "Preservation of Myocardial Function and Metabolism at Subzero Nonfreezing Temperature Storage of the Heart", The Journal of Heart and Lung Transplantation 15(11):1101-1107 (1996).
Serracino-Inglott et al., "Hepatic ischemia-reperfusion injury", The American Journal of Surgery 181:160-166 (2001).

(56) References Cited

OTHER PUBLICATIONS

Soltys et al., "Successful Nonfreezing, Subzero Preservation of Rat Liver with 2,3-Butanediol and Type I Antifreeze Protein", Journal of Surgical Research 96(1):30-34 (2001).
St Peter et al., "Extended preservation of non-heart-beating donor livers with normothermic machine perfusion", British Journal of Surgery 89:609-616 (2002).
Sugimachi et al., "Nonmetabolizable glucose compounds impart cryotolerance to primary rat hepatocytes", Tissue Eng 12(3):579-588 (2006).
Taylor et al., "Twenty-Four Hour Hypothermic Machine Perfusion Preservation of Porcine Pancreas Facilitates Processing for Islet Isolation", Transplantation Proceedings 40:480-482 (2008).
Tolboom et al., "A Model for Normothermic Preservation of the Rat Liver", Tissue Engineering 13(8):2143-2151 (2007).
Tolboom et al., "Recovery of Warm Ischemic Rat Liver Grafts by Normothermic Extracorporeal Perfusion", Transplantation 87(2):170-177 (2009).
Tolboom et al., "Sequential Cold Storage and Normothermic Perfusion of the Ischemic Rat Liver", Tranplantation Proceedings 40(5):1306-1309 (2008).
Afonso et al., "Critical parameters in blood processing fort-cell assays: validation on elispot and tetramer platforms," J Immunol Methods, 2010, 359(1-2):28-36.
Almanza et al., "Endoplasmic reticulum stress signalling—from basic mechanisms to clinical applications," FEBS J., 2019, 286(2):241-278.
Amir et al., "Improved viability and reduced apoptosis in sub-zero 21-hour preservation of transplanted rat hearts using anti-freeze proteins," J. Heart Lung Transplant., 2005, 24(11):1915-1929.
Amir et al., "Prolonged 24-hour subzero preservation of heterotopically transplanted rat hearts using antifreeze proteins derived from arctic fish," Ann. Thorac. Surg., May 2004, 77(5):1648-1655.
Amir et al., "Subzero nonfreezing cryopresevation of rat hearts using antifreeze protein I and antifreeze protein III," Cryobiology, Jun. 2004, 48(3):273-282.
Ardehali et al., "Ex-vivo perfusion of donor hearts for human heart transplantation (Proceed II): a prospective, open-label, multicentre, randomised non-inferiority trial," The Lancet, Jun. 2015, 385(9987):2577-2584, 8 pages.
Armstrong et al., "The hydrodynamic radii of macromolecules and their effect on red blood cell aggregation," Biophys. J, Dec. 2004, 87(6):4259-70.
Arrington and McNamara, "Effect of agitation on platelet aggregation and microaggregate formation in banked blood," Ann. Surg., 1975, 181 (2):243-44.
AU Office Action in Australian Appln. No. 2015301303 dated Sep. 28, 2020, 4 pages.
Avruch et al., "A novel model for ex situ reperfusion of the human liver following subnormothermic machine perfusion," Technology (Singap World Sci.), Dec. 2017, 5(4):196-200, 5 pages.
Bang et al., "Antifreeze peptides and glycopeptides, and their derivatives: Potential uses in biotechnology," Marine Drugs, Jun. 2013, 11(6):2013-2041.
Baskin-Bey et al., "Cathepsin B inactivation attenuates hepatocyte apoptosis and liver damage in steatotic livers after cold ischemia-warm reperfusion injury," Am. J. Physiol. Gastrointest. Liver Physiol., Feb. 2005, 288(2):G396-G402.
Baskin-Bey et al., "Clinical Trial of the Pan-Caspase Inhibitor, IDN-6556, in Human Liver Preservation Injury," Am J Transplant, 2007, 7(1):218-25.
BDJ.co.jp [online], "BD Vacuteina Blood Collecting Tube," 2022, retrieved on Aug. 16, 2022, retrieved from URL<https://www.bdj.co.jp/pas/products/mekkin/1f3pro00000ntpw3.html>, 2 pages (with English translation).
Behrends et al., "Network organization of the human autophagy system," Nature, Jul. 2010, 466(7302):68-76.
Berendsen et al., "Supercooling Enables Long-Term Transplantation Survival Following 4 Days of Liver Preservation," Nat. Med. Jul. 2014, 20(7):790-793, 5 pages.

Bergan et al., "Low molecular weight dextran in treatment of severe ischemia," Arch. Surg., 1965, 91(2):338.
Best, "Cryoprotectant Toxicity: Facts, Issues, and Questions," Rejuvenation Res., Oct. 2015, 18(5):422-436.
Boteon et al., "Mechanisms of autophagy activation in endothelial cell and their targeting during normothermic machine liver perfusion," World J. Gastroenterol., Dec. 2017, 23(48):8443-8451.
Brenner et al., "Decoding cell death signals in liver inflammation," J Hepatol, Sep. 2013, 59(3):583-94.
Briard et al., "Small molecule ice recrystallization inhibitors mitigate red blood cell lysis during freezing, transient warming and thawing," Sci. Rep., 2016, 29(6):23619, 10 pages.
Brill et al., "Neutrophil extracellular traps promote deep vein thrombosis in mice," J Thromb. Haemost., 2012, 10(1):136-44.
Brinkmann and Zychlinsky, "Neutrophil extracellular traps: is immunity the second function of chromatin?," J Cell Biol., 2012, 198(5):773-83.
Brown et al., "Morphological, biochemical, and functional changes in human platelets subjected to shear stress," J Lab. Clin. Med., 1975, 86(3):462-71.
Bruinsma and Uygun, "Subzero organ preservation: the dawn of a new ice age?," Curr. Opin. Organ Transplant., 2017, 22(3):281-286, 6 pages.
Bruinsma et al., "Determination and Extension of the Limits to Static Cold Storage with Subnormothermic Machine Perfusion," The International Journal of Artificial Organs, 2013, 36(11):775-780.
Bruinsma et al., "Metabolic profiling during ex vivo machine perfusion of the human liver," Sci. Rep., 2016, 6:22415, 13 pages.
Bruinsma et al., "Subnormothermic Machine Perfusion for Ex Vivo Preservation and Recovery of the Human Liver for Transplantation: Subnormothermic Machine Perfusion of Human Livers," Am. J. Transplant., 2014, 14(6):1400-1409.
Bruinsma et al., "Supercooling preservation and transplantation of the rat liver," Nat. Protoc., Mar. 2015, 10(3):484-494.
Burkey et al., "Understanding Poly(vinyl alcohol)-Mediated Ice Recrystallization Inhibition through Ice Adsorption Measurement and pH Effects," Biomacromolecules, 2018, 19(1):248-55, 40 pages.
CA Office Action in Canadian Appln. No. 2,957,535, dated Aug. 20, 2021, 5 pages.
Campbell et al., "Restoration of ovarian function and natural fertility following the cryopreservation and autotransplantation of whole adult sheep ovaries," Hum. Reprod., Jun. 2014, 29(8):1749-1763.
Celik et al., "Microfluidic experiments reveal that antifreeze proteins bound to ice crystals suffice to prevent their growth," Proc. Nat'l Acad. Sci. U S A, 2013, 110(4):1309-1314.
Chawade et al., "Normalyzer: a tool for rapid evaluation of normalization methods for omics data sets," J. Proteome Res., 2014, 13(6):3114-3120.
Chen et al., "A Versatile Polypharmacology Platform Promotes Cytoprotection and Viability of Human Pluripotent and Differentiated Cells," Nature Methods, 2021, 18:528-541.
Cheng et al., "A microfluidic device for practical label-free CD4(+) t cell counting of HIV-infected subjects," Lab Chip, Feb. 2007, 7(2):170-78.
Chien et al., "Blood viscosity: influence of erythrocyte aggregation," Science, Aug. 1967, 157 (3790): 829-31.
Chinese Office Action in Application No. 201580054390.3, dated Mar. 19, 2018, 8 pages (with English translation).
Cho et al., "Changes in the expression of cell cycle regulators during rat liver regeneration after partial hepatectomy," Exp. Mol. Med., 1996, 28(4):187-191.
CN Office Action in Chinese Appln. No. 201580054390.3, dated Nov. 15, 2021, 17 pages (with English summary).
CN Office Action in Chinese Appln. No. 201580054390.3, dated Feb. 3, 2020, 19 pages (with English translation).
CN Office Action in Chinese Appln. No. 201580054390.3, dated Jun. 28, 2020, 12 pages (with English translation).
Costanzo et al., "Hibernation physiology, freezing adaptation and extreme freeze tolerance in a northern population of the wood frog," J. Exp. Biol., Sep. 2013, 216(Pt 18):3461-3473.

(56) References Cited

OTHER PUBLICATIONS

De Rose et al., "Granulocyte contamination dramatically inhibits spot formation in aids virus-specific elispot assays: analysis and strategies to ameliorate," J Immunol Methods, 2005, 297(1-2): 177-86.

De Vries et al., "Abstract 615.2: Extending the Human Liver Preservation Time for Transplantation by Supercooling," Transplantation, Jul. 2018, 102(7S):S396.

De Vries et al., "Pretransplant sequential hypo- and normothermic machine perfusion of suboptimal livers donated after circulatory death using a hemoglobin-based oxygen carrier perfusion solution," Am. J. Transplant. Off. J. Am. Soc. Transplant. Am. Soc. Transpl. Surg., 2019, 19:1202-1211.

De Vries et al., "Supercooling extends preservation time of human livers," Nat. Biotechnol., Oct. 2019, 37(10):1131-1136, 10 pages.

De Vries et al., "Systems engineering the organ preservation process for transplantation," Curr. Op. Biotechnol., Aug. 2019, 58:192-201.

Devireddy et al., "Liver Freezing Response of the Freeze-Tolerant Wood Frog, Rana sylvatica, in the Presence and Absence of Glucose. I. Experimental Measurements," Cryobiology, 1999, 38:310-326.

Do Amaral et al., "Hepatocyte responses to in vitro freezing and β-adrenergic stimulation: Insights into the extreme freeze tolerance of subarctic Rana sylvatica," J. Exp. Zool. Part Ecol. Genet. Physiol., 2015, 323(2):89-96.

Dobin et al., "STAR: ultrafast universal RNA-seq aligner," Bioinformatics, Jan. 2013, 29(1):15-21.

Eickhoff et al., "Contrasting Behavior of Antifreeze Proteins: Ice Growth Inhibitors and Ice Nucleation Promoters," J. Phys. Chem. Lett., 2019,10(5):966-972.

Emadali et al., "Distinct endoplasmic reticulum stress responses are triggered during human liver transplantation," J. Pathol., Sep. 2005, 207(1):111-118.

EP Extended European Search Report in European Appln. No. 20150503.9, dated Jun. 15, 2020, 10 pages.

Eshmuminov et al., "An integrated perfusion machine preserves injured human livers for 1 week," Nat. Biotechnol., Feb. 2020, 38(2):189-198.

Extended European Search Report in Application No. 15829066.8, dated Mar. 5, 2018, 10 pages.

Fahy et al., "Cryopreservation of organs by vitrification: perspectives and recent advances," Cryobiology, Apr. 2004, 48(2):157-178.

Fahy et al., "Physical and biological aspects of renal vitrification," Organogenesis, 2009, 5(3):167-175.

Fahy, "Analysis of "solution effects" injury: Cooling rate dependence of the functional and morphological sequellae of freezing in rabbit renal cortex protected with dimethyl sulfoxide," Cryobiology, 1981, 18(6):550-570.

Fairlie et al., "Crosstalk between apoptosis and autophagy signaling pathways," Int Rev Cell Mol Biol, 2020, 352:115-158.

Farrant, "Mechanism of cell damage during freezing and thawing and its prevention," Nature, 1965, 205:1284-1287.

Fuchs et al., "Neutrophils release extracellular DNA traps during storage of red blood cell units," Transfusion, 2013, 53(12):3210-16.

Fuchs et al., "Novel cell death program leads to neutrophil extracellular traps," J Cell Biol., Jan. 2007, 176(2):231-41.

Galluzzi et al., "Caspases Connect Cell-Death Signaling to Organismal Homeostasis," Immunity, 2016, 44:221-31.

Garcia-Romo et al., "Netting neutrophils are major inducers of type i ifn production in pediatric systemic lupus erythematosus," Sci. Transl. Med., Mar. 2011, 3(73):73ra20.

GE Healthcare, Data File 18-1158-27 AB, Cell preparation, 2007, 6 pages.

Gearing et al., "CiiiDER: a tool for predicting and analysing transcription factor binding sites," PLoS One, 2019, 14:e0215495, 12 pages.

Gervin et al., "The effect of agitation of stored human blood on microaggregate formation," Transfusion, Jan. 1978, 18(1):73-78.

Giwa et al., "The promise of organ and tissue preservation to transform medicine," Nat Biotechnol., 2017, 35(6):530-542.

Graw et al., "proteiNorm—A User-Friendly Tool for Normalization and Analysis of TMT and Label-Free Protein Quantification," ACS Omega 2020, 5(40):25625-25633.

Grimberg et al., "p53-Dependent and p53-Independent Induction of Insulin-Like Growth Factor Binding Protein-3 by Deoxyribonucleic Acid Damage and Hypoxia," J. of Clin. Endocrinology & Metabolism, Jun. 2005, 90(6):3568-74.

Gringeri et al., "Subnormothermic machine perfusion for non-heart-beating donor liver grafts preservation in a Swine model: a new strategy to increase the donor pool?," Transplant. Proc., 2012, 44(7):2026-2028.

Gu et al., "circlize Implements and enhances circular visualization in R," Bioinformatics, Oct. 2014, 30(19):2811-2, 2 pages.

Guicciardi and Gores, "Apoptosis: a mechanism of acute and chronic liver injury," Gut, 2005, 54:1024-33.

Guicciardi et al., "Apoptosis and necrosis in the liver," Compr Physiol, 2013, 3(2):977-1010.

Hamilton et al., "Successful preservation of canine small intestine by freezing," J. Surg. Res., 1973, 14(4):313-318.

Hardwick, "Blood processing," ISBT Sci. Ser., 2008, 3:148-76.

Harrison et al., "A randomized, placebo-controlled trial of emricasan in patients with NASH and F1-F3 fibrosis," J Hepatol, 2020, 72:816-827.

Hasan et al., "Ice Recrystallization Inhibiting Polymers Enable Glycerol-Free Cryopreservation of Microorganisms," Biomacromolecules, 2018, 19(8):3371-3376.

Hoglen et al., "A caspase inhibitor, IDN-6556, ameliorates early hepatic injury in an ex vivo rat model of warm and cold ischemia," Liver Transpl, 2007, 13:361-6.

Hoglen et al., "Characterization of IDN-6556 (3-{2-(2-tert-Butylphenylaminooxaly1)-amino]-propionylamino}-4-oxo-5-(2,3,5,6-tetrafluoro-phenoxy)-pentanoic Acid): a Liver-Targeted Caspase Inhibitor," The Journal of Pharmacology and Experimental Therapeutics, 2008, 309(2):634-640.

Huang et al., "A microfluidics approach for the isolation of nucleated red blood cells (NRBCs) from the peripheral blood of pregnant women," Prenat Diagn, Oct. 2008, 28(10):892-99.

Huber et al., "Variance stabilization applied to microarray data calibration and to the quantification of differential expression," Bioinformatics, 2002, 18(Suppl 1):S96-104.

Huestis and Glasser, "The neutrophil in transfusion medicine," Transfusion., Jul. 1994, 34(7):630-46.

Hunt et al., "Freeze-substitution and isothermal freeze-fixation studies to elucidate the pattern of ice formation in smooth muscle at 252 K (-21° C.)," J. Microsc., 1982, 125(2):177-186.

Hunt, "Studies on cellular structure and ice location in frozen organs and tissues: The use of freeze-substitution and related techniques," Cryobiology, 1984, 21(4):385-402.

IN Office Action in Indian Appln. No. 201717004487, dated Sep. 25, 2020, 7 pages.

International Preliminary Report on Patentability in International Application No. PCT/US2015/043269, dated Feb. 7, 2017.

International Search Report and Written Opinion in International Appln. No. PCT/US2020/017310, mailed on Jul. 21, 2020, 24 pages.

International Search Report and Written Opinion in International Appln. No. PCT/US2022/072229, mailed on Oct. 6, 2022, 15 pages.

International Search Report and Written Opinion mailed Oct. 26, 2015 in International Application No. PCT/US15/43269, 22 pages.

Invitation to Pay Additional Fees And, Where Applicable, Protest Fee in International Appln. No. PCT/US2020/017310, mailed on Apr. 30, 2020, 3 pages.

Invitation to Pay Additional Fees And, Where Applicable, Protest Fee in International Appln. No. PCT/US2022/072229, mailed on Jul. 18, 2022, 3 pages.

Ishiguro and Rubinsky, "Mechanical interactions between ice crystals and red blood cells during directional solidification," Cryobiology, 1994, 31(5):483-500.

Ishine et al., "A Histological Analysis of Liver Injury in Freezing Storage," Cryobiology, 1999, 39(3):271-277.

Ishine et al., "Transplantation of Mammalian Livers Following Freezing: Vascular Damage and Functional Recovery," Cryobiology, 2000, 40(1):84-89.

(56) References Cited

OTHER PUBLICATIONS

Jan et al., "The disaggregation effect of dextran 40 on red cell aggregation in macromolecular suspensions," Biorheology, 1982, 19(4):543-54.
Jassem et al., "Normothermic machine perfusion (NMP) inhibits proinflammatory responses in the liver and promotes regeneration," Hepatology, 2019, 70(2):682-695, 34 pages.
JP Office Action in Japanese Appln. No. 2017-50678, dated May 28, 2019, 7 pages (with English translation).
JP Office Action in Japanese Appln. No. 2020-066388, dated Mar. 23, 2021, 10 pages (with English translation).
Karabacak et al., "Microfluidic, marker-free isolation of circulating tumor cells from blood samples," Nat Protoc, Mar. 2014, 9(3):694-710.
Karimian et al., "Ex Situ normothermic machine perfusion of donor livers," J. Vis. Exp., 2015, 99:e52688, 9 pages.
Katenz et al., "Cryopreservation of primary human hepatocytes: The benefit of trehalose as an additional cryoprotective agent," Liver Transplant., 2007, 13(1):38-45.
Klopfleisch et al., "Excavation of a buried treasure—DNA, mRNA, miRNA and protein analysis in formalin fixed, paraffin embedded tissues," Histol Histopathol, 2011, 26(6):797-810.
Kotz et al., "Clinical microfluidics for neutrophil genomics and proteomics," Nat. Med., Sep. 2010, 16(9): 1042-47.
Kramer et al., "Differentiation between cell death modes using measurements of different soluble forms of extracellular cytokeratin 18," Cancer Res, 2004, 64(5):1751-6.
Kuhne et al., "Flow Cytometric Evaluation of Platelet Activation in Blood Collected Into EDTA vs. Diatube-H, a Sodium Citrate Solution Supplemented With Theophylline, Adenosine, and Dipyridamole," Am J Hematol, Sep. 1995, 50(1),40-45.
Kuiper et al., "The biological function of an insect antifreeze protein simulated by molecular dynamics," eLife, 2015, 4:e05142, 14 pages.
Laing et al., "Viability testing and transplantation of marginal livers (VITTAL) using normothermic machine perfusion: study protocol for an open-label, nonrandomised, prospective, single-arm trial," BMJ Open, 2017, 7(11):e017733, 15 pages.
Lamming et al., "Hepatic signaling by the mechanistic target of rapamycin complex 2 (mTORC2)," FASEB J., 2014, 28(1):300-15, 16 pages.
Layne et al., "Freeze duration influences postfreeze survival in the frog Rana sylvatica," J. Exp. Zool., 1998, 280(2):197-201.
Libbrecht, "Physical Dynamics of Ice Crystal Growth," Annu. Rev. Mater. Res., 2017, 47(1):7.1-7.25.
Lin and Carroll, "The effect of calcium and magnesium on frozen rat uteri, and the calcium content of uteri frozen by various procedures," Cryobiology, 1968, 5(2):105-108.
Liu and Green, "Endoplasmic reticulum stress and liver diseases," Liver Res., 2019, 3(1):55-64.
Livak and Schmittgen, "Analysis of relative gene expression data using real-time quantitative PCR and the 2(-Delta Delta C(T)) Method," Methods, Dec. 2001, 25(4):402-8.
Lowe, "Blood rheology in vitro and in vivo," Baillieres. Clin. Haematol., 1987, 1(3):597-636.
Luu and Storey, "Solving Donor Organ Shortage with Insights from Freeze Tolerance in Nature: Activating endogenous antioxidant systems with non-coding RNA to precondition donor organs," BioEssays News Rev. Mol. Cell. Dev. Biol., 2018, 40(10):e1800092, 5 pages.
Maheswaran et al., "Detection of mutations in egfr in circulating lung-cancer cells," N. Engl. J. Med., Jul. 2008, 359( 4):366-77.
Martins et al., "The role of normothermic machine perfusion in liver transplantation," Int J Surg, 2020, 82(S):52-60, 9 pages.
Med.Kyushu-u.ac.jp [online], "Kyushu University Hospital Laboratory Inspection Section Newsletter," Apr. 20, 2007, retrieved on Aug. 16, 2022, retrieved from URL<https://www.med.kyushu-u.ac.jp/cclm/html/tayori/kensa32.htm>, 15 pages (with English translation).
Mergental et al., "Transplantation of Declined Liver Allografts Following Normothermic Ex-Situ Evaluation," Am. J. Transplant. Off. J. Am. Soc. Transplant. Am. Soc. Transpl. Surg., 2016, 16(11):3235-3245.
Mergental et al., "Transplantation of discarded livers following viability testing with normothermic machine perfusion," Nat. Commun., 2020, 11:2939, 13 pages.
Michalopoulos and Bhushan, "Liver regeneration: biological and pathological mechanisms and implications," Nat. Rev. Gastroenterol. Hepatol., 2021, 18:40-55, 16 pages.
Miyamoto and Sasakawa, "Studies on granulocyte preservation. III. Effect of agitation on granulocyte concentrates," Transfusion, 1987, 27(2): 165-66.
Moss et al., "Observations on the effects of glycerol on the cold storage of the canine liver," J. Surg. Res., 1966, 6(4):147-151.
Mueller et al., "Caspase 3 inhibition improves survival and reduces early graft injury after ischemia and reperfusion in rat liver transplantation," Transplantation, 2004, 78(9):1267-73.
Mugnano et al., "Antifreeze glycoproteins promote intracellular freezing of rat cardiomyocytes at high subzero temperatures," Am. J. Physiol. Regul. Integr. Comp. Physiol., 1995, 269(2):R474-479.
Murata and Tanaka, "Liquid-liquid transition without macroscopic phase separation in a water-glycerol mixture," Nat. Mater., 2012, 11:436-443.
Nagrath et al., "Isolation of rare circulating tumour cells in cancer patients by microchip technology," Nature, Dec. 2007, 450(7173): 1235-39.
Nasralla et al., "A randomized trial of normothermic preservation in liver transplantation," Nature, 2018, 557(7703):50-56, 23 pages.
Nassar et al., "Ex Vivo Normothermic Machine Perfusion Is Safe, Simple, and Reliable: Results From a Large Animal Model," Surg. Innov., 2015, 22:61-69, 10 pages.
Natori et al., "Apoptosis of sinusoidal endothelial cells occurs during liver preservation injury by a caspase-dependent mechanism," Transplantation, 1999, 68:89-96.
Natori et al., "The caspase inhibitor IDN-6556 prevents caspase activation and apoptosis in sinusoidal endothelial cells during liver preservation injury," Liver Transpl, 2003, 9(3):278-84.
Naullage et al., "Molecular Recognition of Ice by Fully Flexible Molecules," J. Phys. Chem. C, 2017, 121(48):26949-26957.
Neu and Meiselman, "Depletion-mediated red blood cell aggregation in polymer solutions," Biophys. J, Nov. 2002, 83(5):2482-90.
Neu et al., "Aggregation of human RBC in binary dextran-peg polymer mixtures," Biorheology., 2001, 38(1):53-68.
Nicholson et al., "Comparison of T and B cell analyses on fresh and aged blood," J Immunol Methods, Oct. 1984, 73(1):29-40.
Nösser et al., "Development of a Rat Liver Machine Perfusion System for Normothermic and Subnormothermic Conditions," Tissue Eng. Part A, 2020, 26(1):57-65.
Notice of Allowance in Chinese Appln. No. 201580054390.3, dated Mar. 9, 2022, 3 pages (with English translation).
O'Connor et al., "Usefulness of Soluble and Surface-Bound P-Selectin in Detecting Heightened Platelet Activity in Patients With Congestive Heart Failure," Am J Cardiol., May 1999, 83(9), 1345-1349.
Office Action in Canadian Appln. No. 2,957,535, dated Mar. 10, 2022, 4 pages.
Office Action in Chinese Application No. 201580054390.3, dated Dec. 10, 2018, 12 pages (with English translation).
Office Action in Chinese Application No. 201580054390.3, dated Apr. 23, 2019, 25 pages (with English translation).
Office Action in Japanese Appln. No. 2020-066388, dated Aug. 2, 2022, 6 pages (with English translation).
Office Action in Japanese Appln. No. 2020-066388, dated Nov. 22, 2021, 9 pages (with English translation).
Ohman et al., "Activation of autophagy during normothermic machine perfusion of discarded livers is associated with improved hepatocellular function," Am J Physiol Gastrointest Liver Physiol., Jan. 2022, 322(1):G21-G33.
Op den Dries et al., "Hypothermic Oxygenated Machine Perfusion Prevents Arteriolonecrosis of the Peribiliary Plexus in Pig Livers Donated after Circulatory Death," PLoS ONE, 2014, 9;e88521, 10 pages.

(56) References Cited

OTHER PUBLICATIONS

Orning and Lien, "Multiple roles of caspase-8 in cell death, inflammation, and innate immunity," J Leukoc Biol, 2020, 109:121-141.
Orringer et al., "Purified poloxamer 188 for treatment of acute vaso-occlusive crisis of sickle cell disease: a randomized controlled trial," JAMA., Nov. 2001, 286(17):2099-2106.
Ott et al., "Solid-liquid phase equilibria in water + ethylene glycol," J. Chem. Thermodyn., 1972, 4:123-126.
Owen et al., "Loss of T cell responses following long-term cryopreservation," Journal of Immunological Methods, Sep. 2007, 326(1-2):93-115.
Ozkumur et al., "Inertial focusing for tumor antigen-dependent and -independent sorting of rare circulating tumor cells," Sci. Transl. Med., 2013, 5(179): 179ra47.
Pegg, "The relevance of ice crystal formation for the cryopreservation of tissues and organs," Cryobiology, 2010, 60(3 supp):S36-44.
Perk et al., "A fitness index for transplantation of machine-perfused cadaveric rat livers," BMC Research Notes, 2012, 5:325, 7 pages.
Posevitz-Fejfár et al., "Effects of blood transportation on human peripheral mononuclear cell yield, phenotype and function: implications for immune cell biobanking," PLoS ONE, Dec. 2014, 9(12):e115920, 19 pages.
QiagenBioinformatics.com [online], "Ingenuity Pathway Analysis," available on or before Feb. 21, 2019, via Internet Archive: Wayback MachineURL<http://web.archive.org/web/20190221071551/https://www.qiagenbioinformatics.com/products/ingenuity-pathway-analysis/>,retrieved on Aug. 8, 2022,URL<https://www.qiagenbioinformatics.com/products/ingenuity-pathway-analysis>, 4 pages.
Raigani et al., "Pumping new life into old ideas: Preservation and rehabilitation of the liver using ex situ machine perfusion," Artif Organs, 2020, 44(2):123-128, 6 pages.
Raigani et al., "Viability testing of discarded livers with normothermic machine perfusion: Alleviating the organ shortage outweighs the cost," Clin. Transplant., 2020, 34(11):e14069, 26 pages.
Ramanujam et al., "Stabilization of Nucleic Acids in Whole Blood: An Alternative to Guthrie Cards," Biotechniques, Nov. 1993, 15: 825-8.
Ray, "Preserving the liver for transplantation," Nat. Rev. Gastroenterol. Hepatol., 2018, 15(6):327.
Reimers et al., "Potentiation by red blood cells of shear-induced platelet aggregation: relative importance of chemical and physical mechanisms," Blood, Dec. 1984, 64(6):1200-1206.
Ritchie et al., "limma powers differential expression analyses for RNA-sequencing and microarray studies," Nucleic Acids Res., 2015, 43(7):e47, 13 pages.
Robinson and Newsholme, "Some properties of hepatic glycerol kinase and their relation to the control of glycerol utilization," Biochem. J., 1969, 112(4):455-464.
Robinson et al., "edgeR: a Bioconductor package for differential expression analysis of digital gene expression data," Bioinformatics, 2010, 26(1):139-140.
Roman et al., "T-Cell Activation under Hypoxic Conditions Enhances IFN-γ Secretion," Am. J. Respir. Cell Mol. Biol., Jan. 2010, 42(1):123-8.
Rubinsky et al., "The process of freezing and the mechanism of damage during hepatic cryosurgery," Cryobiology, 1990, 27(1):85-97.
Sanders et al., "The effect of rapamycin on DNA synthesis in multiple tissues from late gestation fetal and postnatal rats," Am. J. Physiol. Cell Physiol., 2008, 295:C406-C413.
Schlegel and Dutkowski, "Letter to editor: repair or prevent: what is the real impact of normothermic machine perfusion in liver transplantation?," Hepatology, 2019, 70(6):2231-2232, 4 pages.
Schmid-Schonbein et al., "On the shear rate dependence of red cell aggregation in vitro," J Clin. Invest., 1968, 47(6): 1447-54.
Searle et al., "Chromatogram libraries improve peptide detection and quantification by data independent acquisition mass spectrometry," Nat. Commun., 2018, 9:5128, 12 pages.
Shannon et al., "Cytoscape: a software environment for integrated models of biomolecular interaction networks," Genome Res., 2003, 13(11):2498-504.
Shen et al., "Decreased hepatocyte autophagy leads to synergistic IL-1β and TNF mouse liver injury and inflammation," Hepatology, 2020, 72:595-608, 31 pages.
Sosa et al., "Early cytokine signatures of ischemia/reperfusion injury in human orthotopic liver transplantation," JCI Insight, 2016, 1:e89679, 17 pages.
Spindler et al., "Dimethyl sulfoxide and ethylene glycol promote membrane phase change during cryopreservation," Cryo Lett., 2011, 32(2):148-157.
Sridharan et al., "Metabolomic Modularity Analysis (MMA) to Quantify Human Liver Perfusion Dynamics," Metabolites, 2017, 7(4):e58, 18 pages.
SRTR.org [online], "Organ Procurement Organization (OPO) Reports," Jan. 2020, retrieved on Aug. 9, 2022, retrieved from URL<https://www.srtr.org/reports/opo-specific-reports/>, 6 pages.
Stephens et al., "The dielectrophoresis enrichment of CD34+ cells from peripheral blood stem cell harvests," Bone Marrow Transplant, Oct. 1996, 18:777-82.
Storey et al., "Cryomicroscopic analysis of freezing in liver of the freeze-tolerant wood frog," Am. J. Physiol. Regul. Integr. Comp. Physiol., 1992, 263:R185-R194.
Storey, "Living in the Cold: Freeze-Induced Gene Responses in Freeze-Tolerant Vertebrates," Clin. Exp. Pharmacol. Physiol., 1999, 26:57-63.
Taylor and Pegg "The effect of ice formation on the function of smooth muscle tissue stored at −21 or −60° C.," Cryobiology, 1983, 20(1):36-40.
Taylor et al., "New Approaches to Cryopreservation of Cells, Tissues, and Organs," Transfus. Med. Hemotherapy, 2019, 46(3):197-215.
Tessier et al., "Effect of Ice Nucleation and Cryoprotectants during High Subzero-Preservation in Endothelialized Microchannels," ACS Biomater. Sci. Eng., 2018, 4(8):3006-3015, 25 pages.
Thomas et al., "Extracellular DNA traps are associated with the pathogenesis of TRALI in humans and mice," Blood, Jun. 2012, 119(26):6335-43.
Toner and Irimia, "Blood-on-a-chip," Annu. Rev. Biomed. Eng., 2005, 7:77-103.
Toth et al., "Inhibition of polymer-induced red blood cell aggregation by poloxamer 188," Biorheology, 2000, 37(4):301-12.
Urbańczyk et al., "Antifreeze glycopeptides: from structure and activity studies to current approaches in chemical synthesis," Amino Acids, 2017, 49(2):209-222.
Uygun et al., "Diluted blood reperfusion as a model for transplantation of ischemic rat livers: alanine aminotransferase is a direct indicator of viability," Transplant. Proc., 2010, 42(7):2463-2467.
Van den Ende, "Multifunctional fructans and raffinose family oligosaccharides," Front. Plant Sci., 2013, 4:247, 11 pages.
Van Leeuwen et al., "Transplantation of high-risk donor livers after ex situ resuscitation and assessment using combined hypo- and normothermic machine perfusion: a prospective clinical trial," Ann. Surg., 2019, 270(5):906-914.
Van Rijn et al., "DHOPE-DCD Trial Investigators. Hypothermic machine perfusion in liver transplantation—a randomized trial," N. Engl. J. Med., 2021, 384(15):1391-1401, 12 pages.
Vodkin and Kuo, "Extended criteria donors in liver transplantation," Clin. Liver. Dis., 2017, 21(2):289-301, 13 pages.
Warnecke et al., "Normothermic ex-vivo preservation with the portable Organ Care System Lung device for bilateral lung transplantation (INSPIRE): a randomised, open-label, non-inferiority, phase 3 study," Lancet Respir. Med., 2018, 6(5):357-367.
Watson and Jochmans, "From "Gut Feeling" to Objectivity: Machine Preservation of the Liver as a Tool to Assess Organ Viability," Curr. Transplant Reports, 2018, 5(1):72-81.
Watson et al., "Observations on the ex situ perfusion of livers for transplantation," Am. J. Transplant., 2018, 18(8):2005-2020.
Weng et al., "Molecular Dynamics at the Interface between Ice and Poly(vinyl alcohol) and Ice Recrystallization Inhibition," Langmuir, 2018, 34(17):5116-5123.

(56) References Cited

OTHER PUBLICATIONS

Weng et al., "Role of synthetic antifreeze agents in catalyzing ice nucleation," Cryobiology, 2018, 84:91-94.
Wolanczyk et al., "Ice nucleating activity in the blood of the freeze-tolerant frog, Rana sylvatica," Cryobiology, 1990, 27:328-335.
Wong et al., "The Role of Physical Stabilization in Whole Blood Preservation," Scientific Reports, Feb. 2016, 6: 21023.
Wowk and Fahy, "Inhibition of bacterial ice nucleation by polyglycerol polymers," Cryobiology, 2002, 44(1):14-23.
Wowk et al., "Vitrification enhancement by synthetic ice blocking agents," Cryobiology, 2000, 40(3):228-236.
Xu et al., "Modulating TRADD to restore cellular homeostasis and inhibit apoptosis," Nature, 2020, 587:133-138, 36 pages.
Yamada et al., "Tolerance in xenotransplantation," Curr. Op. Organ Transplant., 2017, 22(6):522-528, 7 pages.
Yeh and Uygun, "Increasing donor liver utilization through machine perfusion," Hepatology, 2019, 70:431-433, 6 pages.
Young et al., "Gene ontology analysis for RNAseq: accounting for selection bias," Genome Biol., 2010, 11(2):R14, 12 pages.
Yu et al., "Circulating tumor cells: approaches to isolation and characterization," J Cell Biol., Feb. 2011, 192(3):373-82.
Yu et al., "Ex vivo culture of circulating breast tumor cells for individualized testing of drug susceptibility," Science, Jul. 2014, 345(6193):216-20.
Zachariassen and Kristiansen, "Ice Nucleation and Antinucleation in Nature," Cryobiology, 2000, 41(4):257-279.
Zhai et al., "Ischaemia-reperfusion injury in liver transplantation-from bench to bedside," Nat. Rev. Gastroenterol. Hepatol., 2013, 10(2):79-89.
Zhu et al., "A microdevice for multiplexed detection oft-cell-secreted cytokines," Lab on a Chip, 2008, 8(12):2197-2205.
Zhu et al., "Lysosomal quality control of cell fate: a novel therapeutic target for human diseases," Cell Death Dis., 2020, 11(9):817, 13 pages.
Arikura et al., "Abstract: UW Solution: A Promising Tool for Cryopreservation of Primarily Isolated Rat Hepatocytes," J. Hepatobiliary. Pancreat. Surg., 2002, 9(6):742-749, 1 page.
Baust et al., "Cryopreservation: An Emerging Paradigm Change," Organogenesis, 2009, 5(3):90-96.
Carpentier et al., "Abstract: Artificial and Bioartificial Liver Devices: Present and Future," Gut, 2009, 58(12):1690-1702, 1 page.
De Vries et al., "Bulk Droplet Vitrification: An Approach to Improve Large-Scale Hepatocyte Cryopreservation Outcome," Langmuir, 2019, 35(23):7354-7363.
Demetriou et al., "Prospective, Randomized, Multicenter, Controlled Trial of a Bioartificial Liver in Treating Acute Liver Failure," Ann. Surg., 2004, 239(5):660-667.
Demirci and Montesano, "Abstract: Cell Encapsulating Droplet Vitrification," Lab Chip, 2007, 7(11):1428, 5 pages.
Dou et al., "High Throughput Cryopreservation of Cells by Rapid Freezing of Sub-M1 Drops Using Inkjet Printing—Cryoprinting," Lab Chip, 2015, 15(17):3503-3513, 11 pages.
Dunn et al., "Abstract: Hepatocyte Function and Extracellular Matrix Geometry: Long-Term Culture in a Sandwich Configuration," FASEB J. Off. Publ. Fed. Am. Soc. Exp. Biol., 1989, 3(2):174-177, 1 page.
Dunn et al., "Abstract: Long-Term in Vitro Function of Adult Hepatocytes in a Collagen Sandwich Configuration," Biotechnol. Prog., 1991, 7(3):237-245, 1 page.
El Assal et al., "Bio-Inspired Cryo-Ink Preserves Red Blood Cell Phenotype and Function During Nanoliter Vitrification," Adv. Mater., 2014, 26(33):5815-5822.
Fitzpatrick et al., "Human Hepatocyte Transplantation: State of the Art," J. Intern. Med., 2009, 266(4):339-357.
Fox and Chowdhury, "Hepatocyte Transplantation," Am. J. Transplant., 2004, 4(Suppl 6):7-13.
Guillouzo et al., "Abstract: Survival and Function of Isolated Hepatocytes after Cryopreservation," Chem. Biol. Interact., 1999, 121(1):7-16, 1 page.
Haridass et al., "Abstract: Hepatocyte Transplantation: Waiting for Stem Cells," Curr. Opin. Organ Transplant., 2008, 13(6):627-632, 1 page.
He et al., "Vitrification by Ultra-Fast Cooling at a Low Concentration of Cryoprotectants in a Quartz Micro-Capillary: A Study Using Murine Embryonic Stem Cells," Cryobiology, 2008, 56(3):223-232, 11 pages.
Heo et al., "'Universal' vitrification of Cells by Ultra-Fast Cooling," Technology, 2015, 3(1):64-71, 9 pages.
Hopkins et al., "Effect of Common Cryoprotectants on Critical Warming Rates and Ice Formation in Aqueous Solutions," Cryobiology, 2012, 65(3):169-178, 13 pages.
Hughes et al., "Current Status of Hepatocyte Transplantation," Transplantation, 2012, 93(4):342-347.
International Preliminary Report in Patentability in International Appln. No. PCT/US2019/064026, mailed on Feb. 17, 2022, 8 pages.
International Search Report and Written Opinion in International Appln. No. PCT/US2019/064026, mailed on Apr. 21, 2020, 11 pages.
Invitation to Pay Additional Fees And, Where Applicable, Protest Fee in International Appln. No. PCT/US2019/064026, mailed on Feb. 3, 2020, 2 pages.
Jitraruch et al., "Cryopreservation of Hepatocyte Microbeads for Clinical Transplantation," Cell Transplant., 2017, 26(8):1341-1354.
Kedem and Katchalsky, "Abstract: Thermodynamic Analysis of the Permeability of Biological Membranes to Non-Electrolytes," Biochim. Biophys. Acta, 1958, 27(2):229-246, 4 pages.
Kuwayama, "Abstract: Highly Efficient Vitrification for Cryopreservation of Human Oocytes and Embryos: The Cryotop Method," Theriogenology, 2007, 67(1):73-80, 1 page.
Manuchehrabadi et al., "Improved Tissue Cryopreservation Using Inductive Heating of Magnetic Nanoparticles," Sci. Transl. Med., 2017, 9(379):eaah4586, 10 pages.
Ott et al., "Perfusion-Decellularized Matrix: Using Nature's Platform to Engineer a Bioartificial Heart," Nat. Med., 2008, 14(2):213-221, 9 pages.
Parmegiani et al., "Sterilization of Liquid Nitrogen with Ultraviolet Irradiation for Safe Vitrification of Human Oocytes or Embryos," Fertil. Steril., 2010, 94(4):1525-1528.
Petersen et al., "Tissue-Engineered Lungs for in Vivo Implantation," Science, 2010, 329(5991):538-541.
Pless, "Artificial and Bioartificial Liver Support," Organogenesis, 2007, 3(1):20-24.
Sakiyama et al., "Clinical Translation of Bioartificial Liver Support Systems with Human Pluripotent Stem Cell-Derived Hepatic Cells," World J. Gastroenterol., 2017, 23(11):1974-1979.
Samot et al., "Blood Banking in Living Droplets," PLoS One, 2011, 6(3):e17530, 6 pages.
Schrader et al., "Correlating Steric Hydration Forces with Water Dynamics through Surface Force and Diffusion NMR Measurements in a Lipid-DMSO-H2O System," Proc. Natl. Acad. Sci. U.S.A., 2015, 112(34):10708-10713.
Shi et al., "High-Throughput Non-Contact Vitrification of Cell-Laden Droplets Based on Cell Printing," Sci. Rep., 2016, 5(1), 10 pages.
Sorodoc et al., "Is MARS System Enough for A. Phalloides-Induced Liver Failure Treatment?," Hum. Exp. Toxicol., 2010, 29(10):823-832.
Sosef et al., "Cryopreservation of isolated Primary Rat Hepatocytes: Enhanced Survival and Long-Term Hepatospecific Function," Ann. Surg., 2005, 241(1):125-133.
Stéphenne et al., "Hepatocyte Cryopreservation: Is It Time to Change the Strategy?," World J. Gastroenterol., 2010, 16(1):1-14.
Tang et al., "Excluded Volume in Solvation: Sensitivity of Scaled-Particle Theory to Solvent Size and Density," Biophys. J., 2000, 79(5):2222-2234.
Terry et al., "Optimization of the Cryopreservation and Thawing Protocol for Human Hepatocytes for Use in Cell Transplantation," Liver Transpl., 2010, 16(2):229-237.
Uygun et al., "Organ Reengineering through Development of a Transplantable Recellularized Liver Graft Using Decellularized Liver Matrix," Nat. Med., 2010, 16(7):814-820.

(56) References Cited

OTHER PUBLICATIONS

Wang et al., "Development of a Modified Vitrification Strategy Suitable for Subsequent Scale-up for Hepatocyte Preservation," Cryobiology, 2012, 65(3):289-300.

Weng et al., "A Highly-Occupied, Single-Cell Trapping Microarray for Determination of Cell Membrane Permeability," Lab Chip, 2017, 17(23):4077-4088.

International Preliminary Report on Patentability in International Appln. No. PCT/US2020/017310, mailed on Aug. 19, 2021, 20 pages.

\* cited by examiner

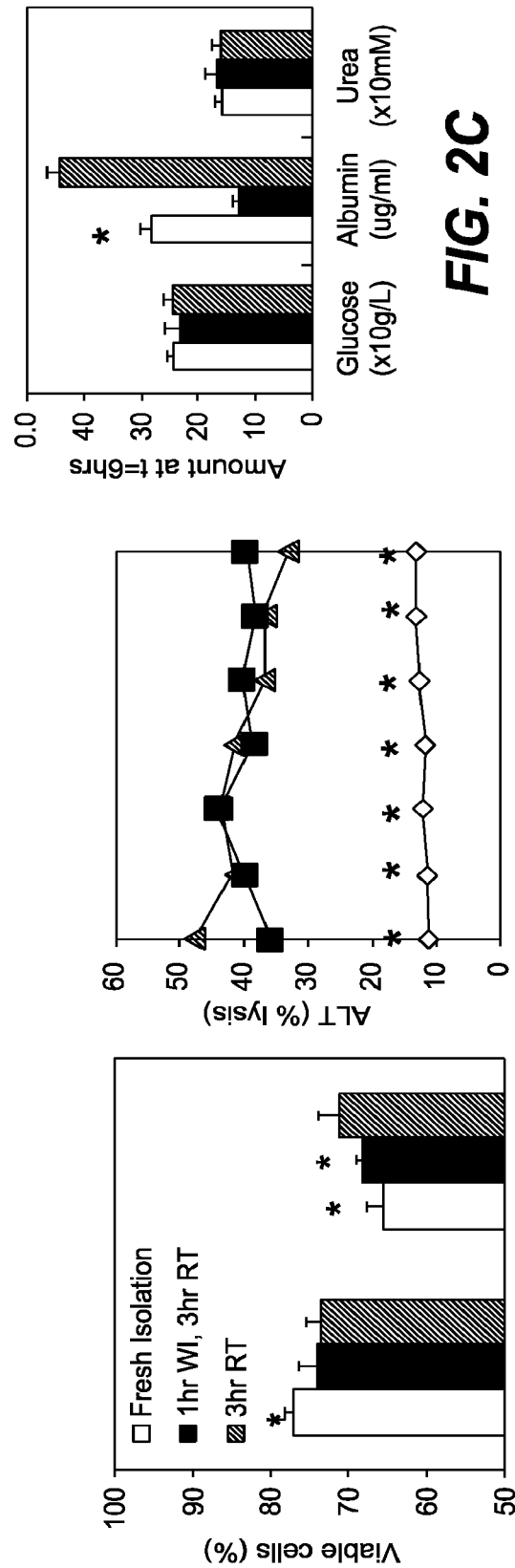
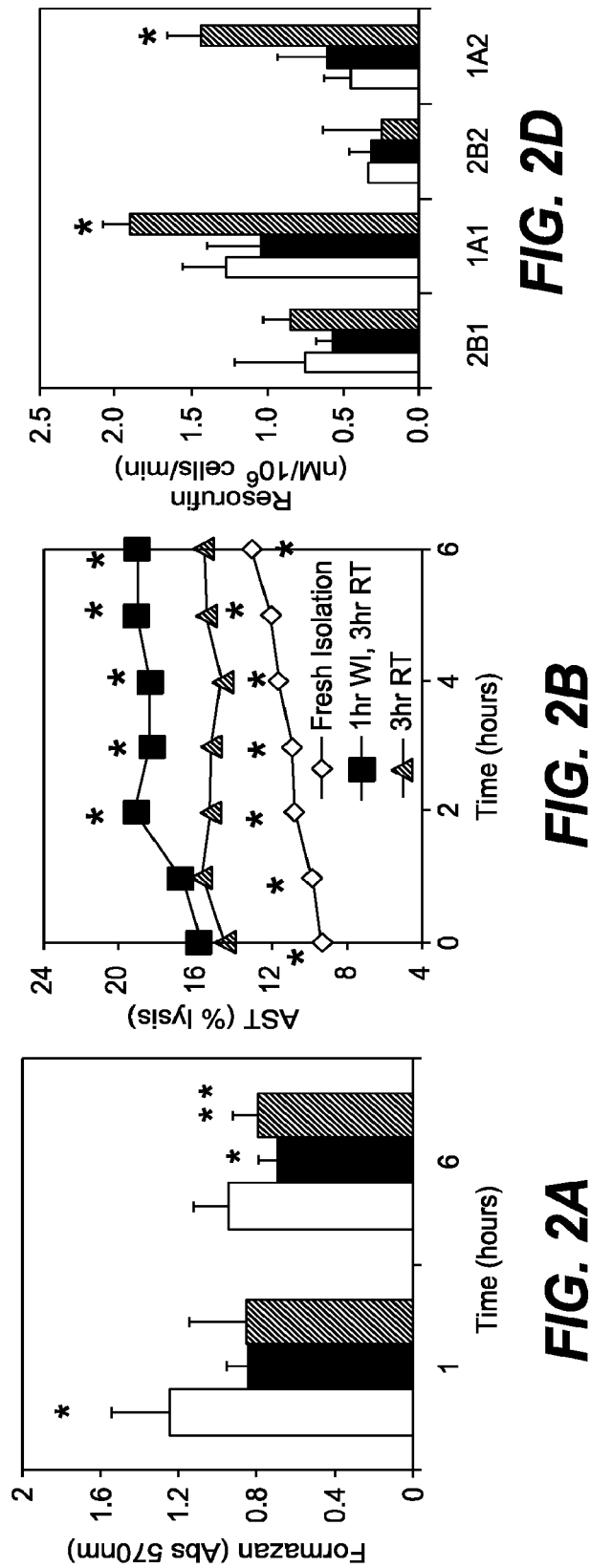

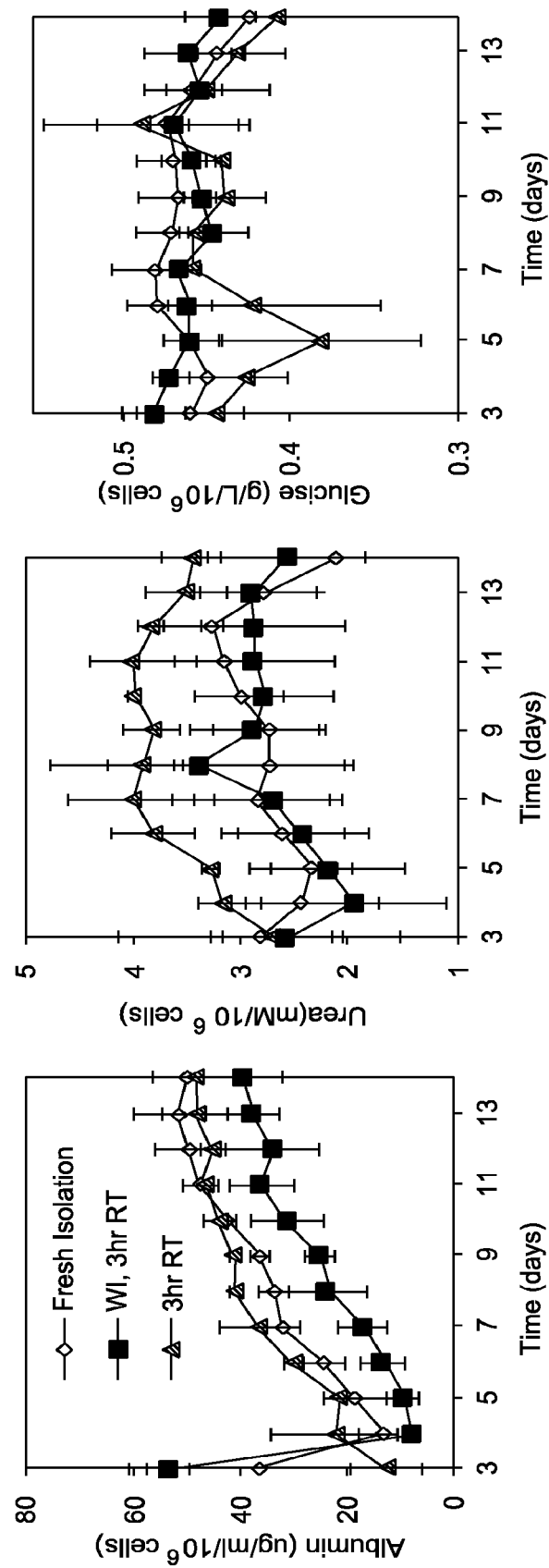

| PARAMETER | SHAM | SUPRAHEPATIC VENA CAVA (SHVC, n=5) | |
|---|---|---|---|
| | | 20% TBSA | 40% TBSA |
| Blood flow (ml/min) | 15±7.4 | 20±9.1 | 20±6.2 |
| Total Hemoglobin (g/dL) | 13±0.55 | 11±1.4 | 11±1.2 |
| Oxyhemoglobin (%) | 24±3.3 | 34±7.3 | 17±6.1* |
| Partial $O_2$ tension (mmHg) | 27±0.63 | 41±16 | 21±6.2 |
| Partial $CO_2$ tension (mmHg) | 52±5.9 | 48±7.8 | 67±5.5* |
| Dissolved $O_2$ (m$O_2$/100ml blood) | 4.2±0.5 | 5.2±1.2 | 2.7±1.1* |
| Total $CO_2$ (mmol/L) | 21±2.8 | 22±1.9 | 25±0.45* |
| pH | 7.28±0.01 | 7.29±0.04 | 7.24±0.02* |
| Glucose (mg/dL) | 210±57 | 165±33 | 144±12 |
| Lactate (mmol/L) | 1.0±0.17 | 0.77±0.17 | 4.3±1.2* |
| β-Hydroxybutyric acid (μmol/L) | 350±251 | 271±141 | 216±189 |
| Acetoacetic acid (μmol/L) | 116±36 | 132±12 | 11±68* |
| Urea nitrogen (mg/dL) | 14±5.0 | 15±1.1 | 17±2.0 |
| Albumin (g/dL) | 1.8±0.17 | 1.2±0.11 | 1.2±0.09 |
| Ammonia (μmol/L) | 41±3.4 | 29±12 | 19±5.7 |
| Alanine (μmol/L) | 261±26 | 163±29 | 149±11 |
| Arginine (μmol/L) | 62±1.5 | 198±30 | 199±23 |
| Ornithine (μmol/L) | 82±9.9 | 85±17 | 124±11* |
| Asparagine (μmol/L) | 28±0.83 | 21±2.6 | 18±0.07 |
| Aspartate (μmol/L) | 13±0.88 | 11±2.6 | 8.3±0.62 |
| Cysteine (μmol/L) | 12±0.46 | 17±1.5 | 19±1.9 |
| Glutamate (μmol/L) | 83±19 | 51±6.8 | 57±18 |
| Glutamine (μmol/L) | 305±42 | 221±53 | 234±8.6 |
| Glycine (μmol/L) | 194±32 | 148±5.3 | 124±14* |
| Histidine (μmol/L) | 56±6.6 | 50±10 | 60±7.1 |
| Proline (μmol/L) | 146±21 | 114±4.7 | 117±14 |
| Serine (μmol/L) | 170±12 | 107±5.4 | 101±15 |
| Methionine (μmol/L) | 38±1.1 | 32±1.9 | 34±1.2 |
| Threonine (μmol/L) | 191±24 | 167±37 | 158±7.5 |
| Valine (μmol/L) | 156±54 | 191±21 | 205±18 |
| Tyrosine (μmol/L) | 60±11 | 63±9.6 | 67±5.5 |
| Isoleucine (μmol/L) | 82±7.5 | 97±12 | 103±11 |
| Phenylalanine (μmol/L) | 54±2.8 | 52±7.7 | 51±2.9 |
| Leucine (μmol/L) | 241±35 | 266±33 | 240±41 |
| Lysine (μmol/L) | 210±42 | 201±33 | 207±24 |
| Sum Amino Acid Nitrogen (μmol/L) | 3683 | 3845 | 3873 |

*Note:*
Liver weights (g) in each group were SHAM: 9.4±0.76; 20% TBSA: 10.6±0.73; 40% TBSA: 9.83±0.35.
Bolded items are significantly different (p<0.05) from SHAM.
* indicates the value for 40% TBSA is significantly different (p<0.05) compared to 20% TBSA burn

FIG. 10A

|  | PORTAL VEIN (PV, n=5) | | |
|---|---|---|---|
|  | SHAM | 20% TBSA | 40% TBSA |
| Blood flow (ml/min) | 15±7.4 | 19±9.1 | 20±6.3 |
| Total Hemoglobin (g/dL) | 15±1.2 | 13±1.0 | 13±0.41 |
| Oxyhemoglobin (%) | 73±8.8 | 81±5.1 | 75±6.3 |
| Partial $O_2$ tension (mmHg) | 68±12 | 57±12 | 66±9.1 |
| Partial $CO_2$ tension (mmHg) | 61±12 | 62±14 | 57±2.0 |
| Dissolved $O_2$ (ml$O_2$/100ml blood) | 15±2.5 | 14±1.9 | 13±0.9 |
| Total $CO_2$ (mmol/L) | 19±2.9 | 23±0.71 | 23±1.1 |
| pH | 7.27±0.02 | 7.28±0.05 | 7.25±0.02 |
| Glucose (mg/dL) | 123±62 | 165±30 | 125 ±12* |
| Lactate (mmol/L) | 1.0±0.18 | 0.75±0.25 | 4.9±0.84* |
| β-Hydroxybutyric acid (μmol/L) | 110±96 | 124±58 | 87±47 |
| Acetoacetic acid (μmol/L) | 110±73 | 143±95 | 98±88 |
| Urea nitrogen (mg/dL) | 13±5.0 | 16±2.2 | 16±2.7 |
| Albumin (g/dL) | 1.9±0.21 | 1.4±0.13 | 1.3±0.11 |
| Ammonia (μmol/L) | 109±33 | 65±30 | 74±5.0 |
| Alanine (μmol/L) | 397±13 | 401±74 | 412±69 |
| Arginine (μmol/L) | 141±93 | 219±36 | 222±5.1 |
| Ornithine (μmol/L) | 120±3.5 | 106±3.3 | 128±9.7* |
| Asparagine (μmol/L) | 49±5.4 | 33±2.5 | 31±0.65 |
| Aspartate (μmol/L) | 21±7.6 | 13±0.54 | 13±3.0 |
| Cysteine (μmol/L) | 15±1.5 | 17±1.5 | 17±0.82 |
| Glutamate (μmol/L) | 68±7.7 | 43±6.7 | 53±16 |
| Glutamine (μmol/L) | 293±46 | 257±29 | 255±5.03 |
| Glycine (μmol/L) | 273±27 | 216±18 | 213±25 |
| Histidine (μmol/L) | 137±26 | 126±14 | 148±10* |
| Proline (μmol/L) | 163±12 | 161±6.7 | 177±20 |
| Serine (μmol/L) | 199±13 | 154±24 | 153±8.3 |
| Methionine (μmol/L) | 44±7.0 | 43±4.6 | 43±1.8 |
| Threonine (μmol/L) | 204±41 | 208±39 | 211±27 |
| Valine (μmol/L) | 165±31 | 199±20 | 205±2.9 |
| Tyrosine (μmol/L) | 68±7.4 | 74±4.6 | 80±5.3 |
| Isoleucine (μmol/L) | 86±16 | 102±6.3 | 101±1.4 |
| Phenylalanine (μmol/L) | 59±3.9 | 66±2.9 | 66±4.1 |
| Leucine (μmol/L) | 261±33 | 310±30 | 340±13 |
| Lysine (μmol/L) | 220±38 | 242±23 | 270±14 |
| Sum Amino Acid Nitrogen (μmol/L) | 4880 | 5039 | 5313 |

*Note:*
Liver weights (g) in each group were SHAM: 9.4±0.76; 20% TBSA: 10.6±0.73; 40% TBSA: 9.83±0.35.
Bolded items are significantly different (p<0.05) from SHAM.
* indicates the value for 40% TBSA is significantly different (p<0.05) compared to 20% TBSA burn

FIG. 10B

|  | HEPATIC ARTERY (HA, n=5) | | |
| --- | --- | --- | --- |
|  | SHAM | 20% TBSA | 40% TBSA |
| Blood flow (ml/min) | 0.66±0.11 | 0.46±0.05 | 0.46±0.27 |
| Total Hemoglobin (g/dL) | 13±1.1 | 12±0.94 | 9.9±1.2* |
| Oxyhemoglobin (%) | 90±4.9 | 92±0.92 | 85±3.6* |
| Partial $O_2$ tension (mmHg) | 114±27 | 115±15 | 96±13 |
| Partial $CO_2$ tension (mmHg) | 45±3.7 | 52±11 | 48±1.1 |
| Dissolved $O_2$ (ml$O_2$/100ml blood) | 15±1.7 | 16±1.1 | 12±1.6* |
| Total $CO_2$ (mmol/L) | 21±1.1 | 20±1.9 | 25±1.8* |
| pH | 7.28±0.03 | 7.29±0.04 | 7.25±0.02 |
| Glucose (mg/dL) | 164±57 | 141±28 | 144±18 |
| Lactate (mmol/L) | 0.94±0.55 | 0.55±0.16 | 3.5±0.6* |
| β-Hydroxybutyric acid (μmol/L) | 245±205 | 62±23 | 141±66 |
| Acetoacetic acid (μmol/L) | 122±21 | 101±67 | 61±36 |
| Urea nitrogen (mg/dL) | 14±4.3 | 13±1.7 | 17±2.6* |
| Albumin (g/dL) | 1.9±0.10 | 1.1±0.14 | 1.3±0.17 |
| Ammonia (μmol/L) | 50±5.4 | 38±1.4 | 23±2.4* |
| Alanine (μmol/L) | 357±35 | 302±14 | 284±33 |
| Arginine (μmol/L) | 107±7.9 | 195±37 | 185±11 |
| Ornithine (μmol/L) | 105±20 | 117±1.8 | 138±21 |
| Asparagine (μmol/L) | 43±3.4 | 35±23 | 33±3.4 |
| Aspartate (μmol/L) | 11±1.2 | 8.6±3.7 | 9.4±2.0 |
| Cysteine (μmol/L) | 16±1.2 | 21±0.7 | 25±1.1* |
| Glutamate (μmol/L) | 78±5.2 | 46±12 | 45±9.0 |
| Glutamine (μmol/L) | 419±36 | 359±29 | 405±15* |
| Glycine (μmol/L) | 218±54 | 187±17 | 163±10* |
| Histidine (μmol/L) | 65±0.17 | 59±5.4 | 67±3.5* |
| Proline (μmol/L) | 169±5.6 | 147±14 | 150±7.5 |
| Serine (μmol/L) | 219±24 | 159±9.6 | 178±19 |
| Methionine (μmol/L) | 54±9.6 | 42±4.1 | 40±5.5 |
| Threonine (μmol/L) | 252±40 | 221±23 | 203±15 |
| Valine (μmol/L) | 202±69 | 193±22 | 193±27 |
| Tyrosine (μmol/L) | 80±10 | 89±1.6 | 82±5.4* |
| Isoleucine (μmol/L) | 122±28 | 106±11 | 100±19 |
| Phenylalanine (μmol/L) | 65±4.4 | 63±2.0 | 67±1.1* |
| Leucine (μmol/L) | 321±88 | 276±33 | 290±62 |
| Lysine (μmol/L) | 237±42 | 193±18 | 224±1* |
| Sum Amino Acid Nitrogen (μmol/L) | 4809 | 4640 | 4759 |

*Note:*
Liver weights (g) in each group were SHAM: 9.4±0.76; 20% TBSA: 10.6±0.73; 40% TBSA: 9.83±0.35.
Bolded items are significantly different (p<0.05) from SHAM.
* indicates the value for 40% TBSA is significantly different (p<0.05) compared to 20% TBSA burn

FIG. 10C

| # | REACTION | PATHWAY | IN VIVO FLUX DATA (umol/h/g liver) | | |
|---|---|---|---|---|---|
| | | | SHAM (n=5) | 20% TBSA (n=5) | 40% TBSA (n=5) |
| 1 | Glucose 6-phosphate ↔ Glucose | Gluconeogenesis | 93±37 | 28±17 | 124±135 |
| 2 | Fructose 6-phosphate ↔ Glucose 6-phosphate | Gluconeogenesis | 99±86 | 58±30 | 129±101 |
| 3 | Fructose 1.6-Bisphosphate ↔ Fructose6-phosphate | Gluconeogenesis | 66±28 | 29±17 | 112±64* |
| 4 | 2 Glyceraldehyde 3-P ↔ Fructose 1,6-Bosphosphate | Gluconeogenesis | 57±26 | 27±18 | 108±55* |
| 5 | Phosphoenolpyruvate + NADH ↔Glyceraldehyde 3-P | Gluconeogenesis | 95±33 | 39±34 | 205±105* |
| 6 | Oxaloacetate ↔ CO2 +Phosphoenolpyruvate | Gluconeogenesis | 90±32 | 37±35 | 203±100* |
| 7 | Pyruvate + CO2 ↔ Oxaloacetate | Gluconeogenesis | 31±18 | 13±30 | 151±70* |
| 8 | Lactate ↔ Pyruvate + NADH | Lactate metabolism & TCA cycle | 5.6±2.6 | -7.0±7.0 | 87±67* |
| 9 | Acetyl-CoA + Oxaloacetate →Citrate | Lactate metabolism & TCA cycle | 68±47 | 68±11 | 120±53* |
| 10 | Citrate ↔ 2-oxo-Glutarate + NADH + CO2 | Lactate metabolism & TCA cycle | 75±46 | 70±12 | 123±52* |
| 11 | 2-oxo-Glutarate → Succinyl-CoA + NADH + CO2 | Lactate metabolism & TCA cycle | 92±45 | 84±11 | 148±53* |
| 12 | Succinyl-CoA ↔ FADH2 +Fumarate | Lactate metabolism & TCA cycle | 102±44 | 89±11 | 153±58* |
| 13 | Fumarate ↔Malate | Lactate metabolism & TCA cycle | 140±47 | 118±34 | 235±75* |
| 14 | Malate ↔ Oxaloacetate + NADH | Lactate metabolism & TCA cycle | 145±47 | 120±32 | 238±80* |
| 15 | Arginine → Ornithine + Urea | Urea cycle | 28±23 | 25±38 | 76±34 |
| 16 | Ornithine + CO2 + NH4 ↔Citrulline | Urea cycle | 34±19 | 32±32 | 75±29 |
| 17 | Citrulline + Aspartate →Arginine + Fumarate | Urea cycle | 28±20 | 27±32 | 73±29 |
| 18 | Arginine uptake | Aminoacid metabolism | 3.6±5.1 | 2.3±1.8 | 2.8±3.1 |
| 19 | Ammonia Output | Urea cycle | -6.2±1.7 | -5.3±0.6 | -6.6±1.6 |
| 20 | Ornithine Output | Urea cycle | -3.4±0.9 | -2.6±2.5 | -0.1±2 |
| 21 | Citrulline Output | Aminoacid metabolism | 5.6±5.2 | 4.6±3.1 | 2.2±4.3 |
| 22 | Alanine → Pyruvate + NH4 + NADH | Aminoacid metabolism | 13±6.7 | 21±11 | 33±9 |

*FIG. 11A*

| # | Reaction | Category | | | |
|---|---|---|---|---|---|
| 23 | Alanine Output | Aminoacid metabolism | -13±6.2 | -24±10 | -31±8 |
| 24 | Serine → Pyruvate + NH4 | Aminoacid metabolism | 6.8±11 | 1.6±18 | 25±16 |
| 25 | Serine Uptake | Aminoacid metabolism | 2.7±1.7 | 4.8±1.6 | 6.4±2.7 |
| 26 | Cysteine → Pyruvate + NH4 + NADH | Aminoacid metabolism | 0.8±3.7 | -2.8±5.9 | 3.3±5.4 |
| 27 | Cysteine Output | Aminoacid metabolism | 02±0.0 | 0±0.1 | -0.3±0.1* |
| 28 | Threonine → NADH + Glycine + Acetyl-CoA | Aminoacid metabolism | 1.2±4 | 2.4±4.9 | 6±3.2 |
| 29 | Glycine ↔ CO2 + NH4 + NADH | Aminoacid metabolism | 4.2±8.2 | 1.3±13 | 18±11 |
| 30 | Glycine Uptake | Aminoacid metabolism | 5.4±1.2 | 7.1±2.5 | 9.2±2.6 |
| 31 | Valine + 2-oxo-Glutarate → Glutamate + propionyl-CoA + 3 NADH + FADH2 + 2 CO2 | Aminoacid metabolism | 0.8±0.4 | 1.2±2.8 | -0.1±0.4 |
| 32 | Isoleucine + 2-oxo-Glutarate → Glutamate + propionyl-CoA +3 Acetyl-CoA + 2 NADH + FADH2 +CO2 | Aminoacid metabolism | -0.2±0.7 | 0.5±1.3 | -0.3±0.1 |
| 33 | Leucine + 2-oxo-Glutarate→ Glutamate + NADH + FADH2 Acetoacetate + Acetyl-CoA | Aminoacid metabolism | -0.2±3.5 | 3.1±3.1 | 5.4±0.1 |
| 34 | Propionyl-CoA + CO2 → Succinyl-CoA | Aminoacid metabolism | 5.1±2.0 | 3.6±3.4 | 2.5±6.1 |
| 35 | Lysine + 2 2-oxo-Glutarate → 2 Glutamate + 4 NADH + FADH2 2CO2 + Acetoacetyl-CoA | Aminoacid metabolism | 1.5±0.4 | 5.1±5.7 | 4.6±2.2 |
| 36 | Phenylalanine + O2 → Tyrosine | Aminoacid metabolism | 0.5±0.4 | 2.2±0.6 | 2±1 |
| 37 | Tyrosine + 2 O2 → NH4 + CO2 + Fumarate + Acetoacetate + NADH | Aminoacid metabolism | 3.7±3.7 | 0.1±5.4 | 6.4±6.8 |
| 38 | Tyrosine Output | Aminoacid metabolism | -1.0±1.1 | -1±0.4 | -1.5±0.3 |
| 39 | Glutamate ↔ 2 oxo-Glutarate + NADH + NH4 | Aminoacid metabolism | 15±7.5 | 27.4±13.7 | 37±9 |
| 40 | Glutamate Output | Aminoacid metabolism | 0.8±1.3 | 1.1±1.1 | 1±3.4 |
| 41 | Glutamine → Glutamate + NH4 | Aminoacid metabolism | 2.0±2.5 | 4±4.4 | 3.2±0.5 |
| 42 | Proline +0.5 O2 →Glutamate + 0.5 NADH | Aminoacid metabolism | 0.7±2.9 | 4.8±1.4 | 6.9±3.4 |
| 43 | Histidine → NH4 + Glutamate | Aminoacid metabolism | 8.0±5.3 | 8±3.8 | 10.7±3.3 |
| 44 | Methionine + Serine → Cysteine + NADH + Propionyl-CoA + CO2 | Aminoacid metabolism | 0.8±0.1 | 0.9±0.4 | 1.1±0.4 |

*FIG. 11B*

| | | | | | |
|---|---|---|---|---|---|
| 45 | Aspartate ↔ Oxaloacetate + NH4 + NADH | Aminoacid metabolism | -24±17 | -30±26 | -68±24 |
| 46 | Aspartate Uptake | Aminoacid metabolism | 0.5±0.4 | 0.2±0.3 | 0.5±0.3 |
| 47 | Asparagine →Aspartate + NH4 | Aminoacid metabolism | 2.0±1.1 | 0.9±0.2 | 1.6±0.4* |
| 48 | Palmitate → 8 Acetyl-CoA + 7 FADH2 + 7 NADH | Lipid, glycerol, fatty acid metabolism | 11.1±7 | 8.5±4.2 | 11.8±8 |
| 49 | 2 Acetyl-CoA → Acetoacetyl-CoA | Lipid, glycerol, fatty acid metabolism | 11±16 | 2.9±19 | -7.1±14 |
| 50 | Acetoacetyl-CoA → Acetoacetate | Lipid, glycerol, fatty acid metabolism | 15±16 | 8.6±18 | -1.6±13 |
| 51 | Acetoacetate Output | Lipid, glycerol, fatty acid metabolism | -1±1 | 1.1±2.7 | 2.2±0.7 |
| 52 | Acetoacetate + NADH ↔ b-Hydroxybutyrate | Lipid, glycerol, fatty acid metabolism | 21±16 | 11±17 | 8.7±9.1 |
| 53 | NADH + 0.5 O2 → NAD | Oxygen uptake and electron transport | 302±181 | 327±31 | 527±205* |
| 54 | FADH2 + 0.5 O2 → FAD | Oxygen uptake and electron transport | 182±87 | 158±25 | 245±97 |
| 55 | O2 Uptake | Oxygen uptake and electron transport | 249±132 | 247±15 | 404±148* |
| 56 | Glucose 6-phosphate → 2 NADPH + CO2 + Ribulose 5-P | PPP | 14±90 | 32±31 | 9.4±134 |
| 57 | Ribulose 5-P ↔ Ribose 5-P | PPP | 3±30 | 10±11 | 2.3±47 |
| 58 | Ribulose 5-P ↔ Xylulose 5-P | PPP | 18±61 | 24±19 | 10±81 |
| 59 | Ribose 5-P + Xylulose 5-P ↔ Fructose 6-P + Erythrose 4-P | PPP | 10±30 | 12±10 | 5.6±40 |
| 60 | Erythrose 4-P + Xylulose 5-P ↔ Glyceraldehyde 3-P + Fructose 6-P | PPP | 15±31 | 14±9.1 | 8.2±36 |
| 61 | CO2 Output | Oxygen uptake and electron transport | 216±30 | 191±19 | 291±20* |

*Note*
BOLDED items are significantly different ($p<0.05$) from SHAM.
* indicates the value for 40% TBSA is significantly different ($p<0.05$) compared to 20% TBSA burn.

FIG. 11C

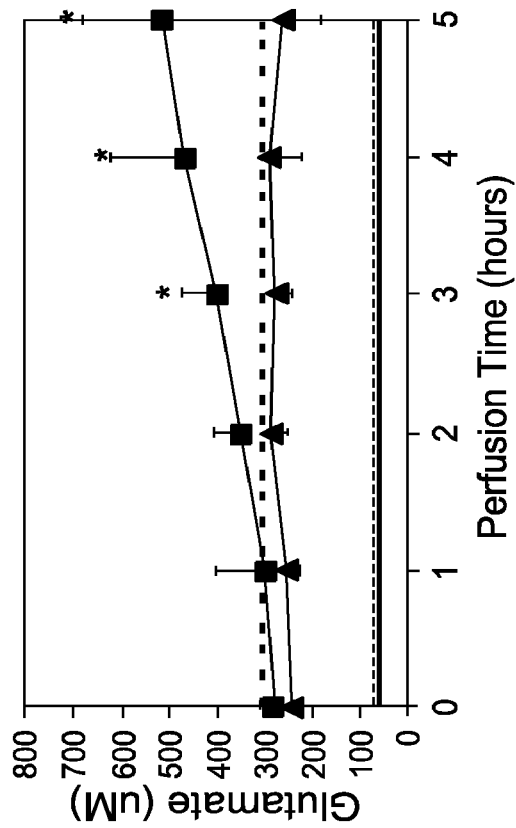
FIG. 19E
FIG. 19F
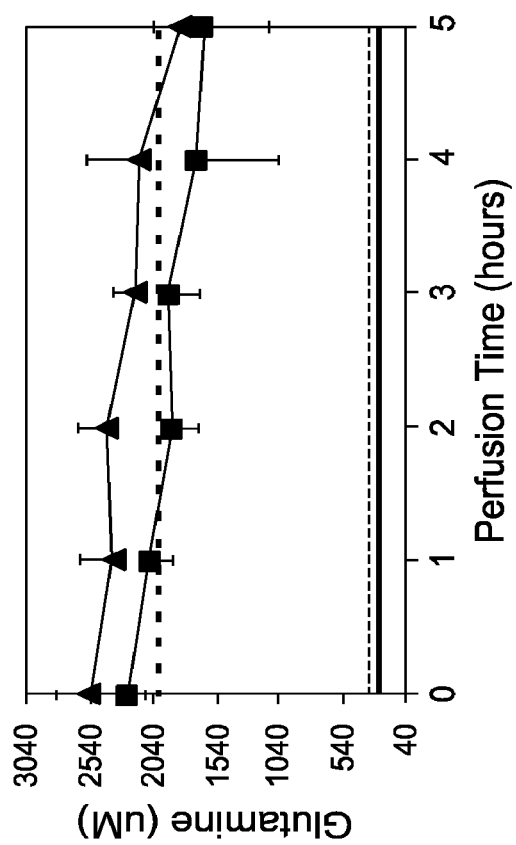
FIG. 19G
FIG. 19H

| # | REACTION | PATHWAY | IN VIVO FLUX DATA (umol/h/g liver) | | | |
|---|---|---|---|---|---|---|
| | | | FRESH T=1-5hr | ISCHEMIC T=0-2hr | ISCHEMIC T=2-5hr | IN VIVO |
| | | | (n=11) | (n=7) | (n=7) | (n=6) |
| 1 | Glucose 6-phosphate ↔ Glucose | Gluconeogenesis | -31±15* | 88±201 | 44±17* | 93±37 |
| 2 | Fructose 6-phosphate ↔ Glucose 6-phosphate | Gluconeogenesis | 24±85 | -26±71* | 22±25 | 79±82 |
| 3 | Fructose 1,6-Biophosphate ↔ Fructose6-phosphate | Gluconeogenesis | -5±21* | -43±51* | 6±8*† | 31±22 |
| 4 | 2 Glyceraldehyde 3-P ↔ Fructose 1,6-Biophosphate | Gluconeogenesis | -5±21* | -43±51* | 6±8*† | 31±22 |
| 5 | Phosphoenolpyruvate + NADH ↔Glyceraldehyde 3-P | Gluconeogenesis | -24±26* | -94±99* | 4±14*† | 37±29 |
| 6 | Oxaloacetate ↔CO2 +Phosphoenolpyruvate (Gluconeogenic) Phosphoenolpyruvate + ADP → Pyruvate (Glycolytic) | Gluconeogenesis | -24±26* | -94±99* | 4±14*† | -31±15* |
| 7 | Pyruvate + CO2 ↔ Oxaloacetate (Gluconeogenic) Pyruvate + CoA + NAD + → Acetyl-CoA + CO2 + NADH (Glycolytic) | Gluconeogenesis | -37±23* | 110±101* | -24±12*† | 24±19 |
| 8 | Lactate ↔ Pyruvate + NADH | Lactate metabolism & TCA cycle | -57±21* | -124±98* | -40±12*† | 6±3 |
| 9 | Acetyl-CoA + Oxaloacetate →Citrate | Lactate metabolism & TCA cycle | 31±14* | 20±26* | 12±9* | 71±47 |
| 10 | Citrate ↔ 2-oxo-Glutarate + NADH + CO2 | Lactate metabolism & TCA cycle | 31±14* | 20±26* | 12±9* | 71±47 |
| 11 | 2-oxo-Glutarate → Succinyl-CoA + NADH + CO2 | Lactate metabolism & TCA cycle | 35±14* | 30±26* | 34±9* | 80±46 |
| 12 | Succinyl-CoA ↔ FADH2 +Fumarate | Lactate metabolism & TCA cycle | 32±14* | 26±26* | 32±9* | 82±46 |
| 13 | Fumarate ↔ Malate | Lactate metabolism & TCA cycle | 69±19* | 56±27* | 56±17* | 107±53 |
| 14 | Malate ↔ Oxaloacetate + NADH | Lactate metabolism & TCA cycle | 69±19* | 56±27* | 56±17* | 107±53 |

FIG. 20A

| | | | | | | |
|---|---|---|---|---|---|---|
| 15 | Arginine → Ornithine + Urea | Urea cycle | 35±12 | 35±4 | **57±4*†** | 28±23 |
| 16 | Ornithine + CO2 + NH4 ↔ Citrulline | Urea cycle | 31±10 | 25±8 | **56±4*†** | 32±20 |
| 17 | Cirulline + Asparate → Arginine + Fumarate | Urea cycle | 29±10 | 25±8 | 20±13 | 25±20 |
| 18 | Arginine uptake | Aminoacid metabolism | 4.3±1.6 | 9.3±6.7 | 2.6±0.6*† | 3.6±5.1 |
| 19 | Ammonia Output | Urea cycle | 0.7±0.2* | 0.8±0.9* | 0.5±0.1* | -6.2±1.7 |
| 20 | Ornithine Output | Urea cycle | 2.3±1.2* | 9.3±6* | 0.7±1.1*† | -3.4±0.9 |
| 21 | Citrulline Output | Aminoacid metabolism | 2±1.9* | -0.1±9 | 2±1.2* | 7±5.2 |
| 22 | Alanine → Pyruvate + NH4 + NADH | Aminoacid metabolism | 8.6±2.4 | 4.9±8.3 | 7.2±1.8 | 12±6.8 |
| 23 | Alanine Output | Aminoacid metabolism | -7.1±1.4* | -3.9±7.6* | 7.2±1.8* | 12.7±6.2 |
| 24 | Serine → Pyruvate + NH4 | Aminoacid metabolism | 8.6±6.3 | 6.7±13.5 | 6.6±1.5 | 6.4±11.5 |
| 25 | Serine Uptake | Aminoacid metabolism | 0.2±0.3* | -1.2±1.1* | 0.5±0.2*† | 2.7±1.7 |
| 26 | Cysteine → Pyruvate + NH4 + NADH | Aminoacid metabolism | 2.9±3.2 | 3±4.8 | 2.1±0.5 | 0.1±3.8 |
| 27 | Cysteine Output | Aminoacid metabolism | -0.1±2.7 | -1.4±1.9 | 1.2±0.5* | 0.2±0 |
| 28 | Threonine → NADH + Glycine + Acetyl-CoA | Aminoacid metabolism | 0.4±0.7 | 0.6±8.2 | 2.1±1.2 | 1.2±4 |
| 29 | Glycine ↔ CO2 + NH4 + NADH | Aminoacid metabolism | 8.2±4.2 | 7.5±10.2 | 6.9±1.4 | 5.2±8 |
| 30 | Glycine Uptake | Aminoacid metabolism | 4.8±0.9 | 5±0.1 | 4.8±0.8 | 5.4±1.2 |
| 31 | Valine + 2-oxo-Glutarate → Glutamate + propionyl-CoA + 3 NADH + FADH2 + 2 CO2 | Aminoacid metabolism | -2.2±0.9* | -2.9±1* | -0.9±1.4*† | 0.8±0.4 |
| 32 | Isoleucine + 2-oxo-Glutarate → Glutamate + propionyl-CoA + Acetyl-CoA + 2 NADH + FADH2 +CO2 | Aminoacid metabolism | -1.7±0.6* | -1.4±0.3* | -1.7±0.7* | -0.2±0.7 |
| 33 | Leucine + 2-oxo-Glutarate → Glutamate + NADH + FADH2 Acetoacetate + Acetyl-CoA | Aminoacid metabolism | -2.6±2.1 | -4±3.5 | -2.6±2.1 | -0.2±3.5 |
| 34 | Propionyl-CoA + CO2 -> Succinyl-CoA | Aminoacid metabolism | -2.6±1.1* | -3.7±1* | -1.7±1.6*† | 1.4±0.8 |
| 35 | Lysine + 2 2-oxoGlutarate → 2 Glutamate + 4 NADH + FADH2 + 2CO2 + | Aminoacid metabolism | 7.2±4.2* | 2.9±6 | 3.7±1.6* | 1.5±0.4 |

FIG. 20B

| | | | | | | |
|---|---|---|---|---|---|---|
| | Acetoacetatyl-CoA | | | | | |
| 36 | Phenylalanine + O2 → Tyrosine | Aminoacid metabolism | 2.1±0.6* | 2.6±0.4* | 0.9±0.2*† | 0.5±0.4 |
| 37 | Tyrosine + 2 O2 → NH4 + CO2 + Fumarate + Acetoacetate + NADH | Aminoacid metabolism | 7.5±2.2* | 5±4.8 | 3.6±0.2 | 0.8±3.9 |
| 38 | Tyrosine Output | Aminoacid metabolism | -3.9±0.4* | -1.5±2 | -2.7±0.1* | -1±1.1 |
| 39 | Glutamate ↔ 2-oxo-Glutarate + NADH + NH4 | Aminoacid metabolism | 12.1±9.4 | 7.2±24.9 | 24.2±6.8* | 12.8±7.6 |
| 40 | Glutamate Output | Aminoacid metabolism | 5.4±3.5* | 2.3±0.1* | 0.2±0.9† | 0.8±1.3 |
| 41 | Glutamine → Glutamate + NH4 | Aminoacid metabolism | 5.7±3.3* | 9.3±25.9 | 20.4±5.6* | 2±2.5 |
| 42 | Proline +0.5 O2 → Glutamate + 0.5 NADH | Aminoacid metabolism | 2.6±0.4* | 2±1.9 | 1.6±0.9 | 0.7±2.9 |
| 43 | Histidine → NH4 +Glutamate | Aminoacid metabolism | -0.2±0.4* | -0.2±0.3* | 0.1±0.2* | 8±5.3 |
| 44 | Methionine + Serine → Cysteine + NADH + Propionyl-CoA + CO2 | Aminoacid metabolism | 1.3±0.2* | 0.6±0.1* | 0.9±0.2† | 0.8±0.1 |
| 45 | Aspartate ↔ Oxaloacetate + NH4 + NADH | Aminoacid metabolism | -24±8.7 | 20.3±10.9 | 15.9±12.9 | -23±16.7 |
| 46 | Aspartate Uptake | Aminoacid metabolism | 2.5±0.7* | 2.1±1.9 | 2.6±0.1* | 0.5±0.4 |
| 47 | Asparagine → Aspartate + NH4 | Aminoacid metabolism | 0.8±0.4* | 1.2±0 | 1.4±0.3 | 2±1.1 |
| 48 | Palmitate → 8 Acetyl-CoA +7 FADH2 + 7 NADH | Lipid, glycerol, fatty acid metabolism | 4.2±2.3* | 4.1±4* | 3.2±1.3* | 13.2±6.7 |
| 49 | 2 Acetyl-CoA ↔ Acetoacetyl-CoA | Lipid, glycerol, fatty acid metabolism | -0.8±4.9* | 3.9±14.1 | 5.5±2.1 | 17.6±16.4 |
| 50 | Acetoacetyl-CoA → Acetoacetate | Lipid, glycerol, fatty acid metabolism | 6.5±3.5* | 6.7±13.2 | 9.2±1.3 | 19.2±16.4 |
| 51 | Acetoacetate Output | Lipid, glycerol, fatty acid metabolism | 11.4±1.8* | 7.7±11.9 | 10.4±0.9* | -1.3±0.6 |
| 52 | Acetoacetate + NADH ↔ b-Hydroxybutyrate | Lipid, glycerol, fatty acid metabolism | 0±0* | 0±0* | 0±0* | 21±16 |
| 53 | NADH + 0.5 O2 → NAD | Oxygen uptake and electron transport | 164±52* | 109±87* | 119±32* | 317±178 |
| 54 | FADH2 + 0.5 O2 → FAD | Oxygen uptake and electron transport | 62±26* | 49±44* | 53±16* | 176±87 |
| 55 | O2 Uptake | Oxygen uptake and electron transport | 132±38* | 92±63* | 95±24* | 249±132 |

FIG. 20C

| | | | | | | |
|---|---|---|---|---|---|---|
| 56 | Glucose 6-phosphate → 2 NADPH + CO2 + Ribulose 5-P | PPP | 43±100 | 25±61 | 25±29 | 73±97 |
| 57 | Ribulose 5-P ↔ Ribose 5-P | PPP | 14±33 | 8±20 | 8±10 | 24±32 |
| 58 | Ribulose 5-P ↔ Xylulose 5-P | PPP | 29±67 | 17±40 | 16±19 | 49±65 |
| 59 | Ribose 5-P + Xylulose 5-P ↔ Fructose 6-P + Erythrose 4P | PPP | 14±33 | 8±20 | 8±10 | 24±32 |
| 60 | Erythrose 4-P + Xylulose 5-P ↔ Glyceraldehyde 3-P + Fructose 6-P | PPP | 14±33 | 8±20 | 8±10 | 24±32 |
| 61 | CO2 Output | Oxygen uptake and electron transport | 120±97* | 81±39* | 60±23 | 216±30 |
| 62 | Glycogen ↔ Glucose-6-P | Glucose metabolism | -13±26* | 139±208* | -34±14*† | 87±43 |

*Note:*

Bolded items are significantly different ($p<0.05$) from FRESH.
\* Items significantly different ($p<0.05$) from IN VIVO.
† Items significantly different from ISCHEMIC T=0-2hrs

FIG. 20D

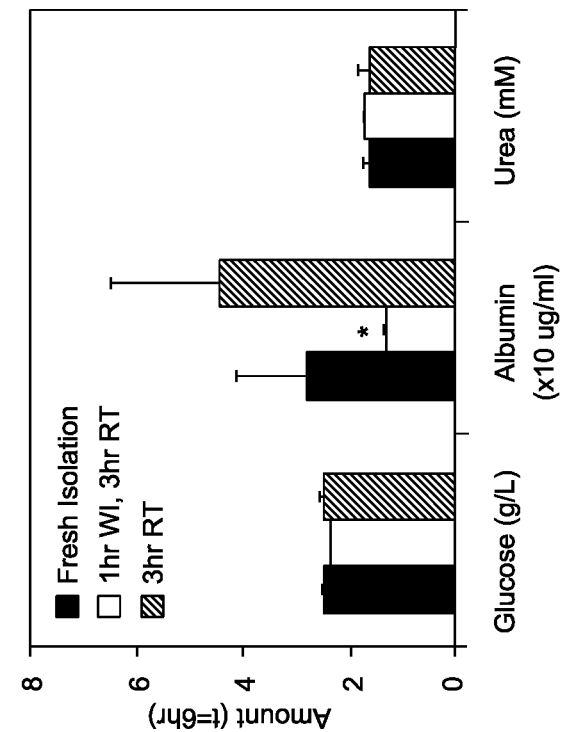
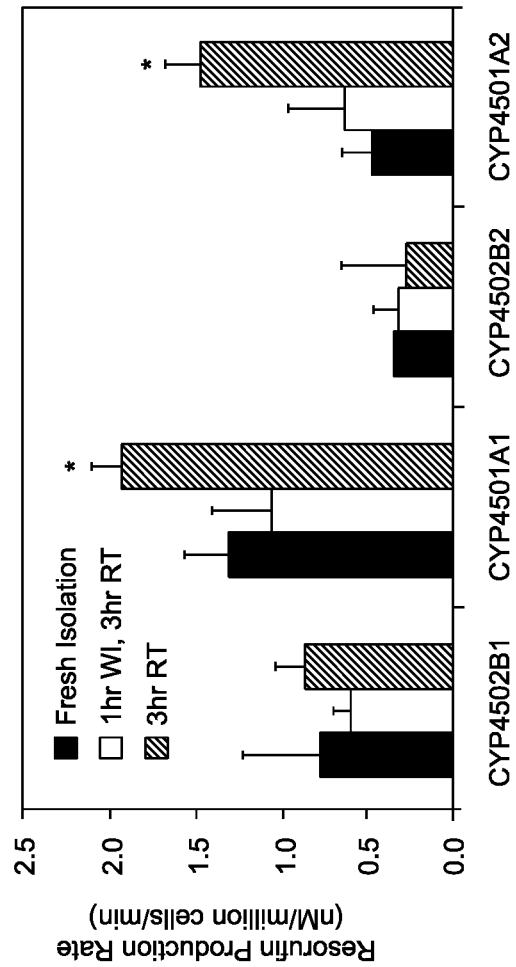
FIG. 28E
FIG. 28F

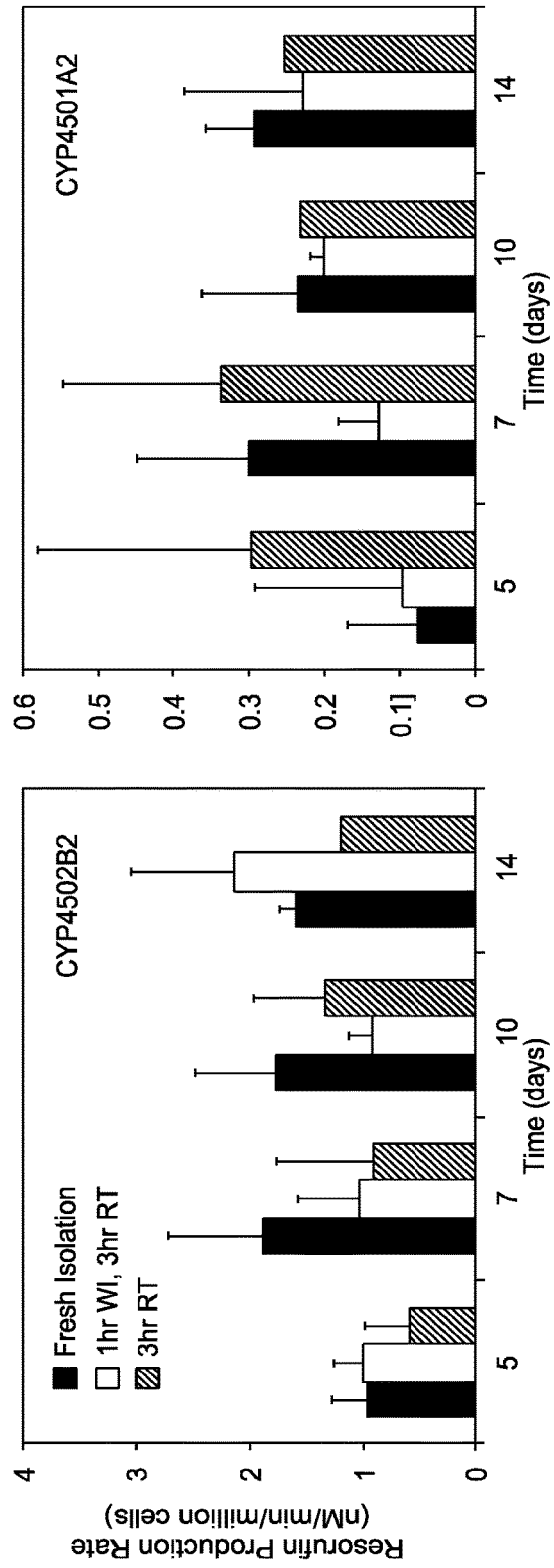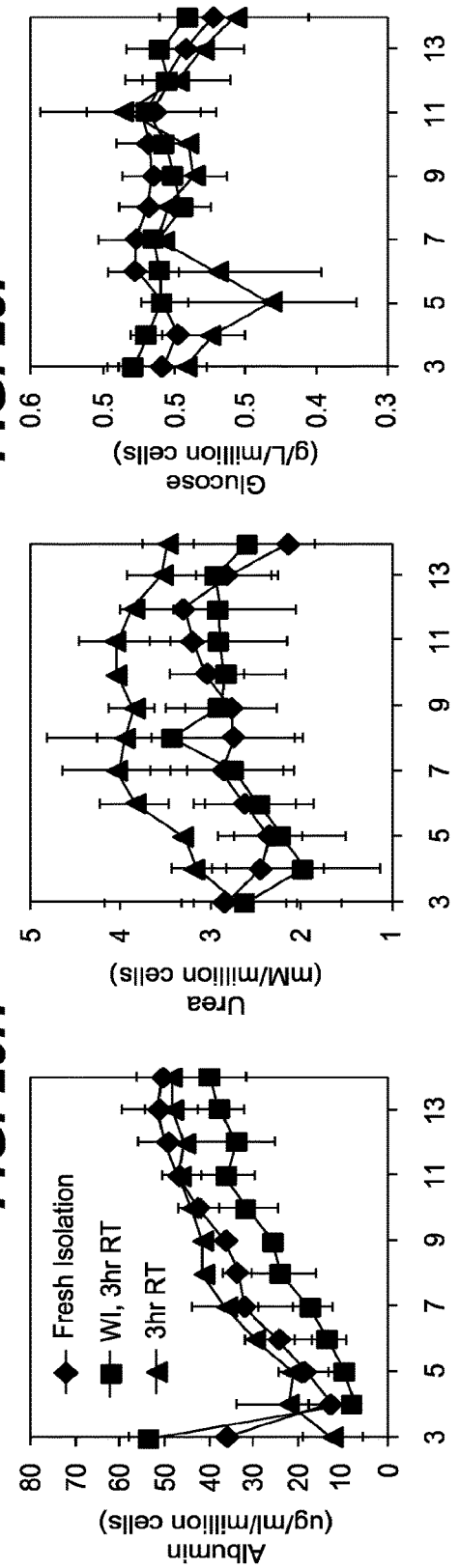

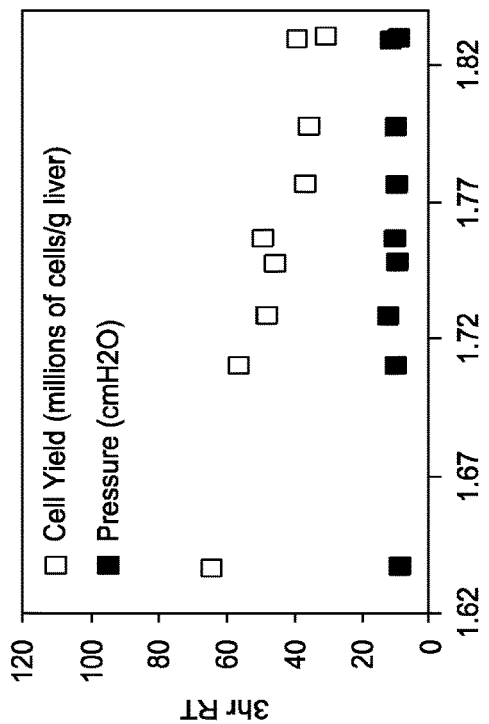
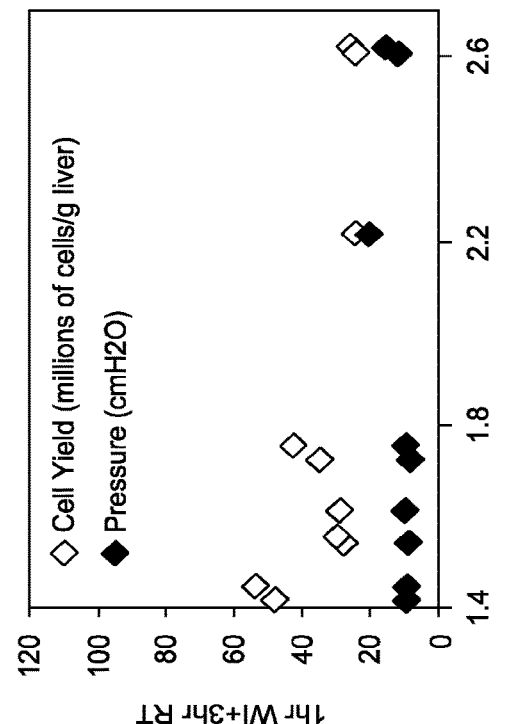
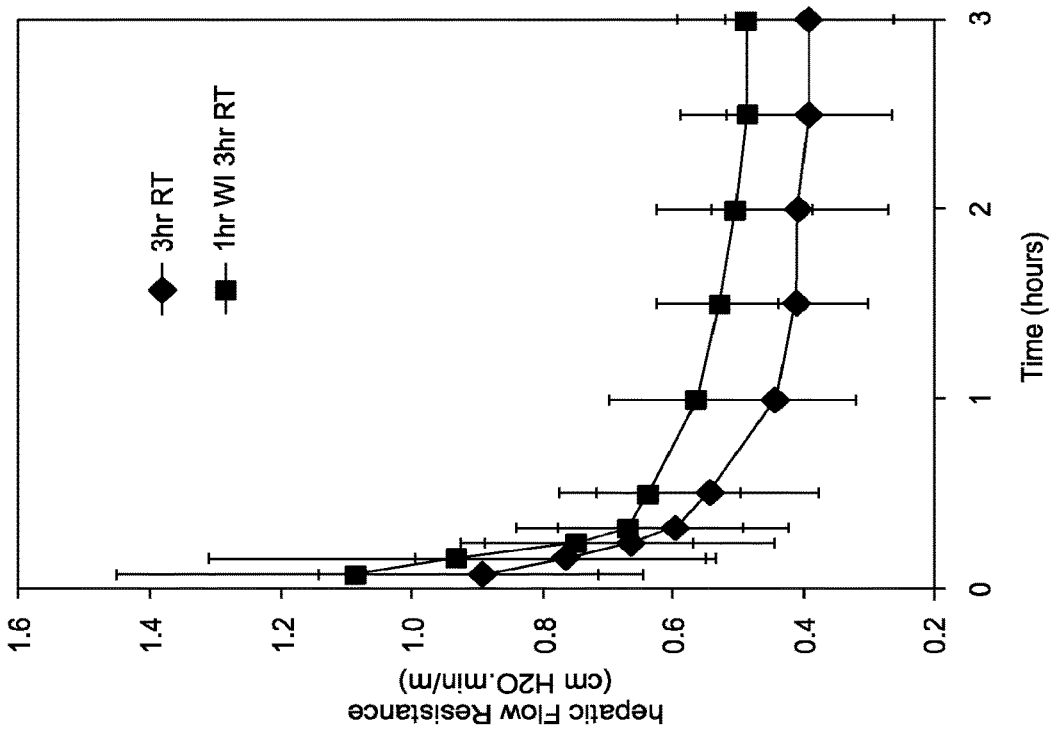
FIG. 32A
FIG. 32B
FIG. 32C

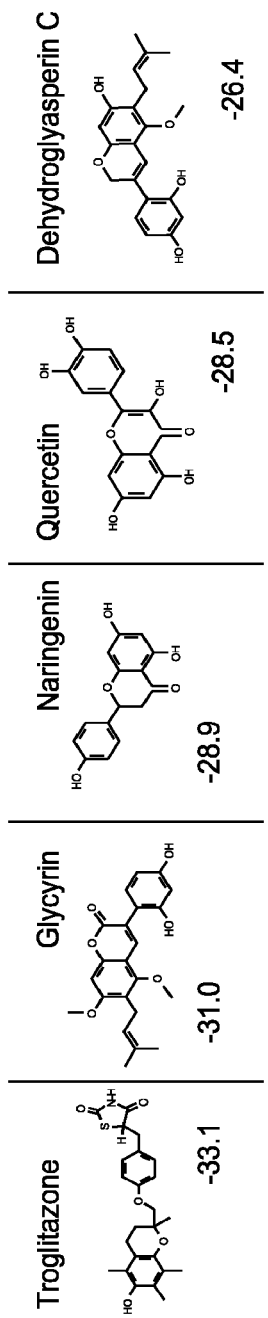
FIG. 35
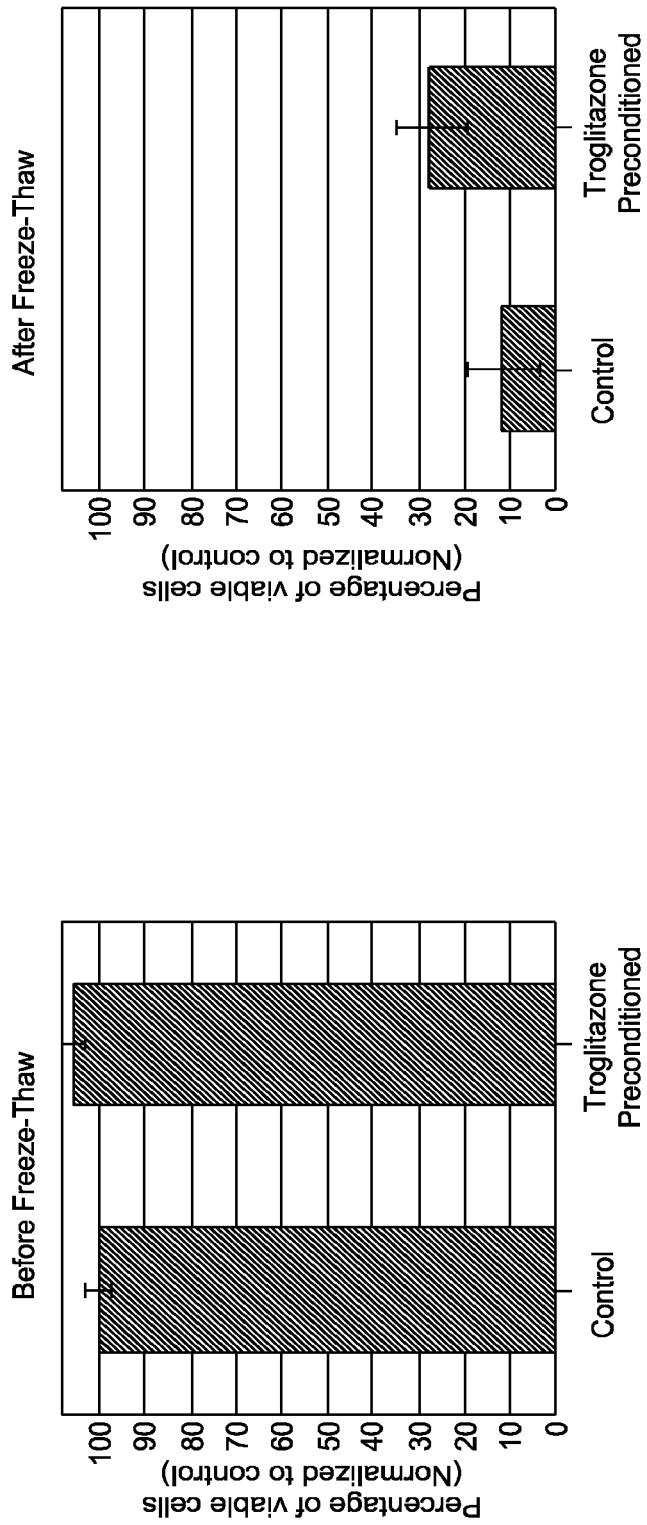
FIG. 36A
FIG. 36B

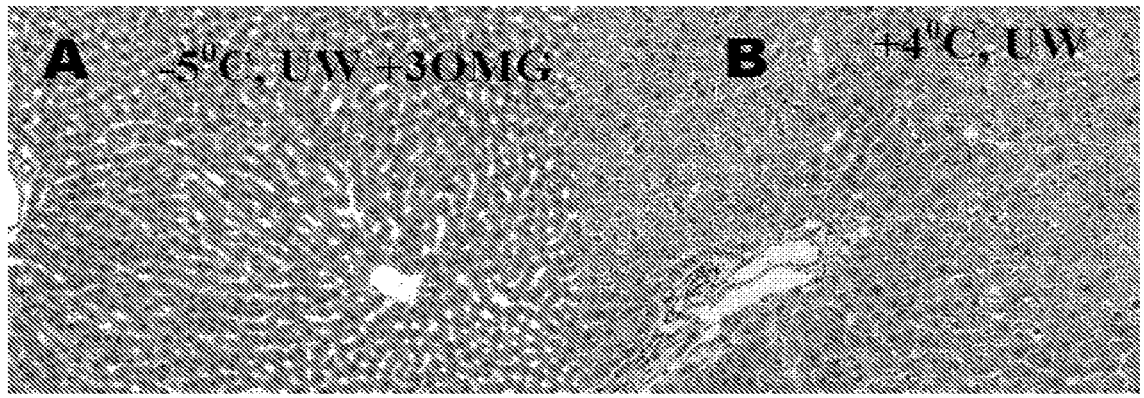
FIG. 45A  FIG. 45B
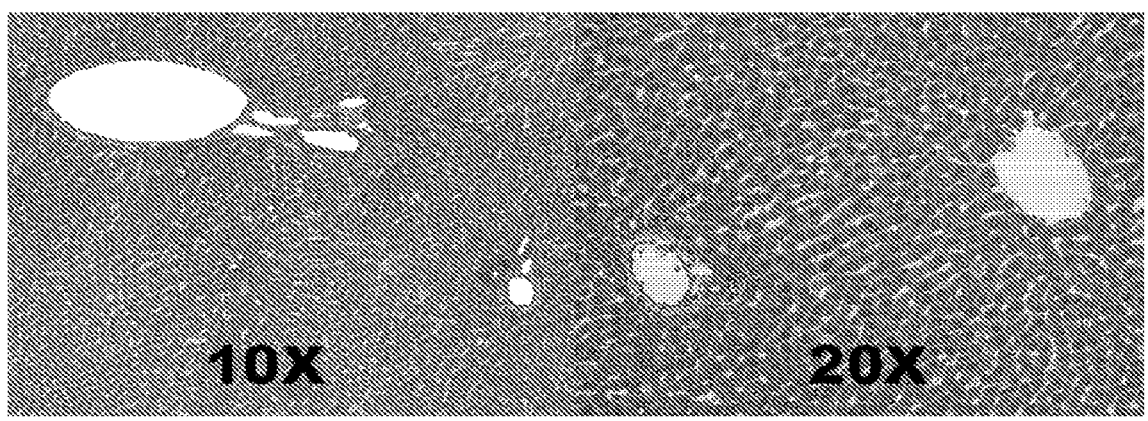
FIG. 46

METHODS AND COMPOSITIONS FOR PRESERVING TISSUES AND ORGANS

CROSS REFERENCE TO RELATED APPLICATIONS

This application is a Divisional of Ser. No. 13/695,459 filed on Oct. 3, 2013, which is a 35 U.S.C. 371 National Stage Application of International Application No. PCT/US2011/035223 filed on May 4, 2011, which designates the United States, and which claims the benefit under 35 U.S.C. § 119(e) of U.S. Provisional Patent Application Ser. No. 61/330,959 filed on May 4, 2010, U.S. Provisional Patent Application Ser. No. 61/364,186 filed on Jul. 14, 2010, and U.S. Provisional Patent Application Ser. No. 61/447,905 filed on Mar. 1, 2011, the contents of each are incorporated herein in their entity by reference.

GOVERNMENT SUPPORT

The present application was made with Government support under Grant Numbers NIBIB-R01EB008678, NIDDK-R00DK080942, NIDDK-K99DK088962, NTDDK-R01DK59766, awarded by the National Institutes of Health (NIH). The Government of the United States has certain rights in the invention.

FIELD OF THE INVENTION

The present invention generally relates to analysis of viability of organs for transplantation, and to methods, compositions and systems for preservation of organs for transplantation or other uses in the future, where the methods, compositions and systems relate to preserving the viability of organs and storing the organs for extended periods of time whereby they remain viable by metabolic suppression and/or by storing at subzero temperatures.

SEQUENCE LISTING

The instant application contains a Sequence Listing which has been submitted in ASCII format via EFS-Web and is hereby incorporated by reference in its entirety. Said ASCII copy, created on Oct. 30, 2012, is named 20121031_SequenceListing-TextFile_030258_070451_US and is 3,111 bytes in size.

BACKGROUND OF THE INVENTION

Demand for viable organs far exceeds the current supply. In 2011, it is predicted that over 70% of the people placed on the waiting list for organ transplantation will not receive a donor organ (see world wide web at: "opt.transplant.hr-sa.gov" as of 04/22/2011), and this disparity between the number of organs available and the number of organs required continues to grow: the increasing rate at which organ transplantation is prescribed outpaces the slow increase in the number of donors each year. It has been suggested that the actual need is much larger, and if the demand could be entirely met, over 30% of all deaths in the United States could be substantially postponed. Additionally, there is a constant demand for enormous numbers of high quality cells such as hepatocytes in the fields of cell transplantation, pharmacotoxicology, tissue engineering, and bioartificial assist devices. The scarcity of viable organs, for example liver and resultant necessitates the use of suboptimal sources including damaged donor organs that are not transplantable. Many of these organs have potentially reversible pathologies however, that could be treated via ex vivo perfusion thereby increasing their cell yield.

One of the greatest problems in donor organ transplantation is the storage and preservation of organs from the time of harvest from a donor to the time of transplantation into a recipient. The amount of time that can lapse between the two events is quite limited because the cells and tissues of the donor organ deteriorate over time, even if they are stored at refrigerated temperatures. Once harvested, cells and tissues are deprived of the oxygen that is required to maintain internal metabolism and cell volume integrity. To counteract the ill effects of low oxygen, standard techniques for modern organ preservation involve the exposure of a harvested organ to preservation solutions at cold temperatures not below 0° C. Although colder temperatures are a solution to oxygen deprivation in donor organ tissue, they present their own problems. Cold or hypothermic conditions may lead to cellular damage including a reduced ability to generate energy, maintain cell volume integrity, and also swelling and/or cell death.

Organs can only be kept viable for transplant for a limited time between the donation and the transplant operation. As soon as an organ is recovered from a donor, the clock starts ticking to meet the deadline to get it transplanted into a waiting recipient. Currently, the organs that can be transplanted and how long the organ can be out of the body before transplantation are as follow: heart and lungs 4-6 hours; pancreas, liver, and intestine 12-24 hours, kidneys 48-72 hours. Further hepatocytes are usually only viable for transplanting within 12 hours.

There are currently approximately 100,000 patients on the organ transplant waiting list in the US; a number that far exceeds the supply of available organs and the waiting list continues to grow at about 5% each year. The most promising strategies that are being explored as a means for addressing this critical shortage are: 1) bioartificial tissue and organ construction, which aims to manufacture tissue and organ analogues in vitro, and 2) donor organ revitalization methodologies, the goal of which is to recondition marginally damaged organs for transplantation. For both these approaches to be clinically successful, considerable effort must be expended on developing effective biopreservation methodologies. The current gold standard for whole organ preservation is cold storage on ice during which time the organ continuously deteriorates, and does not remain viable for any length of time, e.g., heart and lungs remain only viable for only 4-6 hours; pancreas, liver, and intestine remain only viable for only 12-24 hours, and kidneys remain only viable for only 48-72 hours Currently, the vast majority of efforts to develop improved cryopreservation and desiccation techniques focus on the preservation of individual cell populations, as the necessary strict control of temperature and concentration gradients are impossible to achieve in macroscopic tissues and organs, whether they be artificial or natural.

Simple cold storage remains the only option for tissue preservation. While cryopreservation has the potential, in theory, for very long storage of organs, successful and viable preservation of tissues and organs has proven elusive and very difficult (Fahy, G. G., Wowk, B. and Wu, J. Cryopreservation of complex systems: the missing link in the regenerative medicine supply chain. Rejuvenation Research 9, 279-291 (2006). A superior biopreservation method that extends the tissue storage time beyond current limits has yet to be developed. Such a method would be truly transformative for tissue and organ preservation, tissue and organ transport, and tissue and organ transplantation.

Storage of organs at sub-zero temperatures is extremely difficult because the tissue and water in the organ usually freezes. These relatively lower temperature ranges cause damage or destruction to the cells and tissues. There are some preservations solutions currently available for organ storage purposes, e.g., Viaspan™, which is used for cold (above 0° C.) storage, although their capacity to store organs effectively is significantly limited to the fact that they can only extend the storage of organs to a maximum of 36 hours before organs begin to deteriorate. For example, the preservation of donor organs using Viaspan™ preservation solution (also commonly known as University of Wisconsin (UW) solution, manufactured by DuPont) only extends the storage of kidney organs to a maximum of 36 hour period before the organs begin to deteriorate. For example, if kidneys are perfused with UW solution and packed on ice, surgeons will attempt to use them within 24 hours but not later than 36 hours after harvesting. A principal problem however is that the viability of the donor kidney decreases over time of storage so that by 36 hours there is at least some damage to the tubular cells. This generally results in decreased viability of the kidney cells so that urine production and proper kidney function are delayed after transplant. As a result, artificial kidney function or dialysis is generally required for full recovery of a recipient after transplantation.

Perfusion systems are capable of significantly impacting the viability of transplantable organs by optimally supporting donor organs during storage, and recovering reversibly damaged tissues through perfusate-based treatment protocols (Tolboom, et al., Transplantation, 2009, 87 (2): p. 170-7.; St Peter, et al., British Journal of Surgery, 2002, 89: p. 609-616.).

In summary, there is an urgent need for improved preservations technologies, especially for tissues and organs. Accordingly, there is a need for improved solutions and methods for effective organ preservation for extended periods of time. To facilitate the translation of this technology to clinical use, comprehensive and dynamic analyses of organ function during perfusion are needed that identify parameters critical to organ stability and recovery.

It is estimated that every year 27,000 people die because of liver-failure; currently the twelfth leading cause of death in the US. The only known treatment is orthotopic liver transplantation. According to the Organ Procurement and Transplantation Network, over 10,000 patients are added to the waiting list and less than 7,000 receive transplants each year. Clinically, the decision to use a non-ideal donor liver for transplantation is a difficult choice that to date lacks an accurate measure, and is done primarily based on gross organ morphology and donor statistics such as age and cause of death. A large number of organs, for instance kidneys, are not transplanted due to fear of graft failure based on qualitative tests that are open to interpretation. It is estimated that with the current practice about 3,000 viable cadaveric livers go unused. It is further estimated that about 6,000 ischemic livers could be reconditioned for transplantation, dramatically increasing the availability of grafts; currently these organs are discarded due to lower survival rates for these marginal grafts.

Accordingly, an accurate and reliable system for the analysis, prediction, and optimization of to predict organ viability, and to determine best method of organ preservation is greatly needed, and would provide significant benefit to increase the number of organs in a viable condition for transplant, and reduce the number of deaths caused by inaccessibility to organ transplantation, e.g., such methods may reduce liver failure caused deaths in the order of hundreds to thousands of patients per year. The broader impacts of such a method for prediction of liver viability would be very tangible both clinically and scientifically.

SUMMARY OF THE INVENTION

The present invention is related generally to methods and compositions to determine viability of an organ for transplantation and other medical purposes. Accordingly, one aspect of the invention relates to a method and assay for assessing the viability of an organ, and provides a quantitative standard for "transplantability" of an organ or future medical uses, or use of an organ to harvest cells. In some embodiments, a method for assessing the viability of an organ, cells or tissues evaluates the energy levels of the organ, which can be used to predict or anticipate (i) likely success of a transplant, (ii) can be used to determine the optimal preservation and storage protocols of the organ for extended storage of the organ, (iii) determine the ideal use of the organ, whether for transplantation, cell isolation, or recovery of organ scaffold for cell transplantation.

The lack of a practical approach to objectively quantify organ viability and identify suboptimal organs is a major problem and consequently, only a fraction of the available donor organs are actually used in organ transplants. Herein, the inventors have demonstrated a simple and effective method to determine the viability of an organ that allows the dynamic assessment of organ performance and, importantly, a highly accurate and reliable prediction of viable cell yield through tissue ATP content. In some embodiments, viability of an organ, and/or amount of viable cell yields can be determined by the amount of other energy molecules in the organ, for example, but not limited to, NADH, NADPH, ADP, AMP and glycogen (for liver)

As disclosed herein, the inventors have demonstrated that a direct correlation between cell yield and tissue ATP content provides an objective measure of organ viability and recovery during perfusion. In particular, one can use energy parameters in the organ as a measure of organ or tissue viability.

The viability of an organ over a particular time is a function of two measurements, (i) stored cellular energy (e.g., ATP levels), and (ii) energy consumption over a particular time period of viability. For example, without wishing to be bound by theory, if an organ has a cellular energy level at the maximum possible level of 100%, and a high metabolic activity and therefore high energy consumption, the organ may have a viability of, for example, 12 hours. However, if the organ has a cellular energy level at 50% of the maximum ATP level, but had very low metabolic activity and therefore low energy consumption, the organ may have the same viability of, for example, 12 hours. Thus, by modifying the energy content (e.g., ATP levels) and/or decreasing the energy consumption and/or metabolic activity of the organ, one can extend the time of viability of an organ.

Accordingly, the present invention relates to measuring the viability of an organ by measuring energy content (e.g., ATP levels) and optionally, the energy consumption, and using this to determine the viability of an organ over a period of time. Other aspects of the invention relate to methods to preserve or extend the time period of viability of an organ by either (i) increasing the energy content of the organ by preservation perfusion of the organ, and/or (ii) by metabolic suppression of the organ chemically, e.g., using metabolic suppressants, and/or by physical or environmental conditions, e.g., sub-zero non-freezing storage, as disclosed herein.

Accordingly, one aspect of the present invention relates to a measure of viability of an organ by measuring one or more energy parameters. In one embodiment, a energy parameter is the level of ATP (or ATP content) of the tissue which is an indication of the amount of ATP stored and thus the cellular energy content of the organ at that specific period in time. Based on a known average consumption of an organ of that organ type, the level of ATP can be used to accurately and reliable predict the length of time the organ will remain viable. In some embodiments, the level of ATP is about at least 60% or about 70% or about 80%, or about 90% or greater than 90% reliable at predicting the length of time the organ will remain viable for transplantation or other uses, e.g., cell harvesting.

In another embodiment, one can also measure the metabolic activity of the cell, e.g., using a metabolic flux assay (MFA) as disclosed herein, which can be used to determine the rate of energy consumption. Accordingly, based on the energy stores (e.g., ATP levels) and the rate of energy consumption, (e.g., determined by the MFA), one can accurately and reliable predict the length of time the organ will remain viable. In some embodiments, a prediction of the viability of an organ can be determined on energy stores alone (e.g., ATP, or other energy molecules, e.g., NADH, NADPH, ADP, AMP and glycogen (for liver)). In some embodiments, a prediction of the organ viability via a combination of other parameters indirectly related to ATP synthesis/use. In some embodiments, transplant success can be predicted via blood gas analysis and/or on (ii) degree of ischemia, which can be predicted via metabolite levels.

In some embodiments, the method to measure the viability of an organ as disclosed herein, e.g., by measuring stored cellular energy (e.g., ATP levels), and/or energy consumption over a particular time (e.g., using the MFA) can be used to predict the success of the transplant with high reliability. For example, in some embodiments, the methods disclosed herein to assess the viability of an organ as disclosed herein are at least about 50% reliable, or at least about 60% reliable, or at least about 70% reliable, or at least about 80% reliable, or at least about 90% reliable, or greater than 90% reliable at predicting the successful outcome of the implantation of the organ into the subject.

Another aspect of the present invention relates to methods and compositions to extend or preserve the length of time an organ can remain viable. The inventors designed three methods of extending the viable preservation time of organ tissue: 1) perfusion 2) metabolic suppression by metabolic suppressor agents, and 3) metabolic suppression by sub-zero non-freezing storage. Such methods have allowed inventors to extend the viable preservation time of an organ and thereby increase the range of organ distribution and allocation, minimizing effects related to geography, and allowing for better donor/recipient matching, thereby potentially saving many lives.

In some embodiments, one can use any one, or a combination, in any order of 1) perfusion, 2) chemical mediated metabolic suppression, and 3) sub-zero non-freezing storage to extend the preservation time of organs. For example, one could increase the length of time of viability by first increasing ATP stores by perfusing with a preservation perfusion solution as disclosed herein, which also serves to remove cytotoxins from the organ, then subsequently decrease the rate of metabolic activity of the organ by perfusing the organ with a metabolic suppressant and/or supercoolant agent as disclosed herein followed by sub-zero non-freezing storage, and storing the organ for a predetermined period of time at a sub-zero temperature. After storage of the organ, the organ can be rewarmed in a perfusion based system and optionally evaluated for viability by measuring (i) ATP levels, and/or (ii) metabolic activity (e.g., energy consumption) to determine the viability of an organ after preservation.

In some embodiments, the methods and compositions enable one to preserve or extend the viable preservation time of an organ by at least double or at least about triple the current storage time. In some embodiments, the methods as disclosed herein provide for increasing the viable preservation time by at least 1.5-fold, or at least about 2-fold, or at least 3-fold the current preservation times. In some embodiments, the methods as disclosed herein provide increasing the viable preservation time to at least about 5 days, or at least about 6 days or at least about 7 days or more than 7 days, or at least about 10-fold, or at least about 14-fold increase in preservation times as compared to current preservation methods. This is a significant increase in the extension of period of viability of an organ, providing additional time to allow for cross-matching of donors and recipients, and for transnational and trans-international transport of donor organs, which are not possible under the current preservation procedures.

Accordingly, one aspect of the present invention relates to a reliable method to measure the viability of an organ by measuring the cellular energy content in the cell, (e.g., the energy stored in the cell) by measuring the ATP levels in the cell. In particular, ATP levels can be measured by direct measurement of ATP levels in a biopsy tissue sample obtained from the organ. One can use any method to measure ATP levels known to one of ordinary skill in the art, for example, one can use the method of measuring ATP content as disclosed herein in the examples.

In some embodiments, the MFA can measure the cellular energy status of the cell by measuring a energy parameter. In some embodiments, a energy parameter is the level of ATP in the cell. In particular, the inventors have demonstrated herein that in a biopsy sample from an organ, there is a linear correlation between the cell-yield and the tissue ATP content, normalized to the total protein. In particular, in some embodiments the level of ATP in a cell is a useful energy parameter to enable a direct measure of organ viability and organ recovery during organ preservation, e.g., by using the methods as disclosed herein. Where the ATP level is above a predefined threshold, it indicates the organ is of good viability and can be used for organ transplant, or other medical uses.

Another aspect of the present invention relates to a reliable method for assessing the viability of an organ by determining the energy consumption of an organ, and is referred to herein as a "metabolic flux assay" or "MFA, and provides an efficient pre-screening method for qualitatively evaluating the viability of an organ at any time, for example, after harvesting the organ from a donor, and/or before preservation and/or after preservation. In particular, the MFA can measure the change in the level of at least one viability metabolite as it is consumed or produced by the organ, and can be used to provide an indication of the time of recovery of an ischemically damaged organ, and/or organ stability during perfusion and/or the impact of perfusion on organ metabolism.

In some embodiments, the MFA is used in a method to measure the consumption of cellular energy by an organ, and comprises perfusing the organ with a MFA perfusion solution (e.g., a MFA perfusate) and measuring the input and output levels of metabolites to determine the level of metabolic activity, and therefore the energy consumption of the organ. In some embodiments, the organ is perfused with a MFA perfusate, which comprises a modified culture media. In some embodiments, the MFA perfusate comprises erythrocytes as oxygen carriers to provide physiological flow rates of oxygen delivery. However, in some embodiments, the MFA perfusate does not comprise erythrocytes.

In some embodiments, the MFA measures the metabolic status of an organ by measuring any one or a combination of (i) oxygen uptake (e.g., oxygen consumption), (ii) glucose levels, and (iii) nitrogen metabolism of the organ over a defined period of time. In some embodiments, the MFA measures the input and output levels of at least about 10 metabolites, or at least about 15 metabolites, or at least about 20 metabolites, or about 28 metabolites during the perfusion of the organ with the MFA perfusate, and where the level of the metabolite falls below or uses above a predefined threshold for each metabolite is indicative of the energy status of the cell and the viability of the organ.

Accordingly, the present invention relates to measuring the viability of an organ by measuring energy content (e.g., ATP levels) and optionally, the energy consumption, and using this to determine the viability of an organ over a period of time. Accordingly, as disclosed herein, measuring the level of metabolic activity (e.g., energy consumption) over a particular time and measuring the stored cellular energy (e.g., ATP levels) can be used as a highly reliable method to determine viability of the organ. In some embodiments, the method is at least about 50% reliable, or at least about 60%, or at least about 70%, or at least about 80%, or at least about 90%, or at least about 98% reliable as to the viability of the organ over a period of time.

Additionally, the inventors have demonstrated herein a method to extend or preserve the viability of an organ includes rewarming the organ by normothermic perfusion with a preservation perfusion solution reduces reperfusion and/or ischemic damage. In particular, the inventors have demonstrated that normothermic perfusion can significantly reduce or partially reverse, or prevent the damaging effects of ischemia.

In some embodiments, after assessing the viability status of an organ, one can proceed with methods to extend the time period of viability of the organ by either (i) increasing the energy content of the organ, e.g., by preservation perfusion of the organ, or (ii) by metabolic suppression of the organ chemically, e.g., using metabolic suppressants, and/or by physical or environmental conditions, e.g., sub-zero non-freezing storage, as disclosed herein.

Additionally, the inventors also demonstrated methods to extend or preserve the viability of an organ by suppressing the metabolic activity of the organ either by using metabolic suppressants, and/or by supercooling preservation of the organ to sub-zero temperatures using a minimally toxic supercoolant agent to avoid antifreeze toxicity, and further slowing the organ metabolism thereby reducing anoxic/ischemic damage to minimal levels.

For example, the inventors have demonstrated herein that significant ischemic damage to the organ can be prevented, or can be partially or fully, restored or reversed by ex vivo perfusion of the organ with a preservation perfusion solution to distribute nutrients and remove cytotoxins. For example, the inventors demonstrate by perfusing livers with a preservation perfusion solution enables fully functional hepatocytes to be recovered from liver organs that would otherwise, without the perfusion, have been considered to be deteriorated and be discarded. Accordingly, the present invention provides a methodology to enable greater cell yields per donor organ in addition to increasing the number of organs eligible for treatment.

Accordingly, one aspect of the invention relates to a preservation perfusion solution to maintain the viability of the organ, and for distributing nutrients to the organs via the vasculature and to remove cytotoxins. In some embodiments, the preservation perfusion solution can be perfused through the organ tissue to unblock any blocked vascularization of the organ. In some embodiments, the preservation solution comprises an admixture of agents to promote the energy status of cells in the organ tissue, for example, can comprise an energy source to support cellular functions including the Krebs cycle. In some embodiments a preservation perfusion solution comprises a quick and ready source of ATP, or agents to quickly increase ATP levels in the organ. In some embodiments, a preservation perfusion solution comprises about 10%, or about 20%, or about 40%, or about 80%, or about 100%, or about 2-fold, or about 3-fold or about 5-fold or more than 5-fold greater levels of adenosine, a precursor to ATP synthesis, or other agents which increase ATP levels in a cell, as compared to standard media. In some embodiments, the preservation perfusion solution can be used to prevent ischemic damage to organs, for example, before or after sub-zero storage.

Another aspect of the present invention relates to preservation of an organ by metabolic suppression of the organ. In some embodiments, this can be chemical suppression, e.g., using metabolic suppressants, and in alternative embodiments, it can be physical or environmental conditions, e.g., sub-zero non-freezing storage, as disclosed herein. Metabolic suppression is used to decrease metabolic activity of an organ and thereby decrease consumption/utilization of ATP in the cell, thereby extend the viable preservation time an organ.

Accordingly, one embodiment relates to a method of metabolic suppression of the organ in order to extend the viable preservation time of an organ. In some embodiments, for chemical mediated metabolic suppression of an organ, the organ can be perfused with a solution comprising a metabolic suppressant agent. In some embodiments, the metabolic suppressant agent is magnolol or a derivative or analogue thereof, where magnolol is a biphenic compound with an antioxidant and functions as a tumor suppressant. In some embodiments, an organ can be perfused with a preservation solution, as disclosed herein, before being perfused with a metabolic suppressant agent.

Another aspect of the present invention relates to preservation of an organ by sub-zero storage of the organ. In some embodiments, the sub-zero storage, also referred to herein as "sub-zero non-freezing" or "SZNF" occurs in a sub-zero freezing media comprising at least one supercoolant agent or at least one hypothermic preservatives. In some embodiments the sub-zero freezing media comprises the supercoolant agent 3-O-methyl-glucose (3OMG), which lowers the achievable freezing temperature without cytotoxic side effects.

As the rate of biological reactions are roughly halved every 10° C. decrease, the method of sub-zero non-freezing storage as disclosed herein can be used to decrease temperatures by at least −10° C., or by at least about −15° C., or at least about −20° C., or at least about −25° C., or colder than about −25° C., to extend or preserve viability of the more than at least double the viable preservation duration for biological and artificial tissues.

Accordingly, one aspect of the invention relates to a method of assessing viability of an organ, comprising measuring a least one energy parameter and determining a measure of viability as a function of the at least one energy parameter. In some embodiments, the energy parameter is an energy parameter to measure the level of energy stores in the organ, e.g. the level or one or more of ATP, NADH, NADPH, ADP, AMP and glycogen (for liver) can be measured. In alternative embodiments, the energy parameter is an energy which measures the amount of energy consumed by the organ over a defined period of time.

In some embodiments, the energy parameters can be compared to reference energy parameters to provide a highly accurate and reliable prediction of viable cell yield in the organ and organ viability. In some embodiments, the determining a measure of viability comprises comparing a measured energy parameter to a representative threshold of a transplantability of an organ. In some embodiments, the reference energy parameter is based on the energy parameters for a healthy organ and/or the energy parameters of an organ which has a good viability and upon immediate implantation into a subject results in a successful transplantation, and provides a threshold of a transplantability. For example, in some embodiments, where the energy parameters measured in the organ are the same or above a threshold of a transplantability, e.g., a reference energy parameter for a healthy organ and/or the energy parameters of an organ which has a good viability and upon immediate implantation into a subject results in a successful transplantation, it indicates good viability of the organ.

In some embodiments, a measure of viability comprises comparing a measured energy parameter to a preservation threshold of an organ. In some embodiments, where the measured energy parameter above a representative preservation threshold, the organ can be selected for preservation according to the methods as disclosed herein. In some embodiments, the representative preservation threshold is based on the levels of energy parameters of an organ which has viability and will respond well to preservation according to the methods as disclosed herein.

In some embodiments, a measure of viability comprises comparing a measured energy parameter to a threshold representative of cell harvesting threshold of an organ. For example, in some embodiments, where the measured energy parameter is above a cell harvesting threshold, the organ can be selected for cell harvesting of cell of the organ. In some embodiments, the representative cell harvesting threshold is based on the levels of energy parameters of an organ or cells which can result in a level of yield of cells harvested from the cell for future use.

In some embodiments, an energy parameter is a measure of the metabolic activity of the organ. In some embodiments, an organ is preserved or stored prior to, during or after the method of assessing its viability.

In some embodiments, after assessing the viability of an organ, it can optionally be implanted into a subject, for example, a mammalian subject, e.g., a human subject. In some embodiments, cells can be harvested from an organ after assessing its viability according to the methods as disclosed herein.

In some embodiments, the methods for assessing an organs viability is at least about 50% reliable at predicting the viability of the organ and/or successful outcome of implantation of the organ into a subject, or at least about 60%, or at least about 70% or at least about 80%, or at least about 90% or greater than 90% reliable at predicting the viability of the organ and/or successful outcome of implantation of the organ into a subject.

In some embodiments, after assessing the viability of an organ, the method further comprises implanting the organ in a subject. In some embodiments, a least one energy parameter measured is the level of ATP in the organ. Any means to assay for ATP is encompassed for use in the methods of the invention as disclosed herein. In some embodiments, a least one energy parameter measured is measuring the cellular energy status of the organ (e.g., ATP stores).

In some embodiments, at least one energy parameter can be measured during normothermic or subnormothermic perfusion of the organ. In some embodiments, before, or after assessing the viability of an organ, one can perfuse the organ with a preservation perfusion solution as disclosed herein. In some embodiments, the preservation prefusion solution comprises sources of cellular energy or ATP, e.g., adenosine at least about 2-fold, or 3-fold, or 3-5 fold, or 5-10 fold greater than conventional media. In some embodiments, the preservation perfusion solution can comprises erythrocytes, and in alternative embodiments, the preservation perfusion solution lacks erythrocytes.

In some embodiments, a least one energy parameter measured is measuring the energy consumption as disclosed herein, by measuring the changes in at least one metabolite as disclosed herein. In some embodiments, an energy parameter which is measured is the level of a plurality of metabolites. For example, in some embodiments, a plurality of metabolites can be selected from any or a combination from the group consisting of: Glucose, Urea, Nitrogen, Total Carbon dioxide, AST, ALT, ALP, total protein, total bilirubin, Creatinine, Sodium, Potassium, Calcium, Chloride, Total Cholesterol, triglycerides (high density and/or low density), very low density lipoproteins, Amino acids, Lactate, Free fatty acids, Glycerol, Insulin, Glucagon, 3-hydroxybutyrate, Acetoacetate, Nitric Oxide, Gluthatione, Glutathione disulfide, bile, principle bile acids, steroids, O2 and CO2, Hematocrit, Hemoglobin (Free, oxygenated), electrolytes, TNF-α.

In some embodiments, where an energy parameter is the rate of energy consumption, one can measure the change in the levels of a plurality of metabolites over a predefined period of time, wherein the change in the plurality of metabolites is selected from any or a combination from the group consisting of: Oxygen uptake, carbon dioxide output, glucose output, lactate uptake, acetoacetate output, β-Hydroxybutyrate output, urea output, ammonia uptake, alanine uptake, arginine uptake, ornithine uptake, asparagine uptake, aspartate uptake, cysteine output, glutamate output, glutamine uptake, glycine uptake, histidine uptake, proline uptake, serine uptake, methionine uptake.

In some embodiments, at least about 10 metabolites are measured, or at least about 15, or at least about 20 or about 28 or more metabolites are measured. In some embodiments, an energy parameter which is measured is the oxygen consumption by the organ, and/or the level measuring the gluconeogeneis of the organ, and/or the nitrogen metabolism by the organ. In some embodiments, where the energy parameter measured in the organ is above a predetermined level it is indicative that the organ is suitable for preservation and/or implantation into a subject.

Another aspect of the present invention provides a method for extending the viable preservation of the organ, comprising perfusing the organ with a preservation perfusion solution. In some embodiments, the preservation perfusion solution comprises at least 3 of the following: insulin, L-glutamine, hydrocortisone heparin penicillin, streptomycin sulfate, adenosine. In some embodiments, the normothermic or subnormothermic perfusion with a preservation perfusion solution removes cytotoxins from the organ.

Another aspect of the present invention provides a method for preventing ischemic damage in an organ, comprising perfusing the organ with a preservation perfusion solution. In some embodiments, the methods prevents at least about 10%, or at least about 20%, or at least about 30%, or a least about 40%, or a least about 50%, or at least about 60%, or a least about 70%, or a least about 80%, or a least about 90%, or greater than 90% of ischemia due to cold or warm ischemic exposure. In some embodiments, the perfusion with the preservation perfusion solution is performed prior to, or after, the ischemic damage. In some embodiments, the preservation perfusion solution comprises at least 3 of the following: insulin, L-glutamine, hydrocortisone heparin penicillin, streptomycin sulfate, adenosine. In some embodiments, the perfusion with the preservation perfusion solution occurs at normothermic or subnormothermic temperatures.

Another aspect of the present invention relates to a method of extending the viable preservation time of an organ, comprising contacting at least a portion of the organ with a solution comprising at least one metabolic suppressant agent. In some embodiments, the organ is contacted with a solution comprising a metabolic suppressant agent decreases utilization of ATP in the cell. In some embodiments, contacting comprises contacting at least a portion of the organ with a solution comprising the metabolic suppressant agent by immersing the organ, either partially or completely, and/or perfusion of the organ or tissue with a solution comprising the metabolic suppressant agent. In some embodiments, contacting at least a portion of the organ with a solution comprising a metabolic suppressant agent increases the cellular energy (e.g., ATP stores) in the cell. In some embodiments, the method of extending the viable preservation time of an organ further comprises measuring a least one energy parameter, e.g., an ATP utilization parameter such as the metabolites as disclosed herein, and comparing the measured energy parameter, e.g., an ATP utilization parameter to a threshold representative of a quantitative standard for ATP in the cell.

In some embodiments, the metabolic suppressant agent is selected from the group consisting of: Troglitazone, Glycyrin, Naringenin, Quercetin, Dehydroglyasperin C (Pubchem CID 480775), Magnolol, and derivatives thereof. In some embodiments, the metabolic suppressant agent is Magnolol and derivatives thereof. In some embodiments, the metabolic suppressant agent is an inhibitor of PPARγ, such as, for example, a RNAi agent inhibitor or nucleic acid inhibitor of PPARγ. In some embodiments, an inhibitor of PPARγ is selected from any or a combination of agents selected from the group consisting of: troglitazone and rosiglitazone, T0070907, GW9662 and BADGE, or derivatives thereof.

Another aspect of the present invention relates to a method of preserving an organ by sub-zero non-freezing (SZNF) comprising: (i) contacting an organ with a media comprising a supercoolant agent; (ii) cooling said organ to a predetermined sub-zero temperature; (iii) storing said organ at the predetermined sub-zero temperature; and (iii) re-warming said organ.

In some embodiments, the method further comprises measuring a least one energy parameter, and determining a measure of viability as a function of the at least one energy parameter as disclosed herein. In some embodiments, the method further comprises implanting the organ in a subject, e.g., a mammalian subject, e.g., a human subject.

In some embodiments, the method of method of preserving an organ by sub-zero non-freezing (SZNF) further comprises harvesting the cells of the organ after the rewarming the tissue and/or organ.

In some embodiments, the method of preserving an organ by sub-zero non-freezing (SZNF) is at least 50% reliable at predicting the viability of the organ and/or successful outcome of implantation of the organ into a subject, or at least about 60%, or at least about 70%, or a least about 80%, or at least about 90% or greater than 90% reliable at predicting the viability of the organ and/or successful outcome of implantation of the organ into a subject.

In some embodiments, re-warming the organ in the method of preserving an organ by sub-zero non-freezing (SZNF) is by normothermic perfusion, or subnormothermic perfusion of the organ. In some embodiments, the normothermic or subnormothermic perfusion is with a preservation perfusion solution as disclosed herein. In some embodiments, the normothermic or subnormothermic perfusion is with a preservation perfusion solution removes cytotoxins from the organ.

In some embodiments, the method of preserving an organ by sub-zero non-freezing (SZNF) cools and stores the organ at a predefined sub-zero temperature without freezing. In some embodiments, the predefined sub-zero temperature is at least $-5°$ C. or below, or at least $-10°$ C. or below, or at least $-15°$ C. or below, or at least $-20°$ C. or below, or at least $-30°$ C. or below, or between $-30°$ C. and $-80°$ C. In some embodiments, the organ is stored (e.g., held) at the predefined sub-zero temperature for at least about 1 hour, or at least about 2 hrs, or a least about 3-5 hours, or at least about 5-12 hours, or at least about 12-24 hours, or at least about 24 to 48 hours, or at about 3 days, or about 4 days, or about 5 days, or about 6 days or about 7 days or longer than 7 days.

In some embodiments, the supercoolant agent is a hypothermic preservative. In some embodiments, the supercoolant agent can be selected from any in the group consisting of: 3-O-methyl-glucose (3OMG), hypothermosol, trehalose, polyvinyl alcohol, polyvinylpyrrolidone, DMSO, polygylcerol, K3Glc (Kaempferol 3-O-O-D-glucopyranoside); K7Glc (Kaempferol 7-O-β-D-glucopyranoside), Q7Glc (Quercetin 7-O-β-D-glucopyranoside), Q3Gal (Quercetin 3-O-β-D-galactopyranoside), Polyethylene glycol. In some embodiments, the supercoolant agent is 3-O-methyl-glucose (3OMG) or a derivative thereof.

In some embodiments, a supercoolant can be used at a concentration between 0.1-2 mg/ml, or alternatively, it can be used at a concentration between 50 mM and 1M.

In some embodiments, the organ is cooled to the predefined sub-zero temperature at a rate of at least 1° C. per 10 minutes, or at a rate of at least 1° C. per 5 minutes or at least 1° C. per 1 minute, or at least 1° C. per 10 minutes. In some embodiments, the organ is re-warmed from the predefined sub-zero temperature at a rate of at least about 1° C. per 5 minutes, or at least 1° C. per 1 minute or faster than 1° C. per 1 minute.

BRIEF DESCRIPTION OF THE DRAWINGS

FIG. 1A shows a liver perfusion system; FIG. 1B shows the experimental groups; FIG. 1C shows cell yield and viability normalized to wet liver weight before and after Percoll purification; FIG. 1C shows biopsy ATP content normalized to total protein content.* denotes significantly less than all other groups (p<0.05). ** denotes significantly more than all other groups (p<0.05). Data shown are means±s.d. (n=8 in each group).

FIGS. 2A-2E illustrate cell function in suspension for WI+3hrRT and 3hrRT groups compared to fresh hepatocytes. Percent viability of cells using: FIG. 2A shows Trypan Blue exclusion. Fresh hepatocytes are significantly reduced in viability at t=6 hrs (p<0.05), and mitochondrial activity measured by absorbance of formazan produced from MTT at 570 nm. FIG. 2B shows ALT; perfused groups have significantly higher starting values (p<0.05), AST; significant differences exist between all groups (p<0.05). FIG. 2C shows metabolic assays of glucose, albumin and urea. Albumin is significantly reduced in WI+3hrRT cells at t=6 hrs (p<0.05). D. CYP450 activity measured using resorufin production by dealkylation of benzyloxy resorufin (CYP4502B2), pentoxy resorufin (CYP4502B1), ethoxy resorufin (CYP4501A1) and methoxy resorufin (CYP4501A2) after 3,3'-methylene-bis(4-hydroxycoumarin) activation. Activity is significantly higher in 3hrRT cells for CYP4501A1 and CYP4501A2 (p<0.05). E. Gene expression profiling of suspended hepatocytes at t=0 hrs. All data shown are means±s.d.

FIGS. 3A-3F illustrate cell function in double layer collagen gel sandwich plate culture. Viability of cells using: in FIG. 3A Hoechst 33452/Ethidium homodimer-1 double stain and, mitochondrial activity measured by absorbance of formazan produced from MTT at 570 nm; in FIG. 3B CYP450 isoenzyme activity for days 5, 7, 10 and 14 of culture.FIGS. 3C-E show metabolic activity for albumin, urea, glucose. Urea production is significantly increased in 3hrRT livers (p<0.05).F. Phase contrast images for Fresh, WI and WI+3hrRT livers respectively.

FIG. 4A shows clearance of debris within 20 minutes of perfusion. FIG. 4B shows the decline of hepatic resistance and increase in total protein release from livers in perfusion. Correlation of hepatic flow but not portal pressure with total cell yield. Lower oxygen uptake rate and increased rate of lactate performance in WI+3hrRT livers (p<0.05). FIG. 4C shows the bile weight accumulated by t=6 hrs is significantly different between perfusion groups. FIG. 4D shows the perfusate albumin concentration over time.

FIG. 4E shows the pH of perfusate entering and exiting the liver. pH out at t=0.5 hrs is significantly different between 1 hr WI+3hrRT livers (p<0.05). FIG. 4F shows the PAS stain for glycogen content of Fresh, WI and perfused groups at t=3 hrs.

FIG. 5A shows the transmission electron microscopy (10 µm) of Fresh, WI and perfused liver groups at t=3 hrs (FIG. 5A); FIG. 5B shows the ALT and AST release during perfusion by WI+3hrRT livers; values are stable in 3hrRT livers (p<0.05); FIG. 5C shows the unfolded protein response and ER stress of biopsied livers, and performance as cell suspensions through ratio of spliced XBP-1 to non-spliced and gene expression profiles of Grp78 and CHOP1. * denotes significantly different from all other groups (p<0.05)

FIG. 6A shows the perfusion flow rates of 3hrRT and WI+3hrRT livers; FIG. 6B shows the portal pressure profiles are distinct at t=1 hr and 1.5 hrs (p,0.05); FIG. 6C shows hepatic resistances; FIG. 6D shows cumulative protein release captured over the same time frame is distinguished between groups beginning at t=0.5 hrs (p<0.05). Data is expressed as mean±s.d. (n=16).

FIG. 7A shows the oxygen delivery (ODR) and oxygen exit (OER) rates of 3hrRT and WI+3hrRT liver; FIG. 7B shows the glucose levels compared to initial Williams Medium E content; FIG. 7C shows urea levels. Data is expressed as mean±s.d. (n=16).

FIG. 8 A shows H&E; Figures B shows TEM.

FIG. 9A shows Aktl;

FIG. 9B shows Gadd34; FIG. 9C shows anti-apoptotic/anti-autophagy activity using Bcl2/Bax ratio. Data is expressed as mean+/−s.d. (n=4).

FIG. 10 illustrates a table of values of measured in vivo hepatic blood flow and metabolite concentrations.

FIG. 11 illustrates a table of the effect of burn injury on metabolic fluxes based on in situ (in vivo) and perfused liver data.

FIGS. 19A-19J illustrates the average amino acid metabolism during NELP of WI and Fresh livers, compared to Williams Medium E (WE), and in vivo upper bound values (ave+1 std dev) and lower bound values (ave− 1 std dev). * indicates significantly different from Ischemic (p<0.05).

FIG. 20 illustrates a table of the metabolic flux analysis.

FIG. 27A shows the cell yield post-Percoll purification normalized to wet liver weight; FIG. 27B shows the ATP content of biopsied tissue normalized to the total protein content; FIG. 27C shows the viability of cells post-Percoll purification. Data shown are means±std dev. Values for WI and 3hrRT livers are significantly different from other groups (p<0.05); there is no statistical difference between fresh and WI+3hrRT groups FIG. 28A-28F illustrates the cell function in suspension for WI+3hrRT and 3hrRT groups compared to Fresh hepatocytes: FIG. 28A shows the percent viability of cells using Trypan Blue exclusion. Fresh hepatocytes are significantly reduced in viability at t=6 hrs (p<0.05); FIG. 28B shows ALT; perfused groups have significantly higher starting values (p<0.05); FIG. 28C shows mitochondrial activity measured by absorbance of fornazan produced from MTT at 570 mm; FIG. 28D shows AST; significant differences exist between all groups (p<0.05); FIG. 28E shows CYP450 activity measured using resorufin production by dealkylation of benzyloxy resorufin (CYP4502B2), pentoxy resorufin (CYP4502B1), ethoxy resorufin (CYP4501A1) and methoxy resorufin (CYP4501A2) after 3,3'-methylene-bis (4-hydroxycoumarin) activation. Activity is significantly higher in 3hrRT cells for CYP4501A1 and CYP4501A2 (p<0.05). FIG. 28F shows metabolic assays of glucose, albumin and urea. Albumin is significantly reduced in WI+3hrRT cells at t=6 hrs (p<0.05). All data shown are means±std dev.

FIG. 29A-29I illustrates the cell function in double layer collagen gel sandwich plate culture. FIGS. 29A-29C show phase contrast images for Fresh, WI and WI+3hrRT livers respectively;

FIG. 29D show mitochondrial activity measured by absorbance of formazan produced from M'TT' at 570 nm; FIG. 29E shows viability of cells using Hoechst 33452/Ethidium homodimer-1 double stain; FIGS. 29F-29I show CYP450 isoenzyme activity for days 5, 7, 10 and 14 of culture; FIGS. 29 J-29L show metabolic assays for Albumin, urea, glucose. Urea production is significantly increased in 3hrRT livers (p<0.05).

FIG. 30A shows glucose consumption over time; FIG. 30CB shows pH of perfusate entering and exiting the liver. pH out at t=0.5 hrs is significantly different between 1 hr WI+3hrRT livers (p<0.05); FIG. 20C shows albumin production over time; FIG. 20D shows oxygen delivery and exit from the liver measured as a function of the partial oxygen tension and flow rate of perfusate; FIG. 30E shows urea production over time; FIG. 30F show oxygen uptake rate over time; FIG. 30G shows lactate production over time; FIG. 30H shows bile weight accumulated by t=6 hrs.

FIGS. 32A-32C illustrate the hemodynamic relations in perfusion: Figure A shows hepatic resistance of both WI+3hrRT and 3hrRT livers; Figure B shows scatter-plot of individual experiment cell yields and pressures (n=9) vs. corresponding flow rates for 3hrRT livers. Linear correlation between cell yield and flow rate is significant (Pearsons −0.97); FIG. 32C shows the scatter-plot of individual experiment cell yields and pressures vs. corresponding flow rates for WI+3hrRT livers (n=10).

FIG. 35 illustrates the compounds identified as ligands of PPAR-γ, with the binding energies (kJ/mol) calculated.

FIGS. 36A-36B illustrate: FIG. 36A shows the percentages of cell population before cryopreservation, normalized to that of the control cells; FIG. 36B shows the percentages of cell population following cryopreservation.

FIG. 38B shows the cell viability (black bar) and metabolic activity (white bar) of hepatocytes after incubation with isotonic mixtures of various sugars and DMSO for 60 min; this indicates that loading 3OMG affects the cells similar to other glucose variants, and 3OMG is minimally toxic at concentrations used FIG. 39A shows past-thaw cell viability (percentage of unfrozen control), shows more than 50% viability after one week storage in liquid nitrogen. FIGS. 39B and 39C show typical phase-contrast images of cryopreserved hepatocytes at 48 h after thawing (FIG. 39B), no-glucose control (FIG. 39C), 3OMG. FIGS. 39D and 39E show cells in control group remained unattached, whereas 3OMG loaded cells were very well spread.

FIGS. 45A-45B illustrate that SZNF preserves liver microstructure during 5 days storage. H&E staining: FIG. 45A shows -5'C in 3OMG-supplemented University of Wisconsin medium, FIG. 45B shows conventional UW storage.

FIG. 46 illustrates a preservation protocol (3OMG loading, SZNF storage, rewarming in the NELP system).

DETAILED DESCRIPTION OF THE INVENTION

Figure 1A:
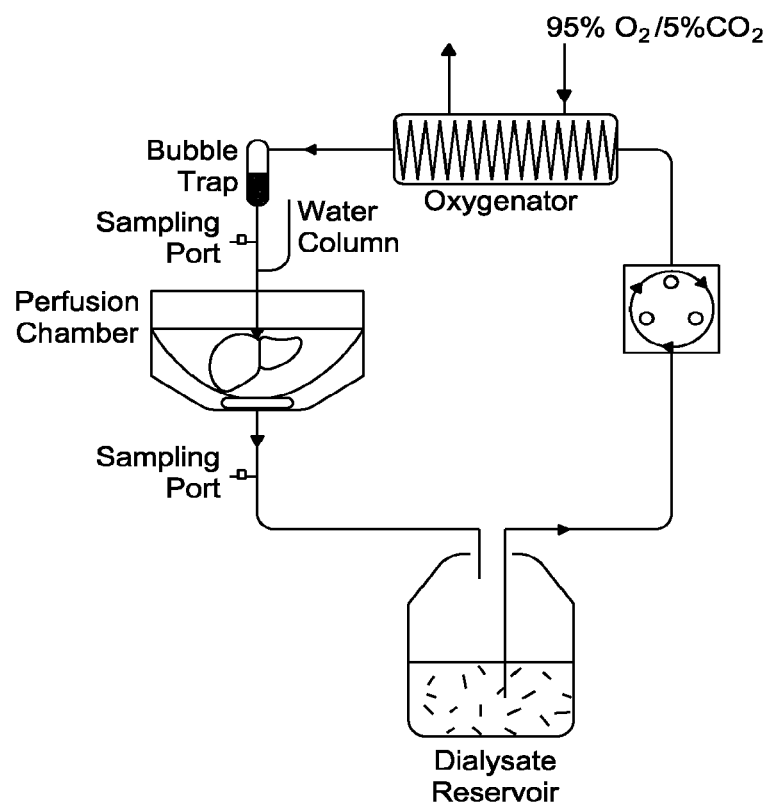
FIGS. 1A-1D illustrate.
Figure 1B:
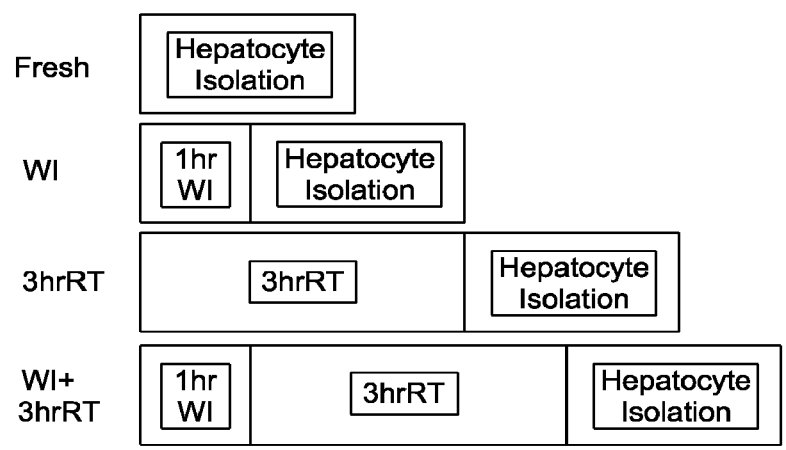

Current organ preservation, storage and transplantation procedures are limited because organs are so vulnerable to damage after removal from a donor. Once harvested, cells and tissues are deprived of the oxygen that is required to maintain internal metabolism and cell volume integrity. This low oxygen state is called ischemia and leads to hypoxia, which prevents oxygen from being delivered to the organ tissue. Without oxygen, cellular tissue can suffer injury as cell metabolism fails and individual cells can be subject to swelling or inflammation.

To counteract the ill effects of ischemia, standard techniques for modern organ preservation involve the exposure of a harvested organ to preservation solutions at cold temperatures not below 0° C. This treatment essentially creates hypothermic conditions that reduce a cell's need for metabolic oxygen. Components of the solution and the cold environment combine to protect the cell from ischemic conditions and thereby prevent the onset of injury. This procedure is known as cold flush preservation, in which the preservation solutions are designed to eliminate chemical potential gradients across the cell membranes of the cells composing the organ. By doing so the solution tends to mimic the intracellular environment and prevent the donor organ cells from activating metabolic pathways. Although hypothermia is a solution to oxygen deprivation in donor organ tissue, it presents its own problems. The cells of an organ preserved under hypothermic conditions lose their ability to replenish ATP stores, and therefore cannot produce the energy required to regulate the sodium-potassium pump, which is one of the most important modulators of internal cell volume. Also the hypoxic environment induces the release of intracellular calcium and elevated concentrations of calcium can lead to subsequent activation of multiple metabolic inflammatory pathways. As a result, the cells may exhibit endothelial cell swelling, a loss of blood vessel integrity, including the reduction in the internal diameter of blood vessels called a vasospasm, and even cell death in tubules.

One of the most widely used solutions in organ preservation and storage is known as University of Wisconsin (UW) solution or Viaspan, which is manufactured by DuPont. However, preservation of donor organs using Viaspan is generally limited to a 36-hour period in kidneys before the organs begin to deteriorate.

Generally

One aspect of the present invention relates to a method to assess the viability of an organ. In some embodiments, the cellular energy status (e.g., energy store) of the organ is determined, which is determined by measuring ATP content of the organ. The cellular energy status (e.g. level of ATP) in the organ can be used by itself as an efficient and reliable an indication of organ viability, or it can be combined with a measure of energy consumption (e.g. determined by a metabolic flux assay), where viability is a function of the two measures, to provide a reliable and quantitative measure of an organ's viability, and serves as a measure to determine the optimal preservation method of the organ.

In particular, one aspect of the present invention relates to a method of assessing the viability of an organ by measuring cellular energy content (e.g. ATP levels) and/or energy consumption (e.g., metabolic activity) using a metabolic flux assay (MFA) as disclosed herein.

Another aspect of the present invention relates to methods and compositions to preserve the viability of organs for transplantation, and methods to extend the time period of viability of an organ by either (i) increasing the energy content of the organ by preservation perfusion of the organ, or (ii) by metabolic suppression of the organ by chemical suppression, e.g., using metabolic suppressants, and/or by physical or environmental conditions, e.g., sub-zero non-freezing storage, as disclosed herein.

In some embodiments, based on the organ's viability as determined by measuring cellular energy content (e.g. ATP levels) and/or energy consumption (e.g., metabolic activity)

using a metabolic flux assay (MFA) as disclosed herein, one or a combination of methods to extend viable preservation time of organ tissue can be used, which include, 1) perfusion with a preservation perfusion solution, and/or 2) metabolic suppression or the organ, and/or 3) sub-zero non-freezing storage (SZNF). Accordingly, as disclosed herein the inventors have demonstrated a reliable method for extending the viable preservation time organ, as well as a quantitative method to determine the organ's viability and thus usability for organ transplantation or other medical uses, thereby increasing the range of organ distribution and allocation, minimizing effects related to geography, and allowing for better donor/recipient matching, thereby potentially saving many lives.

In some embodiments, the methods and compositions enable extending the viable preservation time of an organ to at least 36 hours, or at least about 48 hours, or about 3 days or about 4 days or about 5 days or longer than 5 days. Accordingly, in some embodiments, the methods and compositions enable extending the viable preservation time of an organ to at least about 12 hours, or 36 hours, or 2.5 days, or about 3.5 days longer than the current achievable period of time of storage time. This is a significant increase in the extension of period of viability of a transport of an organ, providing additional time to allow for cross-matching of donors and recipients, and for transnational and trans-international transport of donor organs, which are not possible under the current preservation procedures.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "organ" as used herein refers to a structure of bodily tissue in a subject, e.g., a mammalian subject such as a human, wherein the tissue structure as a whole is specialized to perform a particular bodily function. Organs which are transplanted within the meaning of the present invention include for example, but without limitation, cornea, skin, heart, lung, kidney, pancreas, liver, spleen. In some embodiments, the term "organ" also encompasses decellularized and recellularized organs, as well as engineered and artificial organs and tissues, including engineered organs (e.g., tissue engineered constructs), engineered organs comprising a bioscaffold, tissues, organ slices and partial organs.

The term "viability" as used herein refers to the state of an organ's survival capability, e.g., capable of survival after transplantation into a recipient. Viability can be used as a measure of the entire organ's survival or a part of the organ, or the viability of cells within the organ.

The term "reliability" as used herein refers to the extent to which a measure, procedure or instrument yields the same result on repeated trials. Stated another way, reliability as used herein refers how well a particular assessment method provides consistent results, regardless of who uses the method or when it is used.

The term "damaged organ" as used herein shall be understood to indicate an organ that is in less than ideal condition for transplantation, such that the expected probability of transplant success is reduced. Examples of damaged organs include, but are not limited to, organs that suffer warm ischemia for more than 30 minutes, organs that suffer cold ischemia for more than 12 hours, moderate or highly steatotic livers (e.g., livers with greater than 30% fat), fibrotic livers, cirrhotic livers, livers from patients afflicted with hepatitis C or HIV, and the like.

The term "implant" refers to insert of an organ, graft, tissue, or inert substance into the body of a subject.

The term "transplant" as used herein refers to an organ, part of an organ, engineered tissue, or other body tissue that has been transferred from its site of origin in one subject to a recipient site in the same or a different subject. Specifically in an allograft transplant procedure, the site of origin of the transplant is in a donor individual and the recipient site is in another, recipient individual.

The term "transplantation" refers to the method of transferring of an organ, or other bodily tissue from its site of origin in one subject to a recipient site in the same or a different subject, whether or not autologous, homologous or heterologous and whether or not it is performed directly or subsequently to further processing or preservation of the tissue or organ.

The term "Hypothermic" shall be understood to mean temperatures below room temperature. For example, "hypothermic" temperatures include, but are not limited to, temperatures between about 0° C. to about 15° C., temperatures between about 1° C. to about 8° C., temperatures between about 3° C. to about 5° C., and the like.

The term "in vitro model" shall be understood to be a model created outside of an organism of a subset of the organism's constituent parts, for example, for studying the function of the constituent parts. An "in vitro drug model" shall be understood to be an in vitro model created to study the interaction of a drug, pharmaceutical, test agent, and the like with a subset of an organism's constituent parts. Interactions can include absorption, distribution, metabolism, toxicity, and the like.

The term "room temperature" as used herein shall be understood to mean a temperature between about 15° C. and about 25° C. For example, "room temperature" includes, but is not limited to, temperatures between about 18° C. and about 23° C., temperature between about 19° C. and about 21° C., temperatures between about 24° C. and about 25° C., temperatures between about 20° C. and about 21° C., and the like.

The term "normothermic" shall be understood to mean temperatures above room temperature. For example, "normothermic" temperatures include, but are not limited to, temperatures between about 25° C. and about 42° C., temperatures between about 30° C. and about 38° C., temperatures between about 37° C. and about 37.5° C., and the like.

The term "subnormothermic" shall be understood to mean a temperature of about room, and is generally between 15° C. and 25° C., and in some embodiments can be at 20° C.

The term "sub zero" as used herein refers to any temperature below 0° C. For example, a sub-zero temperature can be in a range, for example, but is not limited to, about −5° C. and about −10° C., a temperature of about −10° C. and about −15° C., a temperature of about −15° C. and about −25° C., a temperature of about −25° C. and about −30° C., a temperature of about −30° C. and about −50° C., a temperature of about −50° C. and about −80° C., or below about −80° C.

The term "metabolic suppressant" refers to an agent which decreases the metabolic activity of an organ by at least about 10% as compared to the organ in the absence of a metabolic suppressant. In some embodiments, a metabolic suppressant can result in diapause (state of metabolic arrest) of the organ.

The term "perfusion" as used herein refers to the flowing of fluid through the tissue or organ. Stated in anther way, perfusion or to "perfuse" refers to suppling an organ, tissue with a fluid by circulating it through blood vessels or other natural channels. Techniques for perfusing organs and tissue are well known in the art, and are disclosed in International Patent Application WO2011/002926, and U.S. Pat. Nos. 5,723,282 and 5,699,793 which are both incorporated herein in their entirety by reference.

The term a "perfusate" as used herein shall be understood to be any fluid capable of improving or maintaining the vitality of a cell, tissue, organ (including decellularized and recellularized organs), bioscaffold, and the like. Improving or maintaining vitality can include one or more of the following: maintenance of appropriate osmotic pressure, maintenance of appropriate oncotic pressure, maintenance of appropriate temperature, inhibition of decay, inhibition of microbial growth, and the like.

The term "storage medium" as used herein shall be understood to be any substance for preserving vitality of a cell, tissue, organ (including decellularized and recellularized organs), bioscaffold, and the like. Preservation of vitality can include one or more of the following: maintenance of appropriate osmotic pressure, maintenance of appropriate oncotic pressure, maintenance of appropriate temperature, inhibition of decay, inhibition of microbial growth, and the like.

The term "supercoolant agent" as used herein refers to an agent which, when added to a solution or organ, prevents freezing, or the solution becoming a solid at the normal freezing temperatures, and allows the solution or organ to stay in a liquid state at the desired sub-zero temperature. A supercooling agent aids supercooling, which is the cooling of a liquid below its freezing point without it becoming solid. Supercoolant agents are often confused with cryoprotectant agents, which may also aid in freezing point depression but are actually aimed at preserving the tissue where the water has reached a solid state (either ice of vitrification). A supercooling agent prevents freezing of a tissue or organ when the tissue is cooled to subzero temperatures and results in an preserving the viability after warming, in comparison to the effect of cooling without a supercoolant.

The term "cryoprotectant" as used herein refers to an agent which minimizes ice crystal formation in a tissue or organ when the tissue is cooled to subzero temperatures or freezes.

The term "recellularize" shall be understood to be any process for engrafting one or more cells within a decellularized organ or bioscaffold.

The term "rejection" as used herein refers to the process or processes by which the immune response of an organ transplant recipient mounts a reaction against the transplanted organ, cell or tissue, whether native or bioartificial, such as a recellularized tissue, sufficient to impair or destroy normal function of the organ. The immune system response can involve specific (antibody and T cell-dependent) or non-specific (phagocytic, complement-dependent, etc.) mechanisms, or both.

The term "effective" as used herein refers to a characteristic of an amount of preservation perfusion solution, and/or metabolic suppression, and/or subzero storage, or any combination thereof, to achieve the goal of preventing, avoiding or retarding tissue damage in tissue, such as a harvested organ, whether the tissue damage results from ischemia, reperfusion, degradation of high-energy phosphates, inflammatory responses, edema, or any other tissue response to a stimulus such as the disruption of function and the manipulation that attends harvesting and storage of the organ.

The term "cells," "host cells" or "recombinant host cells" are terms used interchangeably herein. It is understood that such terms refer not only to a particular cell type, but to the progeny or potential progeny of such a cell. Because certain modifications can occur in succeeding generations due to either mutation or environmental influences, such progeny can not, in fact, be identical to the parent cell, but are still included within the scope of the term as used herein.

The term "agent" refers to any entity which is normally not present or not present at the levels being administered in the cell. Agent can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, minibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, "gene silencing" or "gene silenced" in reference to an activity of an RNAi molecule, for example a siRNA or miRNA refers to a decrease in the mRNA level in a cell for a target gene (e.g. P2-AR regulator gene) by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

The terms "activate" or "increased" or "increase" as used in the context of biological activity of a cell herein generally means an increase in the biological activity of a cell by a statically significant amount relative to in a control condition. For the avoidance of doubt, an "increase", or "activation" of a cell means a statistically significant increase of at least about 10% of the level and/or activity of ATP as compared to non-treatment of an organ according to the methods including an increase of at least about 20%, at least about 30%, at least about 40%, at least about 50%, at least about 60%, at least about 70%, at least about 80%, at least about 90%, at least about 100% or more, including, for example at least 2-fold, at least 3-fold, at least 4-fold, at least 5-fold, at least 10-fold increase or greater of level of ATP as compared to if the organ was not treated according to the methods and compositions as disclosed herein.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "optional" or "optionally" means that the subsequent described event, circumstance or substituent may or may not occur, and that the description includes instances where the event or circumstance occurs and instances where it does not.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Methods to Determine the Viability of an Organ

In accordance with the various embodiments of the invention, the viability of an organ over a particular time can be determined as a function of at least one measurement selected from (i) stored cellular energy (e.g., ATP levels), and/or (ii) energy consumption over a particular time period of viability.

Accordingly, the present invention relates to measuring the viability of an organ by measuring energy content (e.g., ATP levels) and optionally, the energy consumption, and using this to determine the viability of an organ over a period of time. Accordingly, disclosed herein is a reliable screening method for qualitatively evaluating the viability of an organ at any time. In some embodiments, the viability of an organ can be assessed using the ATP levels and/or MFA after harvesting the organ from a donor, and/or before preservation and/or after preservation.

Other aspects of the invention relate to viability status of the organ to determine optimal methods to preserve the organ. In some embodiments, where it is desirable to increase the duration of viability of the organ, the present invention provides methods to extend the time period of viability of an organ by either (i) increasing the energy content of the organ by preservation perfusion of the organ, and/or (ii) by metabolic suppression of the organ chemically, e.g., using metabolic suppressants, and/or by physical or environmental conditions, e.g., sub-zero non-freezing storage, as disclosed herein.

ATP assay

As disclosed herein, the inventors have demonstrated that a direct correlation between cell yield and tissue ATP content provides an objective measure of organ viability and recovery during perfusion. In particular, one can measure energy parameters in the organ as a measure of viability. Accordingly, one aspect of the present invention relates to a measure of viability of an organ by measuring one or more energy parameters. In one embodiment, a energy parameter is the level of ATP (or ATP content) of the tissue which is an indication of the amount of ATP stored and thus the cellular energy content of the organ at that period of time. Based on a known average consumption of an organ of that organ type, the level of ATP can be used to determine the length of time the cell is viable for.

One aspect of the present invention relates to a method to assess the viability of an organ. In some embodiments, the cellular energy status (e.g., energy store) of the organ is determined, which is determined by measuring ATP content of the organ. The cellular energy status (e.g. level of ATP) in the organ can be used by itself as an efficient and reliable an indication of organ viability, or it can be combined with a measure of energy consumption (e.g. determined by a metabolic flux assay), where viability is a function of the two measures, to provide a reliable and quantitative measure of an organ's viability, and serves as a measure to determine the optimal preservation method of the organ. In particular, one aspect of the present invention relates to a method of assessing the viability of an organ by measuring cellular energy content (e.g. ATP levels) and/or energy consumption (e.g., metabolic activity) using a metabolic flux assay (MFA) as disclosed herein.

One aspect of the present invention relates to a reliable method to measure the viability of an organ by measuring the cellular energy content in the cell, e.g., the energy stored in the cell by measuring the ATP levels in the cell. In some embodiments, ATP levels can be measured by direct measurement of ATP levels in a biopsy tissue sample obtained from the organ. In other embodiments, one can use any method to measure ATP levels known to one of ordinary skill in the art, for example, one can use imaging without taking biopsy samples, or a method of measuring ATP content as disclosed herein in the examples. Where the ATP level is above a predefined threshold, it indicates the organ is of good viability and can be used for organ transplant, or other medical uses.

In some embodiments, the biopsy location for ATP measurements can be performed based on location in the organ. As an exemplary example, for a liver organ, the 3 largest lobes are identified, from the center of the lobe to the periphery, a slice was cut and divided into three (center, center-periphery, periphery). ATP was measured in each and averaged for the value of ATP in that liver. In some embodiments, e.g., for humans organs, a core biopsy using 18-14 G catheter can be used in a variety of location in the organ. Typically, the amount of tissue required for accurate measurement of ATP levels is about 10-20 mg:

In some embodiments, ATP content can be measured in tissue segments homogenized with a mortar and pestle under liquid nitrogen and resuspended in 500 µL of nucleotide releasing buffer (Biovision, #K254-200). Each sample can be spun down at 16000 rpms for 2 minutes. 100 µL of biopsy sample was subsequently placed in a cuvet and the assay continued as described according to the ATP assay kit. In some embodiments, data of ATP levels can be plotted against a standard and normalized to the total protein present in the sample supernatant using a standard Bradford assay.

In some embodiments, direct measurement of ATP can be performed, e.g., for example, in humans, core biopsies can be conducted in the liver in 3 places of one lobe, starting at the hepatic vein, and moving away from the hepatic vein to the periphery. Care should clearly be taken when near the veins to avoid bleeding.

Additionally, in some embodiments, an ATP assay can be performed from at least one biopsy taken from the organ, or from multiple biopsy sites from the organ, for example, at least 2, or 3, or 4, or 5, or more than 5 biopsy sites from the organ. In some embodiments, the biopsy sites are taken from specific locations in the organ based on visual analysis of the organ. In some embodiments, the sites for biopsies can be standardized locations for each organ type.

For example, in some embodiments, an organ's viability can be graded based upon ATP levels. For example, in some embodiments, where ATP level is 0.8 umol/g total protein or above, an organ is predicted to be viable and suitable for transplantation or grade 1 quality. In some embodiments, where the ATP level between about 0.8 umol/g and 0.4 umol/g total protein, an organ is predicted to be suitable for preservation according to the methods as disclosed herein, or grade 2 quality. In some embodiments, where the ATP level between about 0.4 umol/g and 0.2 umol/g total protein, an organ is predicted to have low viability, or grade 3 viability. In some embodiments, where the ATP level less than about 0.2 umol/g total protein, an organ is predicted to be non-viable, or a grade 4 quality. It is encompassed within the present invention that the viability of the organ can be classified into many different levels of viability, for example, about at least 4 grades, or 5 grades, or 6 grades, or 7 grades and the like. There can also be other methods to characterize the degree of viability, for example, based on percentages of likelihood of successful transplant of the organ. Metabolic Flux Assay (MFA)

One aspect of the present invention provides a method to assess the viability of an organ by measuring energy consumption using a Metabolic Flux Assay as disclosed herein. In some embodiments, the viability of an organ is dependent on measuring the input and output of a variety of metabolic factors and determining the metabolic activity and therefore the energy consumption of the organ.

In some embodiments, the "metabolic flux assay" as disclosed herein provides an efficient and reliable screening method for qualitatively evaluating the viability of an organ at any time. In some embodiments, the MFA can be used to indicate the time of recovery of an ischemically damaged organ, organ stability during perfusion and the impact of perfusion on organ metabolism. In some embodiments, the MFA comprises measuring cellular energy status of an organ by perfusing the organ with a MFA perfusion solution, and measuring the energy status of the cell.

In some embodiments, the method of the MFA comprising perfusing the organ with a MFA perfusate, which comprises a modified culture media. In some embodiments, the MFA perfusate comprises erthyrocytes as oxygen carriers to allow physiological flow rates of oxygen delivery. However, in some embodiments, the MFA perfusate does not comprise erthrocytes, as the erthrocytes, while increasing the oxygen delivery rates to the tissue, increases the viscosity which can lead to increased pressure and limits flow rate of the perfusate. In some embodiments, the MFA perfusate can be optimized to comprises an erthyrocytes concentration for efficient oxygen delivery but does not limit flow rate or increase pressure in the organ during perfusion.

In some embodiments, the perfusion of the organ for the MFA is performed at normothermic temperatures or at subnormothermic temperatures. In some embodiments, the MFA perfusion is performed at 37° C., or about 30° C. or about 20° C., or at any temperature between about 20° C. and 37° C. In some embodiments, where the entire organ is not required or parts of the organ are only required, the perfusion can be performed at subnormothermic about 20° C., or about 25° C. or about 30° C.

In some embodiments, the MFA measures the metabolic status of an organ by measuring any one or a combination of (i) oxygen uptake (e.g., oxygen consumption), (ii) glucose levels, and (iii) nitrogen metabolism, as disclosed in Examples 2 and 3. In particular, the MFA measures changes in metabolism in major pathways including amino acid metabolism, gluconogeneis, TCA, lipid metabolism, oxidative phosphorylation and the urea cycle and the like. Methods for measuring metabolite concentrations to determine oxygen uptake (e.g., oxygen consumption), glucose levels, and nitrogen metabolism, as well as amino acid metabolism, gluconogeneis, TCA, lipid metabolism, oxidative phosphorylation and the urea cycle as well known to one of ordinary skill in the art, and are encompassed for use in the methods as disclosed herein. In some embodiments, methods to measure such metabolites are disclosed in Table 1.

As disclosed herein, metabolic flux models have been performed on organs (e.g., liver and hepatocytes), including detailed stoichiometric balances of TCA and urea cycles, oxygen uptake, glycolytic/gluconeogeneic pathways, fatty acid metabolism, NADH and NADPH balance, and albumin

TABLE 1

Variables to be measured in perfusate/reservation medium, and methods of analysis.

| Metabolite to be measured | Methods |
| --- | --- |
| Glucose, Urea Nitrogen, Total Carbondioxide, AST, ALT, ALP, Total protein, Total bilirubin, Creatinine, Sodium, Potassium, Calcium, Chloride | Piccolo Comprehensive Metabolic Panel, Piccolo ® Point-of-Care Chemistry & Electrolyte System, Abaxis Inc., Union City, CA. |
| Total Cholesterol, triglycerides, high density, low density and very low density lipoproteins | Piccolo Lipid Panel |
| Amino acids | HPLC [Yamaguchi, Y. et al., Surger 121, 295-303] |
| Lactate | Assay kit, Pointe Scientific |
| Free fatty acids | FFA Assay (Boehringer-Mannheim GmbH, Germany) |
| Glycerol | Based on Pointe Scientific TG kit [Chan, C. et al., Biotechnology and Bioengineering 81, 33-49 (2003)] |
| Insulin | Insulin Assay kit, Alpco Diagnostics, \Mndham, NH |
| Glucagon | Glucagon Assay kit, Wako Chemicals, Richmond, VA |
| β-hydroxybutyrate | Stanbio assay, Boerne, TX |
| Acetatoacetate | See Zupke et al., BiotechonolBioeng 58, 222-230 (1998) |
| Nitric Oxide | Sensor, World Precision Instruments, United Kingdom |
| Gluthatione, Glutathione disulfide | See Schauer et al. [Annals of Surgery 239, 220-231 (2004)] |
| Principle bile acids | Diagnostic Chemicals Limited, Oxford, Connecticut |
| Major steroids | ELISA kits, Invitrogen |
| Dissolved $O_2$ and $CO_2$, Hematocrit, Hemoglobin (Free, oxygenated) | Bayer Diagnostics Blood gas analyzer m865 |
| Online oxygen and other electrolytes | Microelectrodes Inc, Bedford, NH |
| TNF-α | ELISA kit, ebioscience, San Diego, CA |

In some embodiments, one can evaluate the MFA perfusate coming out of the organ for blood gasses. For example, for oxygen consumption, one can measure oxygen delivery rate (ODR) of the concentration of oxygen in the perfusate going into the organ, and can measure the oxygen exit rate (OER) of oxygen concentration in the perfusate coming out of the organ, to determine the oxygen update rate (OUR), which is the difference between the ODR and the OER. In some embodiments, the oxygen uptake (umol/hr/g) of highly viable organ is about 200-300 umol/hr/g, and the oxygen uptake of a good viable organ is about 120-150 umol/hr/g, and the oxygen uptake of a viable organ suitable for preservation according to the methods as disclosed herein is about 50-120 umol/hr/g. Additionally, this threshold of OUR which is indicative of the organ being viable will vary with organ type, age of organ, as well as gender and species variation.

In some embodiments, one can measure glucose levels are a measure of gluconeogeneis, with a reduction in gluconeogeneis a measure of decreased viability.

In some embodiments, the MFA provides the steady-state mass balance on the n metabolites (z) in the system in terms of the m involved reaction rates (fluxes), v (which can be considered as a lumped group of individual reaction rates), and S, the n×m matrix of stoichiometric coefficients of the metabolites in reactions. At steady state, the change in the n metabolites in the system is zero; hence the metabolic balance equations reduce to a set of linear algebraic equations as S. v=0. Therefore fluxes that have not been measured (such as intracellular fluxes that would require destructive assays) can be calculated from available measurements.

synthesis (see for example FIGS. 2-3, and FIGS. 28-29). In some embodiments, the liver metabolic model can be extended by inclusion of insulin, glucagon, bile, cholesterol and nitric oxide metabolism. In some embodiments, one can predict the hormone catalysis rates can be performed which enable optimization of the hormonal supplementation rates in the perfusion system; where insulin and glucagon levels can be assayed and their degradation flux be included in the analysis. In some embodiments, cholesterol, and other principle bile acids and total steroids can be measured so that bile production, a potential indicator of viability, is also included in the analysis. In some embodiments, Nitric Oxide (NO) (arginine to citrulline conversion by inducible nitric oxide synthase in hepatocytes) can also be added to the model (measured by a NO probe online, see Table 1) and connected with the glutathione synthesis flux and utilization (for ROS neutralization). Hence it will be possible to evaluate the effects of vasodilators such as L-arginine and ROS scavengers with the metabolic model.

In some embodiments, the MFA measures the levels of at least about 10 metabolites, or at least about 15 metabolites, or at least about 20 metabolites, or about 28 metabolites during the perfusion of the organ with the MFA perfusate, and where the level of the metabolite falls below or above a predefine threshold for each metabolite is indicative of the energy status of the cell and the viability of the organ.

For example, one can measure at least about 10 of the metabolites selected from any combination of metabolites in Table 2.

TABLE 2

Exemplary metabolites, where their input levels and output levels are measured to determine metabolic activity and therefore energy consumption of the organ.

| | |
|---|---|
| Glucose-6-P | Citrulline |
| Fructose-6-P | Aspartate |
| Fructose-1, 6-P2 | Alanine |
| Glyceraldehyde-3-P | Glutamate |
| PEP | Serine |
| Pyruvate | Cysteine |
| Oxaloacetate | Glycine |
| NADH | Propionyl-CoA |
| Acetyl-CoA | Acetoacetate |
| Citrate | Acetoacetyl-CoA |
| alpha-Ketoglutarate | $O_2$ |
| Succinyl-CoA | Tyrosine |
| Fumarate | Ribulose-5-P |
| $FADH_2$ | Ribose-5-P |
| Malate | Xylulose-5-P |
| Arginine | Erythrose-4-P |
| Ornithine | $CO_2$ |
| $NH^{4+}$ | |

In some embodiments, the samples from the perfused tissue are analyzed for glucose, insulin, lactate, urea, albumin, acetoacetate and β-hydrobutyrate.

In some embodiments, where the organ is a kidney, urine produced during the ex vivo preservation of a kidney can be monitored and analyzed for specific functional characteristics, and in the ranges, such as oxygen consupation and urine creatine. Specific gravity, relating to the number of solute particles, can be also measured by an urinometer. The value reflects the concentrating ability of the kidney. Thus, a value outside (lower) than the reference interval may reflect renal tubular damage, since concentrating ability is one of the first functions to be lost as a result of renal tubular damage.

Measurement of pH reflects the amount of acid produced in the organ as a result of organ metabolism and oxidation. The regulation of the acid-base balance, together with the regeneration of free buffers, is ultimately a function of renal tubular cells. A urine pH which is more acidic than the reference interval, may indicate in renal tubular defects (i.e., defect in which $HCO_3$ is not reabsorbed from the urine). A urine pH which is more alkaline than the reference interval may indicate a renal tubular defect in which ions (i.e. $H^+$ or $K^+$) are not being reabsorbed from the urine. The presence of glucose or casts in the urine is an indicator of renal glomerular function.

In some embodiments, creatinine clearance values, tubular function of the kidney can be assessed by the measurement of urinary creatinine. In functioning tubules, perfusate creatinine is secreted and not reabsorbed during urine production. Thus, creatinine is added to the perfusate as a tracer molecule to be detected by excretion in the urine.

In some embodiments, kidneys exhibiting good ex vivo functional characteristics with the described process/system were found to function well posttransplantation. For example, urine was always found to be negative for protein and perfluorochemical emulsion leakage. In some embodiments, urinary creatinine concentration of a good health kidney always greater than 40 mg/dl, whereas, in contrast, poor functional characteristics i.e., protein or perfluorochemical leakage were associated with renal damage and poor posttransplantation course. Thus, in those kidneys exhibiting urinary creatinine concentrations of <40 mg/dl during MFA assay as disclosed are considered suitable for the preservation methods as disclosed herein to prevent acute tubular necrosis indicative of poor graft function.

Additional means of assessing the function of an organ using the MFA assay as disclosed herein is the amount of oxygen consumption as the perfusate circulates, relative to a selected time interval, through the organ. Decreased oxygen consumption, i.e. a low oxygen consumption compared to the normal range, may be indicative of tissue hypoxia. Yet another example of a measure of organ function is the vascular flow rate of perfusate circulating through the kidney using a standard perfusion pressure relative to a selected time interval. A low flow rate, compared to the normal range, may be indicative of edema, vasoconstriction, vascular endothelial cell swelling and loss of vascular integrity in a damaged organ. The acceptable level of ex vivo function will be determined by the respective clinicians as the range yielding the threshold of clinical function acceptable at each transplant center.

In some embodiments, functional characteristics of an organ can be assessed by measuring energy parameters including, but not limited to, bile concentrations of bile salts, cholesterol, alkaline phosphatase; bile pH; and liver vascular flow rate, oxygen consumption, and glucose utilization (as measured from the perfusate).

In particular, elevated levels of alkaline phosphatase from a liver, as measured in the bile and/or in the perfusate (i.e., above the reference interval determined by the respective clinician) may be an indicator of hepatic or hepatobiliary disease. Concurrent with the measurement of perfusate alkaline phosphatase (ALP) levels, it may be useful to determine perfusate levels of leucine aminopeptidase (LAP) and gamma glutamyl transferase (GGT) which appear to parallel increases of ALP in hepatobiliary disease.

Demonstrating the connection between viability and liver function during extracorporeal perfusion, the inventors demonstrated that using normothermic perfusion of porcine livers was able to correlate recipient survival to bilirubin content in bile. A second swine study also identified bile production as a predictor of graft viability prior to transplantation. However, bile production is highly dependent on metabolic activity: bile synthesis is the major pathway for elimination of cholesterol, and therefore connected to TCA cycle, lipid metabolism, and gluconeogenesis/glycolysis. It is noted that minor modifications in the perfusion medium can change these values significantly.

In some embodiments, the energy parameters to determine the viability of a pancreas can be assessed by measuring energy parameters including, but not limited to, pancreatic enzyme concentrations such as amylase, lipase; the hormone insulin; pancreatic secretion pH, sodium and potassium; and pancreas vascular flow rate, oxygen consumption, and glucose utilization (as measured from the perfusate). In particular, altered activity of amylase and lipase, as measured in the pancreatic juice and/or in the perfusate (i.e., above the reference interval determined by the respective clinician; for example, perfusate amylase activity reference level may be 70-300 U/l and lipase activity reference level up to 10 U/ml, depending on the method used to measure activity) may be an indicator of pancreatitis.

In some embodiments, the energy parameters to determine the viability of a heart can be assessed by measuring parameters including, but not limited to, heart enzymes such as transaminases (aspartate aminotransferase, AST), lactate dehydrogenase (LD), fructose 1,6-diphosphate aldolase (ALS), malate dehydrogenase (MD), glutathione reductase (GR), creatine phosphokinase (CPK), hydroxybutyrate dehydrogenase (HBD); heart vascular flow rate, oxygen consumption, and glucose utilization (as measured from the perfusate). Indicators of cardiovascular disease may include increased levels of AST, LD, ALS, MD, GR, CPK and HBD in circulated perfusate relative to reference levels determined by the respective clinician (exs. of reference levels include AST: <20 U/l; and LD: 0-300 U/L).

In some embodiments, the MFA comprising measuring levels of metabolites in the blood on perfusion with a MFA perfusion media, and evaluating the blood for blood gasses. Any means to measure blood gasses, and/or multiple metabolites is encompassed in the present invention, for example, using commercially available multiple metabolite rapid-assay devices, (e.g., from Comprehensive Metabolics and Lipid Plus panels) as well as biochemical assays and amino acid compositions, (e.g., automated high-performance liquid chromatography systems, Waters, Milford MA), as disclosed herein in the Examples.

Blood gases can easily be measured by one of ordinary skill in the art, for example, determined immediately using a blood gas analyzer (Rapidlab, Chiron Diagnostics, Norwood, MA). Oxygen concentration delivered and removed from an organ, e.g., a liver can be calculated using the following equation:

$$[O_2] = (1.39 \times [Hb] \times FO_2Hb) + 0.00314 \times pO_2 \quad (1)$$

which expresses the concentration of oxygen (ml/dL of blood) as the sum of oxygen bound to hemoglobin and free in plasma. [Hb] (g/dL) is the concentration of hemoglobin, $FO_2Hb$ is the fraction of oxyhemoglobin present, 1.39 ($mlO_2$/g Hb) is the binding capacity of oxygen to hemoglobin and 0.00314 ($mlO_2$/dl/mmHg) is the solubility coefficient of oxygen in plasma, which is dependent on the partial oxygen tension in the blood, $pO_2$ (mmHg). The rate at which oxygen is delivered to the liver (ODR) and exits the liver (OER) is subsequently dependent on the flow rate, (ml/min), and the difference between the two normalized to the weight of the liver W(g) provides the hepatic oxygen uptake rate (HOUR):

$$HOUR = OEF - ODR \quad (2)$$

$$HOUR = \frac{[O_2]_{outlet} \times \dot{V} - [O_2]_{inlet} \times \dot{V}}{W_{Liver}}$$

Similarly, total carbon dioxide release rate (CRR) at each time point can be calculated based on the total carbon dioxide measures in the samples via Piccolo Blood Chemistry Analyzer (Abaxis) as:

$$CRR = \frac{([tCO_2]_{outlet} - [tCO_2]_{inlet}) \times \dot{V}}{W_{Liver}} \quad (3)$$

Urea can be assayed by reaction with diacetylmonoxime using a commercial assay kit (BUN, Sigma-Aldrich, St. Louis, MO). Ketone bodies were measured enzymatically, by following the appearance of NADH in the conversion to acetoacetate and the disappearance of NADH in the conversion to β-hydroxybutyrate in the presence of β-hydroxybutyrate dehydrogenase42. Nineteen of the common amino acids (except tryptophan) and ammonia can be fluorescently labeled using the AccQ-Tag system (Waters Co., Milford, MA), separated by high-performance liquid chromatography (HPLC; Model 2690, Waters Co.) and quantified by a fluorescence detector (Model 474, Waters Co.). Lactate can be measured using the enzymatic conversion to pyruvate and hydrogen peroxide with lactate oxidase from a commercially available kit (Trinity Biotech, Berkeley Heights, NJ). Albumin concentration can be determined by an enzyme-linked immunosorbent assay using a polyclonal antibody to rat albumin. A standard curve can be derived using chromatographically purified rat albumin (Cappel Laboratories, Aurora, OH) dissolved in medium. Glucose measurements can be quantified with an enzymatic assay kit through conversion to 6-phospho-gluconate (Glucose assay kit, Sigma).

Calculation of Fluxes: Fluxes can be calculated as the gradient of concentration of each metabolite (i.e. slope of the linear regression curve) over the selected segments of perfusion, normalized to the weight of the organ and averaged for each group. Oxygen and Carbon Dioxide fluxes can be determined every hour or more frequently for each organ perfused and then averaged over the selected segments of time.

Data Preprocessing and Outlier Analysis: An initial outlier analysis can be performed for each measurement by plotting box-and-whisker diagrams in a statistical software package, e.g., such as MATLAB (MATHWORKS®) and eliminating obvious errors (e.g. negative values). In some embodiments, outlier analysis can be followed by a more stringent analysis where any measurement value above/below mean±2× inter-quartile range for that group were considered outliers. This process can be used to eliminate artefactual values that increase variability.

Metabolic Flux Analysis: MFA can be performed based on a stoichiometric model for the metabolic reaction network developed, as disclosed herein. In some embodiments, the model consistency and validity of the steady state assumption can be confirmed by the method of Wang and Stephanopoulos. Briefly, this approach tests if the errors from the regression for a chi-square distribution, which indicates a normal, expectable measurement error distribution. If the regression errors do not follow a chi-square distribution at $p<0.05$, then the measured fluxes can be eliminated iteratively to identify any issues. This approach can be used identify two artefactual oxygen uptake measurements, which when eliminated resolved the issues observed.

In some embodiments, based on the tissue ATP analysis, it is possible to determine an empirical ATP balance: Assuming a linear trend of ATP change during perfusion, where ATP content of the organ is measured before and after perfusion with the MFA perfusate for three different levels of input oxygenation (120, 80 and 40 mmHg). The difference between calculated ATP consumption and the actual ATP content can be used to correlate with the remaining fluxes empirically through data mining. One can perform a combined linear regression and statistical variable elimination method to identify the minimum set of fluxes that predict the measured ATP flux with an accuracy >90% (e.g., using WEKA data mining software available from WEKA, University of Waikato). In some embodiments, a strong correlation between ATP synthesis and oxygen uptake rate can occur, but can be different due to the presence of other ATP sinks and related futile cycles in the system that are not included in the metabolic flux assay. The identified linear equation can be used to as a measure of residual ATP utilization flux; making it possible to balance ATP levels. This approach in balancing ATP accounts for ATP consuming reactions which are not measured or not known.

In some embodiments, the measurements of metabolites of the perfusate is measured consistently or intermittently over a period of at least about 1 hour, or at least about 2 hours, or at least about 3 hours or more than 3 hours. In some embodiments, the metabolites can be measured at least one, or at least twice or multiple times over the duration of the MFA. In some embodiments, metabolites of the perfusate are measured at least every hour, or at least every 30 minutes, or a least about every 15 minutes or at least about every 10 minutes, or more frequently than every 10 minutes.

Viability Score (VS)

Based on the levels of cellular energy content (e.g. ATP levels) and/or energy consumption (e.g., metabolic activity) using a metabolic flux assay (MFA) as disclosed herein, one can determine the viability of the organ.

The viability and survival of the organ is strongly correlated with oxygen uptake rate during perfusion. Since oxygen uptake rates directly correlate with metabolic activity, this indicates a direct correlation between liver metabolism during perfusion and graft survival. The data from the oxygen consumption and the date from the MFA assays, as well as physiological measurements such as portal pressure, and bile production can be used to construct a Viability Score (LS).

In some embodiments, variables used to predict survival are not unique, and are generally substitutable: for instance, average oxygen levels can be replaced with carbon dioxide levels, though $CO_2$ can often be a less reliable or accurate indicator. Accordingly, one can construct a viability score that has built in redundancy to improve accuracy and ensure that a viability score can generated from an organ even with missing measurements.

In some embodiments, the viability score is based on sub-scores, which can be combined into a final viability score. In such embodiments, time-profiles of variables observed and evaluated with MFA during perfusion can be parameterized via linear regression, to produce three parameters per variable: mean, standard deviation, and slope. This step enables the use of a more diverse selection of data mining techniques by transforming time-dependent variables to a static data set.

Using statistical data mining approaches for feature selection with Minimum-Redundancy-Maximum-Relevance, a minimal set of variables can be identified to predict the transplant success. In some embodiments, multiple classifiers, including artificial neural networks, Bayesian networks, Support Vector Machines, Decision Trees and Decision Rules, and linear regression models (using MATLAB (MATHSWORKS®) and WEKA data mining software (available from WEKA, University of Waikato) can be used to provide a sub-score viability score. In some embodiments, a sub-score model can be cross-validated using a 10-fold cross validation, to determine the accuracy, sensitivity and specificity of the viability. Variables can be removed from the data set, and the data mining procedure can be repeated to identify additional formulas for increased specificity and/or sensitivity up to 80% with cross validations. To construct the final scoring formula, all sub-scores will be combined weighed with respect to their average accuracies to produce a viability score (LVS).

In one embodiment, the Viability Score can be determined by the following equation, where:

$$LVS = 100 \times \frac{\sum_i f_i(v, z) \cdot \alpha_i}{\sum_i \alpha_i}$$

Where $LVS=\alpha_1$ is the expected accuracy of sub-score i (evaluated by cross validations), $f_i$ as a function of flux distribution v and measured concentrations, z. $f_i(v, z)=1$ if the formula predicts survival, and 0 otherwise. Since multiple classifiers will be tested it is possible that sub-scores have a variety of models. If all measurable indices indicate survival, then LVS yields a value of 100. For instance, if one out of five applicable formulas, each with equal expected accuracy C, predicts negative survival, LVS will yield a value of 80. Therefore, if a particular variable is abnormal due to pure measurement error, the index will be only partially affected.

In some embodiments, the viability score (VS) is based on the entire MFA assay, which include measurements from measurements which cannot be measured in real time (e.g., online) such as HPLC of amino acids. In some embodiments, a viability score (VS) is based on measurements of the MFA assay which are measured in real-time, e.g., online to produce an online viability score (oVS). Accordingly, in some embodiments, an online viability score (oVS) can be based on a subset of easily measurable variables (such as electrolytes and dissolved gas levels), so thai the viability of the status of the organ can be evaluated real-time during perfusion.

In some embodiments, if the values of the MFA are above a predefined threshold, it is indicative of the level of viability of the organ. In some embodiments, one can grade an organ based on the levels of metabolites measured in the organ. For example, in some embodiments, the viability of the organ based on energy consumption can be based on variables (e.g., flux) which can be easily characterized. While fluxes are not absolute ranges due to tissue type, species and genetic differences, Table 3 provides exemplary ranges as an indication of liver organ viability.

TABLE 3

Exemplary ranges of metabolites as an indication of liver organ viability

| Parameter | Good Viability (in vivo) | Good Viability (Fresh, 37° C. sanguineous) | Good for Preservation (WI, 37° C. sanguineous, t = 0-2 hrs) | Insufficient Viability (WI) |
|---|---|---|---|---|
| Oxygen uptake (umol/hr/g) | 249 ± 132 | 132 ± 38 | 92 ± 63 | 0 |
| Carbon Dioxide output | 216 ± 30 | 120 ± 97 | 81 ± 39 | 0 |
| Glucose output | 93 ± 37 | −31 ± 15 | 88 ± 201 | NA |
| Lactate uptake | 5.6 ± 2.6 | −57 ± 21 | −124 ± 98 | <124 |
| Acetoacetate output | −1.3 ± 0.6 | 11.4 ± 1.8 | 7.7 ± 11.9 | |
| β-Hydroxybutyrate output | 21 ± 16 | 0 ± 0 | 0 ± 0 | 0 |

TABLE 3-continued

Exemplary ranges of metabolites as an indication of liver organ viability

| Parameter | Good Viability (in vivo) | Good Viability (Fresh, 37° C. sanguineous) | Good for Preservation (WI, 37° C. sanguineous, t = 0-2 hrs) | Insufficient Viability (WI) |
|---|---|---|---|---|
| Urea output | 28 ± 23 | 35 ± 12 | 35 ± 4 | |
| Ammonia uptake | 6.2 ± 1.7 | 0.7 ± 0.2 | 0.8 ± 0.9 | |
| Alanine uptake | 13 ± 6.0 | 7.1 ± 1.4 | 3.9 ± 7.6 | <3.9 |
| Arginine uptake | 3.6 ± 5.1 | 4.3 ± 1.6 | 9.3 ± 6.7 | >9.3 |
| Ornithine uptake | 3.4 ± 0.9 | 31 ± 10 | 25 ± 8 | |
| Asparagine uptake | 2.0 ± 1.1 | 0.8 ± 0.4 | 1.2 ± 0 | |
| Aspartate uptake | 0.5 ± 0.4 | 2.5 ± 0.7 | 2.1 ± 1.9 | |
| Cysteine output | 0.2 ± 0.0 | −0.1 ± 2.7 | −1.4 ± 1.9 | |
| Glutamate output | 0.8 ± 1.3 | 5.4 ± 3.5 | 2.3 ± 0.1 | |
| Glutamine uptake | 2.0 ± 2.5 | 5.7 ± 3.3 | 9.3 ± 25.9 | >9.3 |
| Glycine uptake | 5.4 ± 1.2 | 4.8 ± 0.9 | 5 ± 0.1 | |
| Histidine uptake | 8.0 ± 5.3 | −0.2 ± 0.4 | −0.2 ± 0.3 | |
| Proline uptake | 0.7 ± 2.9 | 2.6 ± 0.4 | 2 ± 1.9 | |
| Serine uptake | 2.7 ± 1.7 | 0.2 ± 0.3 | −1.2 ± 1.1 | <−1.2 |
| Methionine uptake | 0.8 ± 0.1 | 1.3 ± 0.2 | 0.6 ± 0.1 | NA |
| Threonine uptake | 1.2 ± 4.0 | 0.4 ± 0.7 | 0.6 ± 8.2 | |
| Valine uptake | 0.9 ± 0.4 | −2.2 ± 0.9 | −2.9 ± 1 | <−2.9 |
| Tyrosine uptake | 1.0 ± 1.1 | −3.9 ± 0.4 | −1.5 ± 2 | |
| Isoleucine uptake | −0.2 ± 0.7 | −1.7 ± 0.6 | −1.4 ± 0.3 | |
| Phenylalanine uptake | 0.5 ± 0.4 | 2.1 ± 0.6 | 2.6 ± 0.4 | >2.6 |
| Lysine uptake | 1.5 ± 0.4 | 7.2 ± 4.2 | 2.9 ± 6 | |
| Leucine uptake | −0.2 ± 3.5 | −2.6 ± 2.1 | −4 ± 3.5 | <−4 |

How to determine transplant-worthy organs: There is a need for standards to determine viability of an organ for transplantation. A critical issue in transplantation of livers is that no reliable test for viability exists, a major drawback of cold storage. Currently, the viability decision is made based on texture of organ and quality of perfusion at retrieval, and in some cases histology. The development of a measure of viability of organs for transplantation or for grafts would clearly make decision making for transplantation much easier, particularly for marginal donor organs, and potentially save more patients. An important benefit of machine perfusion is that it allows the evaluation of the function of the graft prior to transplant. However, accurate markers are not established. Also, given the regenerative capacity of the liver, pure hepatocyte damage (as measured by ALT levels) may not be the single best indicator of recipient survival.

In one embodiment, in-line measurements can be made of the constituents of the perfusate after is it has gone through the organ, and/or it is collected in the chamber. Thus, in some embodiments, one can automatically monitor and measure one or more functional characteristics such as pH, various pressures, flow rate, vascular resistance, various chemical constituents, oxygenation, carbon dioxide concentration, and oxygen consumption, with a display as means to show measured values, and recording means to provide a record of such measurements. Methods known to those skilled in the art can be utilized for making the in-line measurements. For example, the perfusate after being perfused through the organ can be exposed to a bank of solid state micro-electrodes which generate electrical signals proportional to the chemical characteristics (U.S. Pat. No. 4,535,786, which is incorporated herein in its entirety by reference) of the perfusate leaving the perfused organ. Alternatively, the perfusate may be exposed to a spectroscopy instrument emitting and analyzing near-infrared as may be used to measure a constituent's concentration such as glucose concentration (U.S. Pat. No. 5,077,476, which is incorporated herein in its entirety by reference). In another mode of this embodiment, the level of a specific metabolite, such as glucose, may be measured by wavelength absorbance when tested by a light of known intensity. Another method for providing in-line measurement includes pumping the collected perfusate to a clinical chemistry analyzer system as disclosed in U.S. Pat. No. 4,786,394 (which is incorporated herein in its entirety by reference). Alternatively, the perfusate can be removed from the chamber and measured by similar techniques in an "off-line" manner.

In another embodiment, the vascular flow rate of the perfusate circulating through the organ can be determined by using the means for diverting and collecting the circulated perfusate, by measuring the volume of perfusate collected from the organ in relation to time. As similar to the embodiment above, micro-electrodes may be used as a means to facilitate such determination of vascular flow rate.

Similarly, in some embodiments, there may be a shunt or catheter operatively linked to the organ being perfused, may be used to divert organ product from the organ, such as urine from a kidney, and further comprises a means to collect the diverted organ product for subsequent measurement of energy parameters (e.g., levels of specific metabolites) of the organ product which relate to organ function. Organ product can be measured in-line using the means and methods for measuring the chemical constituents known to those in the art; and means and methods for monitoring the flow rate and volume, as illustrated in the above embodiments. Alternatively, the organ product can be removed from the collection means and the product's constituents can be measured using similar techniques in an "off-line" manner.

In some embodiments, the viability of an organ can be represented in the % viability of the entire organ, based on the calculated percentage of viable cells in an organ. If an organ is determined to have a % viability above a certain threshold, e.g., a threshold of transplantability (e.g., a transplant threshold), it indicates that the organ is suitable for a implanting into a subject with or without further preservation. In some embodiments, this threshold of transplantability is used to provide a measure of the viability of organs where minimal storage is required, e.g., the recipient is ready and available for implantation with the organ immediately, and thus preservation and storage of the organ for any period of time is unnecessary.

In some embodiments, if the organ is determined to have a % viability below the threshold of transplantability, but above the certain threshold required for preservation viability (e.g., a preservation threshold), it indicates the organ is suitable for preservation according to the methods as disclosed herein (e.g., perfusion preservation and/or metabolic suppression by chemical and/or sub-zero non-freezing (SZNF) storage) in order to extend or maintain the viability and then subsequent implantation into a subject.

In some embodiments, if the organ is determined to have a % viability below the preservation threshold, but above a predefined threshold for cell harvesting (e.g., a cell harvesting threshold), it indicates the organ is suitable for harvesting cells from the organ, so they can be used, for example, but not limited to, cell therapy or for artificial organ engineering and the like.

Accordingly, the methods as disclosed herein provide a methods to quantity the viability of an organ, which can be used to categorize an organ or tissue into one of following groups: (i) suitable for immediate implantation into a subject (with or without preservation methods), (ii) suitable for preservation according to the methods as disclosed herein, (iii) suitable for cell harvesting, or (iv) not suitable viability for implantation into a subject even if preservation was performed, or not suitable for cell harvesting.

The pre-defined threshold levels (e.g., transplant threshold, preservation threshold, and cell harvesting threshold) can be determined by the investigator, and is typically determined by the method of measuring the energy content (e.g., ATP levels) and/or (ii) energy consumption of the organ. For example, as disclosed herein, an organ's viability can be graded based upon ATP levels. For example, in some embodiments, the transplant threshold is an ATP level of 0.8 µmol/g total protein, therefore an organ with an ATP level at, or above the transplant threshold (e.g., an ATP level of 0.8 µmol/g total protein) indicates that the organ is suitable for transplantation, whether or not preservation according to the methods as disclosed herein is performed. In some embodiments, the preservation threshold is an ATP level below 0.8 µmol/g but above an ATP level of 0.4 µmol/g total protein, therefore an organ with an ATP level between about 0.8 µmol/g and 0.4 µmol/g total protein is indicated to be suitable for preservation according to the methods as disclosed herein.

In some embodiments, the cell harvesting threshold is an ATP level below 0.4 µmol/g but above an ATP level of 0.2 µmol/g total protein, therefore an organ with an ATP level between about 0.4 µmol/g and 0.2 µmol/g total protein is indicated to be suitable for cell harvesting.

In some embodiments, where the ATP level is below 0.2 mol/g total protein, it is indicative that the organ has low viability and is likely to be unsuitable for implantation into a subject even if preservation was performed, or unsuitable for cell harvesting.

In some embodiments, the pre-defined threshold levels (e.g., transplant threshold, preservation threshold, and cell harvesting threshold) can be determined by the investigator, based on energy consumption of the organ. For example, Table 3 provide exemplary values of levels of metabolites to determine viability thresholds of an organ. One can perform similar MFA on other organs, e.g., heart, lungs, kidney etc., to determine the viability thresholds for different organ types.

In some embodiments, the viability of an organ is considered as the absolute amount of cells in the organ which are viable, and/or as numerical number grade or % value as compared with a reference organ which is 100% viable. For example, in some embodiments, the viability of an organ can be represented as, for example, 70% viable. In some embodiments, the viability of an organ can be represented as a numerical grade. As an exemplary example, but by no way a limitation, a 100-70% cell viability represents a Grade 1 viability of an organ, which is suitable for implantation into a subject, where a 69-50% cell viability of an organ represents a Grade 2 viability of an organ and is suitable for the preservation methods as disclosed herein, and a 49-30% viability of an organ represents a Grade 3 viability of an organ, and is suitable for cell harvesting, and a viability less than 30% represents an organ which is not suitable for implantation, preservation or cell harvesting. Encompassed herein are numerous grades classification systems, and can include at least about 3, or 4, or 5, or 6, or 7, or 8 or 9 or 10 or more different grading levels, and optionally can include sublevels within these grade levels. In some embodiments, the grade classifications can be alphabetical, e.g., grade A, grade B, grade C etc.

In some embodiments, the viability of an organ can be represented as the % difference, and/or the change in absolute number of amount of cells which are viable as compared to a normal healthy organ. Alternatively, in some embodiments, the viability of an organ can indicate that the organ has a 30% ischemic or degraded cells as compared to a normal cell.

Preservation Perfusion Solution

As disclosed herein, the inventors have surprisingly demonstrated that significant ischemic damage to the organ can be prevented, or can be partially or fully, restored or reversed by ex vivo perfusion of the organ with a preservation perfusion solution to distribute nutrients and remove cytotoxins. For example, the inventors demonstrate by perfusing livers with a preservation perfusion solution enables fully functional hepatocytes to be recovered from liver organs that would otherwise, without the perfusion, have been considered to be deteriorated and be discarded. Accordingly, the present invention provides a methodology to enable greater cell yields per donor organ in addition to increasing the number of organs eligible for treatment.

Accordingly, one embodiment of the present invention relates to a method of perfusing an organ to prevent ischemic damage to the organ, the method comprising perfusing the organ with a perfusion preservation media, as disclosed herein. In some embodiments, the method for perfusing an organ results in increasing the cellular energy status (e.g., the level of energy store) and/or ATP levels in the organ. Accordingly, a method of a perfusing the organ with a perfusion preservation media as disclosed herein serves to improve and increase the cellular energy status of the cell and preserve or extend the viability of an organ.

In some embodiments, the preservation perfusion solution can be used to prevent ischemic damage to organs, for example, before or after sub-zero storage.

In some embodiments, a preservation perfusion solution can be used to perfuse an organ to maintain and/or preserve the viability of the organ, and provides a method for distributing nutrients to the organs via the organs vasculature and to remove cytotoxins from the vasculature. In some embodiments, the preservation perfusion solution can be perfused through the organ tissue to unblock any blocked vascularization of the organ.

In some embodiments, the preservation solution comprises an admixture of agents to promote the energy status of cells in the organ tissue, for example, can comprise an energy source to support cellular functions including the Krebs cycle. In some embodiments a preservation perfusion solution comprises a quick and ready source of ATP, or agents to quickly increase ATP levels in the organ.

In some embodiments, the preservation perfusion solution is an asanguineous perfusate comprising one or more of the following: Williams Medium E (#WI878, Sigma), 2 u/L insulin (28.85 units/mg Humulin, Eli Lily, Indianapolis, IN), 100,000 u/L penicillin, 100 mg/L streptomycin sulfate (Gibco, Invitrogen,GrandIsland,NY), 0.292 g/L L-glutamine (Gibco), 10 mg/L hydrocortisone (Solu-Cortef, Pharmacia & Upjohn, Kalamazoo, MI), 1000 u/L heparin (APP, Schaumberg, IL).

In some embodiments, the perfusion step can include perfusing and washing the organ with one or more isotonic washes. In some embodiments, a method for perfusing an organ can be performed in accordance with methods known by one of ordinary skill in the art, and in one embodiment, an organ is perfused according to the methods as disclosed in International Application WO2011/002926, which is incorporated herein in its entirety by reference. The perfusion can be single or multidirectional perfusion. The perfusion is can be machine- or gravity-driven perfusion. In some embodiments, the operating parameters for organ perfusions with a preservation perfusion solution as disclosed herein are follows:

Flow rate=1.84±0.05 ml/min/g;
Portal hydrostatic pressure=12-16 cm $H_2O$ (8-12 mm Hg);
Hematocrit=17.8% ±0.8%;
Inlet oxygen pressure=128.4±8.1 mm Hg;
Outlet oxygen pressure=47.9±1.7 mm Hg;
Inlet carbon dioxide pressure=30.1±1.1 mm Hg; and
Outlet carbon dioxide pressure=34.6±1.6 mm Hg.

In some embodiments, an organ can be perfused with a preservation perfusion solution as disclosed herein to improve the vitality of the adult cells. Perfusion enhances the recovery of cells from damaged organs by improving cell health before the cells are isolated from the organ. Additionally, perfusion with a preservation perfusion solution resuscitates damaged organs.

In some embodiments, a preservation perfusion solution which can be used in the methods as disclosed herein comprises a base solution which is Williams' Medium E solution (available from Sigma-Aldrich Corp. of St. Louis, Missouri), comprising one or more oxygen carriers can include erythrocytes (e.g., about 20% hematocrit). In some embodiments, the preservation perfusion solution can comprise one or more antioxidants can include bucillamine. See FarinAmersi, et al, "Bucillamine, a thiol antioxidant, prevents transplantation-associate reperfusion injury," 99(13) Proc. Nat'l Acad. Sci. 8915-20 (2002). In some embodiments, the preservation perfusion solution can comprise one or more anti-inflammatory agents can include hydrocortisone. In some embodiments, the preservation perfusion solution can comprise one or more vasodilators can include alpha-adrenoceptor antagonists ("alpha-blockers"), endothelin receptor antagonists ("ERAs"), angiotensin converting enzyme inhibitors ("ACE inhibitors"), and the like. In some embodiments, the preservation perfusion solution can comprise one or more amino acids can include L-argenine, L-glutamine, and the like. In some embodiments, the preservation perfusion solution can comprise one or more buffers can include phosphate buffered saline ("PBS"), Krebs-Ringer buffer ("KRB") (available from Sigma Aldrich, Inc. of St. Louis, Missouri), and the like. In some embodiments, the preservation perfusion solution can comprise one or more inorganic salts can include sodium, calcium, potassium, and the like. In some embodiments, the preservation perfusion solution can comprise one or more substrates for metabolism can include glucose and other carbohydrates, lactate, fatty acids, other energy sources, vitamins, and the like. In some embodiments, the preservation perfusion solution can comprise one or more hormones can include insulin (e.g., about 2 U/L). In some embodiments, the preservation perfusion solution can comprise one or more antibiotics can include penicillin (e.g., about 40,000 U/L) and/or streptomycin (e.g., about 40 mg/L). In some embodiments, the preservation perfusion solution can comprise plasma can have a volume-volume percentage of about 10%. The one or more anticoagulants can include heparin (e.g.. about 1000 U/L). In some embodiments, the preservation perfusion solution can comprise one or more agents for maintaining oncotic pressure can include albumin, polyethylene glycol, and the like.

In some embodiments, a preservation perfusion solution comprises about 10%, or about 20%, or about 40%, or about 80%, or about 100%, or about 2-fold, or about 3-fold or about 5-fold or more than 5-fold greater levels of ATP, or agents which increase ATP levels in a cell as compared to standard media.

In some embodiments, the composition of a preservation perfusion solution for perfusion of an organ as disclosed herein to preserve the energy status of a cell can vary to reflect varying species, organs, and organ health. As a general guide, about 50 mL of a preservation perfusion solution is sufficient for a rat liver, however, several litters of a preservation perfusion solution may be required for human livers.

In some embodiments, an exemplary preservation perfusion solution which can be used in the methods as disclosed herein comprises phenol red-free Williams Medium E (Sigma Chemical, St. Louis, MO) supplemented with 2 u/L insulin (28.85 units/mg Ilumulin, Eli Lily, Indianapolis, IN), 100,000 u/L penicillin, 100 mg/L streptomycin sulfate (Gibco, Invitrogen,GrandIsland,NY), 0.292 g/L L-glutamine (Gibco), 10 mg/L hydrocortisone (Solu-Cortef, Pharmacia & Upjohn, Kalamazoo, MI), and 1000 u/L heparin (APP, Schaumberg, IL). In some embodiments, the preservation solution can optionally comprise one or more antimicrobial agents. The one or more antimicrobial agents can be selected from the group consisting of antibiotics and fungicides. In some embodiments, the preservation perfusion solution can comprise varying levels of insulin, e.g., between about 0-4 µg/L, e.g., about 1 Hg/L, or about 2 µg/L, or about 3 µg/L, or about 4 µg/L, or about 5 µg/L, or more than about 5 µg/L. In some embodiments, the preservation perfusion solution can glucagon, for example, in the range of about 0-20 ng/L, or about 10-30 ng/L or about 20-50 ng/L, for example, about 5 ng/L, or about 1Ong/L, or about 15 ng/L, or about 20 ng/L, or about 50 ng/L or more than about 50 ng/L of glucagon.

In some embodiments, the preservation perfusion solution comprises plasma (25% v/v) and erythrocytes (18-20% v/v). In some embodiments, the preservation perfusion solution comprises less than 18% erythrocytes, for example, at least about less than 15%, or less than 10%, or less than 5% or less than 2% erythrocytes. In some embodiments, the perfusion preservation does not comprise erythrocytes.

In some embodiments, a preservation perfusion solution as disclosed herein can include a solution of osmolality ranging from about 100 mOsm to about 500 mOsm, one or more oxygen carriers, one or more antioxidants, one or more anti-inflammatory agents, one or more vasodilators, one or more amino acids, one or more buffers, one or more inorganic salts, one or more substrates for metabolism, and one or more agents to maintain oncotic pressure between about 15 to about 45 mm Hg In some embodiments, a preservation perfusion solution can comprise decellularization agents, for example, one or more agents selected from the group consisting of detergents, vasodilators, buffers, inorganic salts, and enzymes.

The preservation of an organ by perfusing with a preservation perfusion solution can be accomplished in the organ perfusion system as disclosed in WO2011/002926 or in similar devices.

In some embodiments, a preservation perfusion solution includes a solution having an osmolality of about 100 mOsm to about 500 mOsm, one or more oxygen carriers, one or more antioxidants, one or more anti-inflammatory agents, one or more vasodilators, one or more amino acids, one or more buffers, one or more inorganic salts, one or more substrates for metabolism, one or more hormones, one or more antibiotics, plasma, one or more anticoagulants, and/or one or more agents to maintain oncotic pressure for the perfusate between about 15 mm Hg and about 45 mm Hg.

In some embodiments, the preservation perfusion solution is recirculated through an organ to be perfused by means of a peristaltic pump through a jacketed perfusion chamber, a membrane oxygenator, a heat exchanger, and a bubble trap. In some embodiments, the oxygenator was used to gas the preservation perfusion solution with a mixture of 74% $N_2$/21% $O_2$/5% $CO_2$ and 100% $O_2$ to maintain a constant pH. In some embodiments, a fraction of the perfusate can be diverted to the secondary circuit at a rate of 3 mL/min/g wet liver weight. The secondary circuit can be used to dialyze the perfusate by counter-current exposure to dialysate.

In some embodiments, the oxygen tension of a preservation perfusion solution is maintained between about 50 mm Hg and about 150 mm Hg. In some embodiments, the temperature of the a preservation perfusion solution is maintained between about 4° C. and about 42° C.

In some embodiments, the organ is perfused with the preservation perfusion solution at a temperature at 37.5° C. The organs can be perfused by being immersed in perfusate in the perfusion chamber (see FIG. 4), or perfused at a constant flow rate of pressure through the organ at about 10 and 12 cm $H_2O$. Preservation perfusion solution and dialysate samples can be collected hourly from the organ being perfused and used to measure oxygen delivery and exit rate from samples taken immediately prior to entry to the organ and exit from the organ.

The temperature of the preservation perfusion solution or medium can be maintained between about 4° C. and about 42° C. In some embodiments, an organ is perfused with a preservation perfusion solution at about 20° C. or about 30° C., or about 37° C. In some embodiments, an organ is perfused with a preservation perfusion solution at normothermic or subnormothermic temperatures.

In some embodiments, an organ can be perfused from about 4 hours to about 14 days. In some embodiments, an organ can be perfused for between about 4 days and about 7 days. In some embodiments, an organ can be perfused for at least 1 hour, or at least about 2, or 3, or 4, or 5, or 6, or 7, or 8, or 9, or 10 or 11, or 12 hours, or about 24 or about 36 hours, or about 48 hours, or about 3 days or more than 3 days.

In some embodiments, if adult cells can be isolated from the organ after perfusion with a preservation perfusion solution. In one embodiment, adult cells are isolated by perfusing the organ with a collagenase perfusate, for example a collagenase perfusate can include a solution having an osmolality of about 100 mOsm to about 500 mOsm, one or more enzymes (e.g., collagenase I, collagenase II, collagenase III, collagenase IV, collagenase V, collagenase VI, trypsin, hyaluronidase and the like), one or more oxygen carriers, one or more antioxidants, one or more anti-inflammatory agents, one or more vasodilators, one or more amino acids, one or more buffers, one or more inorganic salts, one or more substrates for metabolism, one or more hormones, one or more antibiotics, plasma, and one or more anticoagulants. Collagenase IV can be obtained from *Clostridium histolyticum* bacteria. The base solution and the components of the collagenase perfusate can be the same or similar to the organ culture perfusate described above. The collagenase perfusate breaks the peptide bonds in collagen molecules in the organ to release the adult cells. The adult cells can be recovered from the collagenase perfusate through a variety of tissue culture methods. In one embodiment, the collagenase perfusate is filtered to isolate the adult cells (step 304b). For example, the collagenase perfusate can be filtered through one or more filters having pore sizes ranging from about 1 µm to about 1,000 µm. Additionally or alternatively, density centrifugation can be performed on the perfusate to isolate the adult cells from the collagenase perfusate. In some embodiments, adult cells isolated from an organ can be cultured in accordance with existing tissue culture methods. A variety of hepatocyte isolation and preservation protocols are described in U.S. Pat. Nos. 5,602,026 and 5,942,436, U.S. Patent Application Publication No. 2006/0019326, and James CY. Dunn et al, "Long-Term in Vitro Function of Adult Hepatocytes in a Collagen Sandwich Configuration," 7(3)

In some embodiments, the method of prefusing with a preservation solution as disclosed herein enables one to maintain or extend the viability and storage time of cells, tissues, and organs beyond current limits. In some embodiments, the method of prefusing an organ or tissue with a perfusing preservation solution as disclosed herein is at least about 20% reliable, or about 30% reliable, or about 40% reliable, or about 50% reliable, or about 60% reliable, or about 70% reliable, or about 80% reliable, or about 90% reliable, or about 100% reliable, in that, after perfusing preservation solution (with or without subsequent steps of metabolic suppression via chemical or environmental means) the organ reaches the required threshold of viability for transplantability, or a reaches the required threshold of viability for cell viability for cell harvesting.

In some embodiments, the method of prefusing an organ or tissue with a perfusing preservation solution as disclosed herein prevents ischemic damage in the organ by about 10%, or by about 20%, or by about 30%, or by about 40%, or by about 50%, or by about 60%, or by about 70%, or by about 80%, or by about 90%, or by about 100% as compared to an organ, or tissue which has not been perfused with the preservation solution as disclosed herein.

In another embodiment, the amount of ischemic damage to an organ or tissue is decreased upon perfusion with the preservation solution according to the methods as disclosed herein by about at least 10%, or at least about 20%, or at least about 30%, or at least about 40%, or at least about 50%, or at least about 60%, or at least about 70%, or at least about 80%, or at least about 90%, greater than 90% as compared to an organ which has not undergone perfusion with the preservation solution as disclosed herein. Stated another way, in some embodiments, an organ or tissue which has undergone perfusion with the preservation solution according to the methods as disclosed herein has at least about 10% more viable cells than an organ or tissue which has not undergone the perfusion with the preservation solution, or about 20% more viable cells, or about 30% more viable cells, or about 40% more viable cells, or about 50% more viable cells, or about 60% more viable cells, or about 70% more viable cells, or about 80% more viable cells, or about 90% more viable cells, or more than 90% more viable cells as compared to an organ or tissue which has not undergone the perfusion with the preservation solution as disclosed herein.

Metabolic Suppressant

In some embodiments, the present invention relates to a method to extend the time period of viability of an organ by suppressing, or decreasing the metabolic activity of the organ. In some embodiments, this metabolic suppression of the organ can be induced by chemical suppression, e.g., using metabolic suppressants, and/or by physical or environmental conditions, e.g., sub-zero non-freezing storage, as disclosed herein.

Accordingly, one embodiment relates to a method of metabolic suppression of the organ in order to extend the viable preservation time of an organ. In some embodiments, for chemical mediated metabolic suppression of an organ, the organ can be perfused with a solution comprising at least one metabolic suppressant agent. In some embodiments, an organ can be perfused with a solution comprising at least 2, or 3, or 4, or 5, or 6, or 7 or 8 or about, 10, or about 10-20 or more than 20 metabolic suppressant agents.

Figure 33:
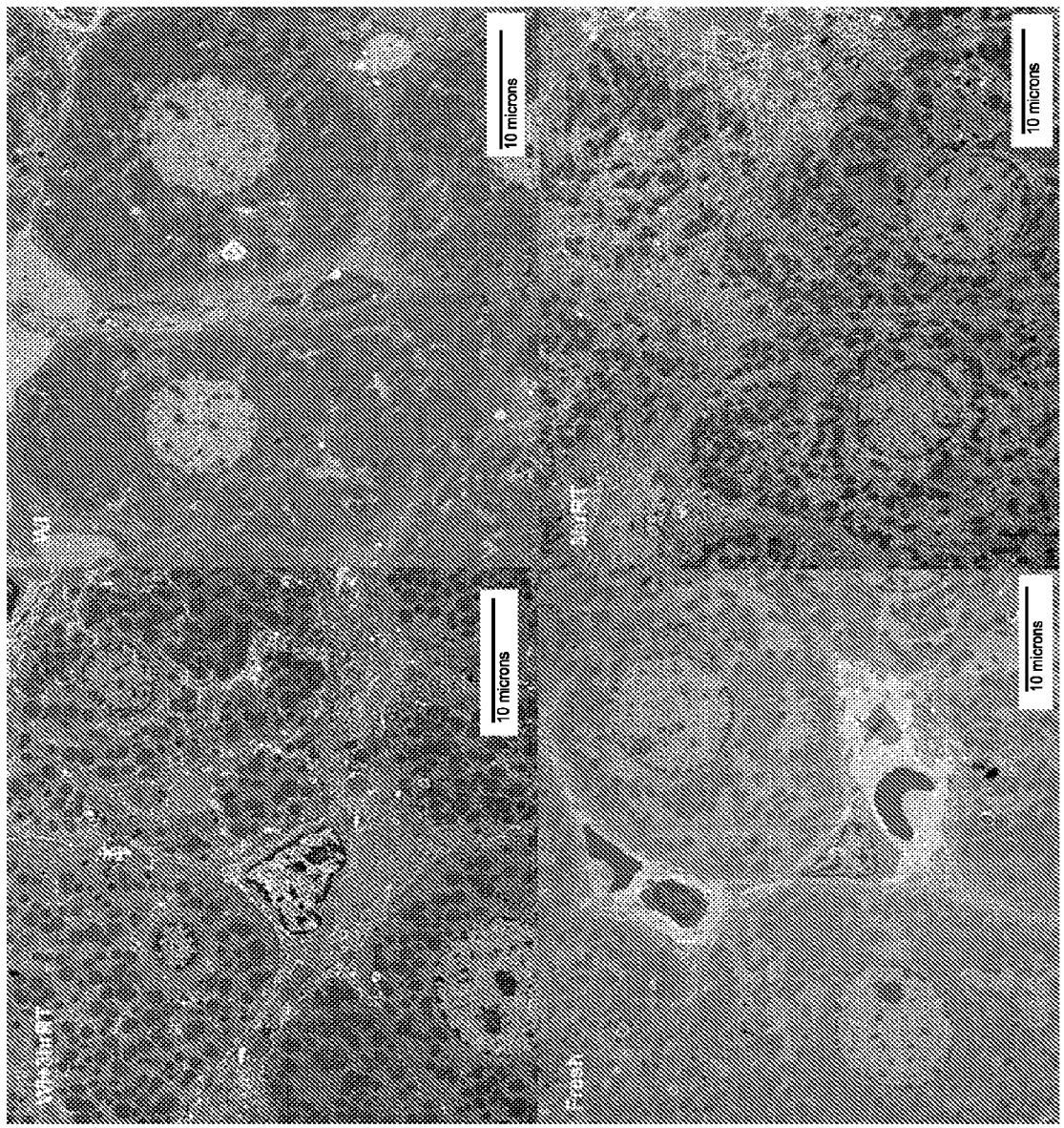
FIG. 33 illustrates the transmission electron microscopy (10 μm) revealing gross edema in WI livers, vacuolation, diminished cytoplasm-to-nucleus ratio and congested sinusoids. Perfused livers have sinusoidal congestion, and variegated cell borders.

In some embodiments, the metabolic suppressant agent is magnolol or a derivative or analogue thereof, where magnolol is a biphenic compound with antioxidant and functions as a tumor suppressant. In some embodiments, an organ can be perfused with a preservation solution, as disclosed herein, before being perfused with at least one metabolic suppressant agent. In some embodiments, a metabolic suppressor agent is selected from the group comprising: Troglitazone, Glycyrin, Naringenin, Quercetin, Dehydroglyasperin C (Pubchem CID 480775), and derivatives thereof, as disclosed in FIG. 33. In some embodiments, the metabolic suppressant agent is magnolol or a derivatives thereof. Magnolol is also known as 5,5'-Diallyl-2,2'-biphenyldiol, respectively 5,5'-di-2-propenyl-[1,1'-Biphenyl]-2,2'-diol (CAS [528-43-8])

In some embodiments, a metabolic suppressant is any agent which inhibits PPAR-gamma transcription factor activity by using any one of the following agents: magnolol (1-50 µM), quercetin (1-200 µM), troglitazone (1-100 µM), taxol (50-500 µM), cromolyn (1-200 µM).

In some embodiments, a metabolic agent for use in the methods and compositions as disclosed herein is a RNAi agent, e.g., a siRNA which gene silences the PPAR-gamma (PPAR-γ) gene, or a regulator of PPAR-gamma gene). As used herein, the term "PPAR-gamma" is also known by aliases PPARG, PPARG1, PPARG2, NR1C3, PPARgamma, and "peroxisome proliferator-activated receptor gamma", and the human PPAR-gamma protein comprises the amino acid sequence NP_005028.4, which is encoded by nucleic acid sequence Genbank Accession number, NM_005037, which is incorporated herein in its entirety by reference. Without wishing to be bound by theory, PPAR-gamma is divided into PPARγ1 and PPARγ2 as two types of isoforms with the sides of different N-termini through the selection of promoters; PPAR γ1 is expressed in the relatively widespread tissues and PPARγ2 is highly expressed mainly in the adipose tissue.

Methods to inhibit PPAR-gamma are commonly known in the art, an include without limitation, T0070907, GW9662 and BADGE, and 2,4-thiazolidinedione, and derivatives thereof, as disclosed in EP application EP 1 214 939, which is incorporated herein in its entirety by reference. Other PPARγ inhibitors are suitable for use as metabolic suppressant agents as disclosed herein, and include for example, specific inhibitors of PPARγ inhibitors troglitazone and rosiglitazone, as disclosed in International patent application WO/2005/077126, which is incorporated herein in its entirety by reference. In some embodiments, other inhibitors of PPARγ function are capable of covalent bonding to PPARγ include those that comprises a nitrogen group, such as 2-chloro-5-nitro-N-pyridinyl-benzamide or 2-chloro-5-nitrobenzanilide, which are believed to covalently modify PPARγ upon binding by reaction of a nitrogen group in the inhibitor with a cysteine residue in the PPARγ binding pocket. Putative inhibitors useful in the method of the invention can be tested using a two-part assay, according to the methods as disclosed in WO/2005/077126. For example, a inhibitor of PPARγ can bind to PPARγ protein, and forms a covalent bond with the PPARγ ligand binding pocket, or to another portion of PPARγ that results in PPARγ protein inactivation.

In some embodiments, one can inhibit PPAR-gamma by RNAi, e.g., with siRNA, shRNA and the like. In some embodiments, inhibition of PPARγ function can be performed using siRNA to reduce PPARγ expression using siRNA. In some embodiments, agents that inhibit a PPARγ regulator gene are nucleic acids. Nucleic acid inhibitors of PPARγ include, for example, but not are limited to, RNA interference-inducing molecules, for example but are not limited to siRNA, dsRNA, stRNA, shRNA and modified versions thereof, where the RNA interference molecule silences the gene expression of a PPARγ gene.

PPARγ can also be inhibited by "gene silencing" methods commonly known by persons of ordinary skill in the art. In some embodiments, the nucleic acid inhibitor of PPARγ is an antisense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

The term "Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA Apr; 9(4):493-501, incorporated by reference herein in its entirety).

The target gene or sequence of the RNA interfering agent can be a cellular gene or genomic sequence, e.g. the PPARγ gene sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target sequence.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting the inhibition of the PPARγ gene can be readily designed and tested. Accordingly, siRNAs useful for the methods described herein include siRNA molecules of about 15 to about 40 or about 15 to about 28 nucleotides in length, which are homologous to the PPARγ gene. Preferably, the PPARγ gene targeting siRNA molecules have a length of about 25 to about 29 nucleotides. More preferably, the PPARγ gene targeting siRNA molecules have a length of about 27, 28, 29, or 30 nucleotides. The PPARγ gene targeting siRNA molecules can also comprise a 3' hydroxyl group. The PPARγ gene targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the PPARγ gene targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the PPARγ gene targeting RNA molecule is double stranded —one strand has a 3' overhang and the other strand can be blunt-ended or have an overhang. In the embodiment in which the PPARγ gene targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The PPARγ gene as disclosed herein have successfully targeted using siRNAs as disclosed herein. For example, gene silencing RNAi of PPARγ are commercially available, for example from Invitrogen. Accordingly, in some embodiments, commercially available siRNAs to PPARγ can be used in the methods of the present invention, for example, from Dharmacon, Lafayette, CO, and include PPARγ siRNA: 5'-GCCCTTCACTACTGTTGAC-3' (SEQ ID NO: 1).

In some embodiments, gene silencing RNAi agents can be produced by one of ordinary skill in the art and according to the methods as disclosed herein. In some embodiments, the assessment of the expression and/or knock down of the PPARγ gene can be determined using commercially available kits known by persons of ordinary skill in the art. Others can be readily prepared by those of skill in the art based on the known sequence of the target mRNA.

To avoid doubt, the sequence of a human PPARγ cDNA is provided at, for example, GenBank Accession Nos.: NM_005037 and can be used to design a gene silencing RNAi modulator which inhibits PPARγ mRNA expression. The sequence of human PPARγ gene is the following sequence:

(SEQ ID NO: 2)

```
  1 ggcgcccgcg cccgccccg cgccgggccc ggctcggccc gacccggctc cgccgcgggc 61 aggcggggcc cagcgcactc ggagcccgag cccgagccgc agccgccgcc tggggcgctt 121 gggtcggcct cgaggacacc ggagagggge gccacgccgc cgtggccgca gaaatgacca 181 tggttgacac agagatgcca ttctggccca ccaactttgg gatcagctcc gtggatctct 241 ccgtaatgga agaccactcc cactcctttg atatcaagcc cttcactact gttgacttct 301 ccagcatttc tactccacat tacgaagaca ttccattcac aagaacagat ccagtggttg 361 cagattacaa gtatgacctg aaacttcaag agtaccaaag tgcaatcaaa gtggagcctg 421 catctccacc ttattattct gagaagactc agctctacaa taagcctcat gaagagcctt 481 ccaactccct catggcaatt gaatgtcgtg tctgtggaga taaagcttct ggatttcact
```

-continued

```
 541 atggagttca tgcttgtgaa ggatgcaagg gtttcttccg gagaacaatc agattgaagc 601 ttatctatga cagatgtgat cttaactgtc ggatccacaa aaaaagtaga aataaatgtc 661 agtactgtcg gtttcagaaa tgccttgcag tggggatgtc tcataatgcc atcaggtttg 721 ggcggatgcc acaggccgag aaggagaagc tgttggcgga gatctccagt gatatcgacc 781 agctgaatcc agagtccgct gacctccggg ccctggcaaa acatttgtat gactcataca 841 taaagtcctt cccgctgacc aaagcaaagg cgagggcgat cttgacagga aagacaacag 901 acaaatcacc attcgttatc tatgacatga attccttaat gatgggagaa gataaaatca 961 agttcaaaca catcaccccc ctgcaggagc agagcaaaga ggtggccatc cgcatctttc 1021 agggctgcca gtttcgctcc gtggaggctg tgcaggagat cacagagtat gccaaaagca 1081 ttcctggttt tgtaaatctt gacttgaacg accaagtaac tctcctcaaa tatggagtcc 1141 acgagatcat ttacacaatg ctggcctcct tgatgaataa agatggggtt ctcatatccg 1201 agggccaagg cttcatgaca agggagtttc taaagagcct gcgaaagcct tttggtgact 1261 ttatggagcc caagtttgag tttgctgtga agttcaatgc actggaatta gatgacagcg 1321 acttggcaat atttattgct gtcattattc tcagtggaga ccgcccaggt ttgctgaatg 1381 tgaagcccat tgaagacatt caagacaacc tgctacaagc cctggagctc cagctgaagc 1441 tgaaccaccc tgagtcctca cagctgtttg ccaagctgct ccagaaaatg acagacctca 1501 gacagattgt cacggaacac gtgcagctac tgcaggtgat caagaagacg gagacagaca 1561 tgagtcttca cccgctcctg caggagatct acaaggactt gtactagcag agagtcctga 1621 gccactgcca acatttccct tcttccagtt gcactattct gagggaaaat ctgacaccta 1681 agaaatttac tgtgaaaaag cattttaaaa agaaaaggtt ttagaatatg atctatttta 1741 tgcatattgt ttataaagac acatttacaa tttacttta atattaaaaa ttaccatatt 1801 atgaaattgc tgatagta
```

In some embodiments, the amount of metabolic suppressant agent administered to an organ can be a delicate balance between a sufficient amount to decrease the metabolic activity (and thus energy consumption) of the organ, yet not too much to result in harm to cells in the organ. For example, the metabolic suppressant should not be of a concentration that renders the cell completely metabolically inactive such that the sodium-potassium pump does not function, which is one of the most important modulators of internal cell volume. As disclosed herein, the hypoxic environment induces the release of intracellular calcium and elevated concentrations of calcium can lead to subsequent activation of multiple metabolic inflammatory pathways, resulting in the cells exhibiting endothelial cell swelling, a loss of blood vessel integrity, including the reduction in the internal diameter of blood vessels called a vasospasm, and even cell death in tubules. Accordingly, in some embodiments, a metabolic suppressant agent does no inhibit the activity of the sodium-potassium pump. In some embodiments, a metabolic suppressant does not cause complete diapause (metabolic arrest). In some embodiments however, a metabolic suppressant can cause diapause.

Accordingly, in some embodiments, an organ can be perfused with a solution comprising at least one metabolic suppressant agent, whereby the concentration of the metabolic suppressant is of an effective amount to decrease the metabolic activity (and thus energy consumption) of the organ, but does not result in inhibition of the sodium-potassium pump, or render the organ completely metabolically inactive.

In some embodiments, the optimal range of concentration of a metabolic suppressant, e.g., such as magnolol is at least 5 µM to about 200 µM, for example, about 5 µM, or about 10 µM, or about 20 µM, or about 40 µM, or about 50 µM, or about 60 µM, or about 70 µM, or about 80 µM, or about 90 µM, or about 100 µM, or about 120 µM, or about 150 µM, or about 200 µM or greater than 200 µM, or any integer between 5 µM and 200 µM.

In some embodiments, the concentration of a metabolic suppressant can be determined and optimized by measuring the viability of an organ according to the methods as disclosed herein. For example, one can measure the energy consumption of an organ using a method such as the MFA as disclosed herein, before and/or during, and/or after perfusing the organ with a perfusate comprising metabolic suppressant agent. One can therefore monitor the effect of the metabolic suppressant agent on the overall organ energy consumption of the organ. Accordingly, the concentration and/or dose of the metabolic suppressant agent in the perfusate can be tailored for a desired reduction in the metabolic activity of the organ. It is envisioned that repeated cycles of monitoring the energy consumption of the organ before and after perfusion with a metabolic suppressant would provide feedback to get the optimal level of inhibition of the metabolic activity of an organ within a desired range for reduced energy consumption while maintaining the delicate balance of keeping the organ in viable state.

In some embodiments, it is contemplated that chemical mediated metabolic suppression, e.g., using metabolic suppressants, the organ can then be subsequently suppressed by physical or environmental conditions, e.g., sub-zero non-freezing (SZNF) storage, as disclosed herein to further enhance the organ and/or cell viability. As disclosed herein, the inventors demonstrated that tandem SZNF in the presence of a metabolic suppressant agent, e.g., magnolol preserves the viability of cells by at least 60% as compared to SZNF in the absence of such a metabolic suppressant agent (as disclosed in Example 7)

Sub Zero Non-Freezing Storage

Another aspect of the present invention relates to preservation of an organ by metabolic suppression by physical or environmental conditions such as sub-zero non-freezing storage of the organ to extend the viable preservation of organs. In some embodiments, sub-zero storage, also referred to herein as "sub-zero non-freezing" or "SZNF" results in decreasing the temperature of the organ to below 0° C. temperatures, without freezing the organ.

In some embodiments, the present invention relates to a method of increasing the viability of an organ by preserving the organ by SZNF, which comprising perfusing the organ with a sub-zero freezing media comprising at least one supercoolant agent or at least one hypothermic preservatives. In some embodiments the sub-zero freezing media comprises the supercoolant agent 3-O-methyl-glucose (3OMG), which lowers the achievable freezing temperature without cytotoxic side effects. In some embodiments, other supercoolant agents or hypothermic preservatives which can be used in the methods of SZNF as disclosed herein include, but are not limited to, hypothermosol (Biolife Solutions, Bothell), trehalose, polyvinyl alcohol, polyvinylpyrrolidone, DMSO, or polygylcerol. In some embodiments, a supercoolant agent is selected from any of the group consisting of: K3Glc (Kaempferol 3-O-β-D-glucopyranoside); K7Glc (Kaempferol 7-O-β-D-glucopyranoside), Q7Glc (Quercetin 7-O-β-D-glucopyranoside), Q3Ga1 (Quercetin 3-O-β-D-galactopyranoside), Polyethylene glycol, or any supercoolant known to persons of ordinary skill in the art. In some embodiments, such a supercoolant agent can be used at between about 0.1-2 mg/ml, for example, at about 0.05 mg/ml, or about 0.1 mg/ml, or about 0.2 mg/ml, or about 0.3 mg/ml, or about 0.4 mg/ml, or about 0.5 mg/ml, or about 0.6 mg/ml, or about 0.7 mg/mil, or about 0.8 mg/mil, or about 0.9 mg/ml, or about 1.0 mg/ml, or about 1.2 mg/ml, or about 1.4 mg/ml, or about 1.6 mg/ml, or about 1.8 mg/ml, or about 2.0 mg/ml, or greater than 2.0 mg/ml concentration, or any integer between about 0.1-2 mg/ml, or about 2 mg/ml and about 5 mg/ml.

In some embodiments, an organ can be perfused with a solution comprising at least 2, or 3, or 4, or 5, or 6, or 7 or 8 or about, 10, or about 10-20 or more than 20 supercoolant agents or other hypothermic preservatives.

In some embodiments, the concentration of a supercoolant agent or hypothermic preservative can be used at a concentration of about 50 mM to 1M, or at any concentration selected from the group of: at about 50 mM, or about 75 mM, or about 100 mM, or about 150 mM, or about 200 mM, or about 250 mM, or about 300 mM, or about 350 mM, or about 400 mM, or about 500 mM, or about 600 mM, or about 700 mM, or about 800 mM, or about 0.9M, or about 1.0 mM or any integer between the range of 50 mM to 1M. In some embodiments, a supercoolant agent is used at a concentration of about 200 mM or about 300 mM or about 400 mM or about 500 mM or greater than 500 mM.

As the rate of biological reactions are roughly halved every 10° C. decrease, the method of sub-zero non-freezing (SZNF) storage as disclosed herein can be used to decrease temperatures by at least −2° C., or at least about −4° C., or at least about −5° C., or at least about −10° C., or by at least about −15° C. or at least about −20° C. or at least about −25° C. or colder than about −25° C. to more than at least double the viable preservation duration for biological and artificial tissues.

In some embodiments, the method of sub-zero non-freezing (SZNF) of an organ follows a specific protocol, involving controlled decreasing the temperature, and once the temperature has reached the desired predefined sub-zero temperature and held for a predefined time, the organ is raised in temperature according to a specific protocol.

For example, in one embodiment, the method for sub-zero non-freezing (SZNF) comprises perfusing the organ with a sub-zero perfusate comprising a supercoolant agent, e.g., 3OMG, during normothermic or subnormothermic perfusion, reducing the temperature to +4° C., optionally perfusing the organ with a cold preservation solution, transferring the organ to a hypodermic chamber for supercooling to a desired temperature and storing at the sub-zero temperature for a predefined time, and then increasing the temperature to +4° C., followed by normothermic or subnormothermic perfusion. In some embodiments, the normothermic or subnormothermic perfusion is with the preservation perfusion solution as disclosed herein. In some embodiments, the normothermic or subnormothermic perfusion is with a MFA perfusate as disclosed herein, and the viability of the organ assessed according to the methods as disclosed herein.

In some embodiments, the temperature of the organ is decreased from normothermic or subnormothermic temperatures to +4° C. at a linear rate of at least 1° C. per 10 mins, or about 1° C. per 5 mins, or about 1° C. per 1 mins, or about 1° C. per 30-seconds, or about 1° C. per 10-seconds, or about 1° C. per 1-second. In some embodiments, the decrease in temperature can be linear, and in other embodiments, it can be tailored to different rates of decreases in temperature over different temperature ranges. In alterative embodiments, the organ is decreased in temperature by steps, e.g., the temperature will decrease by in about 1° C., or about 5° C. or about 10° C. increments, and the temperature will not proceed to the next decrease in the temperature until the organ has come to a steady state of temperature at that increment temperature. In such embodiments, the incremental decreases in temperature need not be the same amount, for example, the temperature may decrease in 2° C. increments between the temperature ranges of about +32° C. and +10° and, decrease in 1° C. increments between the temperature ranges of about +10° and +4° C.

In some embodiments, the organ is perfused before the temperature is decreased. In alternative embodiments, the organ can be perfused with the supercoolant perfusate while the temperature is decreasing from 37° C. to about 1° C. After the organ has reached the 1° C. temperature, the organ is supercooled without continuous perfusion with the supercoolant. In some embodiments, one can continue to perfuse the organ with a supercoolant in temperatures below 1° C., where the supercoolant perfusate is coordinately cooled to the decreasing desired sub-zero temperatures prior to perfusion. However, this may results in undesired freezing and prevent the SZNF temperature from being achieved.

Similarly, in some embodiments, the temperature of the organ is decreased from +4° C. to a predefined sub-zero temperature at a linear rate of at least 1° C. per 10 mins, or about 1° C. per 5 mins, or about 1° C. per 1 mins, or about 1° C. per 30-seconds, or about 1° C. per 10-seconds, or about 1° C. per 1-second until the desired subzero temperature is achieved. In some embodiments, the decrease in temperature can be linear, and in other embodiments, it can be tailored to different rates of temperature decreases in temperature over different temperature ranges. In alterative embodiments, the temperature of the organ is decreased from +4° C. to a predefined sub-zero temperature in steps, e.g., the temperature will decrease in about 1° C., or about 5° C. or about 10° C. increments, and the temperature will not proceed to the next incremental decrease in the temperature until the organ has come to a steady state of temperature at that increment temperature, and the cycle continues until the desired sub-zero temperature is achieved. In such embodiments, the incremental decreases in temperature need not be the same amount, for example, the temperature may decrease in 1° C. increments between the temperature ranges of about +4° C. and −5° and, decrease in 2° C. increments between the temperature ranges of about −5° and −20° C.

In some embodiments, the predefined subzero temperature is about 0° C., or −1° C., or about −2° C., or about −3° C., or about −4° C., or about −5° C., or about −6° C., or about −7° C., or about −8° C., or about −9° C., or about −10° C., or about −11° C., or about −12° C., or about −13° C., or about −14° C., or about −15° C., or between about −15° C. and −20° C., or between about −20° C. and −25° C., or between about −25° C. and −30° C., or greater than about −30° C., e.g., between about −30° C. and −80° C.

Once the organ is at the predefined sub-zero temperature, the organ can be held at the sub-zero temperature for any desired period of time, for example, at least 1 hour, or at least about 6 hours, or at least about 12 hours, or at least about 1 day, or about 2, or 3, or 4, or 5, or 6, or 7, or 8, or 9, or 10, or 11, or 12, or more than 12 hours. In some embodiments, the organ can be held at the sub-zero temperature for about 2 weeks, or about 1 month, or about 2 months, or about 3 months, or about 6 months, or about 1 year or longer than 1 year.

After the predefined period of time that the organ is held at the sub-zero temperature, the temperature can be raised to +4° C. using either a linear increase in temperature, or incremental temperature increases as discussed above. For example, in some embodiments, the temperature of the organ is increased from the predefined sub-zero temperature to +4° C. to at a linear rate of at least 1° C. increase per 10 mins, or about 1° C. per 5 mins, or about PC per 1 mins, or about 1° C. per 30-seconds, or about 1° C. per 10-seconds, or about 1° C. per 1-second until the temperate reaches +4° C. In alterative embodiments, the temperature of the organ is increased from the predefined sub-zero temperature to +4° C. in incremental steps, e.g., the temperature can increase in about 1° C., or about 5° C. or about 10° C. increments, and the temperature will not proceed to the next incremental increase in the temperature until the organ has come to a steady state of temperature at that increment temperature, and the cycle continues until the organ reaches 4° C. In such embodiments, the incremental increases in temperature do not need to be the same range, for example, the temperature may increase in 2° C. increments between the temperature ranges of about −20° and −5° C., and increase in 1° C. increments between the temperature ranges of about −5° and +4° C.

After the organ has reached a temperature of +4° C., the temperature can be raised to normothermic or subnormothermic temperatures using either a linear increase in temperature, or incremental temperature increases as discussed above. For example, in some embodiments, the temperature of the organ is increased from +4° C. to at normothermic or subnormothermic using a linear rate of at least 1° C. increase per 10 mins, or about 1° C. per 5 mins, or about 1° C. per 1 mins, or about 1° C. per 30-seconds, or about PC per 10-seconds, or about 1° C. per 1-second until the temperate reaches +4° C. In alterative embodiments, the temperature of the organ is increased from +4° C. to a normothermic or subnormothermic temperature in incremental steps, e.g., the temperature can increase in about 1° C., or about 5° C. or about 10° C. increments, and the temperature will not proceed to the next incremental increase in the temperature until the organ has come to a steady state of temperature at that increment temperature, and the cycle continues until the organ reaches the normothermic or subnormothermic temperature. In such embodiments, the incremental increases in temperature do not need to be the same range, for example, the temperature may increase in 1° C. increments between the temperature ranges of about +4° and +10° C., and increase in 2° C. increments between the temperature ranges of about +10 and +37° C. In some embodiments, the increase in temperature from +4° C. to normothermic or subnormothermic temperatures occurs while the organ is being perfused, e.g., perfused with a perfusion protection solution as disclosed herein.

In some embodiments, the sub-zero nonfreezing (SZNF) storage enables one to maintain or extend the viability and storage time of cells, tissues, and organs beyond current limits. In some embodiments, the method of preservation by sub-zero nonfreezing (SZNF) storage is at least about 20% reliable, or about 30% reliable, or about 40% reliable, or about 50% reliable, or about 60% reliable, or about 70% reliable, or about 80% reliable, or about 90% reliable, or about 100% reliable, in that, after the sub-zero nonfreezing (SZNF) storage procedure and rewarming step, (with or without the step of perfusion with a preservation solution on warming) the organ reaches the required threshold of viability for transplantability, or reaches the required threshold of viability for cell harvesting.

In some embodiments, sub-zero nonfreezing (SZNF) storage enables one to extend the storage time of cells, tissues, and organs beyond current limits. Isolated organ perfusion systems represent an efficient method for loading the organ with necessary preservation agents, as well as performing the cooling and rewarming protocols in an in vivo like state with minimal additional damage. In addition, perfusion with the MFA perfusate also allows for quantitative evaluation of tissue viability and function after preservation, hence enabling development of standards for transplantation.

Organs

In some embodiments, an organ which is preserved using the methods and compositions as disclosed herein is mammalian organ, and in some embodiments, the mammal is a human. An organ can be selected from the group consisting of, but not limited to, liver, pancreas, kidney, spleen, heart, and lung. The organ can be a liver or heart.

Kits for organ preservation and transplantation

Another aspect of the present invention relates to a kit comprising at least one, or any combination of: the preservation perfusion solution, the MFA perfusate, the metabolic suppression perfusate, and the sub-zero perfusate as these are described herein.

In some embodiments, the kit can comprise a container containing the sub-zero cryopreservation agent 3OMG, and derivatives thereof.

The perfusates as disclosed herein can be stored in separate containers within a single package or kit. Such kits can be marketed to entities engaged in the business or activities of harvesting, storing and preserving and/or transplanting donor organs. These kits can optionally include instructions for methods of organ preparation and storage as described elsewhere herein. In accordance with an aspect of the invention, various types of mammalian organs can be treated and prepared for storage over extended periods of time. While experiments were conducted in the following examples with rat livers, the invention here can be applied to human subjects or other mammals and their respective organs.

In some embodiments of the present invention may be defined in any of the following numbered paragraphs:

1. A method of assessing viability of an organ, comprising: measuring a least one energy parameter, and determining a measure of viability as a function of the at least one energy parameter.
2. The method of paragraph 1, wherein determining a measure of viability comprises comparing a measured energy parameter to a threshold representative of a transplantability threshold of an organ.
3. The method of paragraph 1, wherein determining a measure of viability comprises comparing a measured energy parameter to a threshold representative of cell harvesting threshold of an organ.
4. The method of anyone of paragraph 1 to 3, comprising measuring the metabolic activity of the organ.
5. The method of any of paragraphs 1 to 4, further comprising storing the organ prior to assessing its viability.
6. The method of any of paragraphs 1 to 5, further comprising implanting the organ in a subject.
7. The method of any of paragraphs 1 to 5, further comprising harvesting the cells of the organ.
8. The method of any of paragraphs 1 to 7, wherein the method is at least 50% reliable at predicting the viability of the organ and/or successful outcome of implantation of the organ into a subject.
9. The method of any of paragraphs 1 to 8, wherein the method is at least 60% reliable at predicting the viability of the organ and/or successful outcome of implantation of the organ into a subject.
10. The method of any of paragraphs 1 to 9, wherein the method is at least 70% reliable at predicting the viability of the organ and/or successful outcome of implantation of the organ into a subject.
11. The method of any of paragraphs 1 to 10, wherein the method is at least 80% reliable at predicting the viability of the organ and/or successful outcome of implantation of the organ into a subject.
12. The method of any of paragraphs 1 to 11, wherein the method is at least 90% reliable at predicting the viability of the organ and/or successful outcome of implantation of the organ into a subject.
13. The method of any of paragraphs 1 to 12, wherein the energy parameter is the level of ATP in the organ.
14. The method of any of paragraphs 1 to 13, wherein measuring a least one energy parameter comprises assaying for the level of ATP.
15. The method of any of paragraphs 1 to 14, wherein measuring at least one energy parameter comprises measuring the cellular energy status during normothermic or subnormothermic perfusion of the organ.
16. The method of any of paragraphs 1 to 15, wherein measuring a least one energy parameter comprises cellular energy status.
17. The method of any of paragraphs 1 to 16, further comprising perfusing the organ with a preservation perfusion solution.
18. The method of any of paragraphs 1 to 17, wherein the preservation perfusion solution comprises erythrocytes.
19. The method of any of paragraph 1 to 17, wherein the preservation perfusion solution does not comprise erythrocytes.
20. The method of any of paragraph 1 to 19, wherein the energy parameter measured is the level of a plurality of metabolites.
21. The method of any of paragraph 1 to 20, wherein the plurality of metabolites is selected from any or a combination from the group consisting of: Glucose, Urea, Nitrogen, Total Carbon dioxide, AST, ALT, ALP, total protein, total bilirubin, Creatinine, Sodium, Potassium, Calcium, Chloride, Total Cholesterol, triglycerides (high density and/or low density), very low density lipoproteins, Amino acids, Lactate, Free fatty acids, Glycerol, Insulin, Glucagon, β-hydroxybutyrate, Acetatoacetate, Nitric Oxide, Gluthatione, Glutathione disulfide, bile, principle bile acids, steroids, $O_2$ and $CO_2$, Hematocrit, Hemoglobin (Free, oxygenated), electrolytes, TNF-α.
22. The method of any of paragraph 1 to 19, wherein the energy status is measured by measuring the change in the levels of a plurality of metabolites over a predefined period of time, wherein the change in the plurality of metabolites is selected from any or a combination from the group consisting of: Oxygen uptake, carbon dioxide output, glucose output, lactate uptake, acetoacetate output, 3-Hydroxybutyrate output, urea output, ammonia uptake, alanine uptake, arginine uptake, ornithine uptake, asparagine uptake, aspartate uptake, cysteine output, glutamate output, glutamine uptake, glycine uptake, histidine uptake, proline uptake, serine uptake, methionine uptake.
23. The method of any of paragraphs 1 to 22, wherein the plurality of metabolites comprises at least 10 metabolites.
24. The method of any of paragraphs 1 to 23, wherein the plurality of metabolites comprises at least 15 metabolites.
25. The method of any of paragraphs 1 to 24, wherein the plurality of metabolites comprises at least 20 metabolites.
26. The method of any of paragraphs 1 to 25, wherein the plurality of metabolites is 28 metabolites.
27. The method of any of paragraphs 1 to 26, wherein the energy parameter measured is the oxygen consumption by the organ.
28. The method of any of paragraphs 1 to 27, wherein the energy parameter measured is the level measuring the gluconeogeneis of the organ.
29. The method of any of paragraphs 1 to 28, wherein the energy parameter measured is the nitrogen metabolism by the organ.
30. The method of any of paragraphs 1 to 29, wherein if the energy parameter measured is above a predetermined level it is indicative that the organ is suitable for preservation and/or implantation into a subject.
31. A method for extending the viable preservation of the organ, comprising perfusing the organ with a preservation perfusion solution.
32. The method of paragraph 31, wherein the preservation perfusion solution comprises at least 3 of the following: insulin, L-glutamine, hydrocortisone heparin penicillin, streptomycin sulfate, adenosine.
33. A method for preventing ischemic damage in an organ, comprising perfusing the organ with a preservation perfusion solution.

34. The method of paragraph 31, wherein the perfusion is performed prior to, or after, the ischemic damage.

35. The method of paragraph 33, wherein the preservation perfusion solution comprises at least 3 of the following: insulin, L-glutamine, hydrocortisone heparin penicillin, streptomycin sulfate, adenosine.

36. A method of extending the viable preservation time of an organ, comprising contacting at least a portion of the organ with a solution comprising at least one metabolic suppressant agent.

37. The method of paragraph 36, wherein contacting at least a portion of the organ with a solution comprising a metabolic suppressant agent decreases utilization of ATP in the cell.

38. The method of paragraph 36, wherein contacting at least a portion of the organ with a solution comprising a metabolic suppressant agent increases the cellular energy in the cell.

39. The method of any of paragraphs 36 to 38, further comprising measuring a least one ATP utilization parameter, and comparing the measured ATP utilization parameter to a threshold representative of a quantitative standard for ATP in the cell.

40. The method of any of paragraphs 36 to 39, wherein contacting at least a portion of the organ with a solution comprising comprises immersing, partially or completely the organ with the solution comprising metabolic suppressant agent.

41. The method of any of paragraphs 36 to 40, wherein contacting at least a portion of the organ with a solution comprises perfusing the organ with the solution comprising metabolic suppressant agent.

42. The method of any of paragraphs 36 to 41, wherein the metabolic suppressant agent is selected from the group consisting of: Troglitazone, Glycyrin, Naringenin, Quercetin, Dehydroglyasperin C (Pubchem CID 480775), Magnolol, and derivatives thereof.

43. The method of paragraph 42, wherein the metabolic suppressant agent is Magnolol and derivatives thereof.

44. The method of any of paragraphs 36 to 43, wherein the metabolic suppressant agent is an inhibitor of PPARγ.

45. The method of paragraph 44, wherein the inhibitor of PPARγ is an RNAi agent inhibitor or nucleic acid inhibitor of PPARγ.

46. The method of paragraph 44, wherein the inhibitor of PPARγ is selected from the group consisting of: troglitazone and rosiglitazone, T0070907, GW9662 and BADGE, or derivatives thereof.

47. A method of preserving an organ comprising: (a) contacting an organ with a media comprising a supercoolant agent; (b).cooling said organ to a predetermined sub-zero temperature; (c) storing said organ at the predetermined sub-zero temperature; and (d) re-warming said organ.

48. The method of paragraph 47, further comprising measuring a least one energy parameter, and determining a measure of viability as a function of the at least one energy parameter.

49. The method of paragraph 48, wherein determining a measure of viability comprises comparing the measured energy parameter to a transplantability threshold of an organ.

50. The method of paragraph 47, wherein determining a measure of viability comprises comparing the measured energy parameter to a cell harvesting threshold of an organ.

51. The method of any of paragraph 47 to 50, wherein measuring at least one energy parameter comprises measuring the metabolic activity of the organ.

52. The method of any of paragraphs 47 to 51, further comprising implanting the organ in a subject.

53. The method of any of paragraphs 47 to 51, further comprising harvesting the cells of the organ.

54. The method of any of paragraphs 47 to 53, wherein the method is at least 50% reliable at predicting the viability of the organ and/or successful outcome of implantation of the organ into a subject.

55. The method of any of paragraphs 47 to 54, wherein the method is at least 60% reliable at predicting the viability of the organ and/or successful outcome of implantation of the organ into a subject.

56. The method of any of paragraphs 47 to 55, wherein the method is at least 70% reliable at predicting the viability of the organ and/or successful outcome of implantation of the organ into a subject.

57. The method of any of paragraphs 47 to 56, wherein the method is at least 80% reliable at predicting the viability of the organ and/or successful outcome of implantation of the organ into a subject.

58. The method of any of paragraphs 47 to 57, wherein the method is at least 90% reliable at predicting the viability of the organ and/or successful outcome of implantation of the organ into a subject.

59. The method of any of paragraphs 47 to 58, further comprising harvesting the cells of the organ.

60. The method of any of paragraphs 48 to 58, wherein the energy parameter is the level of ATP in the organ.

61. The method of any of paragraphs 48 to 58, wherein measuring a least one energy parameter comprises assaying for the level of ATP.

62. The method of any of paragraphs 48 to 58, wherein measuring at least one energy parameter comprises measuring the cellular energy status during normothermic perfusion of the organ.

63. The method of any of paragraphs 48 to 58, wherein measuring a least one energy parameter comprises cellular energy status.

64. The method of any of paragraphs 1 to 16, further comprising perfusing the organ with a preservation perfusion solution.

65. The method of any of paragraphs 48 to 58, wherein the preservation perfusion solution comprises erythrocytes.

66. The method of any of paragraph 1 to 17, wherein the preservation perfusion solution does not comprise erythrocytes.

67. The method of any of paragraph 48 to 58, wherein the energy parameter measured is the level of a plurality of metabolites.

68. The method of any of paragraph 48 to 58, wherein the plurality of metabolites is selected from any or a combination from the group consisting of: Glucose, Urea, Nitrogen, Total Carbon dioxide, AST, ALT, ALP, total protein, total bilirubin, Creatinine, Sodium, Potassium, Calcium, Chloride, Total Cholesterol, triglycerides (high density and/or low density), very low density lipoproteins, Amino acids, Lactate, Free fatty acids, Glycerol, Insulin, Glucagon, 3-hydroxybutyrate, Acetatoacetate, Nitric Oxide, Gluthatione, Glutathione disulfide, bile, principle bile acids, steroids, $O_2$ and $CO_2$, Hematocrit, Hemoglobin (Free, oxygenated), electrolytes, TNF-α.

69. The method of any of paragraph 48 to 68, wherein the energy status is measured by measuring the change in the levels of a plurality of metabolites over a predefined period of time, wherein the change in the plurality of metabolites is selected from any or a combination from the group consisting of: Oxygen uptake, carbon dioxide output, glucose output, lactate uptake, acetoacetate output, β-Hydroxybutyrate output, urea output, ammonia uptake, alanine uptake, arginine uptake, ornithine uptake, asparagine uptake, aspartate uptake, cysteine output, glutamate output, glutamine uptake, glycine uptake, histidine uptake, proline uptake, serine uptake, methionine uptake.
70. The method of any of paragraphs 48 to 69, wherein the plurality of metabolites comprises at least 10 metabolites.
71. The method of any of paragraphs 48 to 70, wherein the plurality of metabolites comprises at least 15 metabolites.
72. The method of any of paragraphs 48 to 71, wherein the plurality of metabolites comprises at least 20 metabolites.
73. The method of any of paragraphs 48 to 72, wherein the plurality of metabolites is 28 metabolites.
74. The method of any of paragraphs 48 to 73, wherein the energy parameter measured is the oxygen consumption by the organ.
75. The method of any of paragraphs 48 to 74, wherein the energy parameter measured is the level measuring the gluconeogeneis of the organ.
76. The method of any of paragraphs 48 to 75, wherein the energy parameter measured is the nitrogen metabolism by the organ.
77. The method of any of paragraphs 48 to 76, wherein if the energy parameter measured is above a predetermined level it is indicative that the organ is suitable for preservation and/or implantation into a subject.
78. The method of any of paragraphs 47-77, wherein re-warming the organ is by normothermic perfusion.
79. The method of any of paragraphs 47-78, wherein the normothermic perfusion is with a preservation perfusion solution.
80. The method of any of paragraphs 47-79, wherein the normothermic perfusion removes cytotoxins from the organ.
81. The method of any of paragraphs 47-80, wherein the organ is cooled and stored at the predefined sub-zero temperature without freezing.
82. The method of any of paragraphs 47 to 81, wherein the organ is cooled to at least −5° C. or below.
83. The method of any of paragraphs 47 to 82, wherein the organ is cooled to at least −10° C. or below.
84. The method of any of paragraphs 47 to 83, wherein the organ is cooled to at least −15° C. or below.
85. The method of any of paragraphs 47 to 84, wherein the organ is cooled to at least −20° C. or below.
86. The method of any of paragraphs 47 to 85, wherein the organ is cooled to at least −30° C. or below.
87. The method of any of paragraphs 47 to 86, wherein the organ is cooled to between −30° C. and −80° C.
88. The method of any of paragraphs 47 to 78, wherein the supercoolant agent is a hypothermic preservative.
89. The method of any of paragraphs 47 to 88, wherein the supercoolant agent is selected from the group consisting of: 3-O-methyl-glucose (3OMG), hypothermosol, trehalose, polyvinyl alcohol, polyvinylpyrrolidone, DMSO, polygylcerol, K3Glc (Kaempferol 3-O-f-D-glucopyranoside); K7Glc (Kaempferol 7-O-β-D-glucopyranoside), Q7Glc (Quercetin 7-O-β-D-glucopyranoside), Q3Gal (Quercetin 3-O-β-D-galactopyranoside), Polyethylene glycol.
90. The method of paragraphs 89, wherein the suppercoolant agent is 3-O-methyl-glucose (3OMG) or a derivative thereof.
91. The method of any of paragraphs 47 to 90, wherein the supercoolant is used at a concentration between 0.1-2 mg/ml.
92. The method of any of paragraphs 47 to 90, wherein the supercoolant is used at a concentration between 50 mM and 1 µM
93. The method of any of paragraphs 47 to 92, wherein the organ is cooled at a rate of at least 1° C. per 10 minutes.
94. The method of any of paragraphs 47 to 93, wherein the organ is cooled at a rate of at least 1° C. per 5 minutes.
95. The method of any of paragraphs 47 to 94, wherein the organ is cooled at a rate of at least 1° C. per 1 minute.
96. The method of any of paragraphs 47 to 95, wherein the organ is re-warmed at a rate of at least 1° C. per 10 minutes.
97. The method of any of paragraphs 47 to 96, comprising re-warming the organ at a rate of at least 1° C. per 5 minutes.
98. The method of any of paragraphs 47 to 97, comprising re-warming the organ at a rate of at least 1° C. per 1 minute.

EXAMPLES

The examples presented herein relate to methods and compositions for assessing the viability of organs for transplantation and extending the preservation time of organs based on the viability assessment. In particular, the examples relate to methods of objective measures of organ viability using the MFA, and using this to determine the optimal preservation of the organ using at least one, or a combination of three methods of extending the viable preservation time of organ tissue: 1) perfusion, 2) metabolic suppression, and 3) sub-zero non-freezing storage. Such methods have allowed inventors to extend the viable preservation time, thereby increasing the range of organ distribution and allocation, minimizing effects related to geography, and allowing for better donor/recipient matching, thereby potentially saving many lives. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Example 1

Simple ex vivo perfusion optimizesischemic and freshdonor livers, significantly enhancing hepatocyte yields.

Figure 1C:
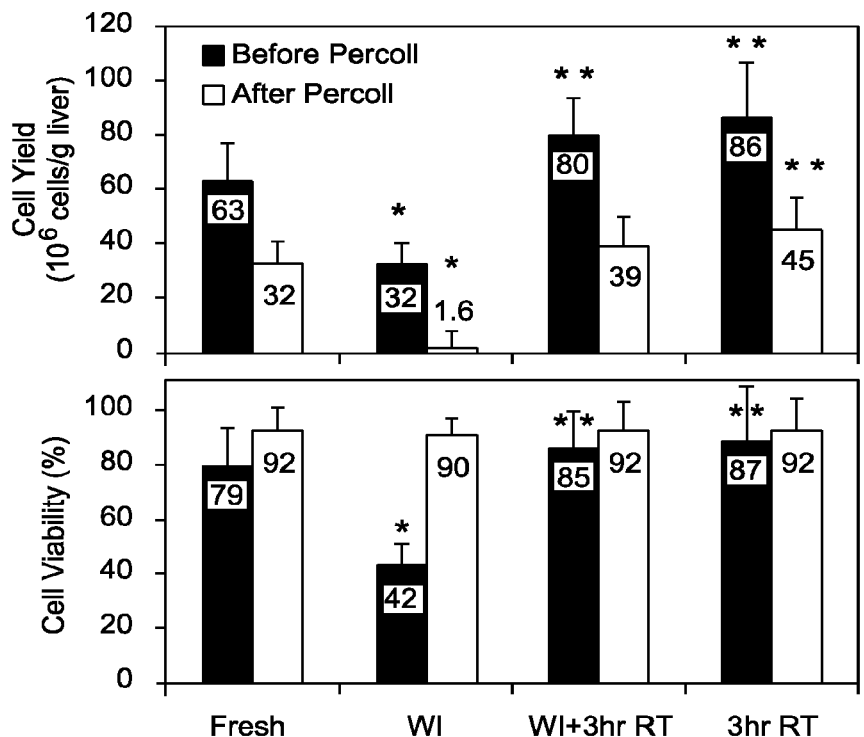

Simple ex vivo organ perfusion significantly enhances hepatocyte yields. Non-premedicated rat livers exposed to 60 minutes of warm ischemia at 34° C. were treated for 3 hours with ex vivo room temperature perfusion (FIG. 1A) prior to hepatocyte isolation. The hepatocyte cell yield from this group (WI+3hrRT) was 39±11 mllion cells/g liver with 92% viability; a 25-fold increase from the 1.6±0.6 mllion cells/g liver with 90% viability procured from non-perfused WI livers. Fresh livers tended to produce fewer cells averaging 32±8.6 mllion cells/g liver with 92%,though this was not statistically significant (p=0.21) (FIG. 1C).

As an additional control group, non-premedicated livers were harvested and placed directly into perfusion. This group, representing fresh perfused livers (3hrRT), produced 45±12 mllion cells/g liver tissue with 92% viability, significantly more than non-perfused Fresh livers (p=0.03).

Figure 1D:
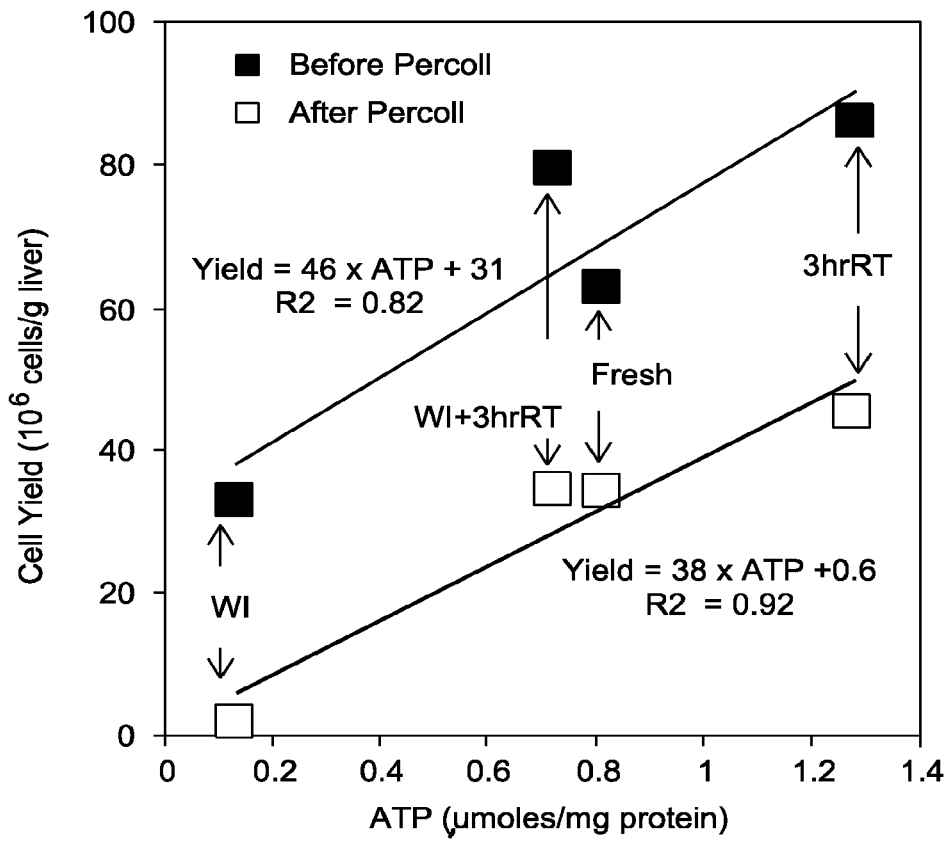

Perfusion-enabled ATP recovery predicts cell yields. ATP depletion occurs rapidly upon the inception of warm ischemia (Abu-Amara, M., Yang, S. Y., Tapuria, N., Fuller, B., Davidson, B., Scifalian, A. Liver ischemia/reperfusion injury: processes in inflammatory networks —A review. *Liver Transpl* 16, 1016-1032 (2010)). As expected, ATP levels from biopsies of WI livers were very low (0.13±0.06 µmoles/mg protein). Perfusion enabled the recovery of WI+3hrRT ATP to levels comparable with Fresh liver ATP (0.8±0.4 and 0.7±0.3 µmoles/mg protein respectively, p=0.5).Not unlike cell yield results, 3hrRT livers were found to have a significantly higher ATP yield than Fresh livers (1.3±0.2 µmoles/mg protein, p=0.001). In fact, a most useful linear correlation (Pearson's correlation 0.96) was found to exist between tissue biopsy ATP levels and final cell yield per gram of liver tissue post-Percoll purification (FIG. 1D) enabling the accurate prediction of the extent of liver recovery during perfusion.

Figure 2E:
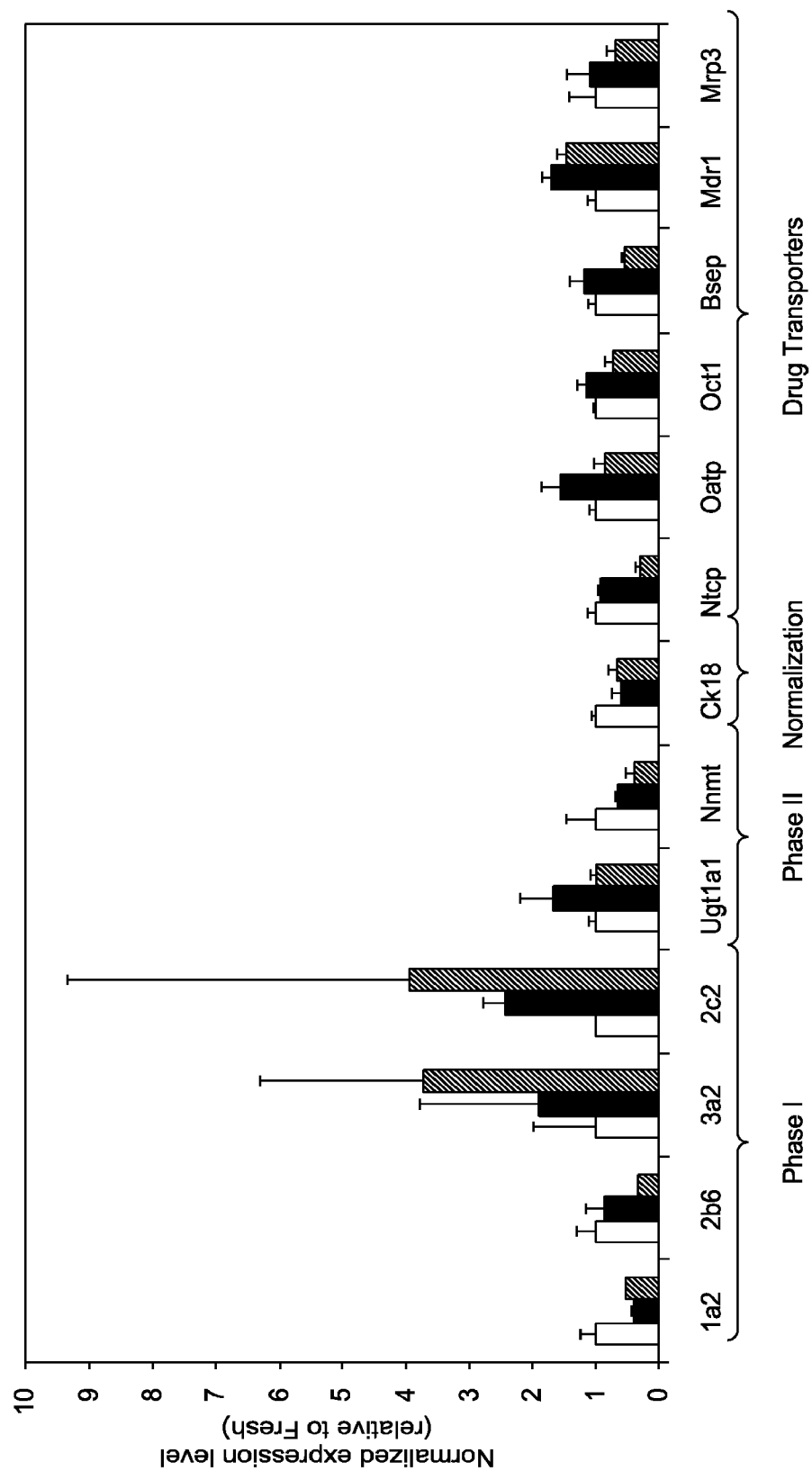

Hepatocyte Performance in Short-term Suspension Cultures. Isolated hepatocytes were evaluated over a 6 hour period of suspension culture (1 mllion cells/vial) to determine their functional capacity and longevity. Cell viability (FIG. 2A), measured by trypan blue exclusion, showed a negligible 3% decline in number of 3hrRT cells from t=1 hr to t=6 hrs of suspension. Fresh cells, by contrast, showed a 15% decline over the same time frame while WI+3hrRT declined by 8%. Cell viability measured by evaluating mitochondrial activity through the reduction of MTT to formazan, showed 3hrRT cell activity declined only 9% by t=6 hrs. Within the same time frame,Fresh livers lost 33% and WI+3hrRT cells lost 28% of their activity. Aspartate (AST) and alanine (ALT) aminotransferase release, indicative of increased membrane permeability, were expressed as a fraction of the total ALT or AST release at 100% hepatocyte lysis (FIG. 2B). At the inception of culture, the perfused groups had significantly higher AST and ALT levels than those of Fresh cells. 3hrRT ALT and AST values were stable or generally declined throughout suspension, while WI+3hrRT cells showed moderate release of both AST and ALT within the first two hours of culture prior to stabilizing. By contrast, Fresh cells produced ALT and AST at a low steady rate throughout culture. General metabolic activity (FIG. 2C) was evaluated as the change in metabolites from t=0 hrs to t=6 hrs. All groups were gluconeogenic, producing similar amounts of glucose (2 g/L at baseline) and they utilized nitrogen at similar rates as measured by urea (0 mM at baseline). WI+3hrRT cells produced 0.4 times as much albumin (0 µg/ml at baseline) as Fresh cells, and 3hrRT cells produced 1.6 times as much. The capacity for drug metabolism was evaluated using a select four cytochrome P450 enzymes. Enzyme activity was measured by dealkylation of benzyloxy resorufin (CYP2B2), pentoxy resorufin (CYP2B1), ethoxy resorufin (CYP1A1) and methoxy resorufin (CYP1A2) after 3,3'-methylene-bis(4-hydroxycoumarin) activation (FIG. 2D). CYP450 activity was similar amongst all groups except for a 1.5 fold increased CYP4501A1 activity and a 3 fold increased CYP4501A2 activity in 3hrRT cells compared to Fresh cells. Expression profiles of liver-specific CYP450 and phase II genes from cells at t=0 hrs of suspension demonstrated higher consistency between perfused liver groups than freshly isolated cells (FIG. 2E) however, mRNA levels were not quantitatively consistent with the observed enzymatic activity (Rodriguez-Antona, C., Donato, M. T. Pareja, E., Gomez-Lechon, M. J., Castell, J. V. Cytochrome P-450 mRNA expression in human liver and its relationship with enzyme activity. *Arch. Biochem. Biophys.*393, 308-315 (2001)).

Figure 3A:
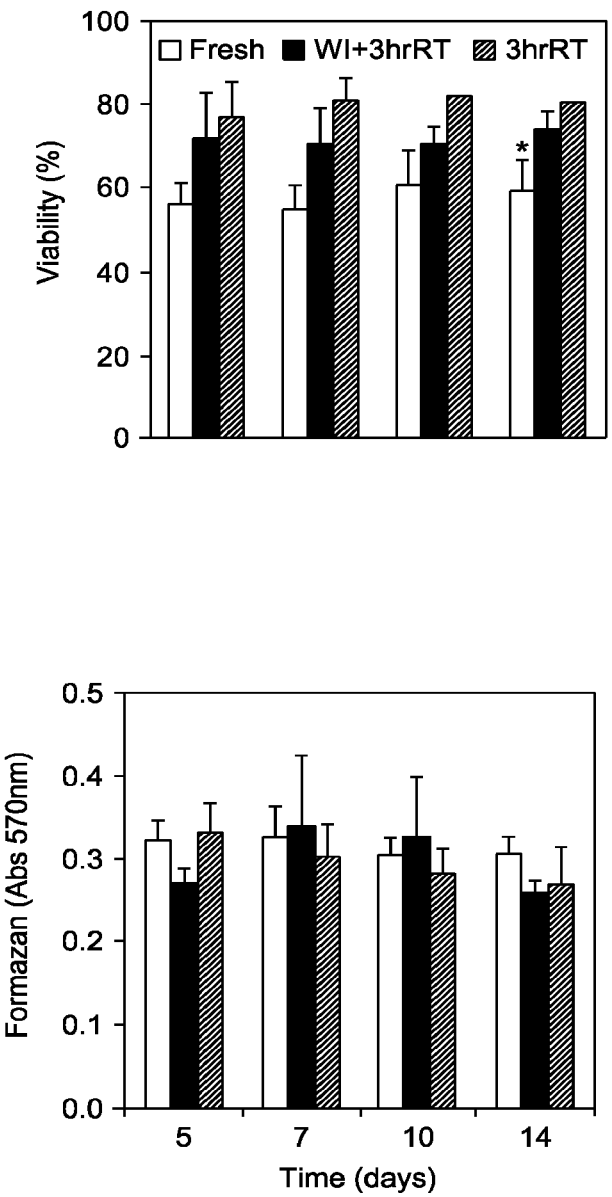
Figure 3B:
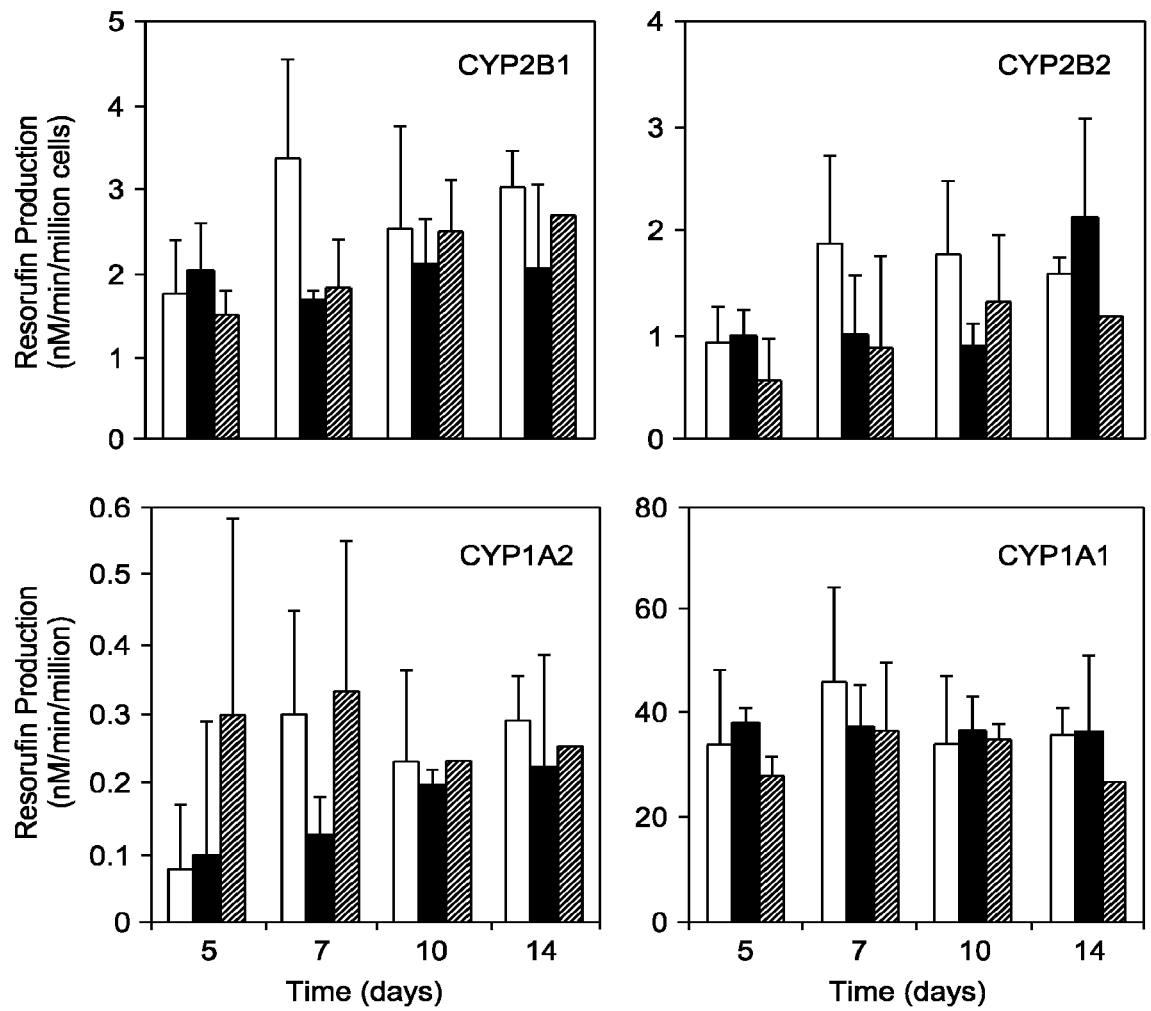
Figure 3F:
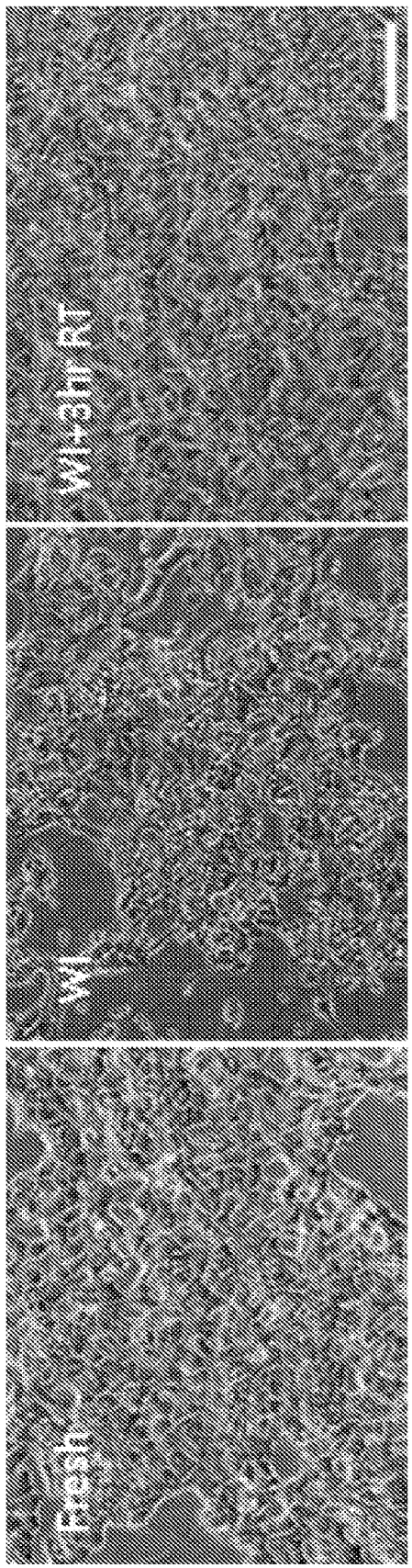

Hepatocyte Performance in Long-term Plate Cultures. In double collagen sandwich plate cultures, isolated hepatocytes were evaluated over a period of 2 weeks. Overall, too few cells were procured from WI livers so they were subsequently excluded from plate culture evaluation. Cell viability counts and mitochondrial MTT reduction to formazan (FIG. 3A) were similar in all groups at each time point. CYP450 activity did not differ significantly across groups though certain trends could be observed; Fresh cells generally peaked in activity within 7 days, while cells from perfused livers appeared to either remain constant throughout culture or gradually increase in activity, peaking at Day 14 (FIG. 3B). Fresh and 3hrRT cells produced comparable amounts of albumin daily (FIG. 3C). Not unlike the suspension cultures, WI+3hrRT cells did not produce as much albumin, though the rate of increase in daily production was similar to Fresh and 3hrRT groups. 3hrRT cells produced significantly more urea than WI+3hrRT or Fresh cells, which were comparable (FIG. 3D). All groups metabolized glucose equally (FIG. 3E).Phase contrast imaging showed confluent, hexagonal, non-steatotic perfused liver cells (FIG. 3F) at day 7. By contrast, WI cells showed poor morphology with little confluent organization, and multiple areas of dead cells.

Figure 6A:
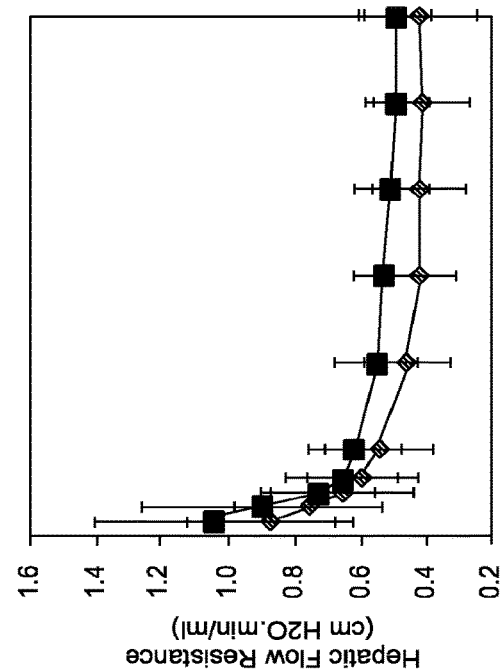
FIGS. 6A-6D illustrate.
Figure 6B:
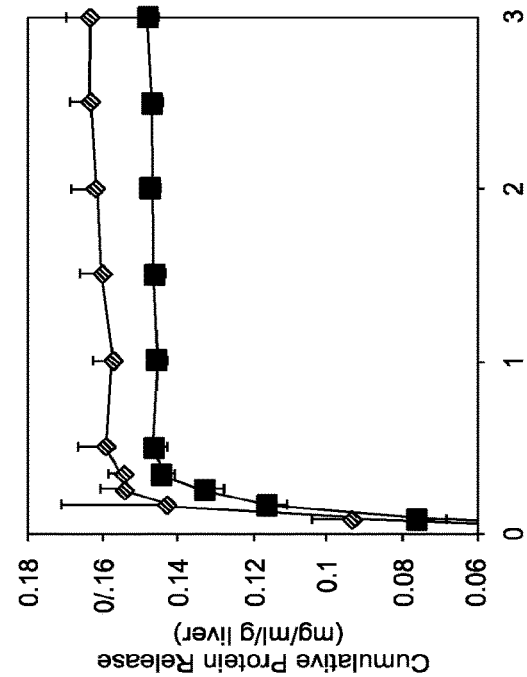
Figure 6C:
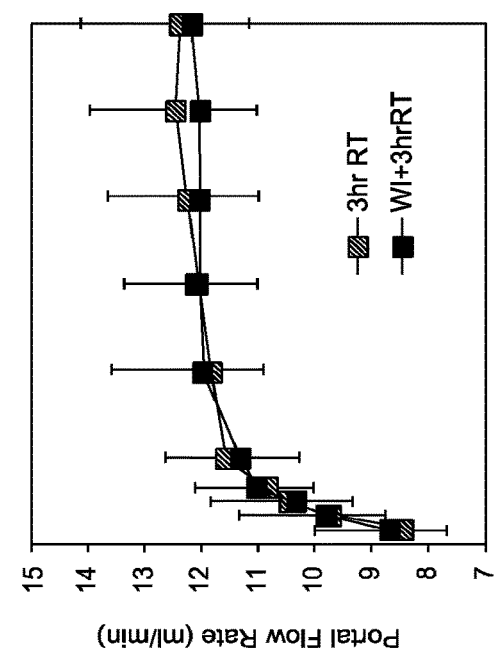
Figure 6D:
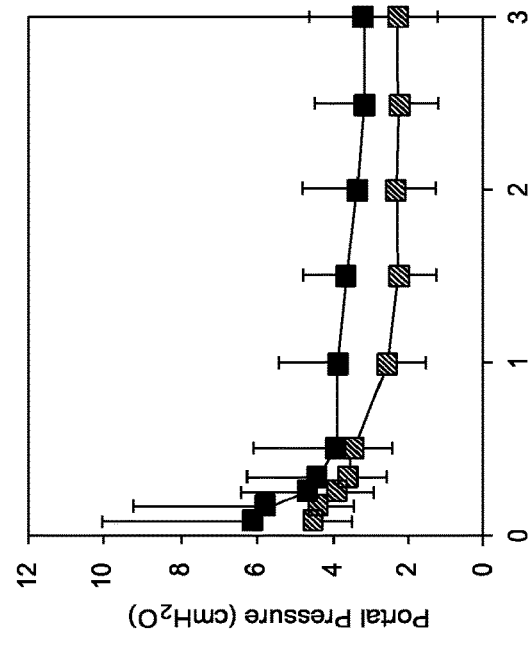

Perfusion removes waste and provides substrates for ATP regeneration. Liver perfusion was initiated at a low flow rate (FIG. 6A), the value of which was gradually raised over time as portal pressure declined (FIG. 6B), resulting in an overall decline in hepatic resistance (FIG. 6C) and removal of debris, measured as total protein (FIG. 6D). The removal of debris was visible during perfusion, with the regions closest to the hepatic veins clearing first, leaving an ever widening-ring of peripheral clots and blood to be washed out. The liver appeared homogeneously perfused within 20 minutes (FIG. 4A), which coincided with the plateau in debris released (FIG. 6D). The extent to which removal of debris reduced total hepatic resistance was also apparent within the first 20 minutes (FIG. 4B), after which hepatic resistance continued to decline without much change in total protein release. For similar flow rate profiles, WI+3hrRT livers tended to consume less oxygen, produce lactate at a higher rate, and have higher portal pressures and hepatic resistances. 3hrRT livers also had a distinct inverse correlation between flow rate and cell yield, producing fewer cells at higher flow rates (Pearson's correlation 0.94). WI+3hrRT livers produced equivalent cell yields to 3hrRT livers at the higher flow rates of 1.8 ml/min/g liver, but failed to increase their yield as flow rate declined (Pearson's correlation of 0.45).These trends, though statistically not different between groups, suggest impaired perfusion in WI+3hrRT livers due to structural differences at the micro-vascular scale.

Synthetic function was not significantly different between groups. WI+3hrRT livers did not initiate bile production immediately, resulting in less accumulation over time (FIG. 4C), though production rate was similar to 3hrRT livers after t=2 hrs. WI+3hrRT livers appeared to degrade albumin content throughout perfusion, while 3hrRT livers did not produce an appreciable amount of albumin during this time frame; there was no significant difference between perfused liver groups and the final concentrations were similar (FIG.

Figure 4A:
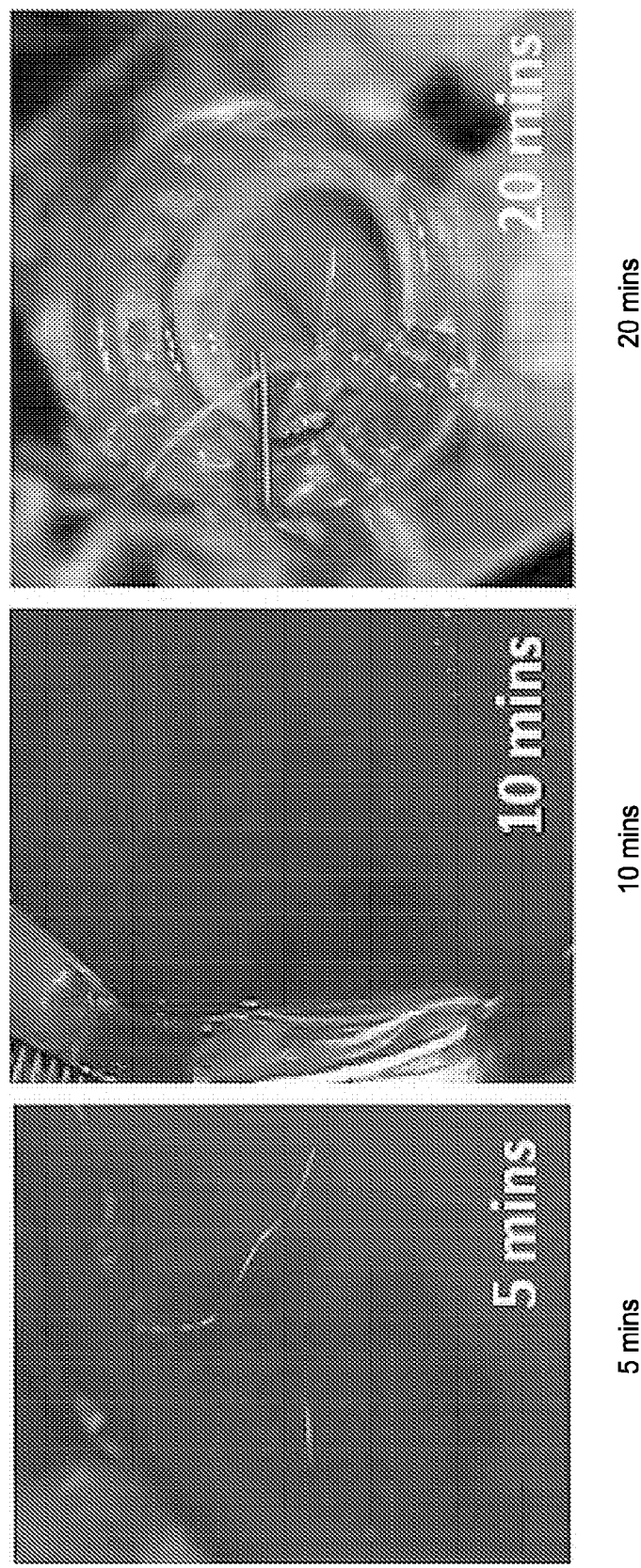
FIGS. 4A-4F illustrate the liver performance in perfusion.
Figure 4B:
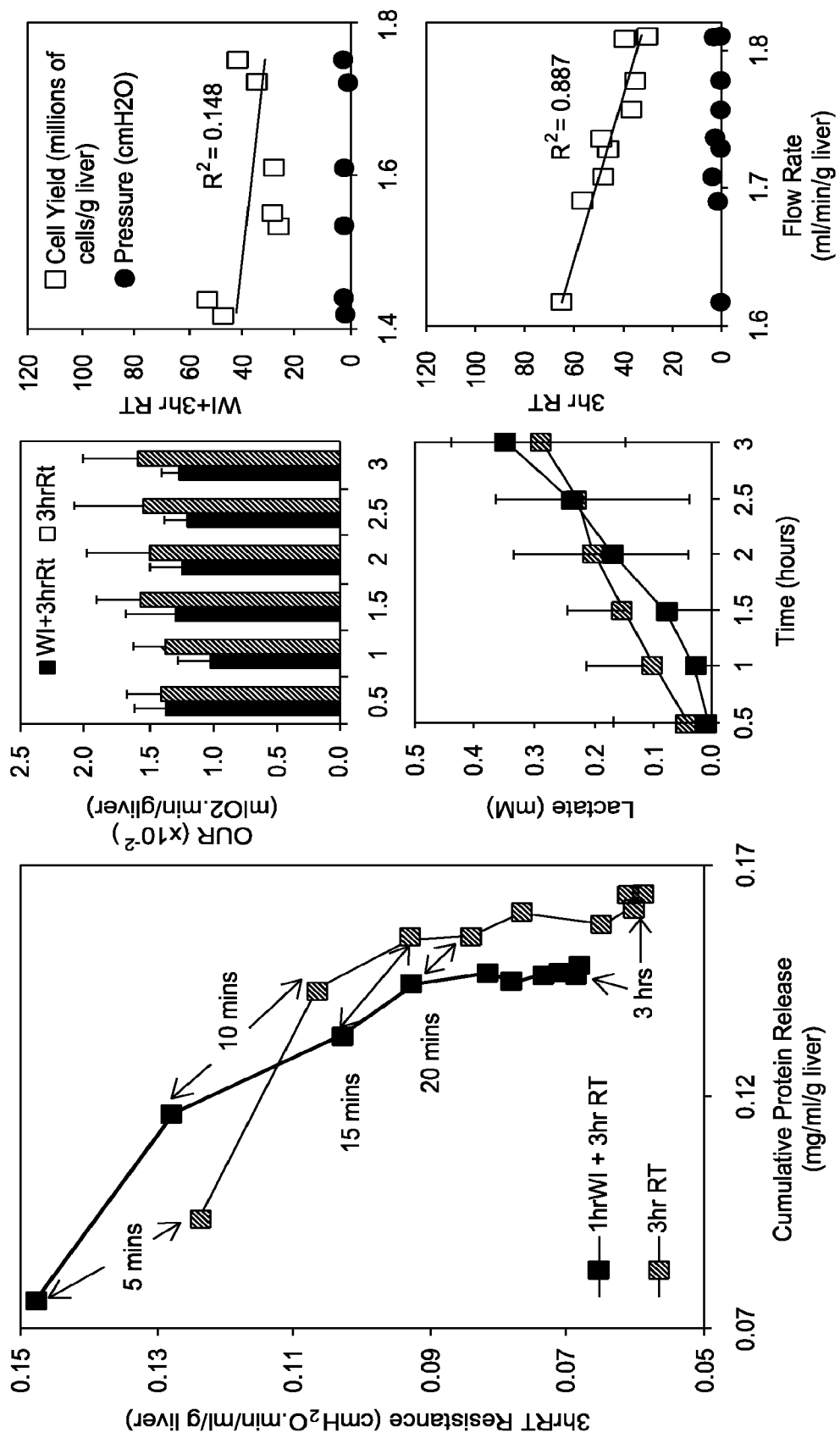
Figures 4C, 4D, 4E:
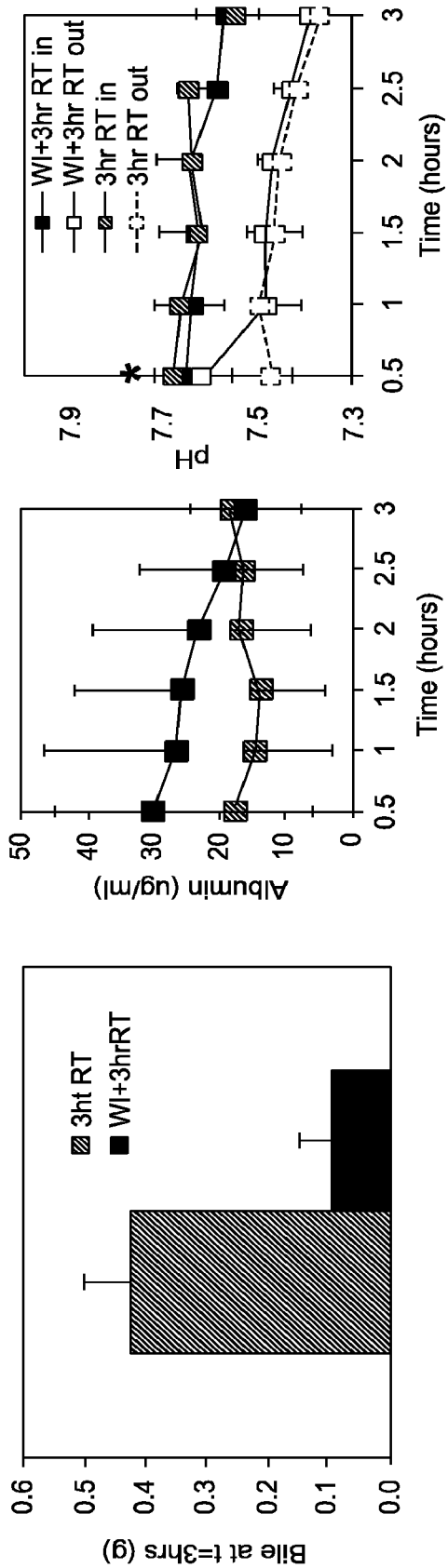
Figure 4F:
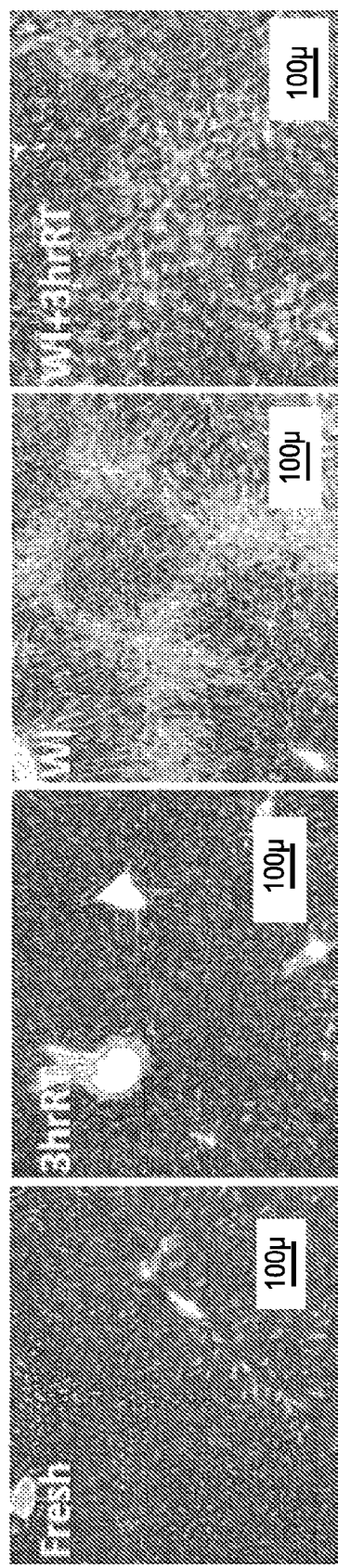
Figure 7A:
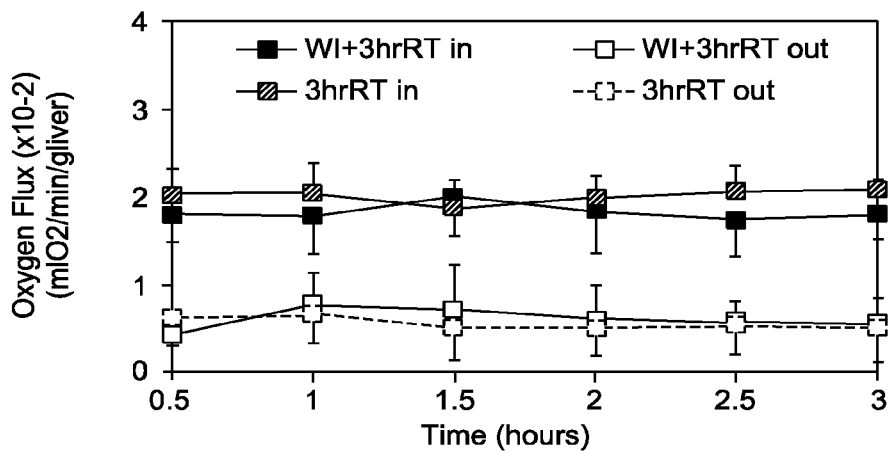
FIGS. 7A-7C illustrate.
Figure 7B:
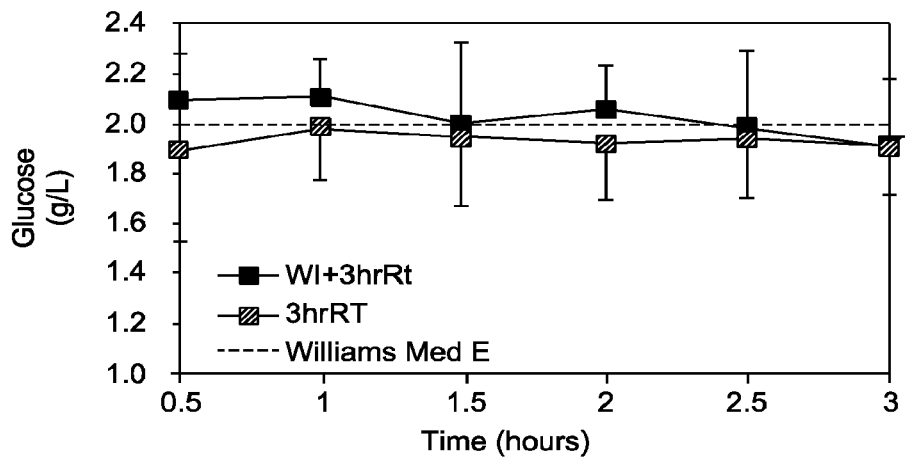
Figure 7C:
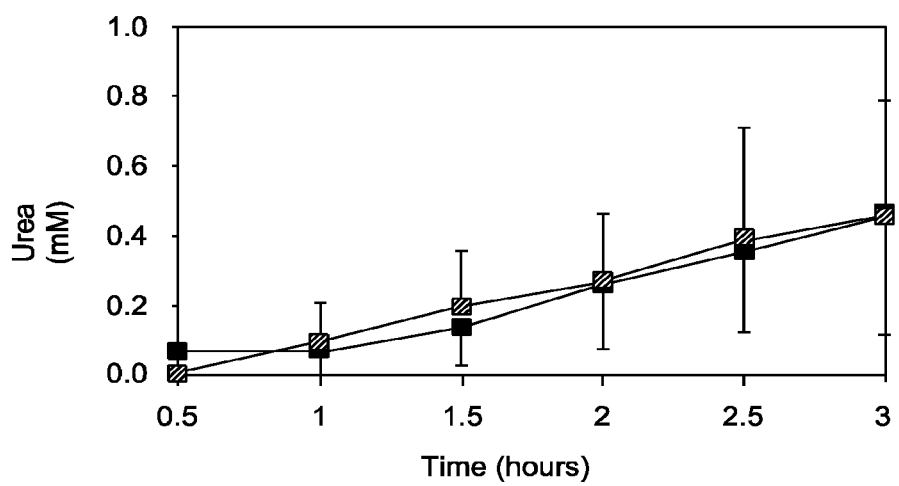

4D). Both groups showed adequate pH regulation (FIG. 4E) and production of urea (FIG. 7). WI+3hrRT livers showed a dramatic, though incomplete, recovery of glycogen stores (FIG. 4F).

Figure 5A:
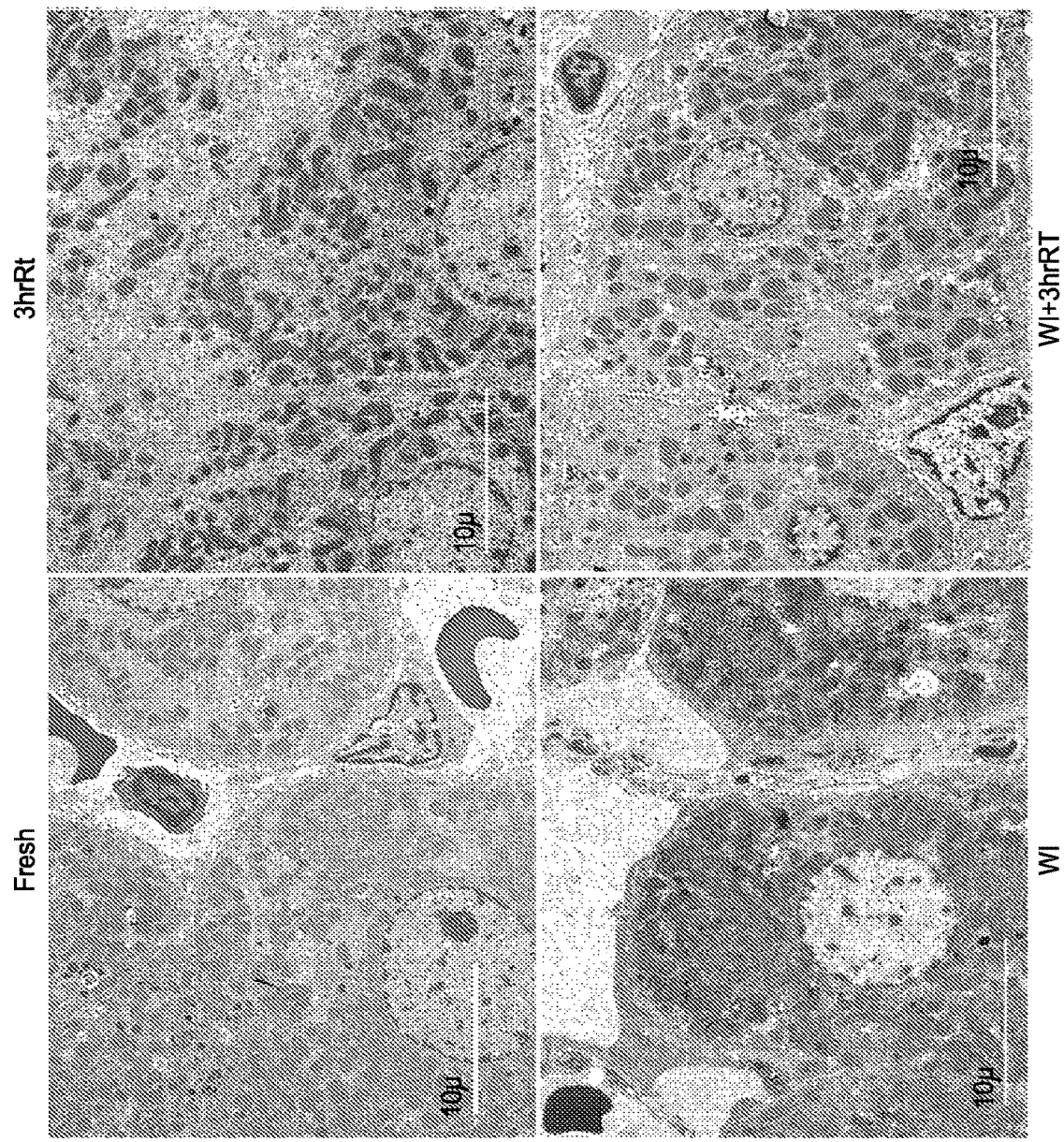
FIGS. 5A-5C illustrate.
Figures 5B, 5C:
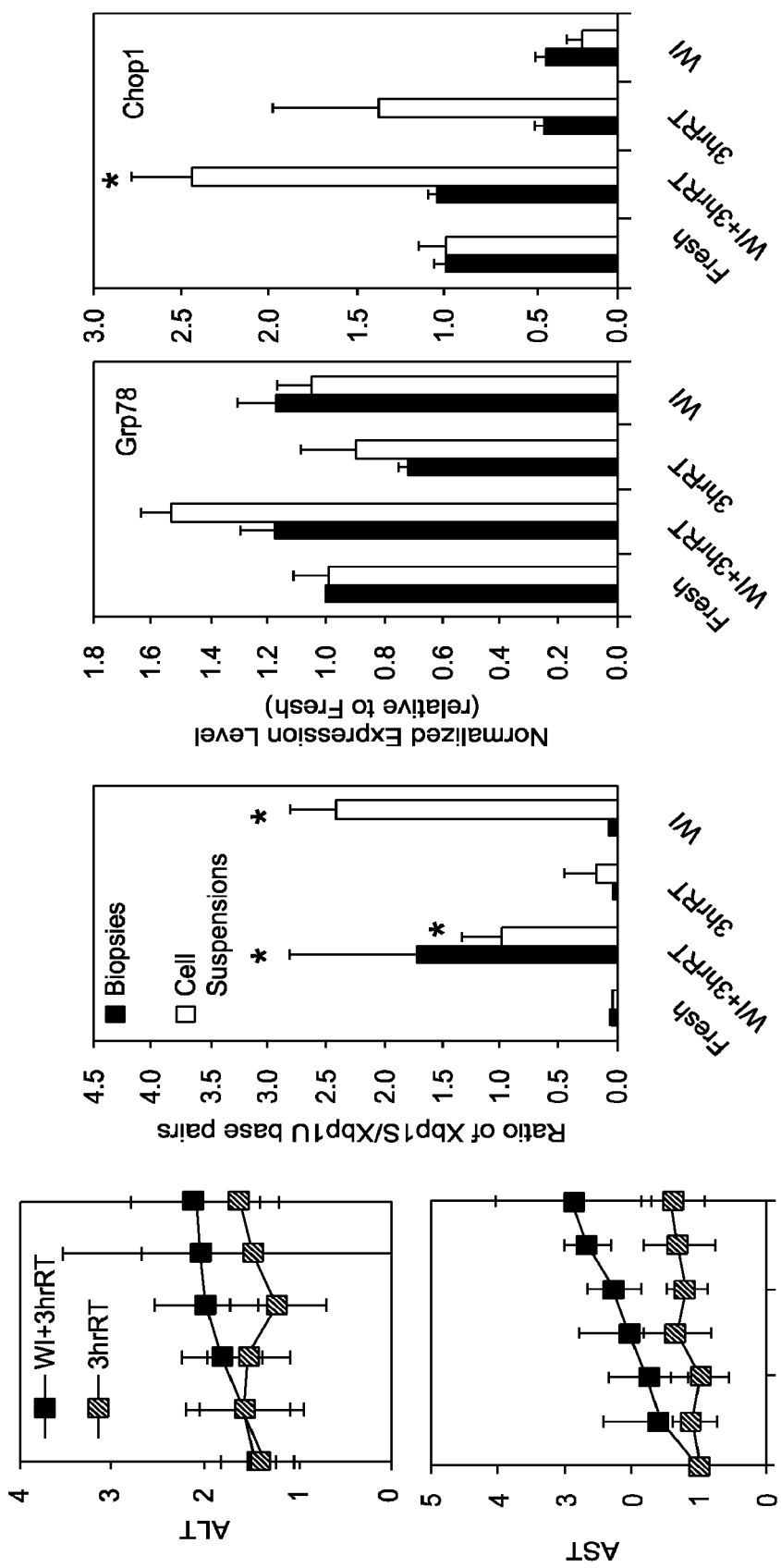
Figure 8A:
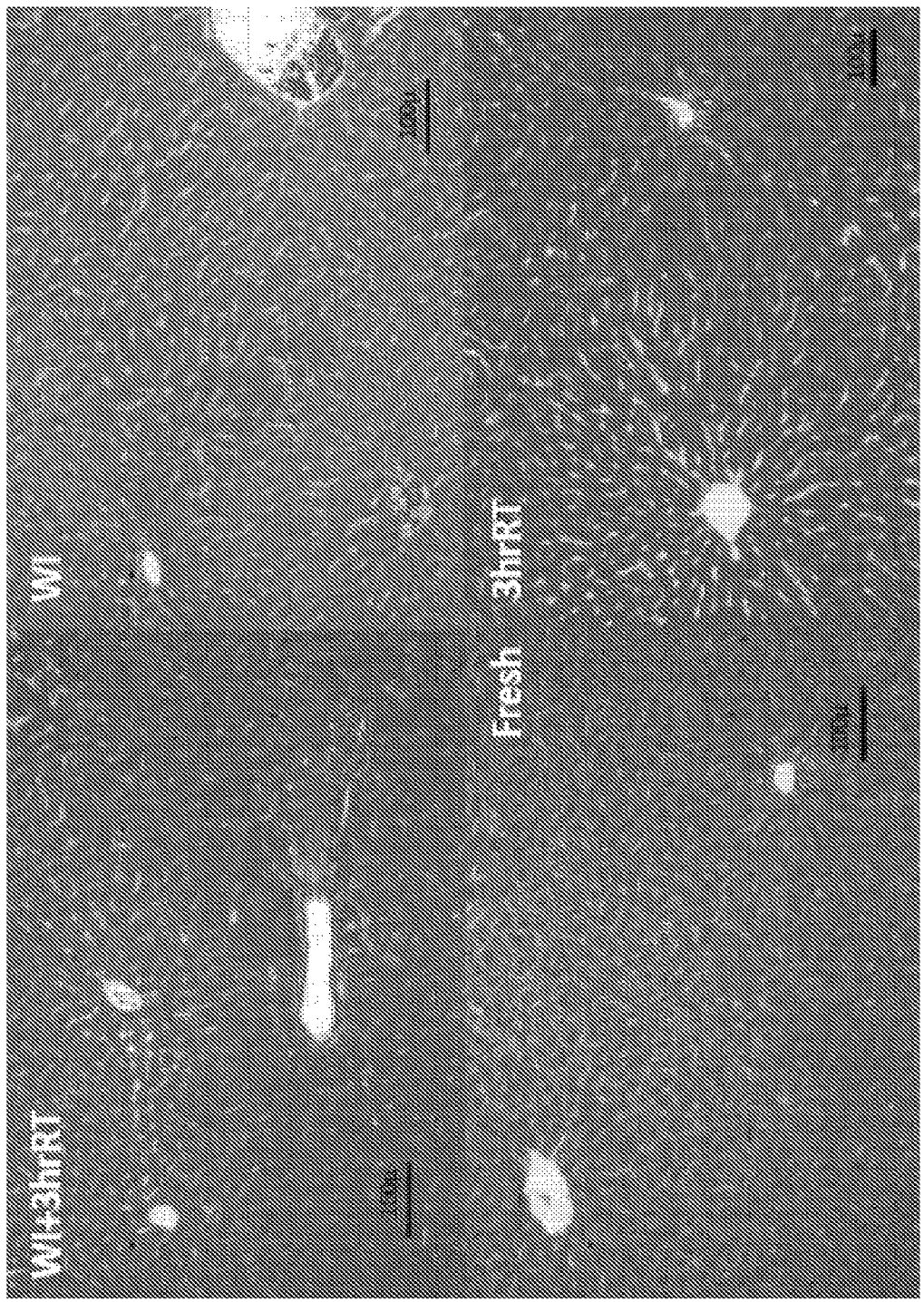
FIGS. 8A-8B illustrate the assessment of ultra-structural changes sustained during ischemia and reperfusion.
Figure 8B:
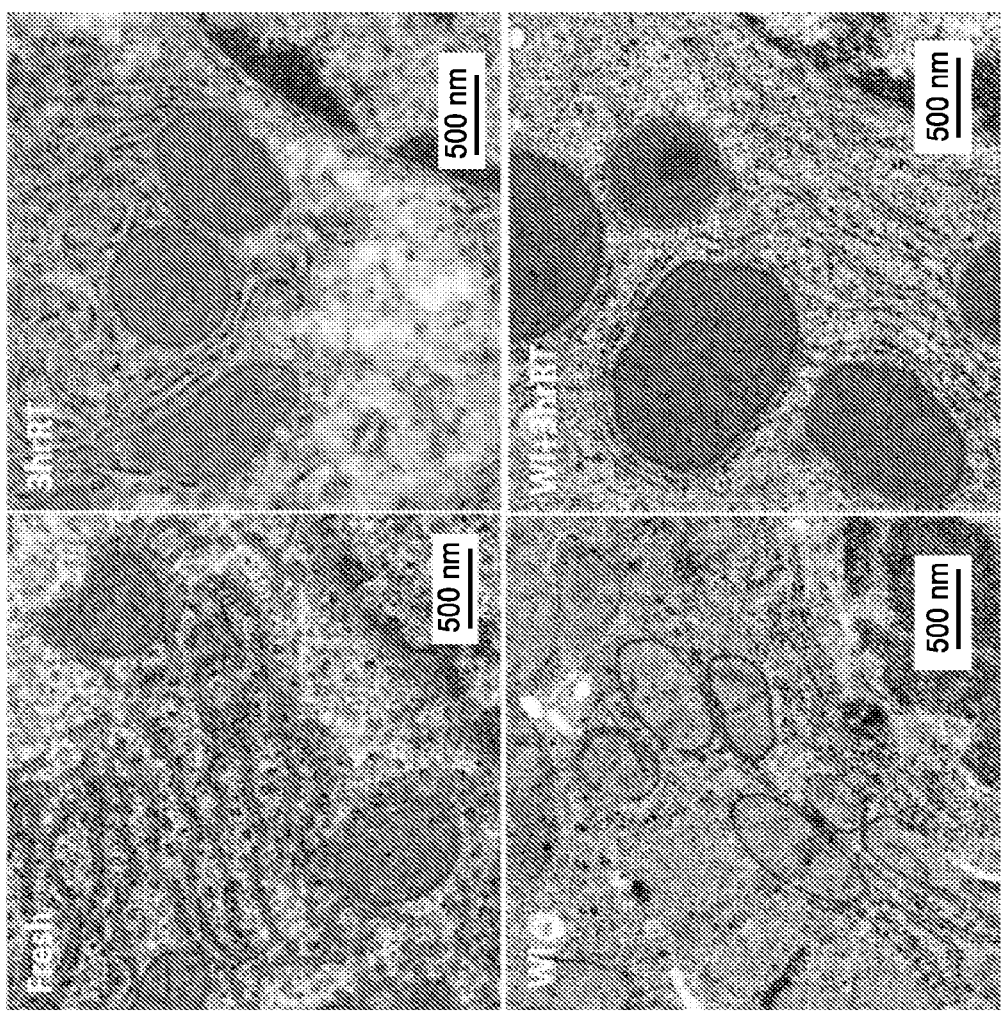

To assess ultra-structural changes sustained during ischemia and reperfusion, microscopic evaluation of WI, Fresh, and perfused liver groups was conducted. II&E (FIG. 8A) revealed intact hepatic architecture with no evidence of cellular necrosis or apoptosis, which was verified by negative fluorescent TUNEL stains (data not shown). Both perfused groups exhibited slight sinusoidal dilatation that correlated with edematous weight gain measured at the end of perfusion of 5.6±2.8% and 1.3±4.8% for 3hrRT and WI+3hrRT livers respectively. At the micron scale, TEM revealed both intra- and intercellular differences between groups (FIG. 5A). Compared to Fresh, WI livers were distinguishable by the retention of cytoplasmic structures but the absence of microvilli at the cell membrane. This was most clearly observed on the free surface of the cell, which was largely shrunken, detached from the endothelium in places and smooth. At higher magnification (FIG. 8B), some cells exhibited loss of rough endoplasmic reticulum (rER) and granularity of mitochondria, with evidence of cytoplasmic vacuoles and aggregation of nuclear material. WI+3hrRT livers by contrast had completely regained normal cell membrane appearance but were notable for enlarged cytoplasm to nuclear ratios, minimal appearance of rER, swollen mitochondria and continued evidence of aggregated nuclear material. 3hrRT livers had indistinct cell membranes; there were no obvious microvilli interjecting clearly demarcated intercellular, sinusoidal and canalicular surfaces, and in some areas, aggregations of blebs were seen within these spaces. At higher magnifications (FIG. 8B) less rER was evident but mitochondria and the nucleus appeared normal and intact. ALT and AST release during perfusion was constant in 3hrRT livers, but gradually and steadily increased with time for WI+3hrRT livers (FIG. 5B).

Figure 9A:
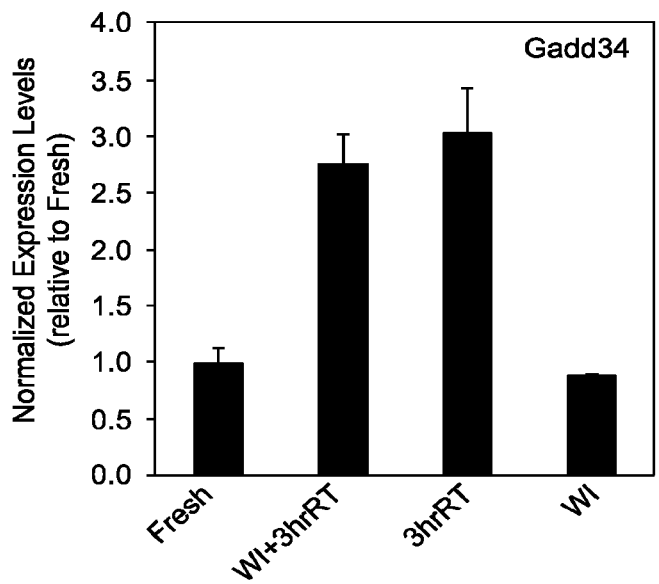
FIGS. 9A-9C illustrates downstream activity of CHOP1 activation.
Figure 9B:
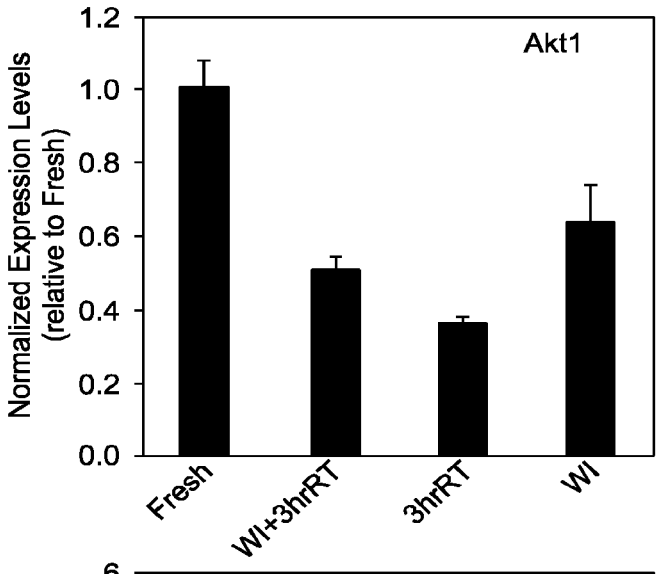
Figure 9C:
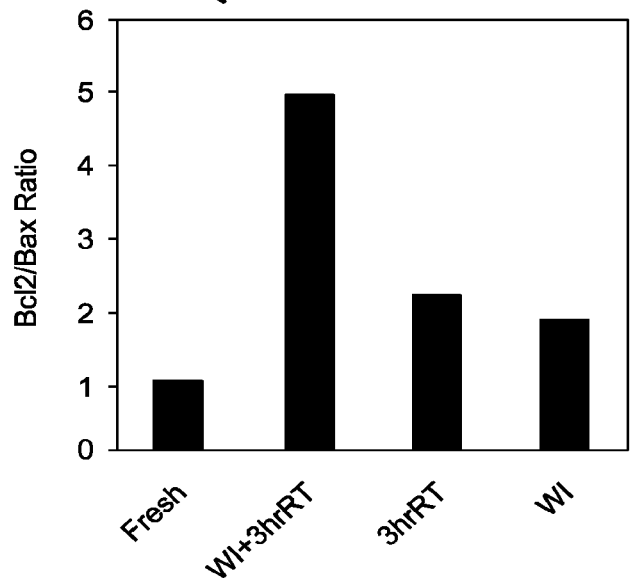

The changes in structure-function relationships, particularly the reduction in albumin synthesis, in association with the reduction in rER present in the cytoplasm of perfused livers, prompted investigation into the possible presence of the unfolded protein response (UPR) and ER stress. Activation of the three pathways associated with ER stress were evaluated with R'T'-PCR; type I trans-membrane protein kinase endoribonuclease (IRE1α), type I transmembrane protein kinase (PERK), and activating transcription factor (ATF6). Specifically, the increased prevalence of spliced X box-binding protein-1 (sXBP-1), C/EBP-homologous protein (CHOP1), and glucose-regulated protein 78 (Grp78 or BiP), were examined respectively in post perfusion biopsy samples and after cell isolation (FIG. 5C). The trends observed in WI+3hrRT tissue biopsies, especially exacerbated in latercell suspension samples, demonstrated up-regulation of all these pathways. By contrast, biopsies of 3hrRT livers were unchanged or down-regulated in these pathways, and comparable to Fresh livers in all cases except CHOP1, which was increased in cell suspension. Downstream evidence of CHOP1 activity was confirmed by up-regulation of protein phosphatase 1 (Gadd34), and down-regulation of Aktl in both groups (FIG. 9). Interestingly, as CHOP1 is also associated with the downregulation of anti-apoptotic B cell lymphoma (Bcl-2) and upregulation of pro-apoptotic BCL-2-associated X protein (Bax), it was surprising to determine that compared to Fresh livers, the Bcl-2/Bax ratio was 5-fold higher in WI+3hrRT livers, and 2-fold higher in both 3hrRT and WI livers (FIG. 9), promoting anti-apoptotic and anti-autophagy (Samali, A., Fitzgerald, U., Deegan, S., Gupta, S. Methods for monitoring endoplasmic reticulum stress and the unfolded protein response. *International Journal of Cell Biology*2010(2009)).

MATERIALS AND METHODS FOR EXAMPLE 1

Experimental Groups. Experiments were conducted on female Lewis rats (160 g-180 g) which were kept in accordance with National Research Council guidelines. The Subcommittee on Research Animal Care, Committee on Research, MassachusettsGeneral Hospital approved the experimental protocols. Animals were randomly divided into four groups: 1) Livers that were exposed to an hour of warm ischemia at 34° C. (WI), 2) Livers that were perfused for 3 hours at room temperature after 1 hr WI (WI+3hrRT), 3) Fresh livers (Fresh), and 4) Fresh livers perfused for 3 hours at room temperature (3hrRT).

Hepatectomy. Livers were excised according to the technique of Delriviere et. al.(Delriviere, L., Gibbs, P., Kobayashi, E., Goto, S., Kamada, N., Gianello, P. Detailed modification technique for safer harvesting and preparation of liver graft in the rat. *Microsurgery*17, 690-696 (1996). Briefly, a transverse abdominal incision was made and the intestines retracted to expose the portal vein (PV), the common bile duct (CBD), and the inferior vena cava (IVC). The CBD was cannulated (12 cm, 22 G polyethylene stent, Surflo, Terumo, Somerset, NJ) and the IVC freed from the right renal and adrenal veins. The portal vein (PV) was freed from the splenic and gastroduodenal veins. The right phrenic vein emptying into the supra-hepatic vena cava (SHVC) was ligated. The hepatic artery was then ligated and the IVC clamped. Finally, the PV was clamped and the clock started for ischemic duration. The diaphragm was opened, the SHVC was transected, and the liver was removed, and weighed. Fresh livers were then immediately prepared for biopsy. 3hrRT livers were placed in a bowl of room temperature saline to be cuffed at the PV and IVC prior to perfusion with an average ischemic time of 5-10 minutes. WI livers were placed in a temperature-controlled chamber filled with saline and maintained at 34±0.1° C. for 1 hr during which time they were cuffed.

Ex Vivo Perfusion.

Perfusate. The perfusate comprised 750 ml phenol red-free Williams Medium E (Sigma Chemical, St. Louis, MO) supplemented with 2 u/L insulin (28.85 units/mg Ilumulin, Eli Lily, Indianapolis, IN), 100,000 u/L penicillin, 100 mg/L streptomycin sulfate (Gibco, Invitrogen,Grand Island,NY), 0.292 g/L L-glutamine (Gibco), 10 mg/L hydrocortisone (Solu-Cortef, Pharmacia & Upjohn, Kalamazoo, MI), and 1000 u/L heparin (APP, Schaumberg, IL).

Perfusion System. The circuit comprised a peristaltic pump which brought perfusate from a reservoir to a membrane oxygenator, through a bubble trap and to an 18 G catheter for portal flow into the liver. The liver was positioned on a fine flexible mesh surface, permeable to perfusate, in a perfusion chamber. Effluent flowed freely from the IVC and SHVC into the chamber where it was then returned to the perfusate reservoir (FIG. 1). The oxygenator was gassed with a mixture of 95% $O_2$/5% $CO_2$. Upon completion of cuffing of 3hrRT livers and after the period of warm ischemia for WI+3hrRT livers, organs were immersed in a drained perfusion chamber into which perfusate dripped at 4 ml/min; perfusion chamber outflow was redirected to a catch basin where effluent from the liver was collected for the first 20 minutes before the circuit was closed.

Samples. Using a simple manometer, portal pressure was recorded every 5 minutes during this flushing, as were flow rates which were gradually increased over time in accordance with the drop in pressures observed. It was desirable to achieve in vivo flow rates of –1.8 ml/min/g liver (Izamis, M., Uygun, K., Berthiaume, F. & Yarmush, M. In vivo metabolic fluxes in rat livers: effect of burn injury. *Biotechnol Bioeng* (2011 Apr; 108(4):839-52)) but preference was given to sustaining an absolute pressure below 4-6cmH$_2$O. At t=30 mins and every half hour after, additional sampling commenced with 1.2 ml perfusate aliquots collected and stored at –80° C. for later analysis. Inflow and outflow blood gas analysis was also performed at this time for pO2 and pH measurements, corrected to 20° C. (Rapidlab, Chiron Diagnostics, Norwood, MA).Bile was collected in a tube outside the perfusion chamber and both it and the livers were weighed at the end of perfusion. Total protein was measured using the Bradford method of dye-binding solubilized protein (BioRad protein assay kit, Hercules, CA). Standard assay reagents were used for glucose (Stanbio 1075-825), urea (Stanbio proc. #0580, Boerne, TX), and lactate (Trinity Biotech proc. #735, Jamestown, NY) and an ELISA was used to detect albumin.

Hepatocyte Isolation. A two-step collagenase perfusion technique described by Seglen (1976), and modified by Dunn et al. (1991) was used to isolate hepatocytes. Briefly, using aseptic technique, after gaining portal vein access with an 18 G catheter, warm oxygenated KRB+EDTA was flowed through the livers at approximately 17 ml/min. For Fresh livers, the IVC was immediately dissected and the liver subsequently removed from the animal into a petri dish until perfusion was completed. Perfused and WI livers were already in petri dishes with cuffed PVs. A collagenase (type IV, Sigma, C5138-1 G) solution with KRB and CaCl$_2$ was introduced to perfusion as the KRB solution was depleted and allowed to flow until successful digestion was observed. The livers were then moved to a sterile hood on ice where approximately 10 mL of sterile, cold KRB were added. The liver capsule was gently broken to release the cells which were then passed through a 250 um filter followed by a 60 um filter. The suspension was divided into 50 mL conical tubes and centrifuged at low speed (15 g-21 g, 4° C., no brake, 5 minutes). The supernatant was aspirated and the pellet resuspended with 10 ml KRB. An initial cell count and viability was performed. A volume of 24 mL of cold Percoll solution (9 parts Percoll: 1 part 1.5M NaCl, pH 5-5.5) was used for every 25 mL of cell suspension. Cells were added at a concentration of 5 mllion cells/mL and inverted several times before being centrifuged (49-58 g, 4° C., no brake, 10 minutes). The buffy coat and supernatant were discarded andresuspended to 10 mL in DMEM+10% FBS+100,000 u/L penicillin+100 mg/L streptomycin sulfate, after which a final count was performed using Trypan Blue exclusion.

Cell Suspension. Cells were diluted to 1 mllion/ml in Williams Medium E and aliquoted into 1.6 mL microcentrifuge tubes, 4 separate vials were used for each assay except for Trypan Blue exclusion where time permitted only 2. The tubes were subsequently rotated at slow speeds in a 37° C. incubator. Light-blocked vials for CYP450 activity were allowed to settle between readings, but manually agitated after each reading.

ALT and AST. 4 vials each were prepared for ALT and AST. At every hourly time point starting at t=0 hrs, 15 ul from each vial was placed into a 96 well plate on ice. At t=6 hours, Triton-X 100 was diluted to 1% concentration with a volume of the remaining cells. The cells were lysed by rapid pipetting, and then diluted 1:4 with PBS; 15 ul from each vial was finally added to the 96 well plate as the positive control. 150 ul of reagent at room temperature was then rapidly pipetted into the wells and a kinetic endpoint assay provided enzyme activity per minute (TR71121 and 7200-006, Thermo Electron, Pittsburgh, PA). The results were subsequently normalized to the completely lysed cells.

CYP450 activity. 4 vials for each of the CYP450 enzymes to be tested were prepared; these included benzyloxy resorufin (CYP4502B2), pentoxy resorufin (CYP4502B1), ethoxy resorufin (CYP4501A1) and methoxy resorufin (CYP4501A2). 20 µl of 6 mM stock solution 3,3'-methylene-bis(4-hydroxycoumarin) was added to each vial (Sigma M1390) and allowed to incubate for 20 minutes. 10 µL of 1 mM solutions of each of the isoenzymes was then added to the vials. The vials were inverted several times and a 50 µL sample was taken at t=0 minutes and stored on ice, away from light. Samples were taken again at 10, 20, 30 and 40 mins. A standard was prepared by serial dilution of 1000 nM resorufin. Samples and standards were read with a fluorescence plate reader (Ex530, Em590) and recorded as rates of resorufin production per million cells.

Glucose, Albumin and Urea. 4 vials were incubated for the entire 6 hr duration, spun down and the supernatant was stored at –80° C. Standard assay reagents were used for glucose (Stanbio 1075-825) and urea (Stanbio proc. No. 0580), and an elisa was used to detect albumin.

Viability. 2 vials were counted hourly using Trypan Blue exclusion to test for viability.

Mitochondrial activity. The MTT assay was performed hourly by pipetting approximately 50,000 cells (50 µL) from 4 vials into 4 wells on a 96-well plate and diluting with 50 µL of Williams Medium E for 4×100 µL of cell suspension. 1 vial of MTT was thawed (Biotium, Inc., 30006) and 10 µL added to each well. Samples were mixed gently while incubating at 37° C., protected from light. The plates were then spun at 800 rpm, the supernatant removed, and 200 µL of DMSO added to dissolve the Formazan. Absorhance was read at $OD_{570}$-$OD_{630}$.

qRT-PCR.RNA was extracted from approximately 20-30 mg of tissue using TRIzol® Reagent extraction process. Total RNA quality was assessed by spectroscopy, and reverse transcribed to cDNA using the Two Step RT-PCR Kit (Invitrogen #11735-040) following the manufacturer's instructions in a Perkin Etus Thermal Cycler 480. cDNA was analyzed by qPCR using the Stratagene mx3005P instrument with the following cycling conditions: step 1) 55° C. for 2 min and 95° C. for 2 min; step 2) amplification at 95° C. for 30 sec, 58° C. for 30 sec, and 72° C. for 50 cycles. A melting curve was used to confirm the specificity of each primer pair. Each sample was run in triplicate to exclude outliers. Gene expression was analyzed using the ΔΔCT method, using β- actin as the normalizer gene.

Plate Culture

Cells were plated in standard 6-well plates using a double layer collagen gel sandwich plate culture (Dunn, J.C., Tompkins, R. G., Yarmush, M. L. Long-term in vitro function of adult hepatocytes in a collagen sandwich configuration. *Biotechnol Progr*7, 237-245 (1991) with C+H as the culture medium; phenol red-free medium was used in the CYP450 assays. Enough plates were prepared for 3 wells to be devoted to each assay on days 5, 7, 10 and 14.

Viability. Hoechst 33452 and Ethidium homodimer-1 double stain was used to detect all nuclei, and dead nuclei, the difference in numbers providing us with a measure of viability. Briefly, 10 µL of a 1 mM solution of Ethd-1 and 5 µL of Hoechst 33452 were added to 5 ml of PBS, while protected from light exposure. Medium from the cells was washed with PBS and 1 ml of the dye-PBS solution was added to each well. The cells were incubated at 37° C. for 10-15 minutes before processing using a Zeiss axiovert 200 microscope. Thirty five snapshots were taken at distinct locations within each well for each dye, overlaid on corresponding phase contrast images. Cell nuclei were subsequently counted using CellProfiler (Broad Institute, Cambridge, MA).

Mitochondrial activity. 100 µL of MTT were added to each well and incubated for 1 hr at 37° C. The medium was subsequently aspirated from the wells and 1 mL of 6 mg/mL collagenase was added and incubated at 37° C. for 15 minutes and pipetted rigorously to dissolve all collagen. 1 mL of DMSO was then added and the contents rigorously pipetted up and down to dissolve the formazan present. 250 µL samples were subsequently placed in triplicate on a 96 well plate (3 wells ×3 samples) and absorbance was read at $OD_{570}$-$OD_{630}$.

CYP450 activity. 48 hours before the assay, 1 mL of a 2 µM solution of 3-methylcholanthrene inducer was added to each well. This medium was left on the cells for the subsequent 48 hours. 5 µM and 80 µM solutions of substrate solution and dicumarol respectively were prepared to a volume of 5 ml (1 ml/well) by diluting in EBSS. After 48 hours, the medium was aspirated and 1 ml of warm EBSS was added to each plate. After 15 minutes, the EBSS was aspirated and 1 ml of the substrate-dicumarol solution was added to each well. 50 µL of medium was subsequently removed at t=5,15 25, and 35 minutes and placed in a 96-well plate protected from light. A standard was prepared by serial dilution of 1000 nM resorufin. Samples and standards were read with a fluorescence plate reader (Ex530, Em590) and recorded as rates of resorufin production per million cells.

Glucose, Albumin, Urea. Plates prepared for analysis on Day 14 were used to provide daily media for metabolic analyses using the same assays as above (in Suspension cultures).

Tissue Biopsies

Tissue sections were rapidly frozen in liquid nitrogen upon resection of Fresh livers, after perfusion was complete for WI+3hrRT and 3hrRT livers, and after 1 hr of warm ischemia for WI livers. Remaining lobes were then perfused with 15 mL of Karnovsky's solution for histological preparation.

ATP. ATP content was measured in tissue segments homogenized with a mortar and pestle under liquid nitrogen and resuspended in 500 µL of nucleotide releasing buffer (Biovision, #K254-200). Each sample was spun down at 16000 rpms for 2 minutes. 100 µL of sample was subsequently placed in a cuvet and the assay continued as prescribed in the kit. Data were plotted against a standard and normalized to the total protein present in the sample supernatant using a standard Bradford assay.

Light Microscopy. Biopsy samples were fixed in 10% formalin, embedded in paraffin, sectioned, andstained with hematoxylin and eosin. Apoptosis was evaluated through TUNEL staining (Promega #G3250, Madison WI).

Transmission Electron Microscopy. Constructs were fixed overnight in modified Karnovsky fixative (2.5% Glutaraldehyde, 2.5% formaldehyde, 0.1M cacodylate buffer, pII 7.2), washed with 0.1M buffer, post fixed in 1% osmium tetroxide in 0.1M cacodylate buffer, and dehydrated in a graded series of ethanol. The samples were infiltrated and embedded in a mixture of Spurrs resin and Quetol according to Ellis_ENREF_51 (Ellis, E. A. Solutions to the problem of substitution of ERL 4221 for vinyl cyclohexane dioxide in Spurr Low Viscosity Embedding Formulations. *Microscopy Today*14(2006)). 60-80 nm cross sections and en face sections were cut on an Ultracut E microtome (Reichert, Depew, NY) using a diamond knife. Thin sections were stained with 5% uranyl acetate and Reynolds lead citrate. The sections were viewed with a JEOL JEM 1010 transmission electron microscope (JEOL, Tokyo, Japan) and images were digitally captured on an AMT XR-41B CCD camera system (Advanced Microscopy Techniques Inc., Danvers, MA) (Bueno, E. M., Saiedi, N., Melotti, S., Ruberti, J. W. Effect of serum and insulin modulation on the organization and morphology of matrix synthesized by bovine corneal stromal cells. *Tissue Eng Part A*15, 3559-3573 (2009)).

qRT-PCR. The same procedure used on biopsy samples was employed on 1 mllion freshly isolated cells stored in 350 ul RA1. Samples were evaluated for select Phase I and II genes as well as XBP1, Grp78 and CHOP1.

Statistical Analysis. Comparisons between groups were done using ANOVA. The criterion for statistical significance was $P<0.05$.

Example 2

Determination of Burn Injury on Hepatic Metabolism.

To determine the effect of burn injury on hepatic metabolism, rats were subjected to a dorsal burn corresponding to 20% of the total body surface area, or a combined dorsal and ventral burn corresponding to a total body surface area of 40%. Three days after burn, the animals were fasted overnight, and on the fourth day, portal vein and hepatic artery flow rates were measured and blood samples were taken. Sham controls consisted of rats that underwent the same procedures, but experienced an immersion in water at 20° C.

Metabolite Concentration Analysis. FIG. 10 displays the group averages of the measured extracellular metabolite concentrations in the portal vein (PV), hepatic artery (HA) and hepatic veins (SHVC) in addition to the flow rates and liver weights. Additional relevant blood chemistry values not used specifically for MFA are represented in Table 4. Nitrogen fluxes are accounted for in Table 5.

There were no elevations in liver enzymes (ALT, AST and ALP) or total bilirubin (Giknis, M. L. A., Clifford, C. B. Clinical Laboratory Parameters for Crl: CD(SD) Rats. (2006); Vollmar, B., Pradarutti, S., Richter, S., Menger, M. D. In vivo quantification of ageing changes in the rat liver from early juvenile to senescent life. Liver 22, 330-341 (2002)) amongst any of the vessels in all groups suggesting that no significant liver damage occurred within four days of burn injury. Plasma creatinine and urea nitrogen values remained within normal range for all rats suggesting unimpaired renal function due to burn injury.

Flow rates generally increased in the portal vein and decreased in the hepatic artery for burn groups compared to sham. Overall values ranged between 1.7-2.2 ml/min/g liver in the portal vein and 0.07-0.05 ml/min/g liver in the hepatic artery for a cumulative inflow of 1.77-2.25 ml/min/g liver.

Trends common to all vessels likely signify the systemic impact due to burn. For example, a significant decrease in albumin and total hemoglobin levels occurred equally in both burn groups. Lactate levels were slightly decreased in the 20% TBSA burn group but elevated 4-fold in the 40% TBSA burn group. This particular finding, combined with reduced dissolved oxygen from low hemoglobin levels, low pH, and high carbon dioxide values suggest a mildly acidotic state induced by the liver in 40% TBSA burn animals.

Obvious dose-dependent changes in concentrations were generally not observed. The most apparent circumstance in which this occurred was a significant four-fold increase in SHVC insulin levels (Table 4). There was also a dose-dependent systemic decrease in VLDL and TG content reflected equally in all vessels (Table 4).

A general appreciation of amino acid metabolism was obtained by accounting for nitrogen. At the bottom of FIG. 10 is a summation of the total circulating amino acid nitrogen in each vessel. Arterial nitrogen, most representative of the systemic state of the body, demonstrates a slight decline in total nitrogen compared to sham (−3.5% and −1% in 20% and 40% TBSA burns respectively). The burn groups had 13 out of 20 amino acids with reduced trends compared to sham, except for arginine, ornithine and cysteine, which were increased systemically, and histidine, valine, tyrosine and phenylalanine, which were unchanged. In the PV, sham nitrogen content remained virtually unchanged from the HA, however the burn groups demonstrated a dose-related increase from intestinal contributions (3.3% and 8.9% in 20% and 40% TBSA burns respectively). SHVC nitrogen content of the burn groups was generally 5% greater than in sham. All groups had a SHVC nitrogen content significantly lower than either the IIA or PV. Nitrogen flux across the liver (Table 2) shows that 20% TBSA burn livers took up as much nitrogen as sham livers but produced more albumin. 40% TBSA burn livers took up the surplus nitrogen but did not alter albumin production; rather they increased their urea nitrogen output suggesting the use of protein preferentially as an energy source.

In order to appreciate the effects of the liver on specific amino acids, influxes (Table 3) and fluxes across the liver were calculated (Table 4). Influxes took the combined contributions of the PV and HA into account, and estimated a total delivery rate of each metabolite to the liver. The efflux subtracted from the influx provided the flux across the liver. Though there were no significant differences in influx across any of the groups, dose-dependent trends of increasing influxes were observed for all amino acids except asparagine, aspartate, glutamate, glutamine, glycine, histidine, and serine, which were similar across groups. Increased uptake from this list of amino acids represents hepatic-specific requirements in the absence of mass-action driving fluxes. Glycine and serine had systemically low concentrations and demonstrated a dose-dependent significant increase in hepatic uptake. Glutamine and glutamate had systemically low concentrations; their uptake by the liver was insignificantly and equally increased. Asparagine and aspartate had systemically low concentrations. Here the flux across livers with the smaller burn was reduced compared to sham while the 40% TBSA burn fluxes were normal. Livers in the bigger burn group preferentially consumed more of these amino acids thereby increasing the flux and significantly lowering the output concentration. Histidine concentration did not vary with burn and its fluxes remained within normal range. Systemically increased concentrations, and the only cases of significantly increased HA concentrations in burn, were those of arginine, cysteine and ornithine (40% TBSA burn only). These subsequently-increased influxes correlated strongly with reduced fluxes across the burn liver groups. Conversely, increases in PV concentrations outweighed concentration values in the HA that were within or below normal range. This resulted in substantially increased fluxes across the liver for proline, phenylalanine, lysine, alanine, threonine, and tyrosine. The BCAAs also had increasing influx trends due to increased PV concentrations. All BCAA fluxes demonstrated a slight upward trend in 20% TBSA burn compared with sham. In the 40% TBSA burn group however, each BCAA differed: valine had a significantly reduced flux, isoleucine was within normal range, and leucine was significantly increased. The resulting SHVC concentration values were below normal for the glucogenic amino acids, normal for the ketogenic ones and elevated for the BCAAs. To determine whether particular increases in influxes were necessary to determine whether the liver would take up or release an amino acid, ratios of burn influxes to sham influxes were calculated. These did not reveal any correlations between change in influx and liver action in any of the groups.

TABLE 4

Non-MFA In vivo Hepatic Blood Chemistry Values.

| PARAMETER | SHAM (n = 12) | 20% TBSA (n = 12) | 40% TBSA (n = 13) |
|---|---|---|---|
| SUPRAHEPATIC VENA CAVA (SHVC) (SHVC) | | | |
| Insulin (ng/ml) | 1.1 ± 0.01 | 3.8 ± 0.02 | 4.5 ± 0.02* |
| AST (u/L) (87-114) | 96 ± 25.7 | 93 ± 26.8 | 122 ± 50.9 |
| ALT (u/L) (28-40) | 48 ± 13.0 | 39 ± 9.50 | 40 ± 7.30 |
| ALP (u/L) (136-188) | 209 ± 66.0 | 166 ± 63.0 | 165 ± 57.4 |
| Total Bilirubin (mg/dL) (0.1-1.0) | 0.32 ± 0.06 | 0.31 ± 0.03 | 0.32 ± 0.06 |
| Creatinine (mg/dL) (0.5-0.6) | 0.25 ± 0.09 | 0.23 ± 0.049 | 0.22 ± 0.04 |
| Cholesterol (mg/dL) (55-89) | 62 ± 21.3 | 71 ± 19.7 | 68 ± 11.2 |
| HDL (mg/dL) | 33 ± 7.41 | 32 ± 8.4 | 32 ± 7.27 |
| LDL (mg/dL) | 28 ± 12.3 | 35 ± 14.9 | 32 ± 3.4 |
| VLDL (mg/dL) | 9 ± 3.3 | 5 ± 1.10 | 4 ± 0.45 |
| Triacylglycerol (mg/dL) (62-92) | 37 ± 17.0 | 22 ± 4.76 | 22 ± 2.38 |
| PORTAL VEIN (PV) | | | |
| AST (u/L) (87-114) | 95 ± 30.0 | 110 ± 2.36 | 47 ± 45.4 |
| ALT (u/L) (28-40) | 53 ± 15.1 | 47 ± 7.20 | 43 ± 7.92 |
| ALP (u/L) (136-188) | 231 ± 81.7 | 188 ± 86.9 | 198 ± 58.9 |
| Total Bilirubin (mg/dL) (0.1-1.0) | 0.32 ± 0.06 | 0.34 ± 0.05 | 0.32 ± 0.06 |
| Creatinine (mg/dL) (0.5-0.6) | 0.21 ± 0.03 | 0.22 ± 0.04 | 0.21 ± 0.03 |
| Cholesterol (mg/dL) (55-89) | 68 ± 20.0 | 86.4 ± 18.6 | 82 ± 8.50 |
| HDL (mg/dL) | 36 ± 3.15 | 42 ± 10.5 | 35 ± 3.56 |
| LDL (mg/dL) | 26 ± 11.1 | 37 ± 12.2 | 41 ± 6.94 |
| VLDL (mg/dL) | 11 ± 4.47 | 6 ± 1.33 | 5 ± 1.03 |
| Triacylglycerol (mg/dL) (62-92) | 48 ± 23.8 | 27 ± 8.15 | 24 ± 4.80 |
| HEPATIC ARTERY (HA) | | | |
| AST (u/L) (87-114) | 109 ± 33.5 | 103 ± 37.6 | 116 ± 44.2 |
| ALT (u/L) (28-40) | 55 ± 15.7 | 40 ± 10.5 | 44 ± 9.87 |
| ALP (u/L) (136-188) | 259 ± 75.6 | 156 ± 93.5 | 186 ± 42.1 |
| Total Bilirubin (mg/dL) (0.1-1.0) | 0.32 ± 0.06 | 0.32 ± 0.04 | 0.35 ± 0.05 |
| Creatinine (mg/dL) (0.5-0.6) | 0.21 ± 0.03 | 0.23 ± 0.05 | 0.25 ± 0.08 |
| Cholesterol (mg/dL) (55-89) | 72 ± 20.4 | 67 ± 22.2 | 74 ± 13.7 |
| HDL (mg/dL) | 32 ± 9.82 | 32 ± 11.6 | 34 ± 4.40 |
| LDL (mg/dL) | 30 ± 13.4 | 32 ± 15.0 | 39 ± 8.10 |
| VLDL (mg/dL) | 12 ± 3.24 | 7 ± 2.4 | 5 ± 0.89 |
| Triacylglycerol (mg/dL) (62-92) | 51 ± 21.2 | 31 ± 10.9 | 24 ± 4.53 |

Bolded items are significantly different ($p < 0.05$) from SHAM.
*value for 40% TBSA is significantly different ($p < 0.05$) compared to 20% TBSA burn.

TABLE 5

Nitrogen Flux Across the Liver.

|  | Sham | 20% TBSA | 40% TBSA |
|---|---|---|---|
| Net Urea Nitrogen Output (umol/min) | 3.6 | 6.4 | 9 |
| Net Albumin Nitrogen Output (umol/min) | 318 | 344 | 298 |
| Net Amino Acid Nitrogen Uptake (umol/min) | 21 | 21 | 31 |

TABLE 6

Measured Influx Values.

| METABOLITE | PV + HA |
|---|---|
| Total Oxygen (ml O2/min/g liver) | 0.26 ± 0.14 |
| Albumin (g/min/g liver) | 0.03 ± 0.01 |
| Lactate (mmol/min/g liver) | 0.07 ± 0.03 |
| Glucose (mg/min/g liver) | 1.81 ± 0.68 |
| Alanine (umol/min/g liver) | 0.64 ± 0.28 |
| Ammonia (umol/min/g liver) | 0.15 ± 0.04 |
| Arginine (umol/min/g liver) | 0.25 ± 0.25 |
| Asparagine (umol/min/g liver) | 0.08 ± 0.04 |
| Aspartate (umol/min/g liver) | 0.03 ± 0.01 |
| Cysteine (umol/min/g liver) | 0.02 ± 0.01 |
| Glutamate (umol/min/g liver) | 0.11 ± 0.04 |
| Glutamine (umol/min/g liver) | 0.48 ± 0.2 |
| Glycine (umol/min/g liver) | 0.43 ± 0.17 |
| Histidine (umol/min/g liver) | 0.22 ± 0.13 |
| Isoleucine (umol/min/g liver) | 0.15 ± 0.08 |
| Leucine (umol/min/g liver) | 0.44 ± 0.22 |
| Lysine (umol/min/g liver) | 0.36 ± 0.18 |
| Methionine (umol/min/g liver) | 0.07 ± 0.03 |
| Ornithine (umol/min/g liver) | 0.19 ± 0.09 |
| Phenylalanine (umol/min/g liver) | 0.09 ± 0.04 |
| Proline (umol/min/g liver) | 0.26 ± 0.1 |
| Serine (umol/min/g liver) | 0.32 ± 0.15 |
| Threonine (umol/min/g liver) | 0.33 ± 0.14 |
| Tyrosine (umol/min/g liver) | 0.11 ± 0.06 |
| Valine (umol/min/g liver) | 0.28 ± 0.16 |

The in vivo influx is the combined portal vein (PV) and hepatic artery (HA) contribution to that flux. "Perfusion" is calculated according to the initial portal perfusate influx.

TABLE 7

Measured In vivo Metabolic Fluxes Across the Liver.

| METABOLITE | SHAM (umol/hr/g) | 20% TBSA (umol/hr/g) | 40% TBSA (umol/hr/g) |
|---|---|---|---|
| Oxygen uptake | 249 ± 132 | 247 ± 15 | 404 ± 148* |
| Carbon Dioxide output | 216 ± 30 | 191 ± 228 | 291 ± 20 |
| Glucose output | 93 ± 37 | 28 ± 17 | 124 ± 135 |
| Lactate uptake | 5.6 ± 2.6 | −7.3 ± 7.0 | 87 ± 67* |
| Acetoacetate output | −1.3 ± 0.6 | 1.1 ± 2.7 | −5.5 ± 10 |
| β-Hydroxybutyrate output | 21 ± 16 | 11 ± 17 | 8.7 ± 9.1 |
| Urea output | 28 ± 23 | 25 ± 38 | 76 ± 34 |
| Ammonia uptake | 6.2 ± 1.7 | 5.3 ± 0.6 | 6.6 ± 1.6 |
| Alanine uptake | 13 ± 6.0 | 24 ± 10 | 31 ± 8.0 |
| Arginine uptake | 3.6 ± 5.1 | 2.3 ± 1.8 | 2.8 ± 3.1 |
| Ornithine uptake | 3.4 ± 0.9 | 2.6 ± 2.5 | 0.1 ± 2.0 |
| Asparagine uptake | 2.0 ± 1.1 | 0.9 ± 0.2 | 1.6 ± 0.4* |
| Aspartate uptake | 0.5 ± 0.4 | 0.2 ± 0.3 | 0.5 ± 0.3 |
| Cysteine output | 0.2 ± 0.0 | 0.0 ± 0.1 | −0.3 ± 0.1* |
| Glutamate output | 0.8 ± 1.3 | 1.1 ± 1.1 | 1.0 ± 3.4 |
| Glutamine uptake | 2.0 ± 2.5 | 4.0 ± 4.4 | 3.2 ± 0.5 |
| Glycine uptake | 5.4 ± 1.2 | 7.1 ± 2.5 | 9.2 ± 2.6 |
| Histidine uptake | 8.0 ± 5.3 | 8.0 ± 3.8 | 11 ± 3.3 |
| Proline uptake | 0.7 ± 2.9 | 4.8 ± 1.4 | 6.9 ± 3.4 |
| Serine uptake | 2.7 ± 1.7 | 4.8 ± 1.6 | 6.4 ± 2.7 |
| Methionine uptake | 0.8 ± 0.1 | 0.9 ± 0.4 | 1.1 ± 0.4 |
| Threonine uptake | 1.2 ± 4.0 | 2.4 ± 4.9 | 6.0 ± 3.2 |
| Valine uptake | 0.8 ± 0.4 | 1.2 ± 2.8 | −0.1 ± 0.4 |
| Tyrosine uptake | 1.0 ± 1.1 | 1.0 ± 0.4 | 1.5 ± 0.3 |
| Isoleucine uptake | −0.2 ± 0.7 | 0.5 ± 1.3 | −0.3 ± 0.1 |
| Phenylalanine uptake | 0.5 ± 0.4 | 2.2 ± 0.6 | 2.0 ± 1.0 |
| Lysine uptake | 1.5 ± 0.4 | 5.1 ± 5.7 | 8.3 ± 5.3 |
| Leucine uptake | −0.2 ± 3.5 | 3.1 ± 3.1 | 13 ± 7.0* |

Values in bold are significantly different from sham group ($p < 0.05$)
*Values significantly different from 20% TBSA group ($p < 0.05$)

Metabolic Flux Analysis

Figure 12:
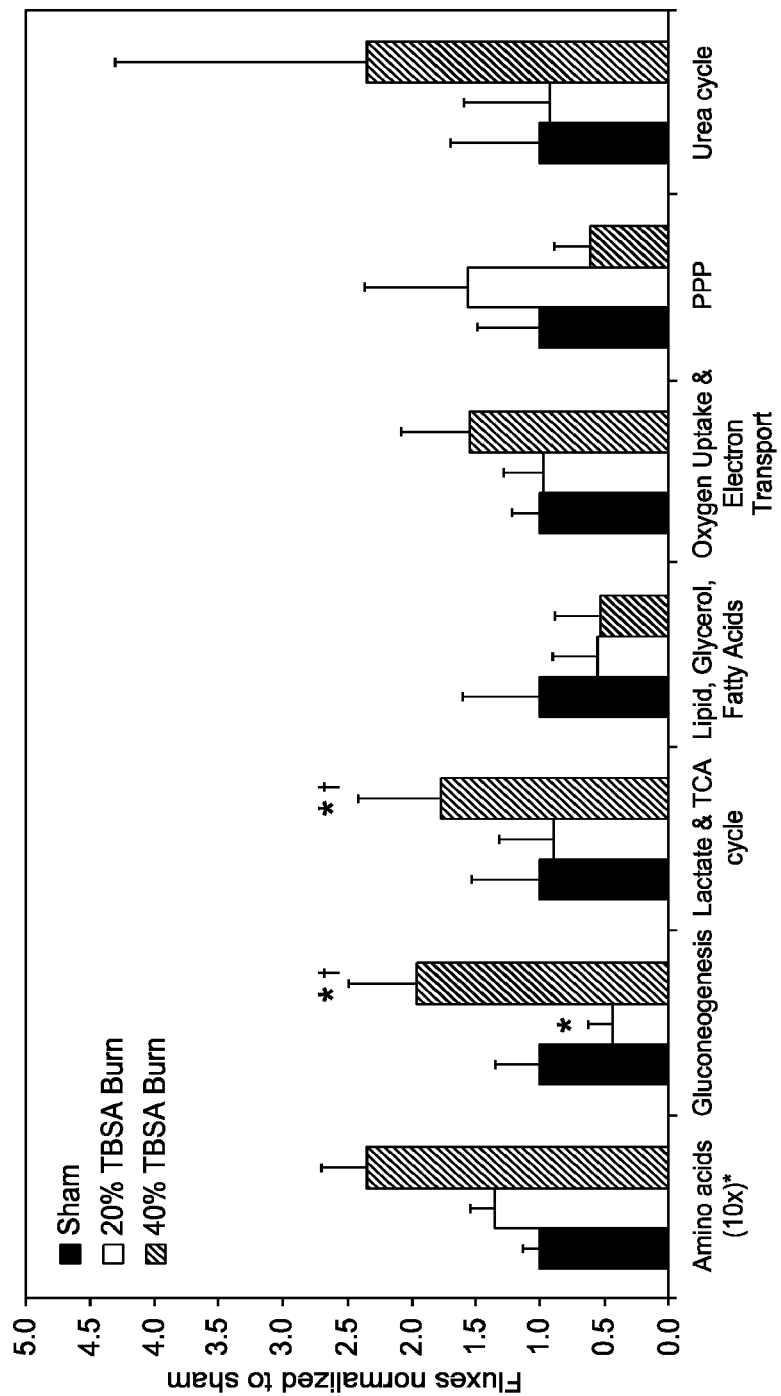
FIG. 12 summarizes the effects of burn injury on the major pathways in the hepatic metabolic network. Values shown are the averages of all fluxes in each pathway group, which were then normalized to the sham group. Pathways (from Table 8) are grouped as follows: Gluconeogenesis: #1-7, Lactate metabolism and TCA cycle: #8-14, Oxidative phosphorylation: #53-55, 61. Pentose phosphate pathway: #56-60. Amino acid metabolism: #18, 21-47, Urea cycle: #15-17, 19-20, Lipid metabolism: #48-52.

A total of 28 fluxes across the liver were calculated from the measured metabolite concentrations, flow rates and liver weights from each rat and averaged (Table 7). MFA then estimated the unmeasured internal metabolic fluxes Table 8 and FIG. 11) using the measured external fluxes. The significant results are mapped in FIGS. 12-15. FIG. 12 represents cumulatively how fluxes in each major pathway were altered (amino acid metabolism, gluconeogenesis, TCA cycle, lipid metabolism, oxidative phosphorylation, and urea cycle). The results show a significant reduction in gluconeogenesis for 20% burn in contrast to a significant increase in 40% burn. Dose dependent responses are seen in increased amino acid metabolism, and the reduced uptake of fatty acids and glycerol. In all other circumstances, the 40% TBSA burn group has increased fluxes compared to 20%, which approximates sham. Only the PIP suggests an increase in 20% burn compared to 40% burn and sham.

Figure 13:
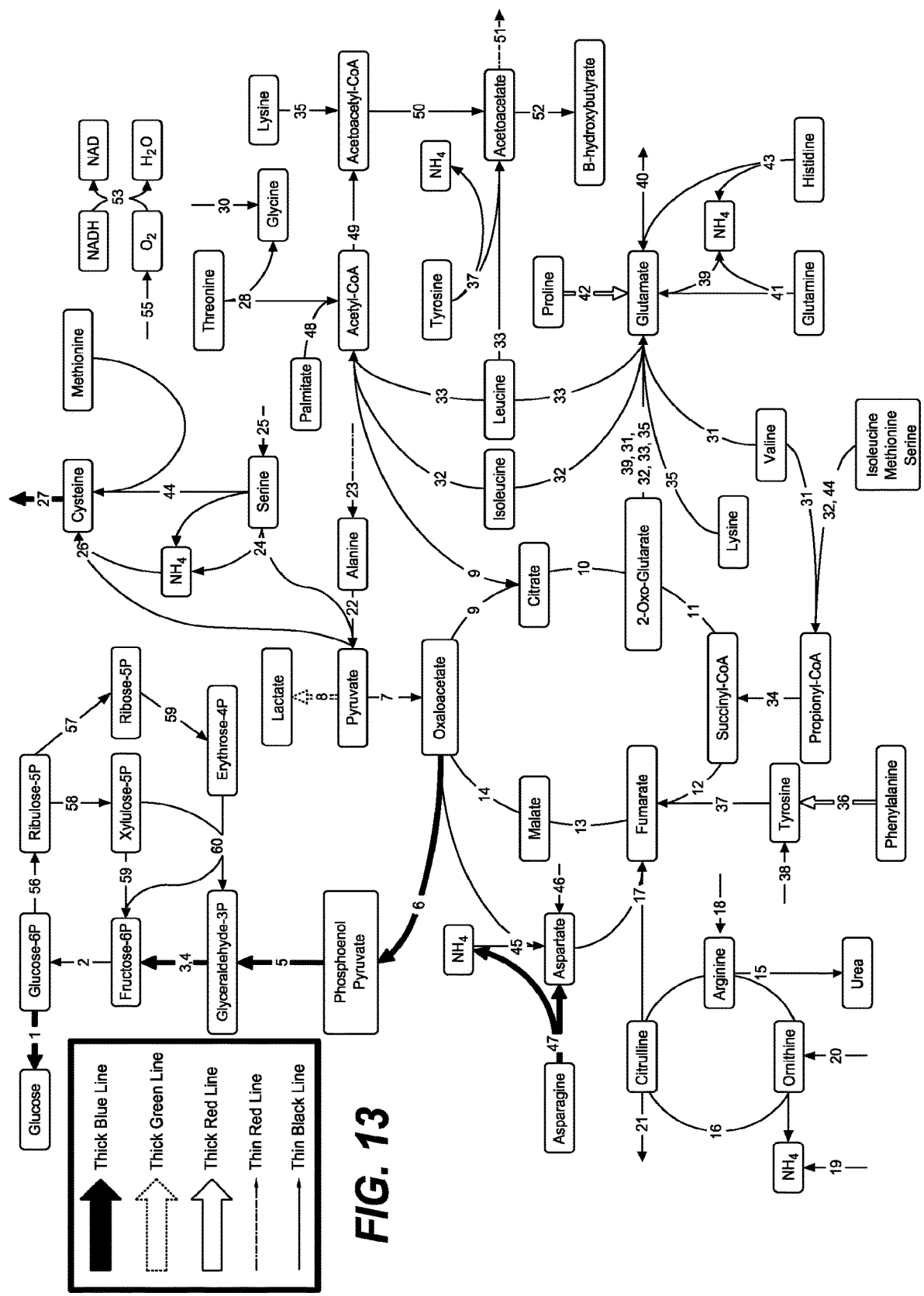
FIG. 13 illustrates flux directions reflecting 20% TBSA results vs. sham controls. Red=Upregulated. Blue=Downregulated, Green=Reversed.
Figure 14:
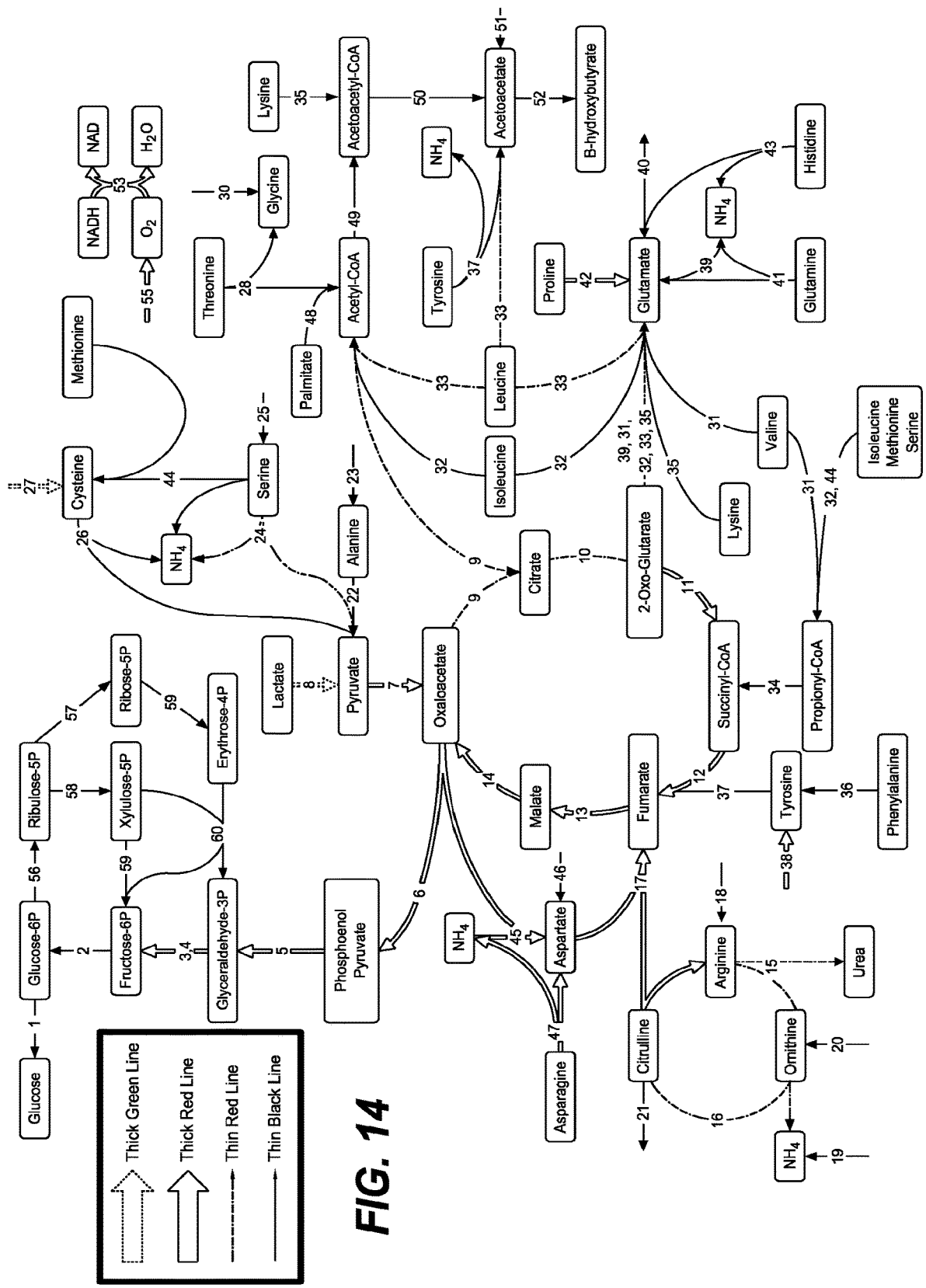
FIG. 14 illustrates flux directions reflecting 40% TBSA results vs. sham controls. Red=Upregulated. Blue=Downregulated, Green=Reversed.

The metabolic flux distributions are depicted as comparisons of the 20% TBSA and 40% TBSA burn groups to the sham controls in FIGS. 13 and 14, respectively. The 20% TBSA burn group demonstrated few significant overall changes compared to sham (FIG. 13). The most prominent finding was a major reduction in gluconeogenesis, despite being fasted, which favors an increase in this pathway. The concentration of glucose exiting the liver was low, but within range of sham values. The impact of reduced gluconeogenesis on oxidative metabolism was to retain TCA fluxes at sham values, but fluxes feeding into the TCA cycle were smaller or diverted. The hydrolysis of asparagine to aspartate and ammonia, for example, was significantly reduced, while acetoacetate production increased ($p<0.1$), a pathway that is favored when the concentration of acetyl CoA exceeds the oxidative capacity of the TCA cycle. Pyruvate tended to be redirected elsewhere, such as to the production of lactate, the plasma concentration of which was reduced systemically. Fluxes contributing to the PPP tended to increase, which coincided with previous results on burn metabolism using isolated perfused rat livers (Lee, K., Berthiaume, F., Stephanopoulos, G. N., Yarmush, D. M., Yarmush, M. L. Metabolic Flux Analysis of Postburn Hepatic Hypermetabolism. *Metabolic Engineering* 2, 312-327 (2000). Though insignificant, amino acid metabolism was generally increased throughout (Table 8) except for asparagine, aspartate, ornithine, arginine and cysteine which were either decreased or unchanged.

By contrast, the 40% TBSA burn group showed a significant increase in gluconeogenesis (FIG. 14); again the glucose concentration levels were lower, but within range of sham upon exiting the liver. Lactate conversion to pyruvate was significantly increased as was the uptake of several gluconeogenic amino acids. In addition, increased uptake of ketogenic amino acids lysine and leucine occurred, resulting in a direct increase of glutamate fueling of the TCA cycle, and a subsequent increase in acetoacetate production. The urea cycle fluxes, as well as the fluxes connecting it to the TCA cycle were all significantly upregulated. The pentose phosphate pathway coincided with sham results.

Figure 15:
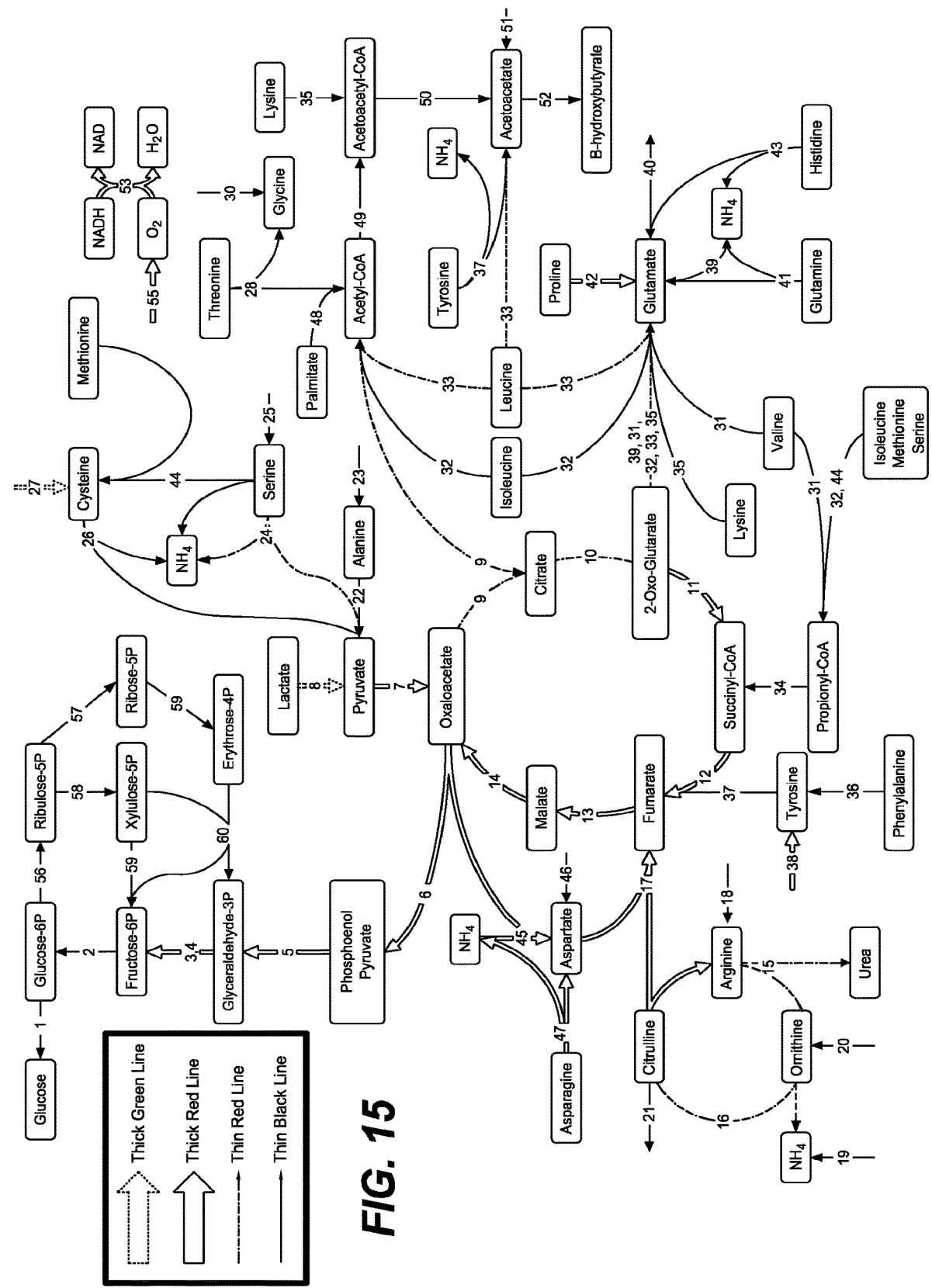
FIG. 15 illustrates flux directions reflecting 40% vs. 20% TBSA burns. Red=Upregulated. Blue=Downregulated, Green=Reversed.

FIG. 15 illustrates the differences in hepatic metabolism of the two burn models. Here it can be appreciated that the energy requirement of the 40% TBSA burn is significantly increased compared to a 20% TBSA burn, with enhanced contributions to the TCA cycle deriving from lactate, acetyl-CoA and amino acids. The consequences of producing more ATP were twice as much oxygen consumption and carbon dioxide output, and three times as much urea output compared to a 20% TBSA burn. Pathways common to both burn groups were significant dose-dependent increases in uptake of proline, phenylalanine and alanine (Table 8; $p<0.01$ in 20% TBSA burn).

TABLE 8

Balanced Metabolites for MFA

| | |
|---|---|
| Glucose-6-P | Citrulline |
| Fructose-6-P | Aspartate |
| Fructose-1, 6-P2 | Alanine |
| Glyceraldehyde-3-P | Glutamate |
| PEP | Serine |
| Pyruvate | Cysteine |
| Oxaloacetate | Glycine |
| NADH | Propionyl-CoA |
| Acetyl-CoA | Acetoacetate |
| Citrate | Acetoacetyl-CoA |
| alpha-Ketoglutarate | O2 |
| Succinyl-CoA | Tyrosine |
| Fumarate | Ribulose-5-P |
| FADH2 | Ribose-5-P |
| Malate | Xylulose-5-P |
| Arginine | Erythrose-4-P |
| Ornithine | CO2 |
| NH4+ | |

METHODS for EXAMPLE 2

Burn Injury Protocol. Male CD rats (Charles River Laboratories, Wilmington, MA) weighing 270-300 g (n≥5 for each group) were housed in a temperature- (25° C.) and light-controlled room (12-h light-dark cycle). The animals were cared for in accordance with the National Research Council guidelines. Experimental protocols were approved by the Subcommittee on Research Animal Care, Committee on Research, Massachusetts General Hospital. Water and rat chow were provided ad libitum. Animals were individually housed and allowed to adjust to their new surroundings for at least 2 days prior to inception of the experiment. On Day 0, rats were randomized into three groups and anesthetized with an intraperitoneal injection of ketamine (62.5 mg/kg of body weight) and xylazine (12.5 mg/kg of body weight). The dorsum of each rat was shaved with clippers, and those receiving a 40% total body surface area (TBSA) burn also had their abdomens shaved. The area to be burned was carefully marked. A full-thickness burn covering ~20% of the TBSA was administered through a 10-s immersion in boiling water (Carter, E. A., Derojas-Walker, T., Tami, S., Tannebaum, S. R., Yu, Y. M., Tompkins, R. G. Nitroc oxide production is intensely and persistently increased in tissue by thermal injury. Biochem J 304(1994)); the remaining 20% burn on the abdomen was administered through a 5-s immersion in boiling water (Baskaran, H., Yarmush, M. L., Berthiaume, F. Dynamics of Tissue Neutrophil Sequestration after Cutaneous Burns in Rats. *Journal of Surgical Research* 93, 88-96 (2000). Sham-treated animals were handled identically, except that room temperature water was used. Animals were then immediately resuscitated with an intraperitoneal saline injection (2.5 ml/kg per rat/% TBSA) and allowed to recover in individual cages. Animals were weighed every 24 hours and food consumption was monitored.

Measurement of Hepatic Flow Rates and Blood Sampling. It has been shown that whole-body parameters of hypermetabolism post-burn injury, including heart rate and temperature, are elevated and/or stable at Day 4 for rats of this age *J Burn Care Res* (2009 Nov-Dec;30(6):993-1001). Subsequently, on the third day following the burn injury, all rats were fasted overnight in preparation for blood sampling on the fourth day. This also coincided with the time point of ex vivo liver perfusions that were performed in earlier studies (Banta, S., Yokoyama, T., Berthiaume, F., Yarmush, M. L. Effects of dehydroepiandrosterone administration on rat hepatic metabolism following thermal injury. *Journal of Surgical Research* 127, 93-105 (2005); Lee, K., Berthiaume, F., Stephanopoulos, G. N., Yarmush, D. M., Yarmush, M. L. Profiling of Dynamic Changes in Hypermetabolic Livers. *Biotechnology and Bioengineering* 83, 400-415 (2003)) enabling the comparison of in vivo and ILP results. Fasting served the dual purpose of providing a baseline measurement of the absolute rate of protein breakdown in the body by which to compare trauma-induced catabolism, and creating a gluconcogenic state for unidirectional fluxes in the MFA model.

On Day 4 each rat was anesthetized with ketamine (62.5 mg/kg) and xylazine (12.5 mg/kg) and the abdomen was shaved from sternum to groin. A transverse abdominal incision was made and the xyphoid process clamped and retracted to expose the proximal abdominal contents. The intestines were moved aside and the caudal lobes of the liver gently elevated to reveal the portal triad. A perivascular ultrasonic flow-probe (Transonic Systems, Ithaca, NY) provided flow rates for the portal vein (PV) and hepatic artery (HA); acoustic resolution was improved with the use of lubricant gel. The sum of flow rates into the liver was assumed to equal the flow rate out via the suprahepatic vena cava (SIIVC).

Following flow rate measurements, a removable clamp was placed on the inferior hepatic vena cava, immediately distal to the liver, and caudal to the renal and adrenal vasculature. After a few minutes, gentle retraction of the liver revealed a markedly reduced SIIVC blood volume. A 23 G heparinized syringe was used to withdraw ~1 ml of blood at the point of confluence of the hepatic veins into the SHVC. This technique did not cause extraneous blood loss. The clamp was carefully removed and then placed on the portal vein proximal to the liver. A 23 G heparinized syringe was used to withdraw ~1 ml of blood from the vein under high pressure. The site was clamped again to prevent exsanguination post-sampling. To obtain a hepatic artery measurement, the abdominal aorta was rapidly isolated caudal to its bifurcation into the common iliacs and catheterized with a heparinized 18 G catheter, again ~1 ml was collected. The liver was excised and a wet weight obtained.

Metabolite Analyses. All blood samples were immediately evaluated for blood gases ( ) and subsequently analyzed for multiple metabolites using a rapid-assay device (Comprehensive Metabolic and Lipid Plus panels, Piccolo, Abaxis). The remaining blood was spun down at 3000× g and the plasma frozen at −80° C. The samples were later analyzed for glucose, insulin, lactate, urea, albumin, acetoacetate and β-hydroxybutyrate, using biochemical assays, and amino acid composition (automated high-performance liquid chromatography system, Waters Co., Milford, MA) as described elsewhere (Arai, K. Lee, K., Berthiaume, F., Tompkins, R. G., Yarmush, M. L. Intrahepatic Amino Acid and Glucose Metabolism in a D-Galactosamine-Induced Rat Liver Failure Model. Hepatology 34, 360-371 (2001)).

Data Preprocessing. An outlier analysis was performed for each variable utilizing box-and-whisker diagrams in MATLAB (The Mathworks, Natick, MA); this resulted in deletion of less than 1% of data. The missing extracellular metabolite concentrations were replaced by the median of the measurements from the other animals from each group, which is a standard procedure in data mining analysis (Witten, I. H. & Frank, E. *Data Mining: Practical machine learning tools and techniques*, (Morgan Kaufmann, San Francisco, 2005)). Fluxes were calculated as:

$$v_i = F_i^{SHVC} c_i^{SHVC} - F_i^{PV} c_i^{PV} - F_i^{HA} c_i^{HA} \quad (3)$$

where F is the flow rate and c is the concentration for metabolite i in the designated vessel (SHVC, PV, or HA). A second outlier analysis was performed for the fluxes, and 58 fluxes out of 405 total were deleted. The average value for each flux (for each group) was calculated for use in MFA, as discussed below.

Metabolic Flux Analysis (MFA). MFA is based on fitting the measured set of fluxes to a stoichiometric model for the hepatic metabolic reaction network have been reported. This model captures the main biochemical reactions involved in central carbon and nitrogen metabolism under fasting conditions. Fasting is used to deplete glycogen stores so that glucose output reflects de novo gluconeogenesis without the confounding effects of glycogen breakdown. Furthermore, under this condition pyruvate dehydrogenase is inhibited, such that both glycogenolysis and pyruvate dehydrogenase fluxes can be set equal to zero. The mathematical model uses a total of 35 metabolites (Table 6) and 61 chemical reactions (Table 8), and was implemented and solved using MATLAB software as described previously(Banta, S., Yokoyama, T., Berthiaume, F., Yarmush, M. L. Effects of dehydroepiandrosterone administration on rat hepatic metabolism following thermal injury. *Journal of Surgical Research* 127, 93-105 (2005)).

The model estimates otherwise inaccessible intracellular reaction fluxes by performing a mass balance around each intracellular metabolite using measured extracellular fluxes. Assuming steady-state conditions (intracellular concentrations of metabolites are constant), these mass balances reduce to a system of linear equations. Briefly, the sum of fluxes to and from a metabolite or its "pool" is assumed to be zero:

$$S \cdot v = 0 \quad (1)$$

where the matrix S contains the stoichiometric coefficients of the biochemical reactions in the hepatic metabolic network. Each element $S_{ij}$ of S is the coefficient of metabolite i in reaction j, and each $v_j$ of vector v is the net flux or conversion rate of reaction j. Equation 1 is separated into measured ($v_m$,) and unknown fluxes ($v_u$), as well as the matrices containing stoichiometric coefficients of known ($S_m$) and unknown reaction ($S_u$) fluxes, as follows:

$$S_u \cdot v_u = -S_m \cdot v_m \quad (2)$$

The measured fluxes represent rates of uptake or release of extracellular metabolites and by solving Equation 2 they also give estimates of unknown intracellular fluxes.

MFA was performed on each individual rat's data, and the results from all the rats in each group pooled to determine average ±standard deviation. The validity of the statistical model was confirmed via the test of Wang and Stephanopoulos (Wang, N. S. & Stephanopoulos, G. Application of macroscopic balances to the identification of gross measurement errors. 25, 2177-2208 (1983)), at a threshold of p<0.05. This method statistically tests for the presence of gross errors that are inconsistent with other measurements, which lead to the violation of the pseudo steady-state assumption. Moreover, in the event of such errors, it can be used to identify the artifactual/erroneous measurements that lead to these inconsistencies. This approach was used to identify and eliminate several gross errors in the data.

Statistics. Comparisons were performed using ANOVA and 2-tailed Student's t-tests. p<0.05 was the criterion used for statistical significance.

Example 3

MFA Comparison of Fresh and Warm Ischemic Livers in NELP

MFA is performed on Fresh and WI livers in perfusion to evaluate the overall performance of the organs in perfusion. The major differences between ischemic and fresh liver metabolism is noted, time to recovery is suggested, and methods of improving perfusion are discussed. In this example inventors examined the temporal profiles of 28 metabolites measured hourly during perfusion. These data provide information on the time frame of recovery of ischemically damaged organs, organ stability during perfusion, and the impact of perfusion on organ metabolism through comparison to in vivo values (Table 9).

Moreover, since the trends in metabolite uptake or production in all groups were generally linear (see Statistical Identification of Linear Response Phases During Perfusion in the Methods section of the selected time segments) it was possible to raise the steady state assumption for the fluxes hence enabling the use of MFA. MFA provided a comprehensive overview of organ function during perfusion by enabling the evaluation of several intracellular fluxes from the measured extracellular fluxes. Inventors also compared the MFA results to an in vivo MFA study (Izamis, M., Uygun, K., Berthiaume, F. & Yarmush, M. In vivo metabolic fluxes in rat livers: effect of burn injury. *Biotechnol Bioeng* (2011 Apr; 108(4):839-52) conducted previously to identify critical differences that could be corrected to enhance the restorative capacity of the perfusion system. It should be noted that the in vivo MFA study (Izamis, M. L., et. al. In vivo metabolic flux analysis of the liver: Effect of burn injury in rats. (2010)) used for comparison here was performed with a different rat strain (Sprague Dawley); although strain-to-strain variations are expected to be minimal in the basic metabolic pathways considered in the model, these comparisons are best interpreted for their overall significance rather than any specific differences in detail.

Oxygen Consumption. Samples of perfusate were taken hourly at the portal vein, to reflect oxygen delivery rate (ODR), and at the infra-hepatic vena cava, to determine oxygen exit rate (OER). Oxygen uptake rate (OUR) was determined as the difference between ODR and OER (FIG. 15A). ODR and OER were also compared to in vivo conditions (FIG. 15B). WI livers consumed significantly less oxygen than Fresh livers during the first hour of perfusion, but by the second hour, consumption had increased to 0.05-0.057 ml $O_2$/min/g liver and was comparable between groups. WI livers showed a slow but steady decline in OUR from t=2-5 hrs, the difference between WI and Fresh livers again becoming statistically different at t=5 hrs. Fresh livers also demonstrated a decline in OUR from t=0-3 hrs after which consumption began to very slowly increase again. FIG. 15B illustrates that the ODR in perfusion averages at 0.14 ml $O_2$/min/g liver in both groups, and falls within one standard deviation of the average in vivo ODR. The OER however, is significantly higher than in vivo, which has negligible variation in value, demonstrating that despite reduced oxygen supply, the liver does not consume all that is available to it in perfusion, regardless of ischemic injury.

Figure 16A:
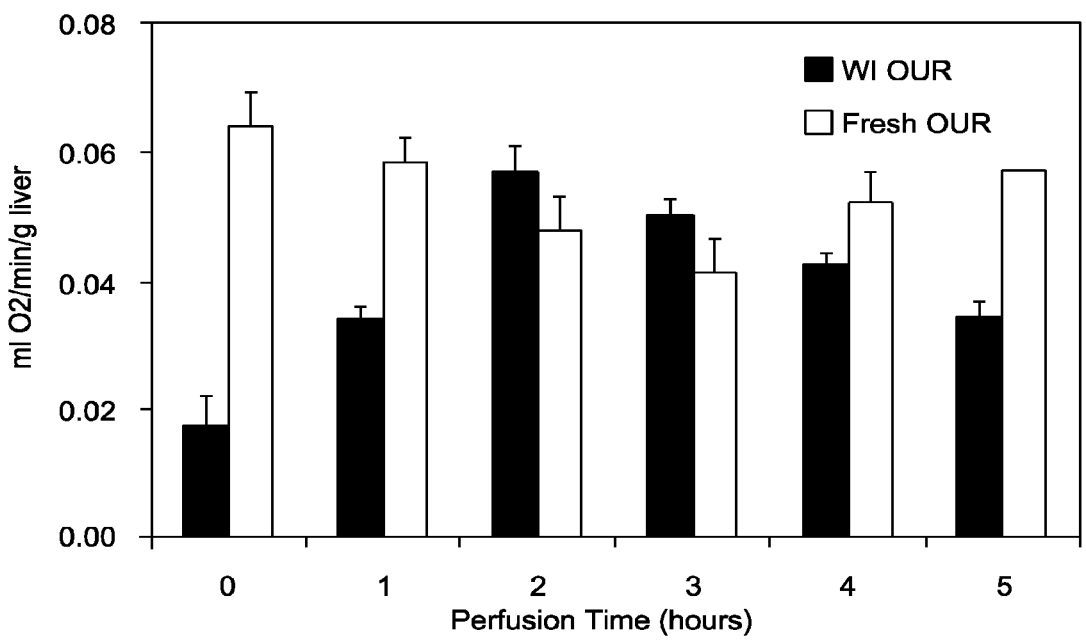
FIGS. 16A-16B illustrate: Figure A shows oxygen uptake rate (OUR) for WI and fresh livers; and Figure B shows oxygen delivery rate (ODR) and exit rate (OER) in perfused livers compared to those in vivo. Red and blue lines represent average ODR and OUR +/−1std dev. * indicates significantly different from fresh (p<0.05)

Glucose. Concentration profiles of glucose in both WI and Fresh livers were generally stable at a value slightly above the original perfusate glucose content of 2 g/L (FIG. 16A). Subtle changes in trends could be appreciated such as an increase in concentration within the first hour of perfusion in both groups to values significantly above the starting value of Williams Medium E, which is similar to the in vivo upper bound level. WI livers continued to increase the glucose concentration, while Fresh livers reduced it during the second hour. During t=3-5 hrs, both groups had similar glucose concentrations that demonstrated a gradual steady increase from 2.18-2.24 g/L for Fresh livers and to 2.29-2.37 g/L for WI livers.

Figure 16B:
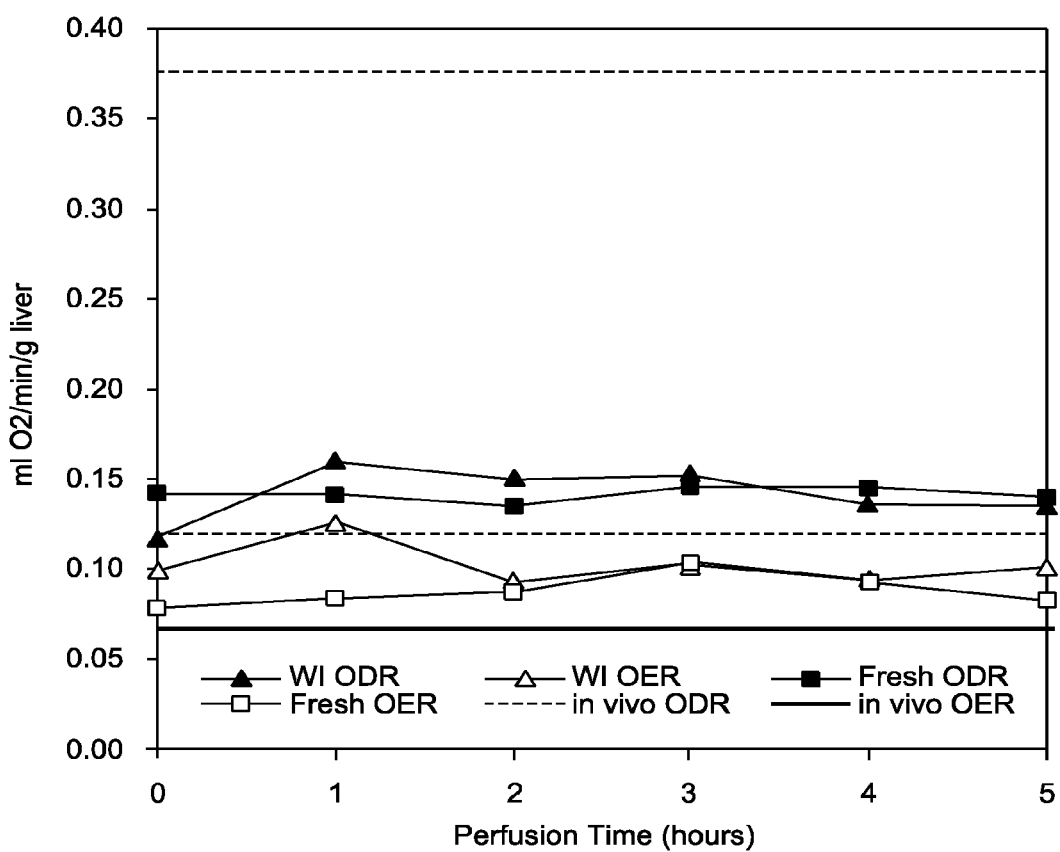
Figure 17A:
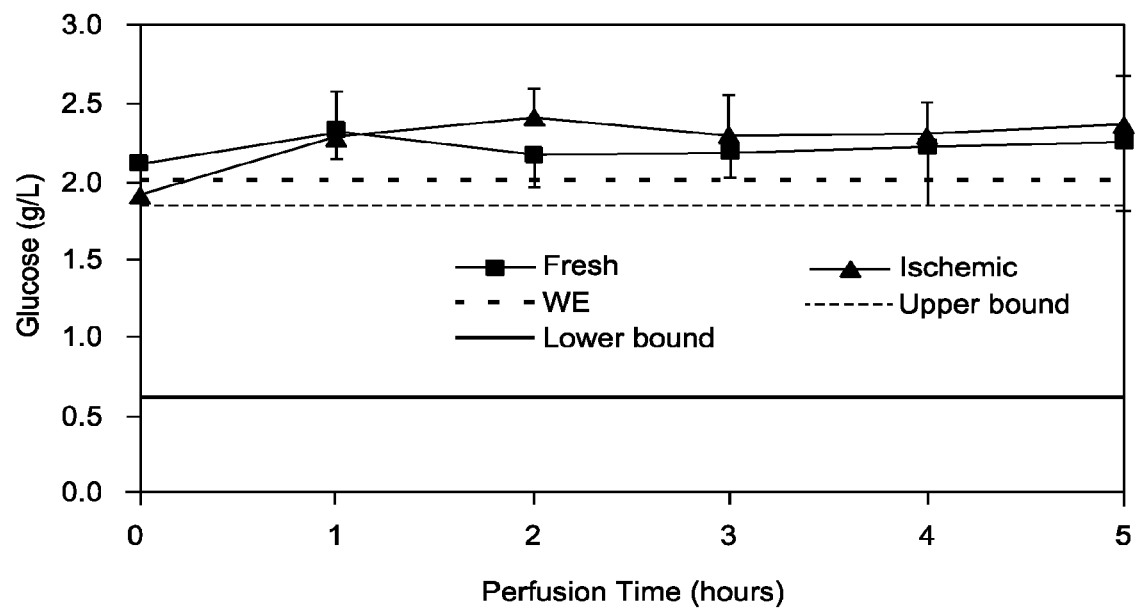
FIGS. 17A-17B illustrate the average concentrations during NELP of WI and Fresh livers, compared to Williams Medium E (WE), and in vivo upper bound values (ave+1 std dev) and lower bound values (ave−1 std dev).
Figure 17B:
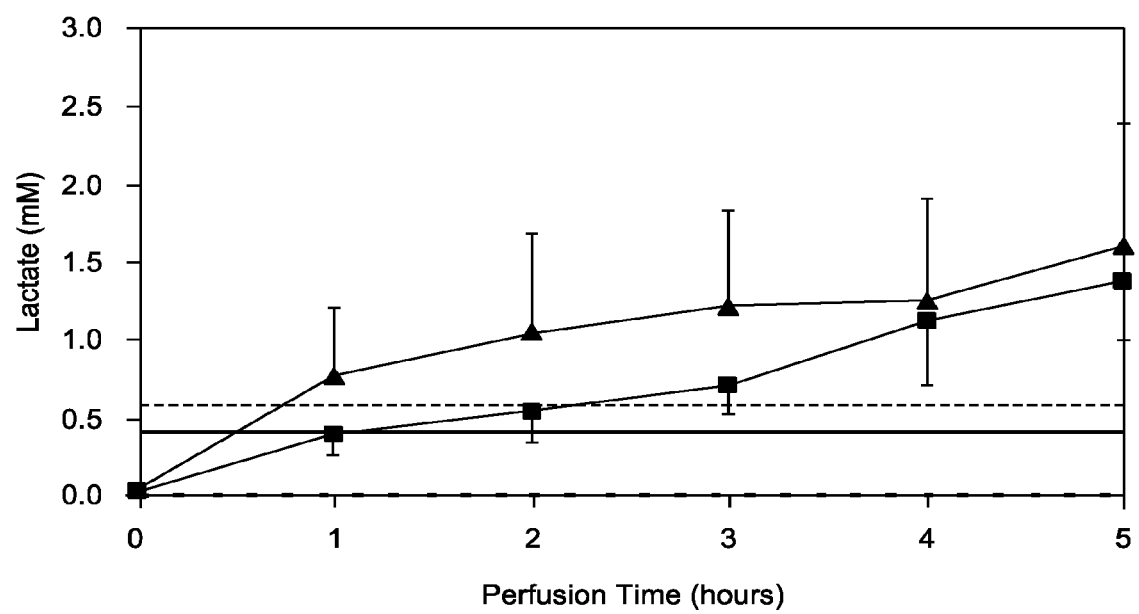

Lactate. WI livers produced more lactate in the first hour than Fresh livers, exceeding the in vivo upper bound value within the first hour (FIG. 16B). The rate of production declined after the first hour resulting in concentrations comparable to Fresh livers by the end of perfusion. Fresh livers produced lactate linearly throughout, also exceeding the in vivo upper limits though this occurred later, a little after 2 hours of perfusion. Note that WE does not contain any lactate.

Figure 19A:
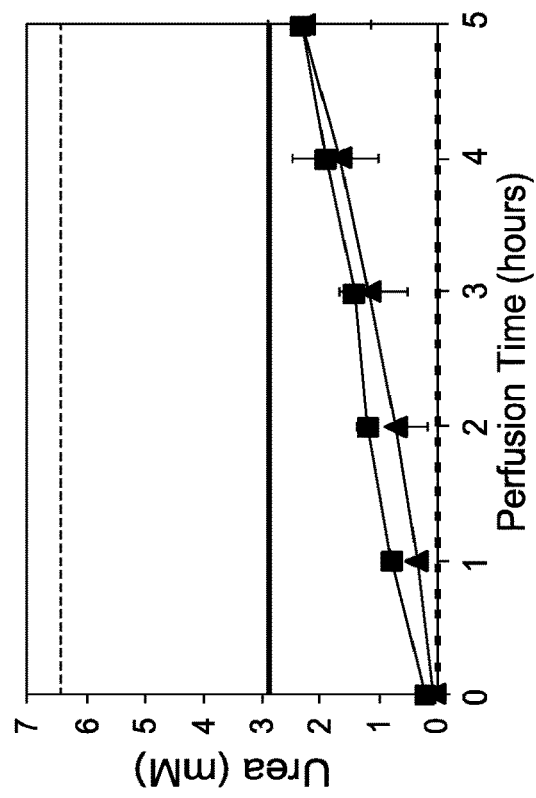
Figure 19B:
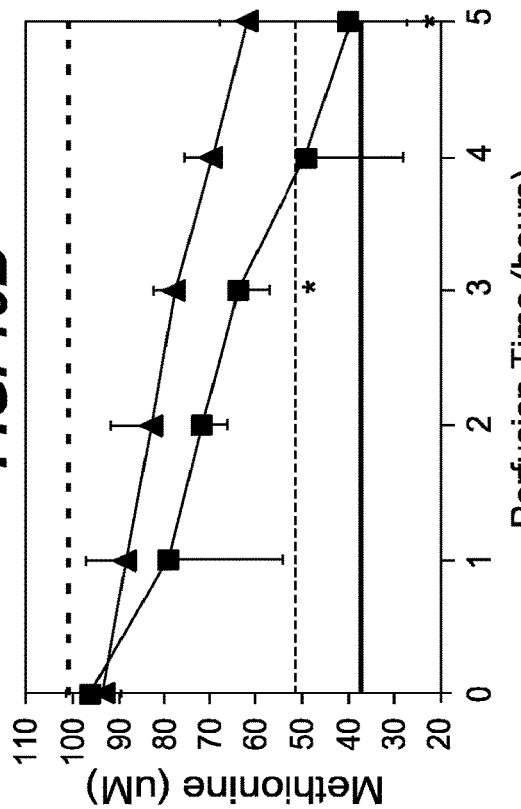
Figure 19C:
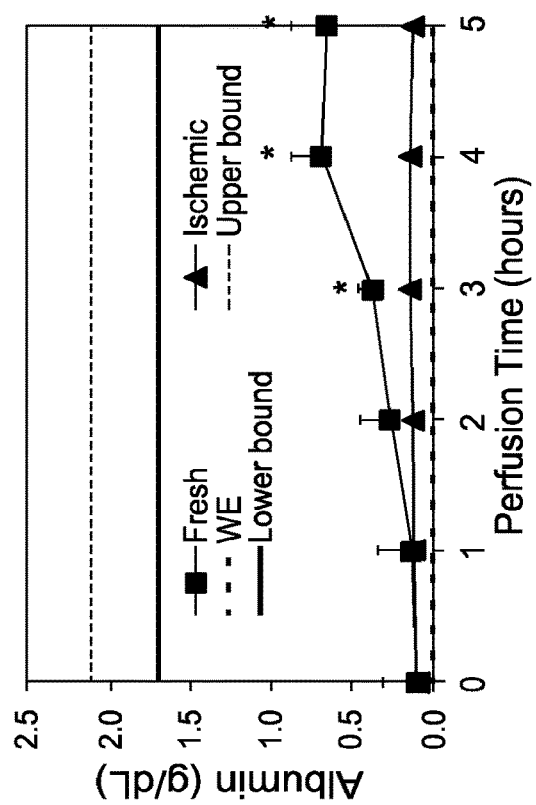
Figure 19D:
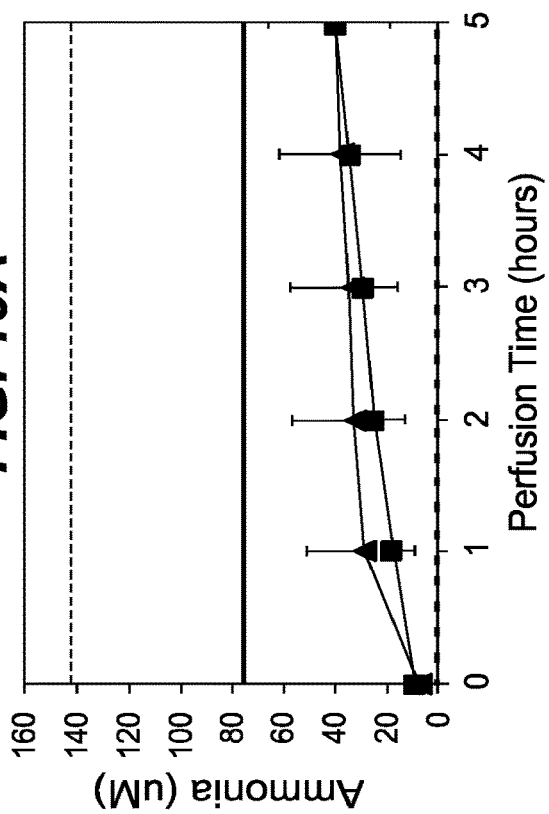
Figures 19I, 19J:
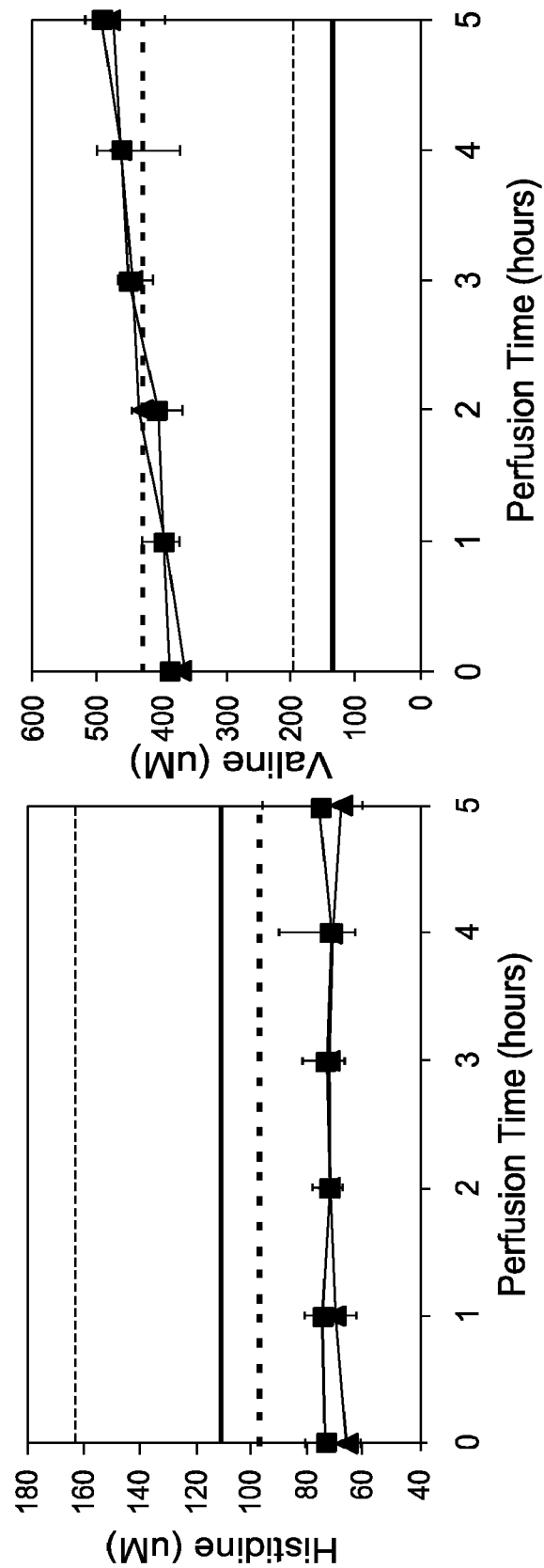

Nitrogen Metabolism. Albumin concentration (FIG. 19A) increased steadily in Fresh liver perfusions, reaching a maximum of 0.68 g/dL at t=4 hrs, approximately 40% of the in vivo lower bound value. By contrast, WI livers produced little to no albumin during this time span (0.0055 g/dL/hr, $R^2$=0.6). Urea concentration increased similarly and linearly in both groups (FIG. 19B) at a rate of 4.1 mM/hr, $R^2$=0.99 for Fresh livers and 4.4 µM/hr, $R^2$=0.98 for WI livers. Urea concentration also did not reach the in vivo lower bound concentration of approximately 2.8 mM at the end of perfusion. Ammonia concentration increased similarly in perfusate from zero to 40 µM in both groups (FIG. 19C). The perfusate values of ammonia were significantly below the in vivo lower bound of approximately 76 µM. The amino acids methionine (FIG. 19D), tyrosine, proline, lysine and phenylalanine were all consumed at significantly lower rates in WI livers than in Fresh livers. Glutamine uptake (FIG. 19E) occurred at a stable rate that was similar for both WI and Fresh livers. Rates of uptake between WI and Fresh livers were also similar for aspartate, alanine, glycine, asparagine, cysteine and threonine (not shown). WI and Fresh livers differed significantly in glutamate metabolism (FIG. 19F). Glutamate concentration increased linearly in Fresh livers but was relatively unchanged in WI livers and remained within the value present in WE. Arginine (FIG. 19G) by contrast was consumed at a significantly higher rate by WI livers, to the extent that it became substrate depleted at t=4 hrs. A reciprocal increase in ornithine was observed (FIG. 19H); a plateau was reached in the significant output by WI livers at t=4 hrs, well above the in vivo upper bound value. A linear increase in ornithine output by Fresh livers resulted in a perfusate concentration within in vivo range at t=5 hrs. Despite WE being deficient in lactate, ornithine, ammonia, urea, albumin, and ornithine, the liver generally increased the concentrations of each of these significantly during perfusion. However, in the case of histidine (FIG. 19I) and serine (not shown), present in WE at values significantly below the in vivo lower bound, neither were utilized or contributed to during perfusion. The branched chain amino acids valine (FIG. 19J), isoleucine and leucine were all produced linearly during perfusion.

Figure 18:
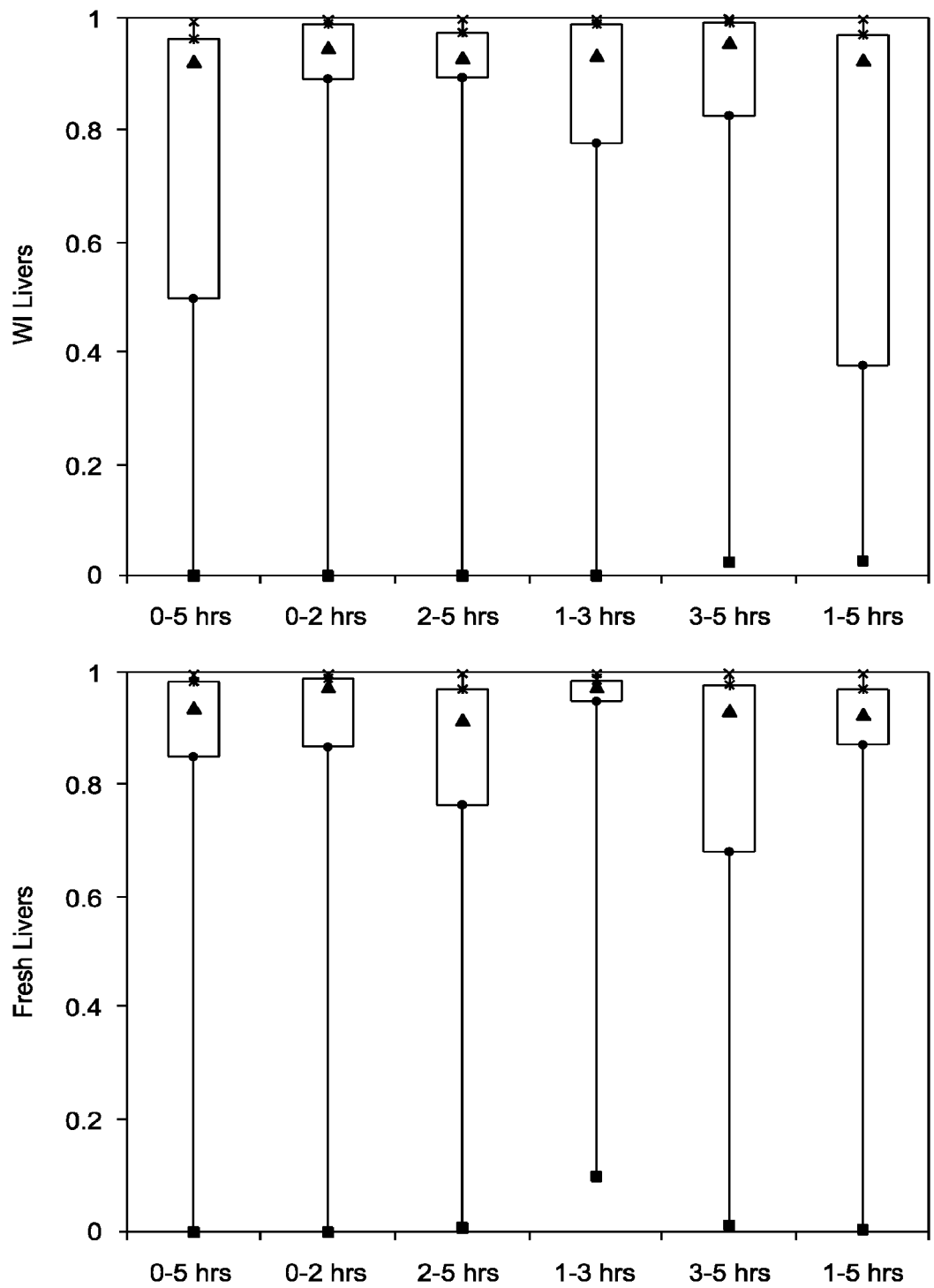
FIG. 18 illustrates box-and-whisker plots of linear regressions performed on the temporal concentration profiles of 28 metabolites measured for WI and Fresh livers.

MFA of Fresh vs. Ischemic Perfused Livers. In order to identify whether there were distinct phases in liver metabolism during perfusion, linear regressions were performed on the temporal concentration profiles of each of the metabolites. Box-and-whisker plots of the resulting $R^2$ values were evaluated for least variation across different segments of time (FIG. 18). Ischemic livers were found to exhibit stable but distinctly different metabolic rates between 0-2 hrs and 2-5 hrs of perfusion; MFA was conducted for both phases. Fresh livers were generally stable throughout perfusion; MFA was performed on the segment with greatest linearity, determined as being t=1-5 hrs. FIG. 19 delineates the results of MFA for all groups.

In FIG. 20, the first two hours of ischemic liver perfusion are compared to fresh liver metabolism using MFA. The map suggests ischemic livers were significantly more glycogenolytic than fresh livers at NELP onset, breaking down glycogen for glycolysis and glucose release. Glycolysis appeared to result in a 116% increase in the production of lactate (Flux #8). Oxygen uptake rate (Fluxes 53-55) and the TCA cycle were comparable between groups. Ischemic livers demonstrated a preferential uptake of the amino acid arginine (118% increased in Flux #18) and a reciprocal, 304% increase, in the release of ornithine into the extracellular space (Flux #20). Ischemic livers also showed a 46% increase in the formation of asparagine from aspartate (Flux #47). Phenylalanine uptake was increased by 24% ($p<0.1$, Flux #36) while tyrosine uptake was reduced by 63% ($p<0.05$, Flux #38) resulting in an overall reduction of fumarate production (Flux #37). Methionine and serine metabolism were significantly reduced (Flux #44); extracellular serine release was observed at this time also (Flux #25). Glutamate production (Flux #40) was 58% of that found in fresh livers, a significant reduction due likely to a decline in contribution from lysine and 2-oxo-glutarate (Flux #35), which were reduced by 61% ($p<0.1$).

Figure 21:
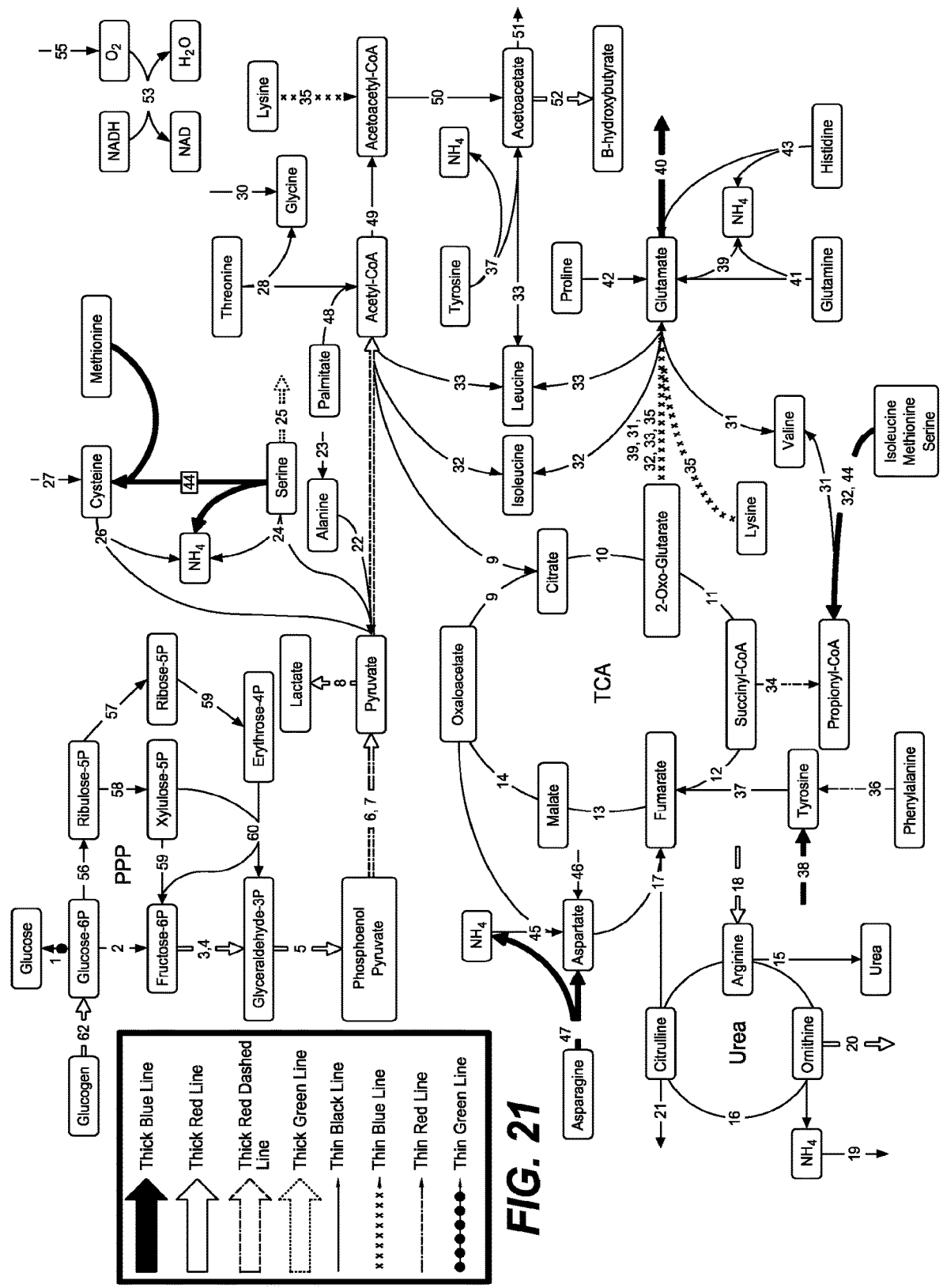
FIG. 21 illustrates the flux directions reflecting Phase I (t=0-2 hrs) of WI vs. Fresh livers. Red arrows=significantly increased. Blue=significantly reduced. Green=reversed. Bold lines=p<0.05, Thin lines=p<0.1, Dotted lines=glycolysis.

Between 2-5 hrs of ischemic liver perfusion (FIG. 21) more differences were apparent between fresh and ischemic livers than at 0-2 hrs. Ischemic livers appeared to be predominantly gluconeogenic and demonstrated a 30% reduction in lactate output compared to fresh livers, despite a further decline in oxygen uptake rate (FIG. 15A). Contributions to the TCA cycle via phenylalanine conversion to tyrosine were reduced, such that fumarate production via this pathway (Flux #37) was only 50% of fresh liver flux values. Reduced acetyl-CoA and oxaloacetate (Flux #9) resulted in a 61% reduction of citrate formation, while threonine conversion to acetyl-CoA was increased 470%. Glutamate output was further reduced to within 4% of Fresh liver fluxes; contributions to its formation from both lysine (50% of fresh livers, Flux #35) and proline (40% of fresh livers, Flux #42) impacted its production substantially. There was however, a 260% increase in glutamate formation via glutamine (Flux #41) which resulted in a 100% increase in glutamate formation of 2-oxo-glutarate (Flux #39). This increased flux converged on the TCA cycle at a point of reduced incoming fluxes from citrate, such that the downstream pathway of the cycle was restored to a value similar to that of fresh livers. Asparagine to aspartate production was further increased to a rate 60% greater than fresh livers, while tyrosine, methionine and serine metabolism remain reduced, though extracellular serine was then actively consumed at a higher rate (Flux #25). Arginine uptake and ornithine output were significantly reduced compared to fresh livers, but the increased metabolism of asparagine, threonine and glutamine resulted in an overall increased urea cycle.

Figure 22:
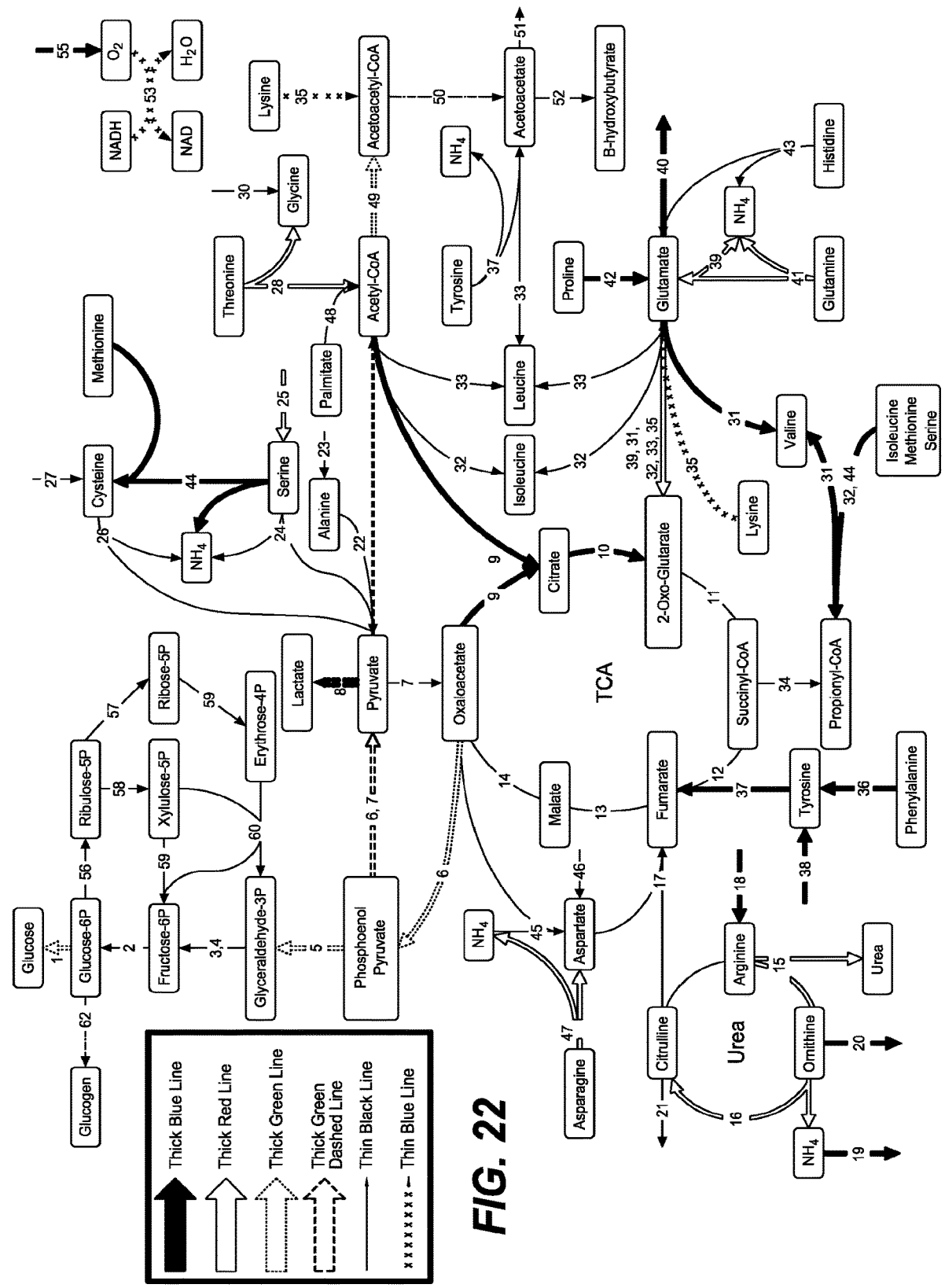
FIG. 22 illustrates the flux directions reflecting Phase II (t=3-5 hrs) of WI vs. Fresh livers. Red arrows=significantly increased. Blue=significantly reduced. Green=reversed. Bold lines=p<0.05, Thin lines=p<0.1, Dotted lines=glycolysis.
Figure 23:
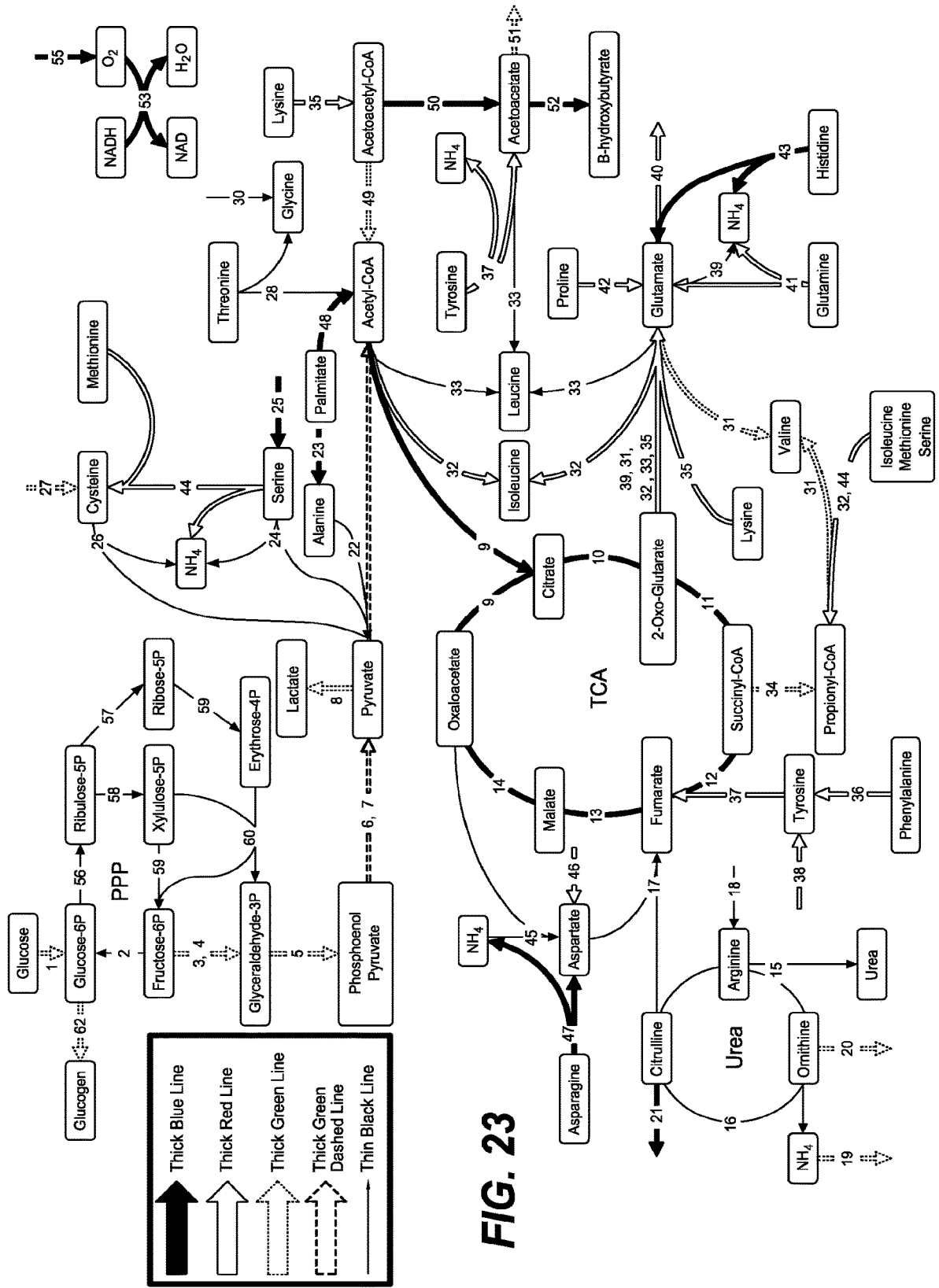
FIG. 23 illustrates the flux directions reflecting fresh vs. in vivo. Red arrows=significantly increased. Blue=significantly reduced. Green=reversed. Bold lines=p<0.05, Thin lines=p<0.1, Dotted lines=glycolysis
Figure 24:
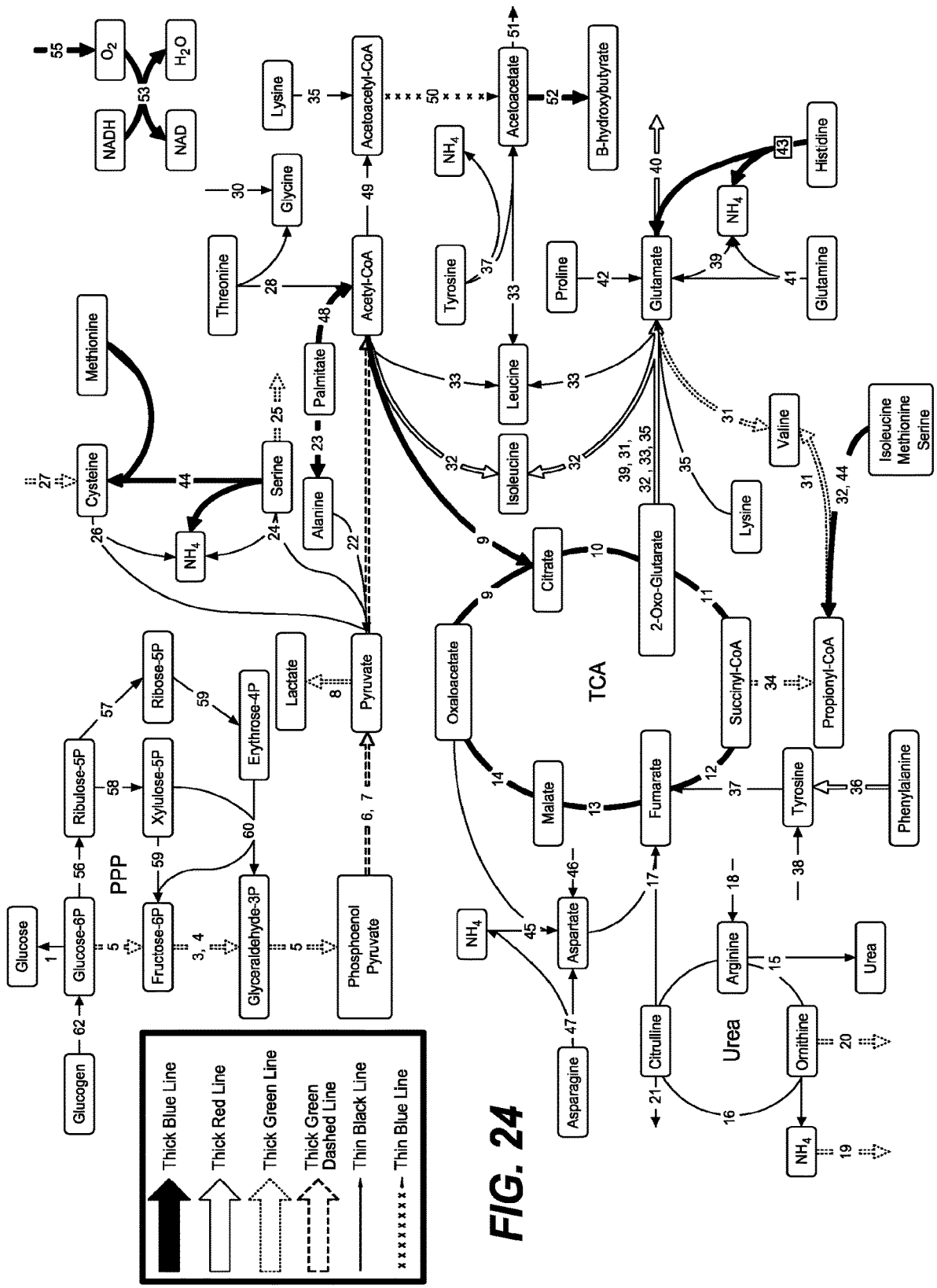
FIG. 24 illustrates the flux directions reflecting Phase I (t=0-2 hrs) of WI vs. in vivo. Red arrows=significantly increased. Blue=significantly reduced. Green=reversed. Bold lines=p<0.05, Thin lines=p<0.1, Dotted lines=glycolysis
Figure 25:
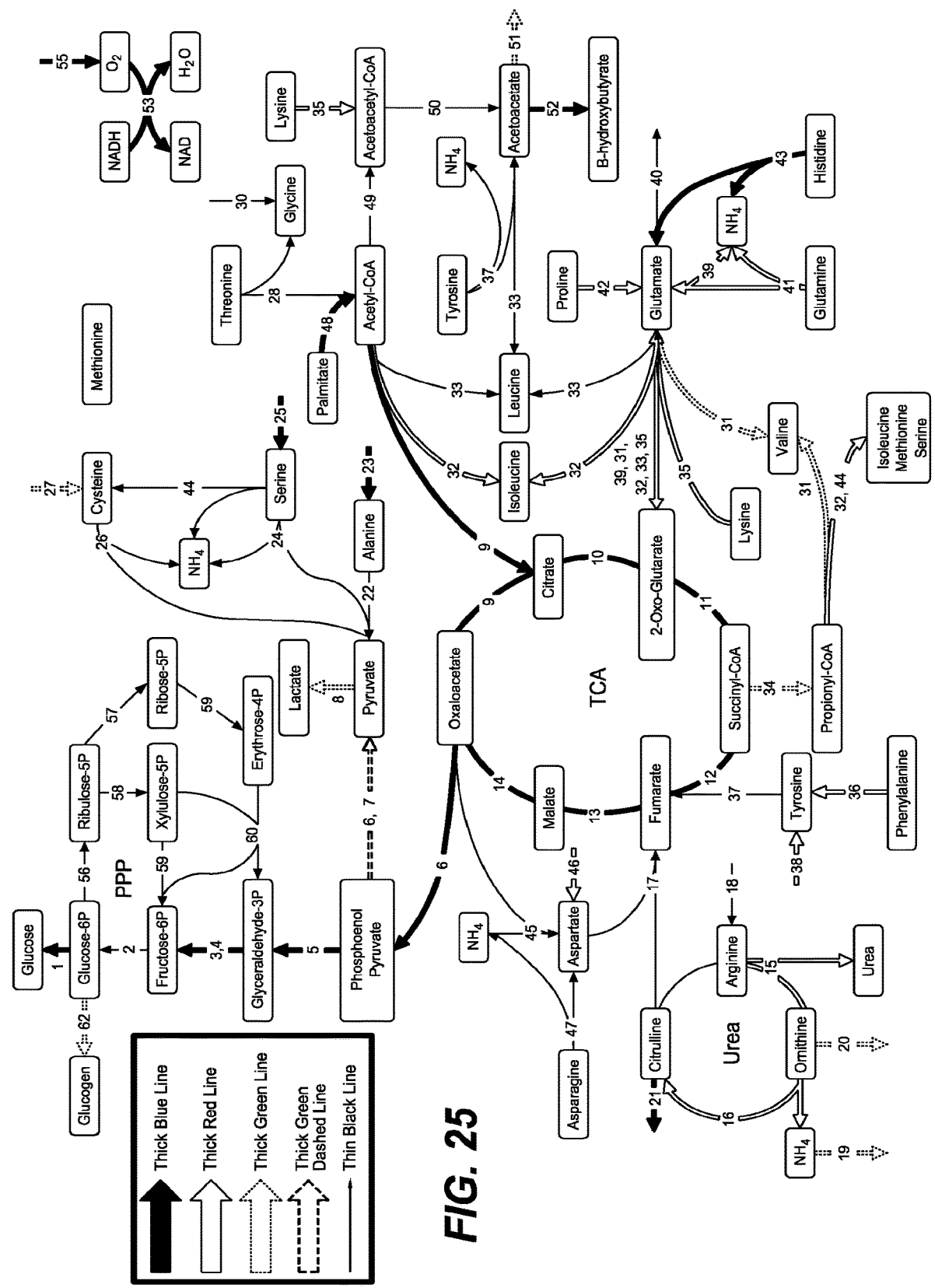
FIG. 25 illustrates the flux directions reflecting phase 11 (t=3-5 hrs) of WI vs. in vivo. Red arrows=significantly increased. Blue=significantly reduced. Green=reversed. Bold lines=p<0.05, Thin lines=p<0.1, Dotted lines=glycolysis.

MFA of perfused vs. in vivo livers. In order to appreciate the impact of perfusion itself on liver metabolism and evaluate potential limitations to the perfusate, a comparison of perfused and in vivo livers was performed using MFA (FIGS. 22-24). FIG. 25 summarizes the MFA findings demonstrating that perfused liver activity of the major pathways of metabolism including oxygen uptake, electron transport, lipid oxidation, the TCA cycle and the PPP was reduced compared to in vivo values. Lactate production was increased in perfusion while amino acids and urea cycle were similar to in vivo livers. The latter findings correlate well with the MFA maps that demonstrate either very little amino acid variation from in vivo as in FIG. 23, or a synchronous increased uptake in some and decreased uptake in others (FIGS. 22 and 24). All perfused livers released branched chain amino acids and had negligible histidine uptake compared to in vivo livers. Further, in the absence of any lipids in the perfusate, and with the unusual formation of branched chain amino acids, the model predicted formation of propionyl-CoA from succinyl-CoA (Flux #34). Perfused livers were generally glycolytic compared to fasted gluconeogenic in vivo livers, though extracellular glucose content varied little in concentration during perfusion.

Fresh livers compared to in vivo livers (FIG. 22) represent the response of a healthy liver in perfusion. Amino acid metabolism was substantially altered. Extracellular glutamate production and 2-oxo-glutarate levels were significantly increased by the catabolism of proline, aspartate, lysine and glutamine (Fluxes #31, #32, #33, and #35). Phenylalanine and tyrosine metabolism were significantly increased contributing to fumarate production, while increased serine and methionine consumption contributed to the pyruvate pool. Conversely, asparagine, histidine, serine and alanine uptake were significantly reduced. The urea cycle remained within in vivo range.

During the first two hours of ischemic liver perfusion glutamate output was significantly increased but in contrast to fresh livers, there were no major amino acid changes except an increase in phenylalanine and a decrease in methionine, serine and alanine (FIG. 23). Between the $2^{nd}$ and $5^{th}$ hours of perfusion, amino acid metabolism picked up to include lysine, glutamine, phenylalanine, tyrosine and aspartate catabolism. Glutamate was oxidized rather than released into the extracellular pool, increasing the 2-oxo-glutarate flux such that downstream TCA activity was comparable to the first two hours of perfusion and the urea cycle was increased. WI livers also reverted to gluconcogenesis (FIG. 24) and possible glycogen formation, though at significantly reduced rates compared to fasted in vivo livers. Lactate formation was reduced 67% from the first two hours of perfusion.

The impact of perfusate content can be appreciated from the concentration of metabolites in Williams Medium E, and the portal influxes (Tables 6 and 7). The content, and subsequent influx, of Williams Medium E exceeded in vivo values for all amino acids except serine and histidine, and their uptake in perfusion was negligible. The converse, exceedingly high influxes (Table 10) as seen in the cases of cysteine, aspartate and glutamine, which were 20×, 10× and 5× higher than the upper bound in vivo influx respectively, resulted in 5-10× higher uptake rates than in vivo. Influxes 1-4× higher than the upper bound in vivo value had variable, less substrate-driven responses by the livers in each of the groups. Arginine was taken up, and ornithine reciprocally released, at a high rate in WI livers and finally demonstrated a plateau when perfusate concentration reached 26μM, suggestive of substrate depletion at t=4 hrs. Only tyrosine in fresh livers demonstrated a similar final concentration, though its concentration profile was linear for the entire duration of the perfusion. All other amino acids exhibited linear concentration profiles and had yet to be depleted at t=5 hrs. The systematic production of branched chain amino acids appeared to be a perfusion artifact. By contrast, methionine metabolism depended on the state of the liver, being upregulated in Fresh liver perfusions but down-regulated in WI perfusions. The metabolism of certain amino acids remained within in vivo ranges across all groups, for example, glycine (Fluxes #28-30) and even aspartate (Fluxes #17, #45, #47) despite the increased aspartate uptake (Flux #46).

TABLE 9

In vivo and Perfusate (WE) Reference Concentrations.

| METABOLITE | Portal Vein[1] | Williams Medium E[2] |
|---|---|---|
| Acetoacetic acid (μM) | 110 ± 73 | 0 |
| Alanine (μM) | 397 ± 13 | 1010 |
| Albumin (g/dL) | 1.9 ± 0.21 | 0 |
| Ammonia (μM) | 109 ± 33 | 0 |
| Arginine (μM) | 141 ± 93 | 287 |
| Asparagine (μM) | 49 ± 5.4 | 151 |
| Aspartate (μM) | 21 ± 7.6 | 225 |
| b-Hydroxybutyric acid (μM) | 110 ± 96 | 0 |
| Cysteine (μM) | 15 ± 1.5 | 330 |
| Glucose (g/dL) | 123 ± 62 | 0 |
| Glutamate (μM) | 68 ± 7.7 | 302 |
| Glutamine (μM) | 293 ± 46 | 2000 |
| Glycine (μM) | 273 ± 27 | 666 |
| Histidine (μM) | 137 ± 26 | 97 |
| Isoleucine (μM) | 86 ± 16 | 381 |
| Lactate (mM) | 1.0 ± 0.18 | 0 |
| Leucine (μM) | 261 ± 33 | 572 |
| Lysine (μM) | 220 ± 38 | 598 |
| Methionine (μM) | 44 ± 7.0 | 101 |
| Ornithine (μM) | 120 ± 3.5 | 0 |
| Phenylalanine (μM) | 59 ± 3.9 | 151 |
| Proline (μM) | 163 ± 12 | 261 |
| Serine (μM) | 199 ± 13 | 95 |
| Threonine (μM) | 204 ± 41 | 336 |
| Tyrosine (μM) | 68 ± 7.4 | 278 |
| Urea nitrogen (mM) | 4.6 ± 1.8 | 0 |
| Valine (μM) | 165 ± 31 | 427 |

[1] Izamis ML, et. al. In vivo metabolic flux analysis of the liver: Effect of burn injury in rats. 2010.
[2] Sigma-Aldrich cat. #W1878.

TABLE 10

Measured Influx Values.

| PARAMETER | PV + HA | Perfusate |
|---|---|---|
| Albumin (g/min/g liver) | 0.02-0.05 | 0.00 |
| Lactate (mmol/min/g liver) | 0.03-0.1 | 0.00 |
| Glucose (mg/min/g liver) | 1.13-2.5 | 3.68 |
| Alanine (umol/min/g liver) | 0.36-0.92 | 1.86 |
| Ammonia | 0.11-0.2 | 0.00 |
| Arginine | 0-0.5 | 0.53 |
| Asparagine | 0.04-0.12 | 0.28 |
| Aspartate | 0.02-0.04 | 0.41 |
| Cysteine | 0.01-0.03 | 0.61 |
| Glutamate | 0.07-0.15 | 0.56 |
| Glutamine | 0.28-0.68 | 3.64 |
| Glycine | 0.26-0.6 | 1.23 |

TABLE 10-continued

Measured Influx Values.

| PARAMETER | PV + HA | Perfusate |
|---|---|---|
| Histidine | 0.1-0.35 | 0.18 |
| Isoleucine | 0.07-0.23 | 0.70 |
| Leucine | 0.21-0.66 | 1.05 |
| Lysine | 0.18-0.54 | 1.10 |
| Methionine | 0.04-0.1 | 0.18 |
| Ornithine | 0.11-0.28 | 0.00 |
| Phenylalanine | 0.05-0.13 | 0.28 |
| Proline | 0.16-0.36 | 0.48 |
| Serine | 0.17-0.48 | 0.18 |
| Threonine | 0.19-0.47 | 0.62 |
| Tyrosine | 0.05-0.17 | 0.51 |
| Valine | 0.12-0.43 | 0.79 |

In vivo influx is the combined portal vein (PV) and hepatic artery (HA) contribution to that flux (ave− 1 std dev, ave+1 std dev). Perfusate influx is calculated according to the initial perfusate concentrations and a flow rate of 1.8 ml/min/g liver.

Example 4

Clinically Translatable Perfusion Technology for the Enhanced Recovery of Transplantable-Grade Cells from all Donor Organs, Particularly Donors after Uncontrolled Cardiac Death.

Using a highly simplified ex vivo perfusion system inventors recovered rat hepatocytes from non-pharmacologically pre-treated rat donors who experienced 10 minutes or 60 minutes of warm ischemia prior to perfusion. The results were compared to freshly isolated hepatocytes and hepatocytes procured from livers exposed to 60 minutes of warm ischemia without treatment.

Figure 26:
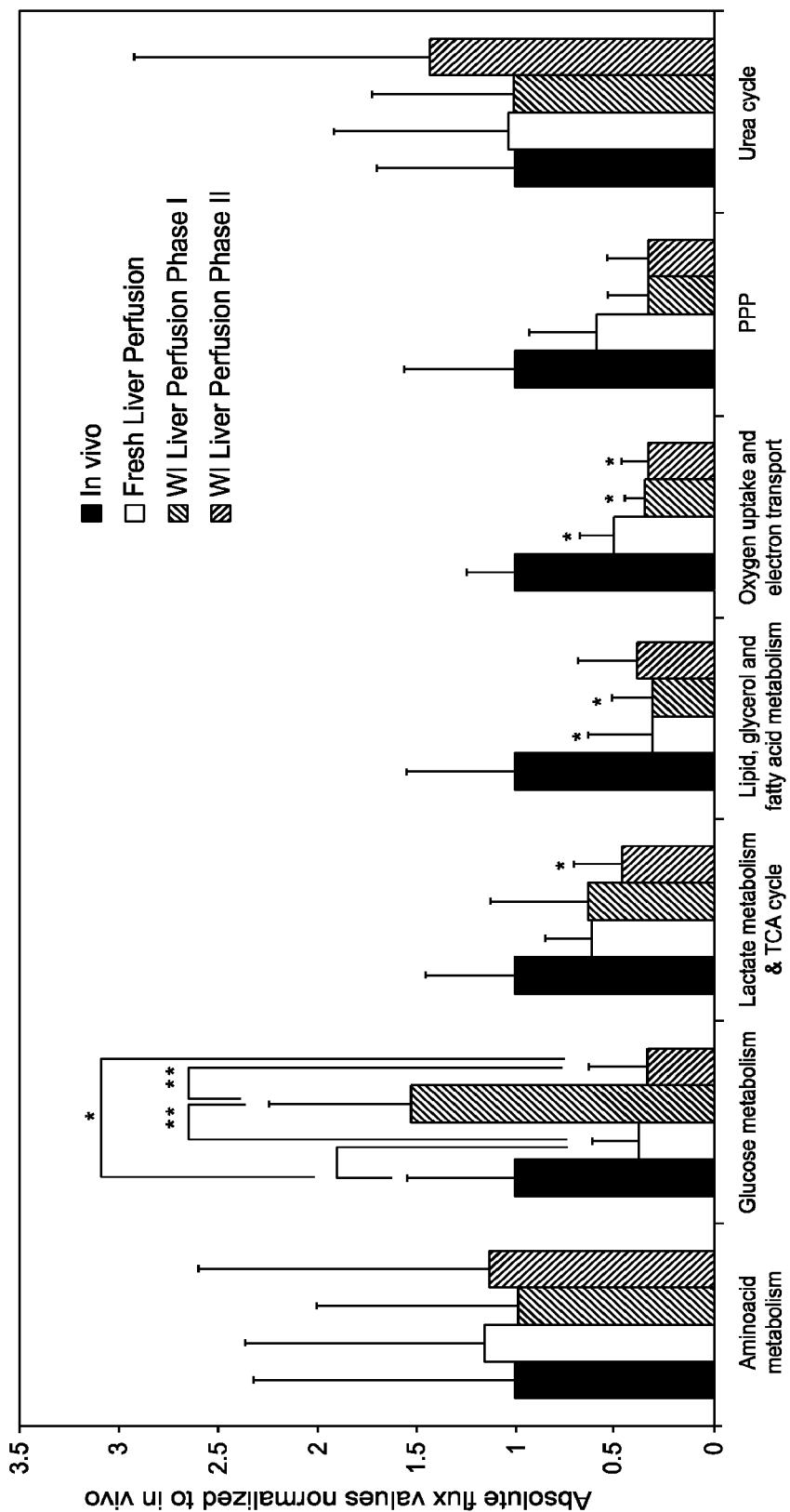
FIG. 26 summarizes the major pathways in perfused livers normalized to in vivo values.

Livers that experienced 10 minutes of ischemia (cooled from 37° C. to approximately 20° C. for cuffing purposes prior to ex vivo perfusion) and livers that experienced 60 minutes of WI (34° C.) were subsequently perfused at 20° C. (room temperature, RT) for 3 hours prior to hepatocyte isolation. FIG. 26a illustrates that there was no significant difference in the number of hepatocytes obtained from WI livers treated with 3 hr RT perfusion (34±11 mllion cells/g liver tissue, n=9) and Fresh livers (34±9 mllion cells/g liver tissue, n=15). By contrast, untreated WI livers yielded significantly fewer hepatocytes (1.7±0.6 mllion cells/g liver tissue, n=8). Further, fresh livers that experienced 10 minutes of ischemia prior to 3 hr RT perfusion resulted in significantly more hepatocytes than untreated Fresh livers (45±10 mllion cells/g liver tissue, n=12). All hepatocyte isolations were treated with Percoll to obtain a viability >90% (625c).

Figure 27A:
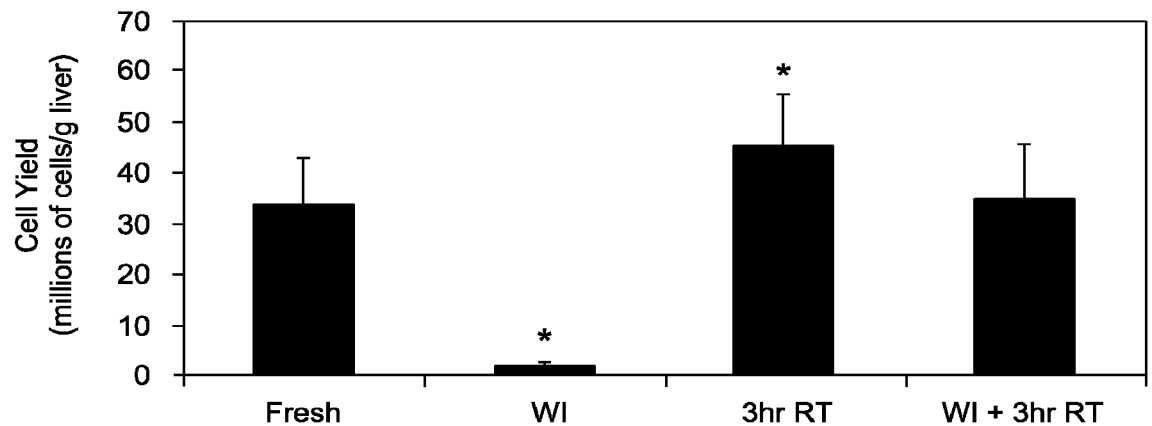
FIGS. 27A-27C illustrate.
Figure 27B:
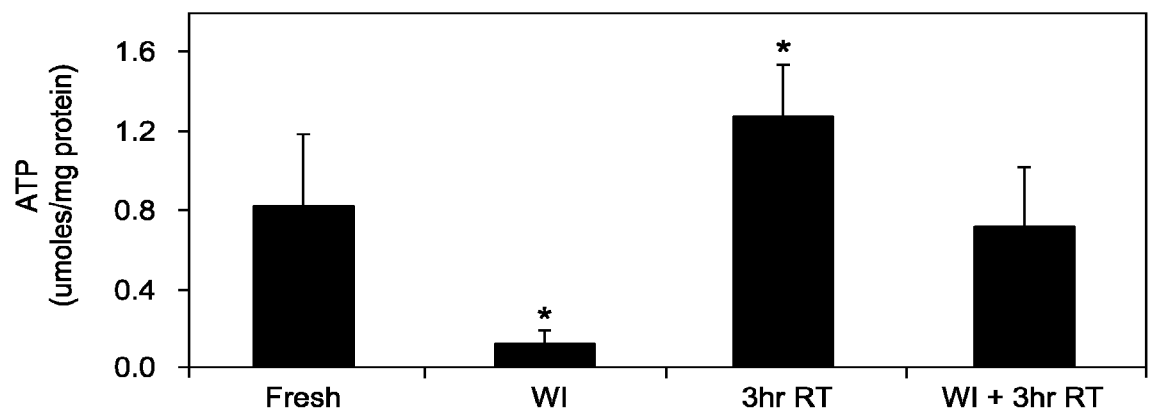
Figure 27C:
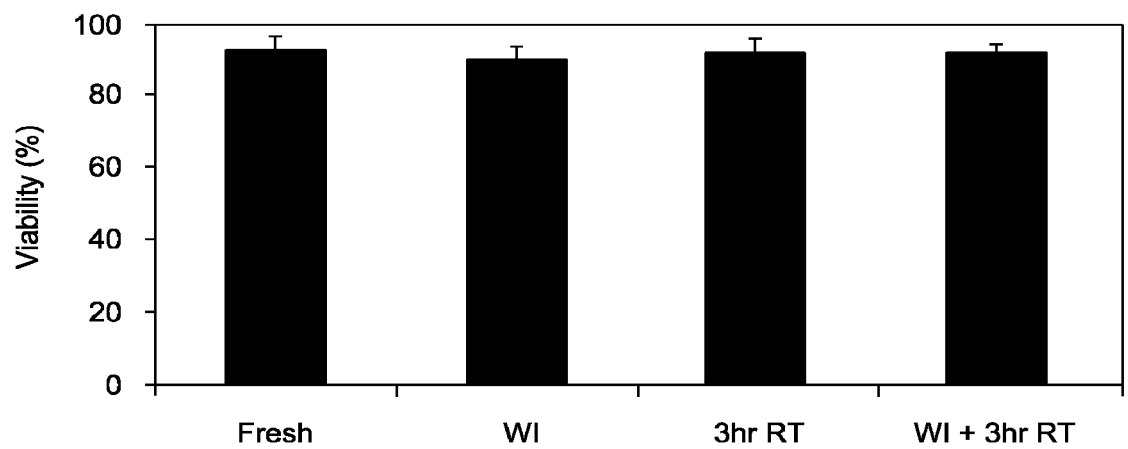

Hepatocyte function was tested under two conditions: 6 hr cell suspension culture and 2 week double layer collagen gel sandwich plate culture. Cell viability and mitochondrial activity were measured in suspension using trypan blue exclusion and MTT reduction to formazan (FIGS. 27A and C respectively). While freshly isolated hepatocytes started with relatively high viability during the first hour of suspension, their viability was the lowest at t=6 hrs. Similarly, while mitochondrial activity of fresh livers was generally higher than that of perfusion-treated groups, they also showed the greatest decline at t=6 hrs, whereas there were no differences between initial and final values in the perfused liver groups. Cell damage in suspension was measured with ALT and AST. FIGS. 27B and D demonstrate that both perfusion groups start with significantly higher ALT and AST values compared to Fresh cells; ALT remains relatively constant in WI+3hrRT cells, gradually degrades in 3hrRT cells and inclines in Fresh cells. AST continues to increase during the first 2 hours before reaching a plateau in WI+3hrRT cells, is stable in 3hrRT cells and inclines steadily for Fresh livers. Cytochrome P450 activity was measured by dealkylation of benzyloxy resorufin (CYP4502B2), pentoxy resorufin (CYP4502B 1), ethoxy resorufin (CYP4501A1) and methoxy resorufin (CYP4501A2) after 3,3'-methylene-bis(4-hydroxycoumarin) activation (FIG. 27E). CYP450 activity was comparable amongst all groups except for 3hrRT cells which exceeded Fresh EROD and MROD activity significantly. Metabolic activity was evaluated at t=6 hrs and it was observed that all groups produced equal amounts of glucose (2 g/L at baseline), and urea (0 mM at baseline), while WI+3hrRT cells produced significantly less albumin than either Fresh or 3hrRT cells.

Figure 28A:
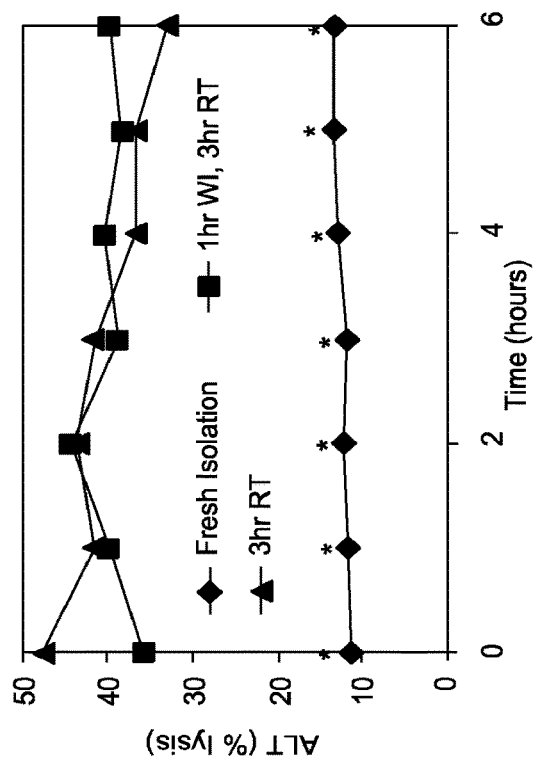
Figure 28B:
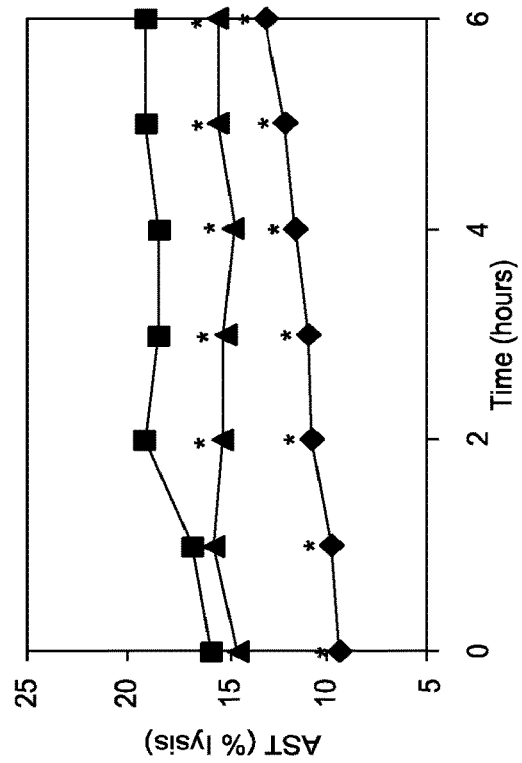
Figure 28C:
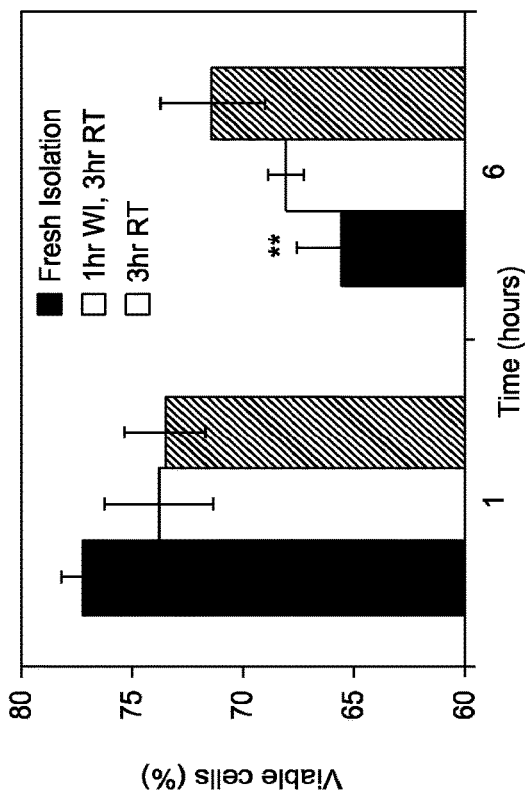
Figure 28D:
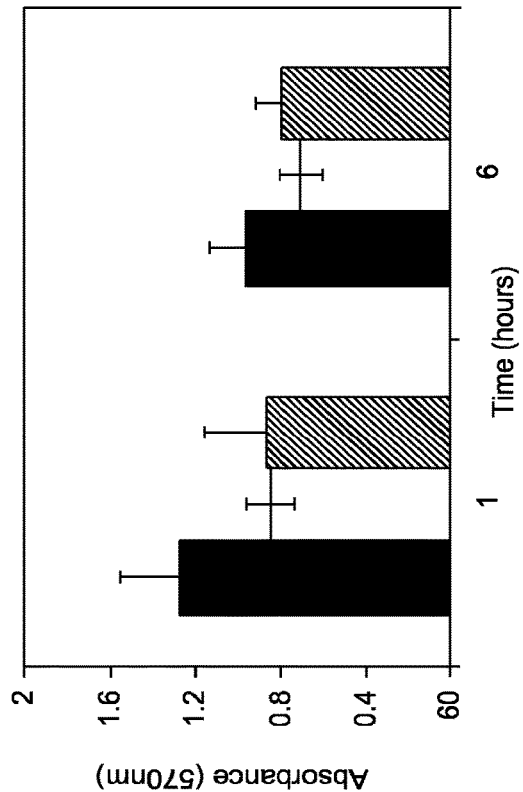

In plate culture, perfused liver cells showed excellent confluency at day 14 when observed using phase contrast imaging (FIG. 28C); better than Fresh hepatocytes (FIG. 28A) and structurally better-preserved compared to WI cells (FIG. 28B). Viability and mitochondrial activity were comparable amongst all groups and displayed a mild but insignificant decline over the two-week culture period. CYP450 activity did not differ significantly across groups. Certain trends could be observed, such as Fresh cells generally peaking in activity within 7 days, while perfused livers appeared to either remain constant throughout culture or gradually pick up in activity, peaking at Day 14. Daily metabolism of albumin shows that Fresh and 3hrRT cells behaved comparably but WI+3hrRT cells did not produce as much. 3hrRT cells produced significantly more urea than either WI+3hrRT or Fresh cells, which were comparable. All groups metabolized glucose equally.

Figures 29A, 29B, 29C:
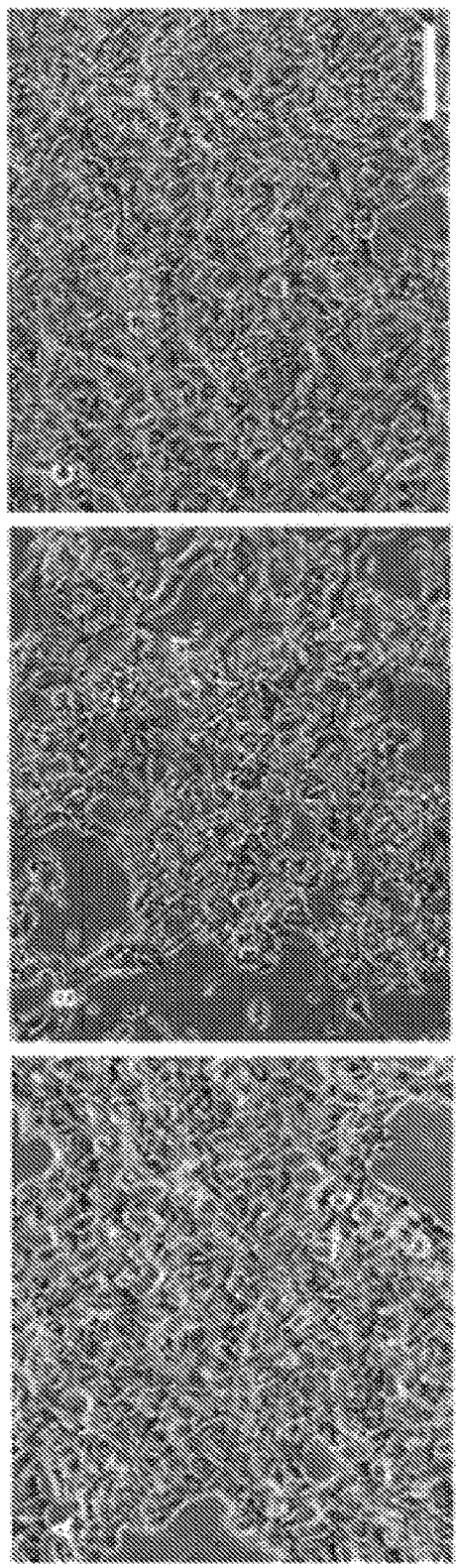
Figure 29D:
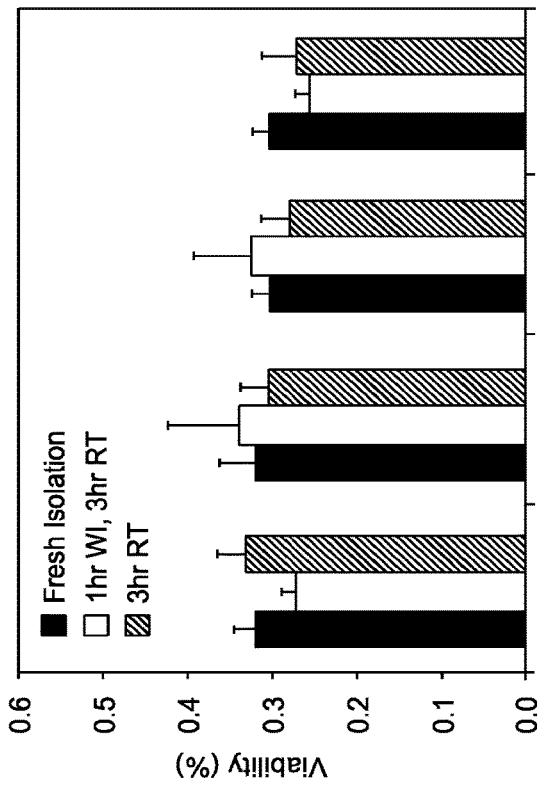
Figure 29E:
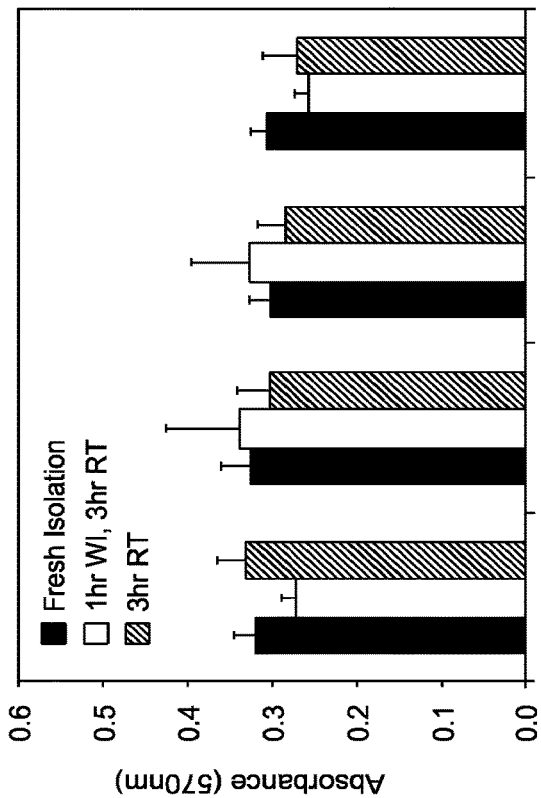
Figure 29F:
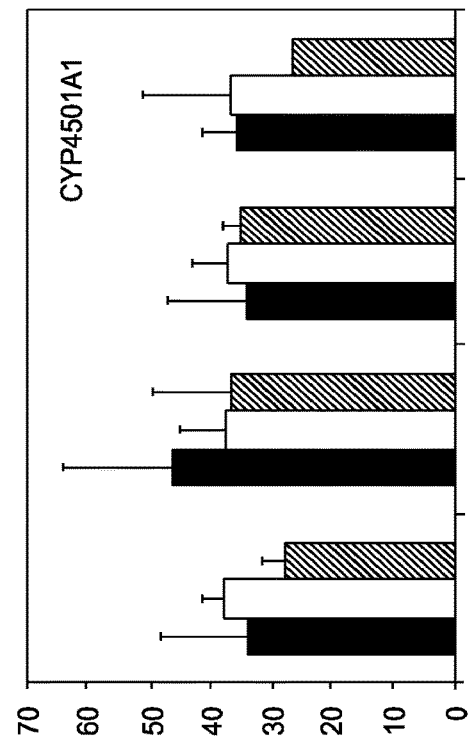
Figure 29G:
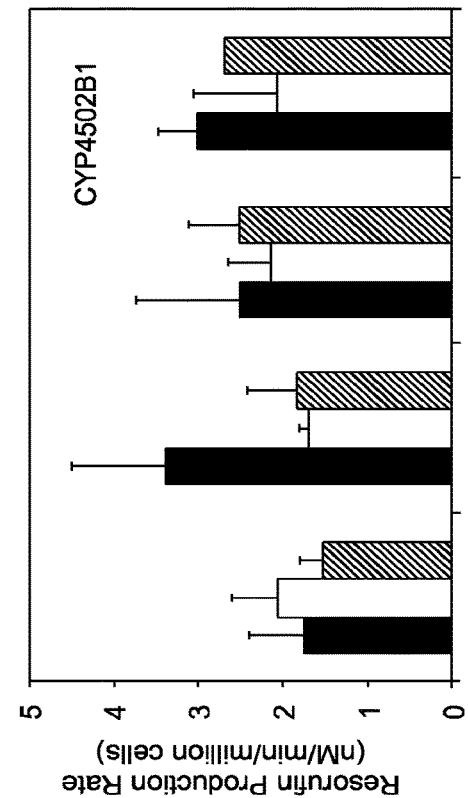
Figure 30B:
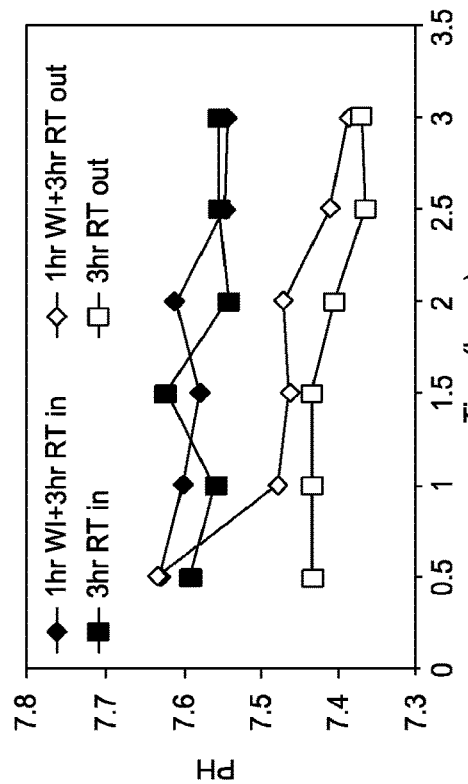
FIGS. 30A-30H illustrate the liver performance in perfusion.
Figure 30D:
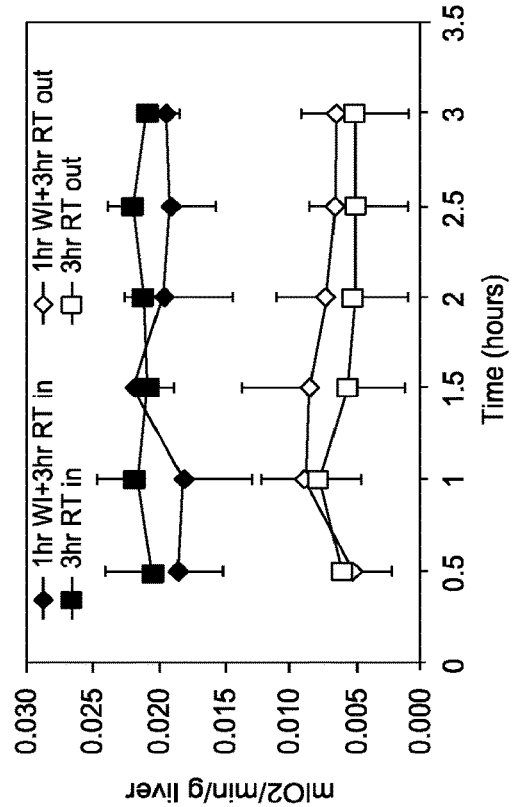
Figure 30A:
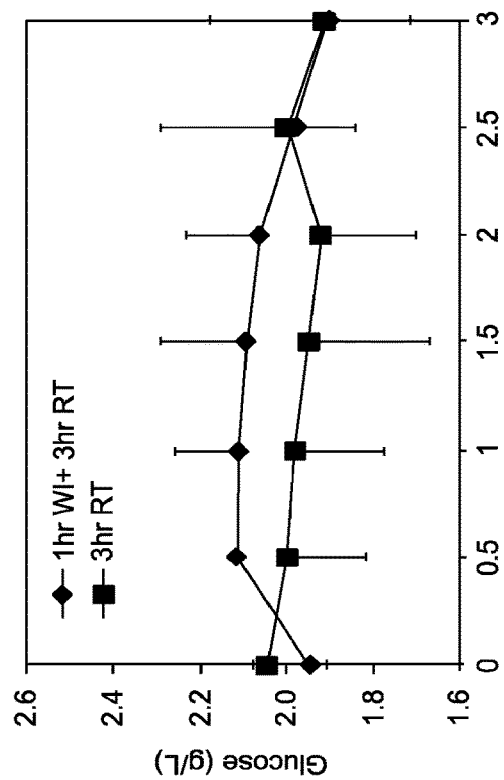
Figure 30C:
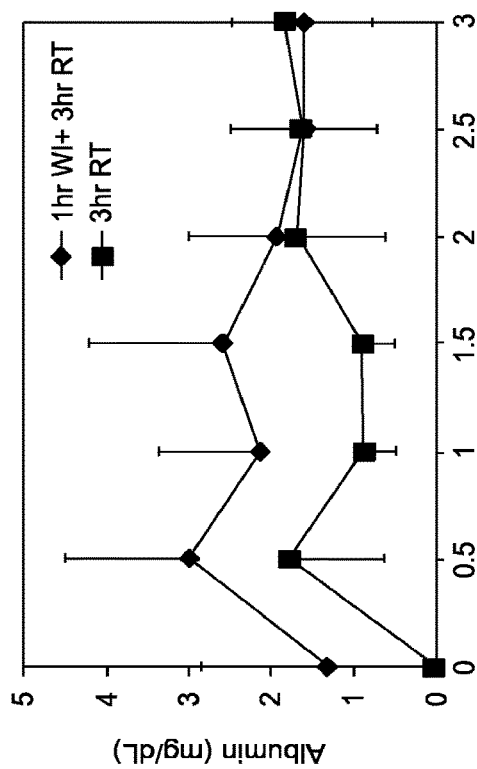
Figure 30E:
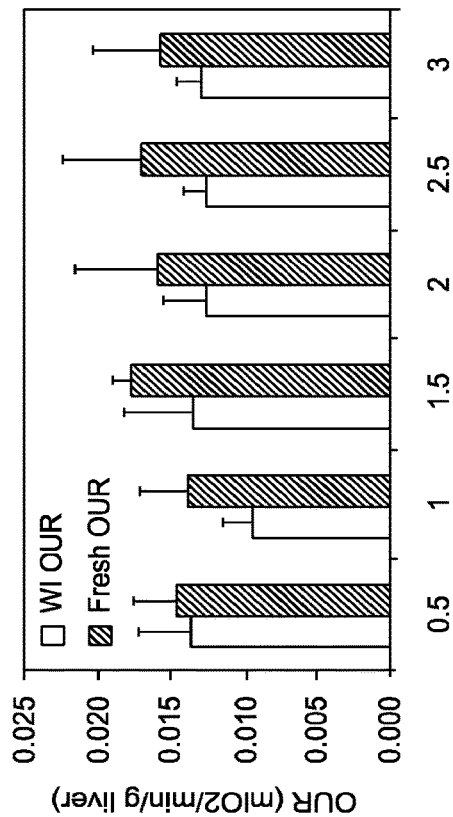
Figure 30F:
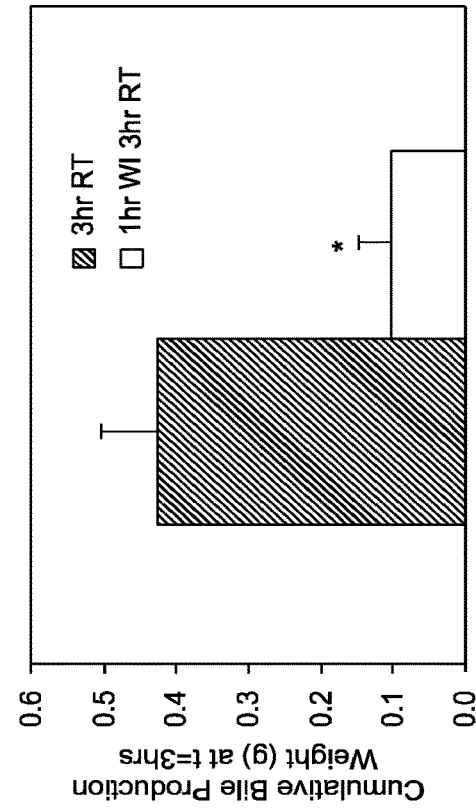
Figure 30G:
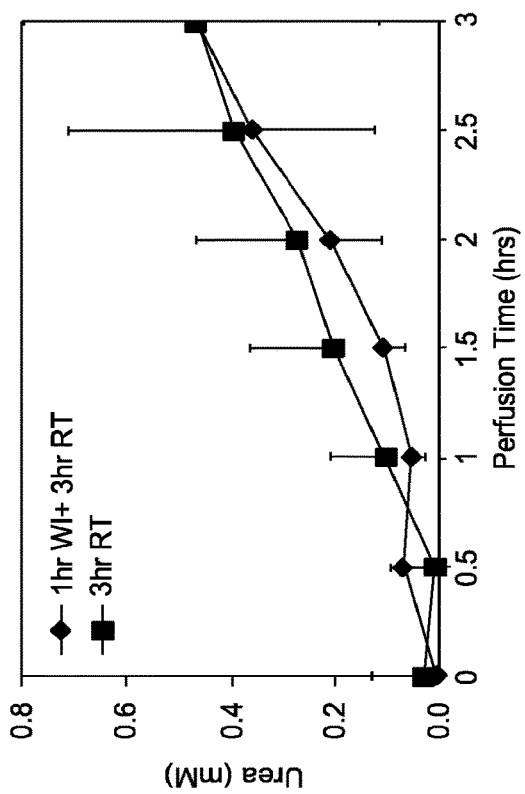
Figure 30H:
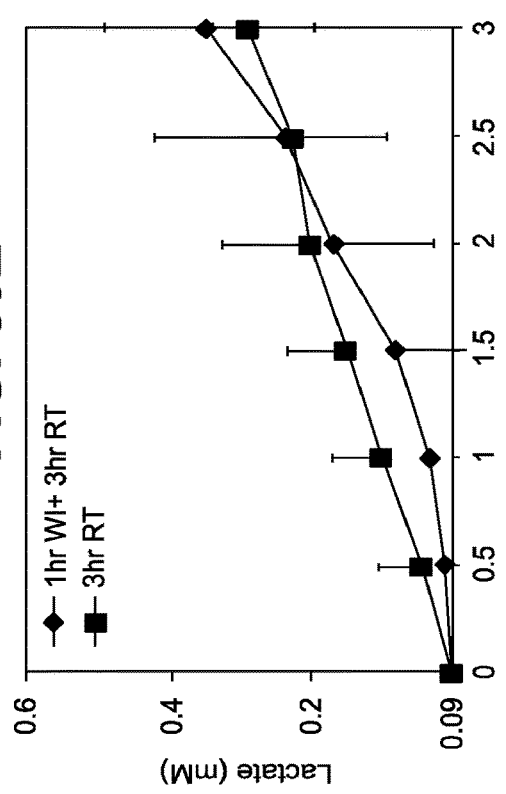

Performance of livers in perfusion was evaluated via several metrics. FIG. 29 illustrates the metabolic characteristics of ex vivo livers perfused at room temperature. The rates of glucose consumption, and lactate (Woods, H. F., Krebs, H. A. Lactate production in the perfused rat liver. *Biochen J* 125, 129-139 (1971)) and urea production were comparable in both groups, and neither demonstrated a net production of albumin (FIGS. 29A, F, G and C respectively). The liver's ability to control pH (Peter, S.D., Imber, C. J., Kay, J., James, T., Friend, P. J. Hepatic control of perfusate homeostasis during normothermic extracorporeal perfusion. *Transpl Proc* 35, 1587-1590 (2003)) was demonstrated from the very beginning of perfusion by 3hrRT livers, while WI+3hrRT livers recovered this function within the first hour (FIG. 29B). Both livers extracted almost all available oxygen in perfusate (FIG. 29D). Overall, 3hrRT livers tended to consumed slightly more oxygen (0.016±0.003 ml O2/min/gliver) than WI+3hrRT livers (0.012±0.003 mlO2/min/gliver), though the difference was insignificant at each measured time point (FIG. 29F). Bile production was delayed in WI+3hrRT, frequently initiating at t=2 hrs compared to the instantaneous production by 3hrRT livers. Subsequently the cumulative amount of bile from WI+3hrRT livers was less at t=3 hrs than that produced by 3hrRT livers (FIG. 29H). Liver weights in WI+3hrRT livers averaged 7.3±0.6 g before ischemia, 7.9±0.91 g after 1 hr of warm ischemia, and 7.6±0.7 g after perfusion. Liver weights in 3hrRT weighed 7.2±0.5 g before perfusion and 7.9±0.6 g after perfusion. None of these increases in weight were significant.

To evaluate the impact of ATP normalized to total protein on cell yield, its content was measured in liver tissue biopsied from organs immediately after harvest, 1 hr of WI, 1 hr WI+3hrRT and 3hrRT. FIG. 25B illustrates that there is a significantly high correlation between ATP content and purified cell yield per gram of liver tissue (Pearson's correlation 0.96). As the ATP measurements were made on biopsied tissue sections, a comparison to initial cell yields was also made (FIG. 30) but this shows a weaker correlation. Percoll subsequently removed 48% of the total yield in Fresh livers, 47% in 3hrRT livers, 51% in WI+3hrRT livers and 96% in WI livers.

Figure 31:
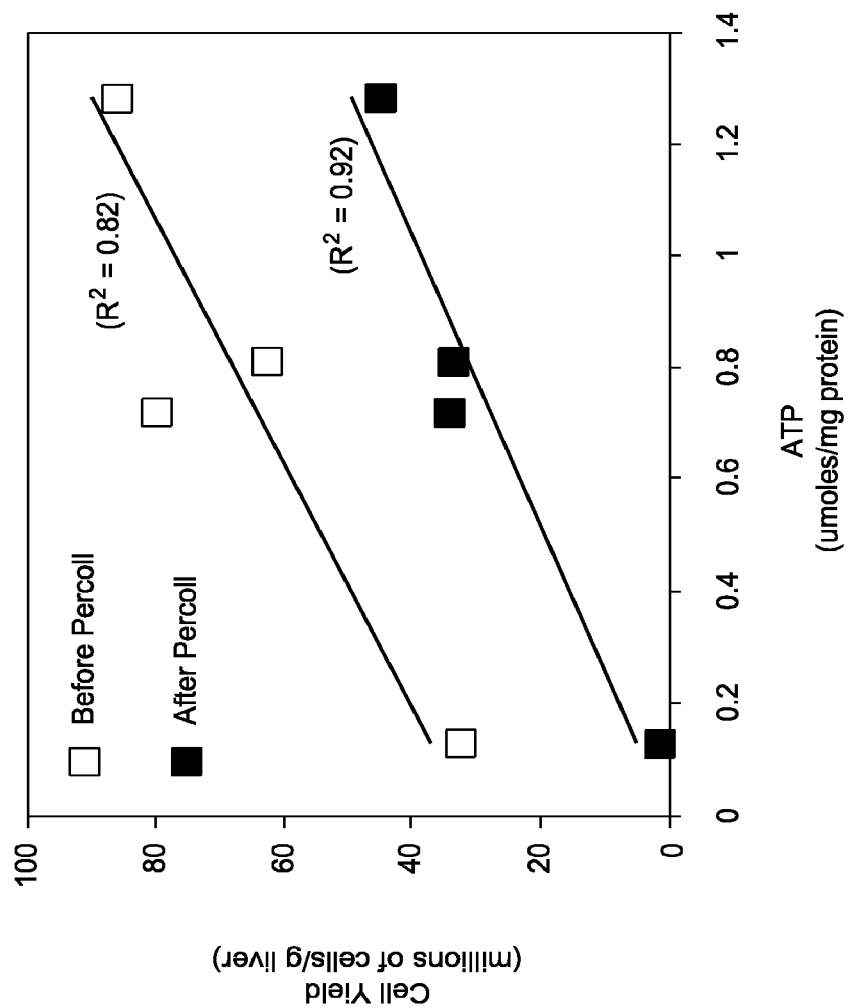
FIG. 31 illustrates a scatter-plot of average cell yields obtained in each group both before and after Percoll purification vs. average ATP content normalized to total protein.

Further differences between WI+3hrRT and 3hrRT livers were highlighted by perfusion hemodynamics. A scatter-plot of final flow rate vs. cell yield and pressure was created for both perfusion groups (FIGS. 31B and C). Both plots show that generally higher yields are obtained at lower flow rates; this relation is distinctly linear in 3hrRT livers (Pearson's correlation −0.94). Pressure across the livers was held generally constant and demonstrated no correlation to cell yield in these experiments. The ratio of pressure drop across the liver and flow rate, initially measured every 5 minutes for the first half hour, and then every half hour thereafter, provided a value of hepatic resistance (FIG. 31A). 3hrRT (n=13) were generally reduced in resistance compared to WI+3hrRT (n=14) livers though there was no consistent statistical difference between the groups. Flow rates for 3 hr RT livers started at 8.5±1.6 ml/min, with initial pressures at 4.5±2.4cmH$_2$O. WI+3hrRT livers experienced a similar initial flow rate of 8.6±2.4 ml/min with initial pressures at 6.25±4.8cmH$_2$O. By the end of perfusion, 3hrRT livers saw flow rates of 13±0.8 ml/min and pressures of 1.9±0.8 cmH$_2$O while WI+3hrRT livers experienced flow rates of 12.6±1.2 ml/min and pressures of 3.3±1.8 cmH$_2$O. This demonstrates that despite slightly lower flow rates in WI+3hrRT, pressure across these livers remained higher.

Histological evaluation using TEM allowed visualization of the presence of edema in WI livers (FIG. 32), with generally reduced cytoplasm-to-nuclear space, a suggestion of rounded or swollen mitochondria and the presence of vacuoles. These were also present in WI+3hrRT livers though to a lesser extent and gross edema was significantly reduced by comparison. However, sinusoids appeared generally dilated and congested while hepatocyte sinusoidal cell boundaries were indistinct. 3hrRT cells did not show significant vacuolation or edema but also suggested evidence of sinusoidal congestion and indistinct sinusoidal hepatocyte borders. At 0.5 microns (FIG. 33), nuclear and mitochondrial membranes appeared intact, and their contents comparable to Fresh livers. Mitochondria appeared more swollen in the WI and perfused livers compared to Fresh livers. Rough endoplasmic reticulum and glycogen rosettes appeared comparable in Fresh and WI livers, less-distinct and discontinuous in perfused livers.

MATERIALS AND METHODS for EXAMPLE 4

Experimental Groups. Experiments were conducted on female Lewis rats (160 g-180 g) which were kept in accordance with National Research Council guidelines. The Subcommittee on Research Animal Care, Committee on Research, Massachusetts General Hospital approved the experimental protocols. Animals were randomly divided into four groups: 1) Livers that were exposed to an hour of WI at 34° C. (WI), 2) Livers that were perfused for 3 hours at room temperature after 1 hr WI (WI+3hrRT), 3) Fresh livers (Fresh), and 4) Fresh livers perfused for 3 hours at room temperature (3hrRT).

Hepatectomy. Livers were excised according to the technique of Delriviere et. al. (Delriviere, L., Gibbs, P., Kobayashi, E., Goto, S., Kamada, N., Gianello, P. Detailed modification technique for safer harvesting and preparation of liver graft in the rat. *Microsurgery*17, 690-696 (1996)). Briefly, a transverse abdominal incision was made and the intestines retracted to expose the portal vein (PV), the common bile duct (CBD), and the inferior vena cava (IVC). The CBD was cannulated (12 cm, 22 G polyethylene stent, Surilo, Terumo, Somerset, NJ) and the IVC freed from the right renal and adrenal veins. The portal vein (PV) was freed from the splenic and gastroduodenal veins. The right phrenic vein emptying into the supra-hepatic vena cava (SHVC) was ligated. The hepatic artery was then ligated and the IVC clamped. Finally, the PV was clamped and the clock started for ischemic duration. The diaphragm was opened, the SIIVC was transected, and the liver was removed, and weighed. Fresh livers were then immediately prepared for biopsy. 3hrRT livers were placed in a bowl of room temperature saline to be cuffed at the PV and IVC prior to perfusion with an average ischemic time of 10 minutes. WI livers were placed in a temperature-controlled chamber filled with saline and maintained at 34±0.1° C. for 1 hr during which time they were cuffed.

Perfusion Circuit. The perfusate comprised 750 ml phenol red-free Williams Medium E (Sigma Chemical, St. Louis, MO) supplemented with 2 u/L insulin (28.85 units/mg Humulin, Eli Lily, Indianapolis, IN), 100,000 u/L penicillin, 100 mg/L streptomycin sulfate (Gibco, Invitrogen,Grand Island,NY), 0.292 g/L L-glutamine (Gibco), 10 mg/L hydrocortisone (Solu-Cortef, Pharmacia & Upjohn, Kalamazoo, MI), and 1000 u/L heparin (APP, Schaumberg, IL). The circuit comprised a peristaltic pump which brought perfusate from a reservoir to a membrane oxygenator, through a bubble trap and to an 18 G catheter for portal flow into the liver. The liver was positioned on a fine flexible mesh surface, permeable to perfusate, in a perfusion chamber. Effluent flowed freely from the PV and SHVC into the chamber where it was then returned to the perfusate reservoir (FIG. 1A). The oxygenator was gassed with a mixture of 95% O$_2$/5% CO$_2$. Upon completion of cuffing of Fresh livers and after the period of warm ischemia for WI livers, organs were immersed in a drained perfusion chamber into which perfusate dripped at 4 ml/min; perfusion chamber outflow was redirected to a catch basin where effluent from the liver was collected for the first 20 minutes before the circuit was closed. Using a simple manometer, portal pressure was recorded every 5 minutes during this flushing, as were flow rates which were gradually increased over time in accordance with the drop in pressures observed. It was desirable to achieve in vivo flow rates of ~1.8 ml/min/g liver (Izamis, M. L., et. al. In vivo metabolic flux analysis of the liver: Effect of burn injury in rats. (2010)). but preference was given to sustaining an absolute pressure below 4-6cmH$_2$O. At t=30 mins and every half hour after, additional sampling commenced with 1.2 ml perfusate aliquots collected and stored at −80° C. for later analysis. Inflow and outflow blood gas analysis was also performed at this time for pO2 and pH measurements, corrected to 20° C. (Rapidlab, Chiron Diagnostics, Norwood, MA). Bile was collected in a tube outside the perfusion chamber and both it and the livers were weighed at the end of perfusion.

Hepatocyte Isolation. A two-step collagenase perfusion technique described by Seglen (1976), and modified by Dunn et al. (1991) was used to isolate hepatocytes. Briefly, using aseptic technique, after gaining portal vein access with an 18 G catheter, warm oxygenated KRB+EDTA was flowed through the livers at approximately 17 ml/min. For Fresh livers, the IVC was immediately dissected and the liver subsequently removed from the animal into a petri dish till perfusion was completed. Perfused and WI livers were already in petri dishes with cuffed PVs. A collagenase (type IV, Sigma, C5138-1 G) solution with KRB and $CaCl_2$ was introduced to perfusion as the KRB solution was depleted and allowed to flow until successful digestion was observed. The livers were then moved to a sterile hood on ice where approximately 10 mL of sterile, cold KRB were added. The liver capsule was gently broken to release the cells which were then passed through a 250 um filter followed by a 60 um filter. The suspension was divided into 50 mL conical tubes and centrifuged at low speed (300-350 RPM, 4° C., no brake, 5 minutes). The supernatant was aspirated and the pellet resuspended with 10 ml KRB. An initial cell count and viability was performed. A volume of 24 ml of cold Percoll solution (9 parts Percoll: 1 part 1.5M NaCl, pII 5-5.5) was used for every 25 mL of cell suspension. Cells were added at a concentration of 5 mllion cells/mL and inverted before being centrifuged (50 g, 4° C., no brake, 5-10 minutes). The buffy coat and supernatant were discarded and resuspended to 10 mL in DMEM+FBS+100,000 u/L penicillin+100 mg/L streptomycin sulfate, after which a final count was performed.

Cell Suspension. Cells were diluted to 1 mllion/ml in Williams Medium E and aliquoted into 1.6 mL microcentrifuge tubes, 4 separate vials were used for each assay except for Trypan Blue exclusion where time permitted only 2. The tubes were subsequently rotated at slow speeds in a 37° C. incubator, except light-blocked vials for CYP450 activity which were allowed to settle between readings so as to reduce pipetting errors.

ALT and AST. 4 vials each were prepared for ALT and AST. At every hourly time point starting at t=0 hrs, 15 ul from each vial was placed into a 96 well plate on ice. At t=6 hours, Triton-X 100 was diluted to 1% concentration with a volume of the remaining cells. The cells were lysed by rapid pipetting, and then diluted 1:4 with PBS; 15 ul from each vial was finally added to the 96 well plate as the positive control. 150 ul of reagent at room temperature was then rapidly pipetted into the wells and a kinetic endpoint assay provided enzyme activity per minute (TR71121 and 7200-006, Thermo Electron, Pittsburgh, PA). The results were subsequently normalized to the completely lysed cells.

CYP450 activity. 4 vials for each of the CYP450 enzymes to be tested were prepared; these included benzyloxy resorufin (CYP4502B2), pentoxy resorufin (CYP4502B1), ethoxy resorufin (CYP4501A1) and methoxy resorufin (CYP4501A2). 20 μL of 6 mM stock solution 3,3'-methylene-bis(4-hydroxycoumarin) was added to each vial (Sigma M1390) and allowed to incubate for 20 minutes. 10 μL of 1 mM solutions of each of the isoenzymes was then added to the vials. The vials were inverted several times and a 50 μL sample was taken at t=0 minutes and stored on ice, away from light. Samples were taken again at 10, 20, 30 and 40 mins. A standard was prepared by serial dilution of 1000 nM resorufin. Samples and standards were read with a fluorescence plate reader (Ex530, Em590) and recorded as rates of resorulin production per million cells.

Glucose, Albumin and Urea. 4 vials were incubated for the entire 6 hr duration, spun down and the supernatant was stored at −80° C. Standard assay reagents were used for glucose (Stanbio 1075-825) and urea (Stanbio proc. No. 0580), and an elisa was used to detect albumin.

Viability. 2 vials were counted hourly using Trypan Blue exclusion to test for viability.

Mitochondrial activity. The MTT assay was performed hourly by pipetting approximately 50,000 cells (50 μL) from 4 vials into 4 wells on a 96-well plate and diluting with 50 μL of Williams Medium E for 4×100 μL of cell suspension. 1 vial of MTT was thawed (Biotium, Inc., 30006) and 10 μL added to each well. Samples were mixed gently while incubating at 37° C., protected from light. The plates were then spun at 800 rpm, the supernatant removed, and 200 μL of DMSO added to dissolve the Formazan. Absorbance was read at $OD_{570}$-$OD_{630}$.

Plate Culture. Cells were plated in standard 6-well plates using a double layer collagen gel sandwich plate culture (Dunn, J.C., Tompkins, R. G., Yarmush, M. L. Long-term in vitro function of adult hepatocytes in a collagen sandwich configuration. *Biotechnol Progr* 7, 237-245 (1991)) with C+H as the culture medium; phenol red-free medium was used in the CYP450 assays. Enough plates were prepared for 3 wells to be devoted to each assay on days 5, 7, 10 and 14.

Viability. Hoechst 33452 and Ethidium homodimer-1 double stain was used to detect all nuclei, and dead nuclei, obtaining a measure of viability. Briefly, 10 μL of a 1 mM solution of Ethd-1 and 5 μL of Hoechst 33452 were added to 5 ml of PBS, while protecting from light exposure. Medium from the cells was washed with PBS and 1 ml of the dye added to each well. The cells were incubated at 37C for 10-15 minutes before processing using a Zeiss axiovert 200 microscope. Thirty five snapshots were taken at distinct locations within each well for each dye, overlaid on corresponding phase contrast images. Cell nuclei were subsequently counted using CellProfiler (Broad Institute, Cambridge, MA).

Mitochondrial activity. 100 μL of MTT were added to each well and incubated for 1 hr at 37° C. The medium was subsequently aspirated from the wells and 1 mL of 6 mg/mL collagenase was added and incubated at 37° C. for 15 minutes and pipetted rigorously to dissolve all collagen. 1 mL of DMSO was then added and the contents rigorously pipetted up and down to dissolve the Formazan present. 250 μL samples were subsequently placed in triplicate on a 96 well plate (3 wells×3 samples) and absorbance was read at $OD_{570}$-$OD_{630}$.

CYP450 activity. 48 hours before the assay, 1 mL of a 2 μM solution of 3-methylcholanthrene inducer was added to each well. This medium was left on the cells for the subsequent 48 hours. 5 μM and 80 μM solutions of substrate solution and dicumarol respectively were prepared to a volume of 5 ml (1 ml/well) by diluting in EBSS. After 48 hours, the medium was aspirated and 1 ml of warm EBSS was added to each plate. After 15 minutes, the EBSS was aspirated and 1 ml of the substrate+dicumarol solution was added to each well. 50 μL of medium was subsequently removed at t=5,15 25, and 35 minutes and placed in a 96-well plate protected from light. Fluorescence intensity was subsequently measured (Ex530, Em590).

Glucose, Albumin, Urea. Media from plates prepared for assay analysis on Day 14 were collected daily and stored for metabolic analysis using the same techniques as above.

Tissue Biopsies. Tissue sections were rapidly frozen in liquid nitrogen upon resection of Fresh livers, after perfusion was complete for WI+3hrRT and 3hrRT livers, and after 1 hr of warm ischemia for WI livers. Remaining lobes were then perfused with 15 mL of Karnovsky's solution for histological preparation.

ATP. ATP content was measured in tissue segments homogenized with a mortar and pestle under liquid nitrogen and resuspended in 500 μL of nucleotide releasing buffer (Biovision, #K354-100). Each sample was spun down at 16 rpms for 2 minutes. 100 μL of sample was subsequently placed in a cuvet and the assay continued as prescribed in the kit. Data were plotted against a standard and normalized to the total protein present in the sample supernatant using a standard Bradford assay.

Transmission Electron Microscopy. Constructs were fixed overnight in modified Karnovsky fixative (2.5% Glutaraldehyde, 2.5% formaldehyde, 0.1M cacodylate buffer, pH 7.2), washed with 0.1M buffer, post fixed in 1% osmium tetroxide in 0.1M cacodylate buffer, and dehydrated in a graded series of ethanol. The samples were infiltrated and embedded in a mixture of Spurrs resin and Quetol according to Ellis (Ellis, E. A. Solutions to the problem of substitution of ERL 4221 for vinyl cyclohexane dioxide in Spurr Low Viscosity Embedding Formulations. *Microscopy Today* 14(2006)). 60-80 nm cross sections and en face sections were cut on an Ultracut E microtome (Reichert, Depew, NY) using a diamond knife. Thin sections were stained with 5% uranyl acetate and Reynolds lead citrate. The sections were viewed with a JEOL JEM 1010 transmission electron microscope (JEOL, Tokyo, Japan) and images were digitally captured on an AMT XR-41B CCD camera system (Advanced Microscopy Techniques Inc., Danvers, MA) (Bueno, E.M., Saiedi, N., Melotti, S., Ruberti, J. W. Effect of serum and insulin modulation on the organization and morphology of matrix synthesized by bovine corneal stromal cells. *Tissue Eng Part A* 15, 3559-3573 (2009)).

Example 5

Molecular Docking Study to Identify Ligands of PPAR-2γ

Figure 34:
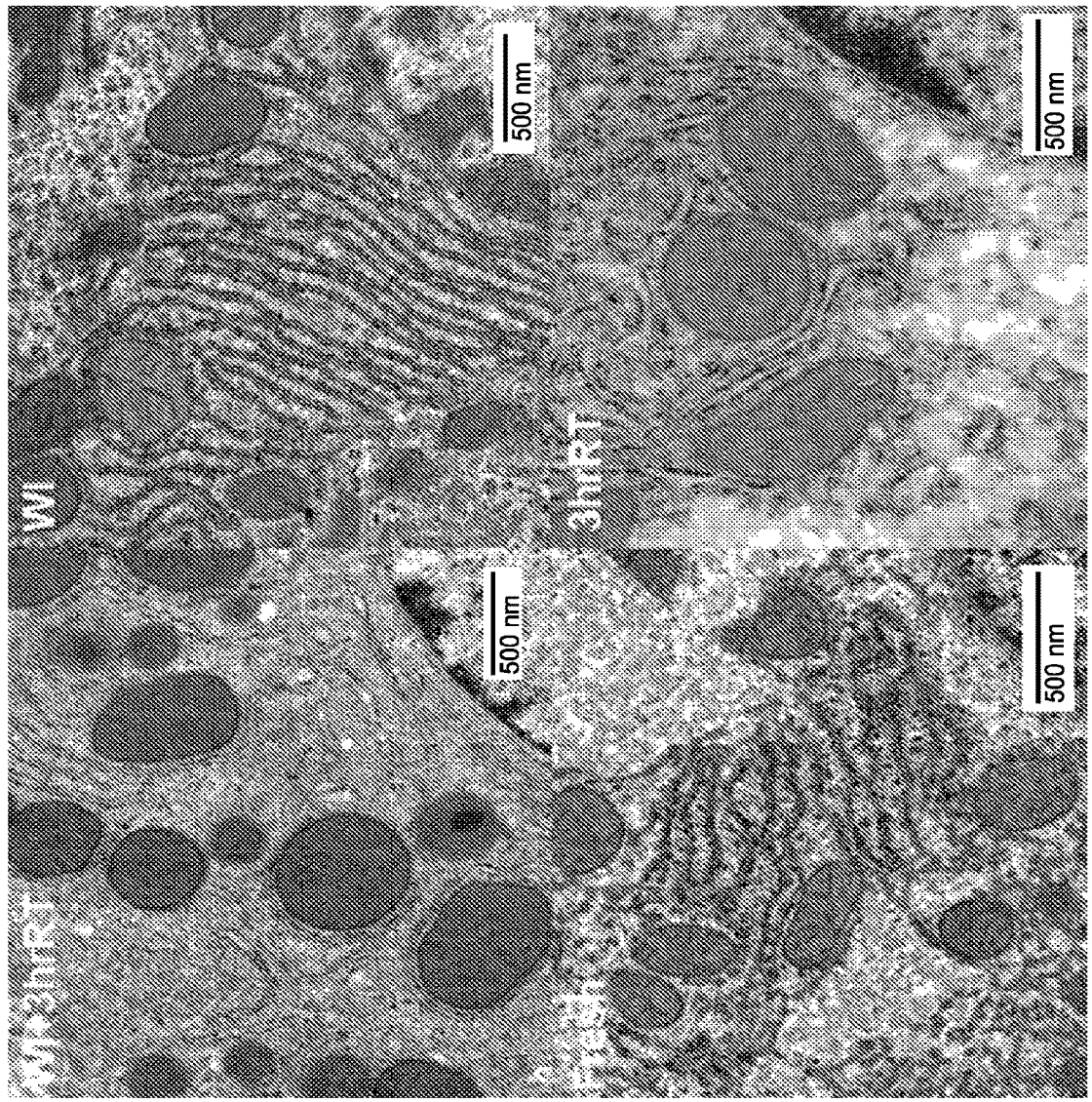
FIG. 34 illustrates the transmission electron microscopy (500 nm) shows WI and perfused livers have swollen mitochondria and potentially disrupted endoplasmic reticulum.

Inventors performed a molecular docking study to identify ligands of PPAR-γ, a transcription factor that is known to have the ability to modulate metabolic rate (see FIG. 34), where inventors identified Troglitazone as a candidate. Inventors also performed preliminary studies to test the effect of supplementation in preservation efficacy. In these initial studies inventors used C3A cells (human liver carcinoma line) and cryopreservation rather than supercooling, due to availability of data to be used as controls. Inventors observed that Troglitazone increased post-thaw viability ~2.5 fold. We are currently testing Troglitazone and other compounds with primary rat hepatocytes both in cryopreservation and supercooled storage.

Methods for Example 5. Nearly confluent C3A cell flasks were trypsinized in PBS solution; cells were sedimented by centrifugation (10 min at 10,000 g at 4 degree c.). The medium was replaced by adding 2 mL of HTS and the cell pallets were re-suspended in the HTS by gentle pipetting. The cell samples in 1 ml, aliquots were put in 1.5 mL, cryovials. The samples were frozen in a controlled rate freezer using a freeze controlled Cryobath (Cryologic, Victoria, Australia) with a CL-8800 temperature controller (Cryologic). A cooling rate of 1 degree c./min was used. The samples were seeded with ice at −4 degrees C. by using a cotton bulb dipped in liquid nitrogen. The freezing was continued 'till the controlled rate freezer temperature reaches −80 degrees C. Cryovials were then taken out of the cryovial holders and put directly into the liquid nitrogen dewar for storage. The cryovials with the cell samples, incubated with and without 25 μM troglitazone for 30 mins, were stored in liquid nitrogen for 5-10 mins. The cell samples in the cryovials were rapidly thawed in a water bath at 37 degree C. The viability (membrane integrity) of the cell samples were found by trypan blue exclusion method.

Example 6

Correlation Between Transplantation Success and Quantity & Viability of Cells Obtained from Ischemic Livers Inventors demonstrated that there is a direct correlation between transplantation success and quantity & viability of cells obtained from ischemic livers (FIG. 36), enabling the use of this as an alternative model to transplantation. Furthermore, inventors established extracorporeal liver perfusion with whole-blood as a surrogate model for ischemic liver transplantation, with ALT being a predictor of transplant success. a) We have recently developed a system where the rat livers can be stably perfused. For testing the system non-ischemic livers were transplanted into syngeneic recipients (inbred Lewis) after 6 hrs of perfusion at 20° C. b) During perfusion AST and ALT levels exceeded normal values until t=3h, and then stabilized. Bile production was linear throughout. Ten out of 11 cases survived at least 1 month after the procedure, indicating the feasibility of normothermic perfusion as a liver preservation environment. c) NELP treatment increased the hepatocyte yield from 1 hr warm ischemic livers significantly, close to the yield obtained from non-ischemic livers. *indicates statistical difference compared to all other groups. (p<0.05). d) Viability of recovered cells was similar in all groups. These results demonstrate that NELP increases the number of cells isolated from ischemic livers by 10 fold. The viability of cells from ischemic livers in all cases was the same. Note that the viability cutoff for cells can be adjusted by altering the final step in cell isolation where live and dead cells are separated by density difference. We normally use 95% viability cutoff, but this results in significant loss of viable cells; inventors found that 80% was the viability was the maximum where inventors could extract some viable cells from ischemic, non-treated livers.

Methods For Example 6.

Lean livers were harvested from Lewis rats and held at 34° C. for 60 mins. After 1 hr of ischemia, livers were perfused in a perfusion system at room temperature. The perfusion system consisted of a closed circuit where perfusate is continuously recycled through a bubble trap and membrane oxygenator before entering the liver. Perfusate passes through the portal vein only and exits via the suprahepatic vena cava, bathing the liver in a perfusion chamber. A parallel circulation system takes the perfusate through a dialyzer. Flow rate through the liver is 1.5 ml/min/g liver wet weight, and portal pressure is maintained between 10 and 15 cm water. The total volume of perfusate is approximately 50 ml and Williams Medium E (Sigma), hydrocortisone (10 mg/l), insulin (2 U/1), heparin (1000U/1), penicillin (40,000 U/1) streptomycin (40 mg/1). The dialysate consists of the same medium and provides a fresh source of glucose as well as a sink for liver byproducts; a separate circuit is used so that protein secretion can be detected easily, and for long-term perfusions media can be replaced simply by replacing the dialysate reservoir. After 3 hrs of perfusion, hepatocytes were isolated using a two-step collagenase perfusion procedure as described previously. The cells were counted using a hemacytometer and the viability was evaluated by trypan blue exclusion. Controls were livers that were undergone 1 hr of warm ischemia (WI), fresh healthy livers with no WI and no perfusion. Group comparisons were performed via ANOVA at p<0.05.

Example 7

3-O-Methyl-Glucose (3OMG) is a Stabilizer in Cryopreservation of Hepatocytes.

Figure 37A:
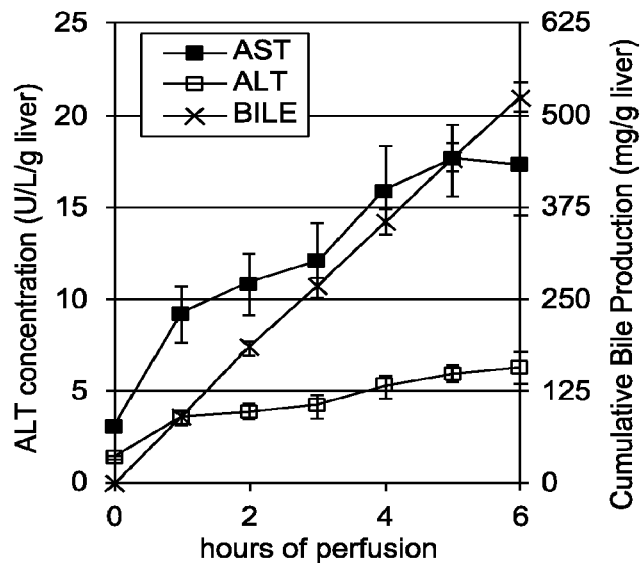
FIGS. 37A-37C illustrate that NELP increases cell yield from ischemic livers by ten-fold.
Figure 37B:
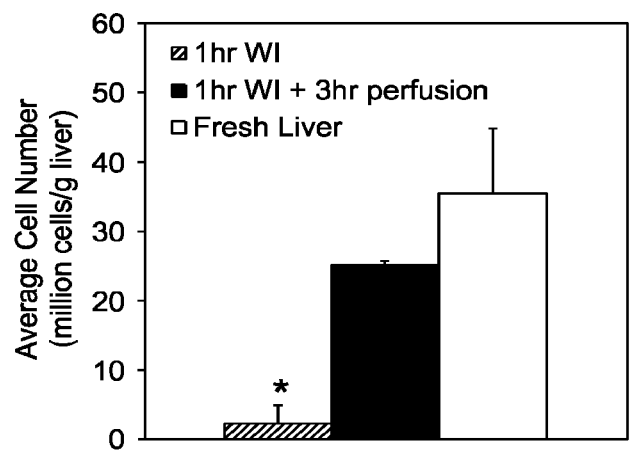
Figure 37C:
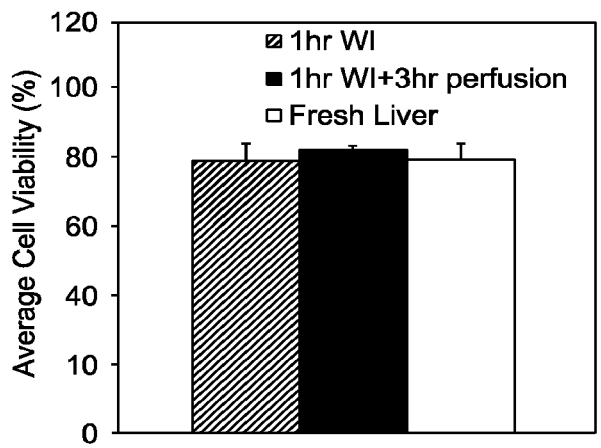

Significant loading of 3OMG can be achieved within 20 minutes (FIG. 37a). The hepatocyte viability when incubated with 3OMG is statistically equal to other saccharides that are not cryopreservative for mammalian cells (FIG. 37b). By comparison, incubation with a common cryopreservative dimethyl sulfoxide (DMSO) under similar conditions reduces viability to 12%. These results indicate 3OMG is minimally toxic for hepatocytes in the concentration range studied; and are in line with the consideration of 3OMG a nontoxic material for studies in humans. The slight viability decrease however indicates that, like glucose and any other substance, 3OMG also can be toxic at high concentrations, and hence optimization of its dosage as proposed in Aim 1 is necessary.

Figure 38A:
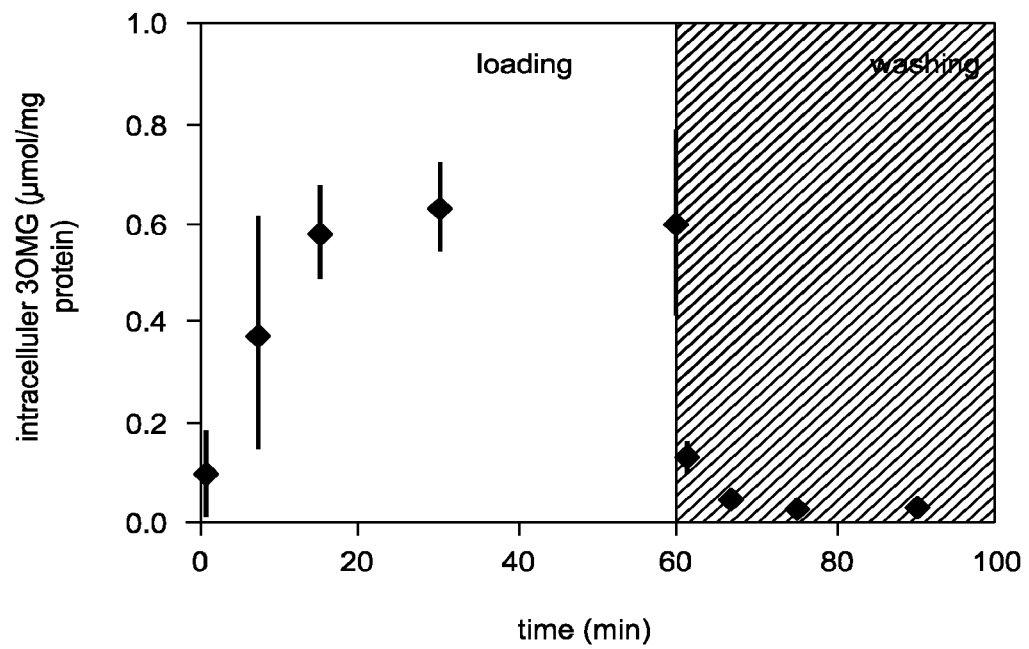
FIGS. 38A-38B illustrate that hepatocytes can be loaded with 3OMG within 20 minutes in vitro. Figure A shows the kinetics of 3OMG uptake show significant loading of cells with 3OMG within 20 minutes, and even more rapid release with washing; perfusion of the livers in stable condition can currently be done for more than 6 hrs, which is more than sufficient for loading with 3OMG.
Figure 38B:
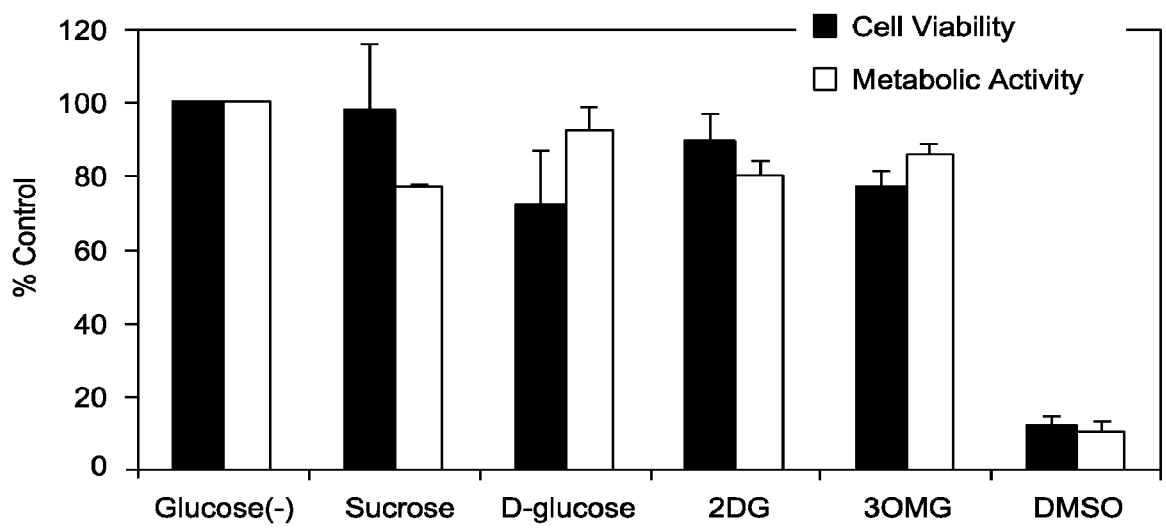
Figure 39A:
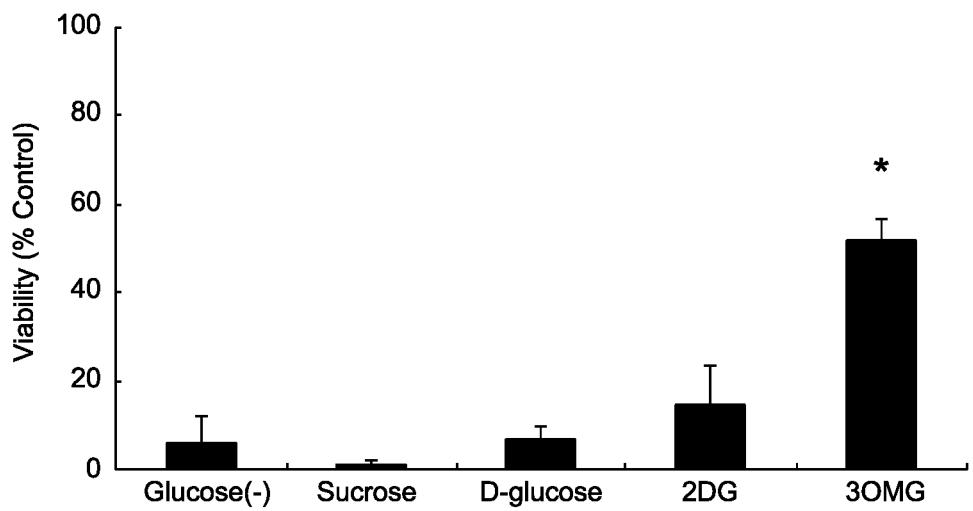
FIGS. 39A-39E illustrate that 3OMG improves past-thaw viability of cryopreserved hepatocytes.
Figures 39B, 39C, 39D, 39E:
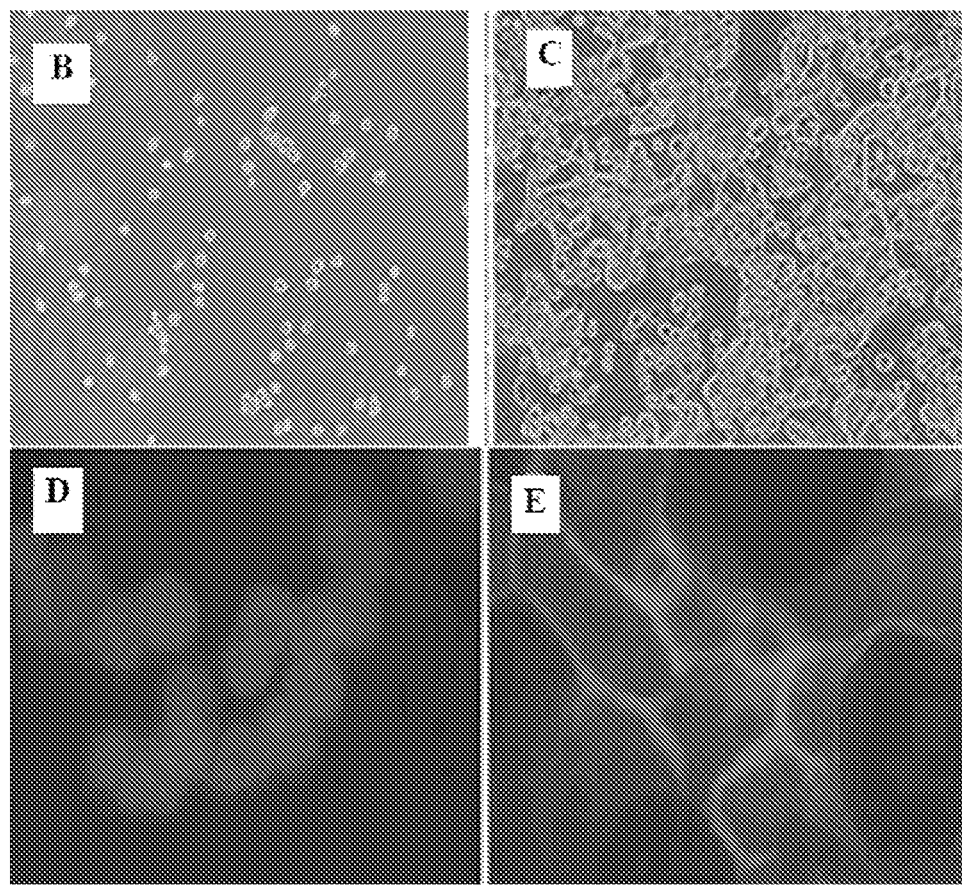

As displayed in FIG. 38, after cryopreservation the viability of cells is above 50% with good morphology with 3OMG, demonstrating its efficacy as a cryopreservant, significantly better then glucose, D-glucose, 2-deoxy-glucose (2 DG), or sucrose. When cultured in vitro, long-term hepatic functions are similar in non-frozen hepatocytes and 3OMG loaded and frozen hepatocytes (FIG. 39). Overall, these studies demonstrate that 3OMG can be loaded and unloaded practically, and that it does perform as a minimally toxic preservative during cryopreservation.

Hepatocytes can be loaded with 3OMG within 20 minutes in vitro. FIG. 37A illustrates that the kinetics of 3OMG uptake show significant loading of cells with 3OMG within 20 minutes, and even more rapid release with washing; inventors can currently perfuse the livers in stable condition for more than 6 hrs, which is more than sufficient for loading with 3OMG. Cell viability (black bar) and metabolic activity (white bar) of hepatocytes after incubation with isotonic mixtures of various sugars and DMSO for 60 min (FIG. 37B); this indicates that loading 3OMG affects the cells similar to other glucose variants, and 3OMG is minimally toxic at concentrations used.

3OMG improves past-thaw viability of cryopreserved hepatocytes. (FIG. 38A) Past-thaw cell viability (percentage of unfrozen control), shows more than 50% viability after one week storage in liquid nitrogen. (FIG. 38B-C) Typical phase-contrast images of cryopreserved hepatocytes at 48 h after thawing (FIG. 38B), no-glucose control (FIG. 38C), 3OMG. Cells in control group remained unattached, whereas 3OMG loaded cells were very well spread. (FIG. 38D-E) Rhodamine phalloidin staining of cryopreserved hepatocytes (original magnification ×400); (FIG. 38D), no-glucose control, (FIG. 38E), 3OMG. No-glucose control hepatocytes completely lost polarity and structure. Actin filaments (F-actin) were found at their normal sites at both the lateral intercellular contacts and the apical canalicular membrane in 3OMG-loaded hepatocytes. These results show that 3OMG is a viable cryoprotectant.

These results demonstrate the 3OMG loaded hepatocytes retain their functions after cryopreservation. Methods: Cells were cultured in a collagen sandwich for 0.5 14 days, and media collected daily were analyzed for albumin and urea. All values were normalized by viable cell number (DNA content) and shown as o the means±se (n >9). Urea secretion and resorufin formation were statistically not different (p=0.51 and p=0.3 respectively). Albumin production on days 7-13 were statistically different at p=0.014 (FIG. 39).

NELP is an accessible short-term liver preservation method. Our NELP system comprises the basic features of an artificially derived blood supply that is heated, oxygenated, cleared of any air bubbles and dialyzed before passing into the liver at a physiological flow rate and pressure via the portal vein (see FIG. 40). Preliminary studies with this system using normal lean rat livers show that livers can be perfused for at least 6 hrs at 37° C. and still exhibit stable metabolic function (FIG. 41). 10 out of 11 perfused livers were successfully with recipients surviving at least 1 month after the procedure.

Figure 40A:
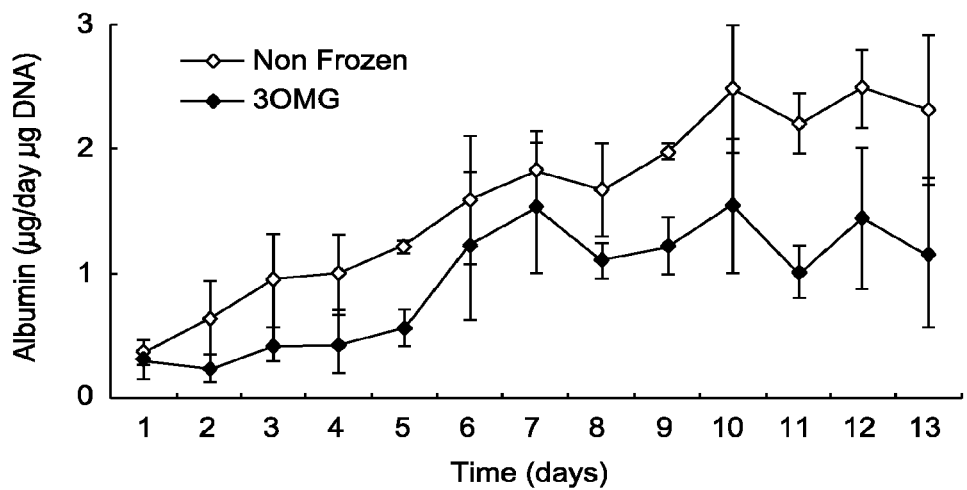
FIGS. 40A-40C illustrate that long-term hepatic functions are similar in non-frozen hepatocytes and 3OMG loaded cryopreserved hepatocytes. Figure A shows albumin, Figure B shows urea and Figure C shows cytochrome P450 activity as assessed by formation of resorufin from ethoxyresorufin.
Figure 40B:
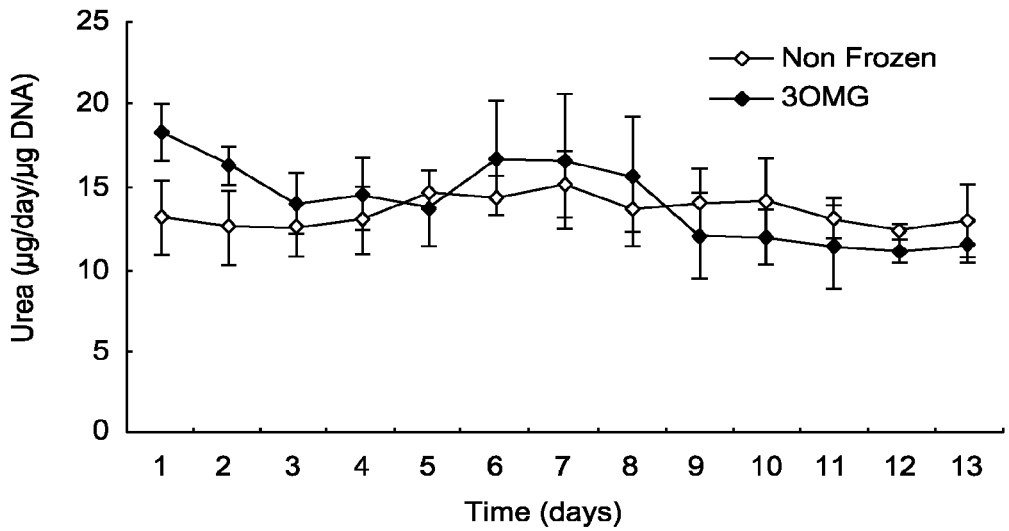
Figure 40C:
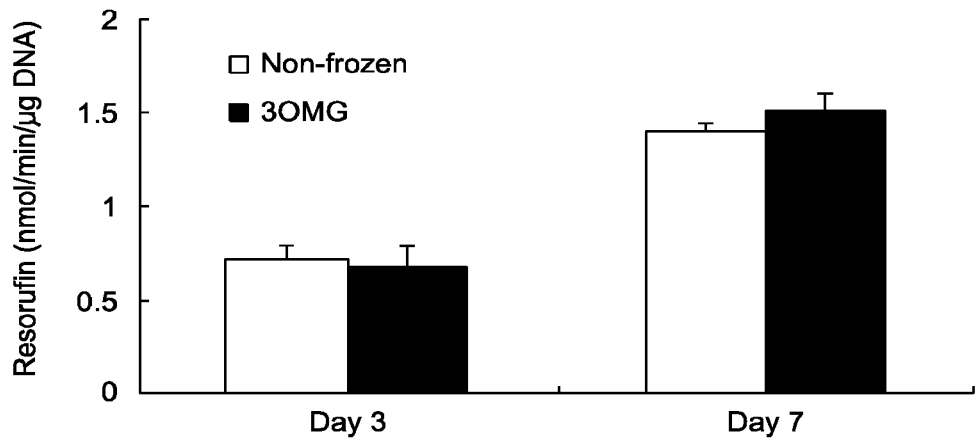

Normothermic Extracorporeal Liver Perfusion (NELP) system (FIG. 40).

Figure 41A:
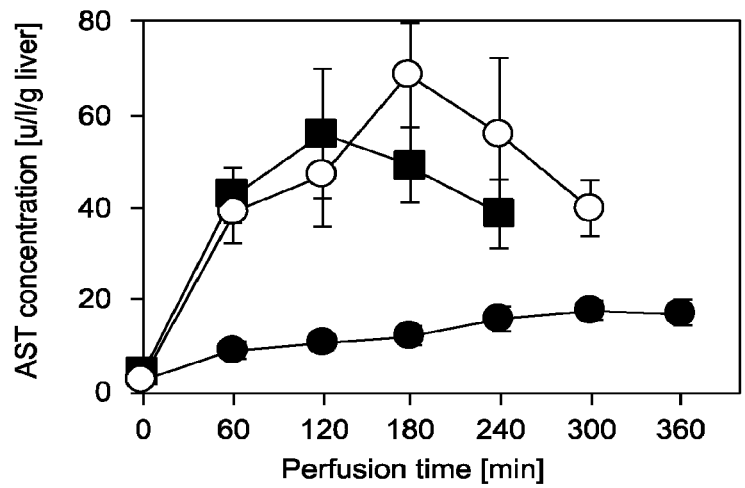
FIG. 41 illustrates that normothermic perfusion of ischemic livers show stable response: AST and ALT release, and bile production compared to normal livers. Solid circles: normal livers, open circles: warm ischemic livers, solid squares: combined warm and cold ischemia.
Figure 41B:
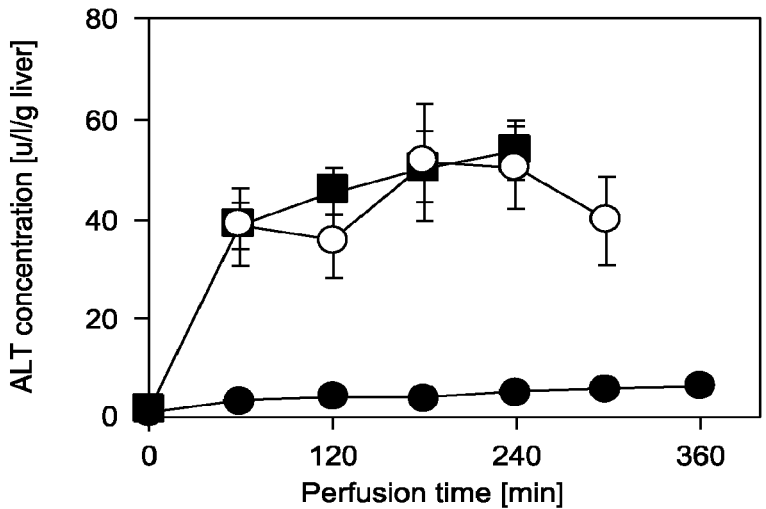
Figure 41C:
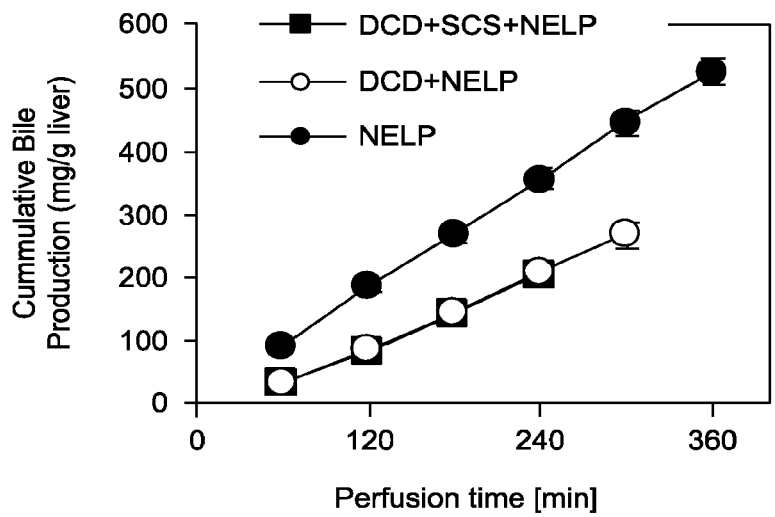

Warm and Cold ischemic livers can be resuscitated with normothermic extracorporeal perfusion: To demonstrate the efficacy of NELP in treating ischemia, livers were harvested from heparinized rats and subjected to warm ischemia at 34° C. for 60 mins, or to combined warm and cold ischemia (45 minutes at 34° C. +2 hrs in UW on ice). Subsequently, the livers were perfused for 5 h in the perfusion normothermically. During perfusion, several parameters were measured and compared to freshly isolated normal livers that were not exposed to any warm ischemia, and perfused for 6 hours in the NELP system (FIG. 41).

Normothermic perfusion of ischemic livers show stable response: AST and ALT release, and bile production compared to normal livers. Solid circles: normal livers, open circles: warm ischemic livers, solid squares: combined warm and cold ischemia (FIG. 41). Ischemic livers displayed similar profiles throughout perfusion regardless of ischemia type. AST & ALT increased several-fold higher than normal livers in the first 3 h of perfusion, and then stabilized or even decreased. Bile production was lower than normal controls, although it was linear throughout, suggesting no further hepatic damage occurred during the perfusion itself. This data demonstrates that normothermically perfused ischemic livers show stable functional response.

Figure 42A:
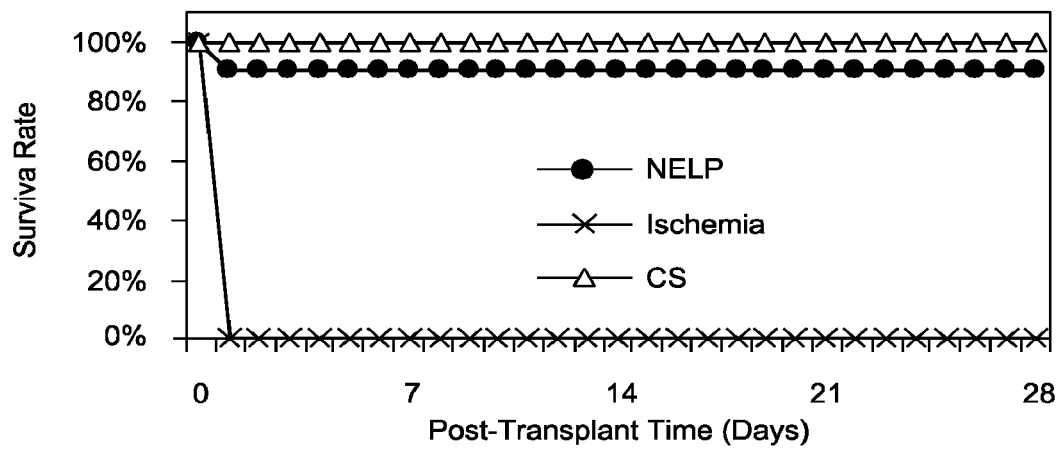
FIG. 42 illustrates that normothermic perfusion resuscitates livers with warm and cold ischemic damage.
Figure 42B:
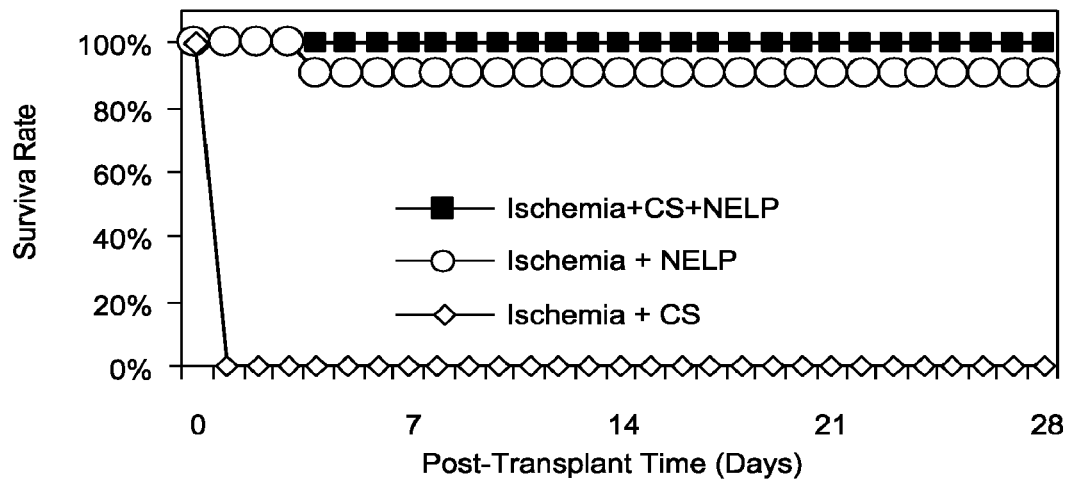

FIG. 42 illustrates that normothermic perfusion resuscitates livers with warm and cold ischemic damage. The survival of rats transplanted with ischemic livers. CS: Cold Storage, NELP: Normothermic Perfusion. Recipients of ischemic livers preserved in UW solution died within 24 hrs. All normothermic perfusion studies demonstrated excellent survival (>90% for ischemic livers treated with NELP), similar to healthy livers with cold storage showing that normothermic perfusion enables rescue of the ischemic livers. Methods: Perfusion protocols are identical to the groups in FIG. 45. For non-perfused groups, Livers were either subjected to 1 hr warm ischemia and kept in CS for 5 hrs, or directly placed in CS and stored for 6 hrs prior to transplantation.

Figure 43A:
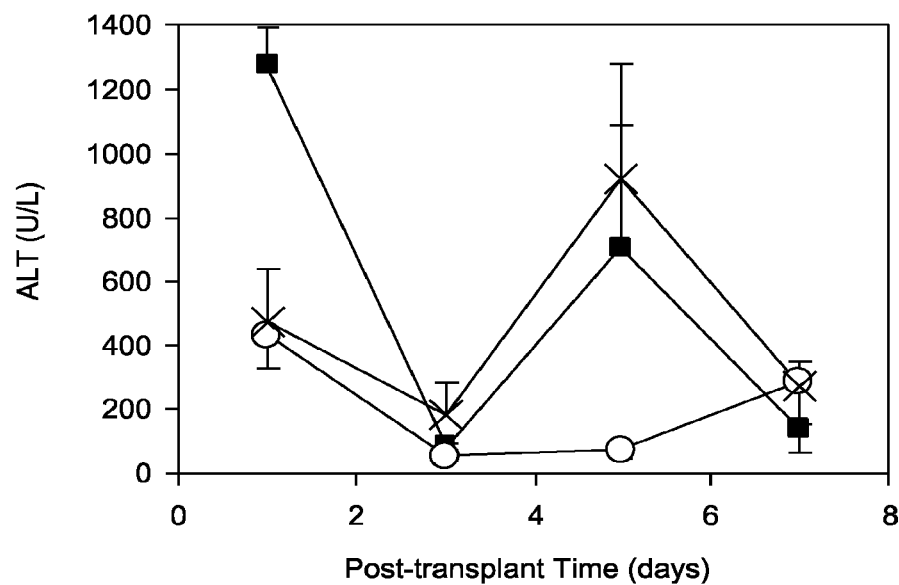
FIGS. 43A-43B illustrate that normothermically perfused grafts perform as well as or better than cold stored organs when transplanted
Figure 43B:
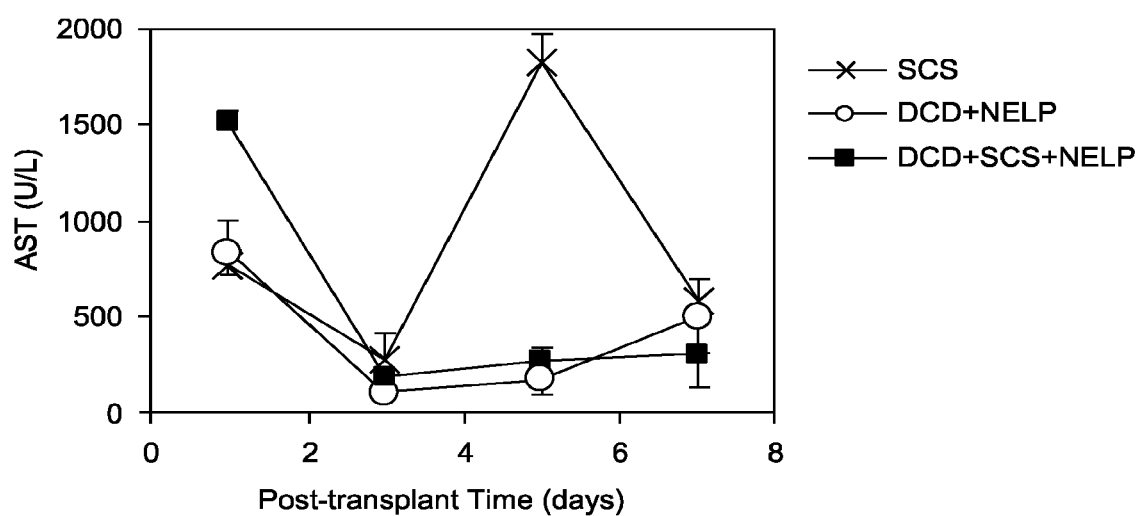

Normothermically perfused grafts perform as well as or better than cold stored organs when transplanted (FIG. 43.). Overall, average transaminase levels of ischemic liver recipients (warm and warm+cold ischemia) were lower compared to recipients of CS grafts at p<0.1.

After normothermic perfusion, ischemic livers were orthotopically transplanted into recipient rats successfully (10/10 warm ischemia, 11/11 combined warm and cold ischemia), with the animals recovering quickly from surgery. The controls did not survive past first day (Cold stored: 0/6, warm ischemia directly transplanted 0/6, see FIG. 42); although animals did wake up from surgery, they died within 24 hrs. Perfused grafts functioned as well or better than cold preserved grafts after transplantation (FIG. 43). These studies clearly show the feasibility of ex vivo normothermic perfusion for the recovery of ischemic livers.

Figure 44:
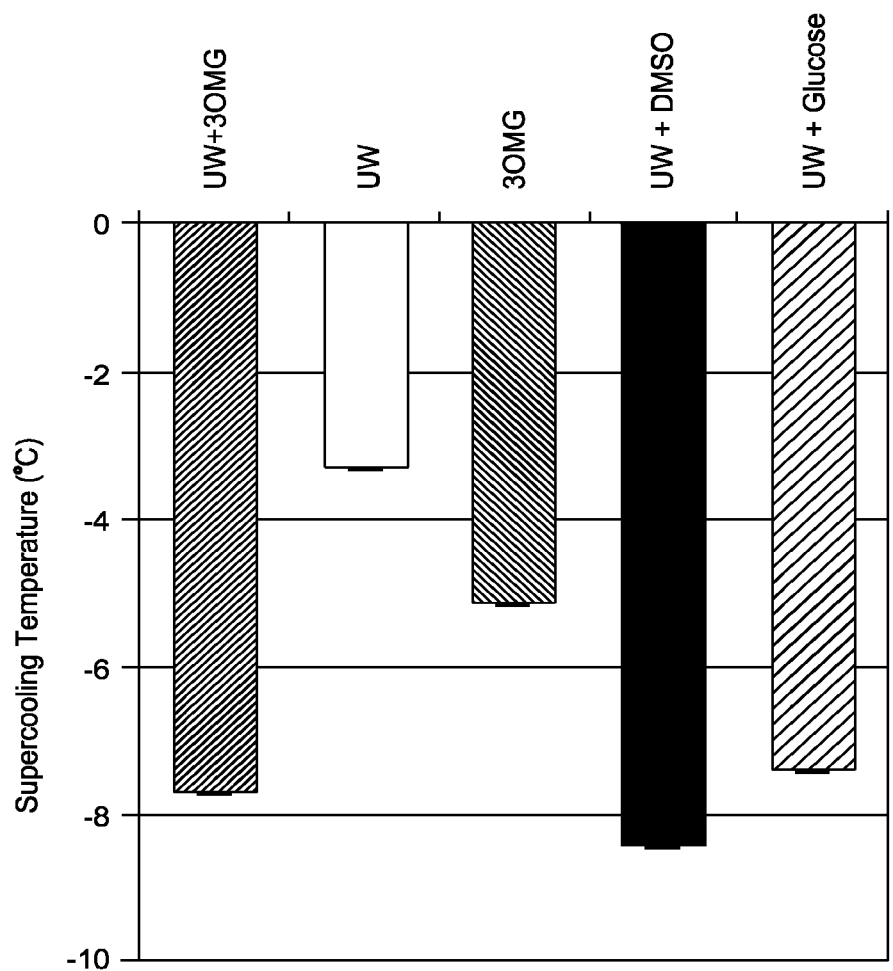
FIG. 44 illustrates that 3OMG significantly reduces achievable SZNF temperature.

3OMG effectively decreases SZNF storage temperature achievable: Using our liver storage equipment, inventors tested the supercooling temperature that can be achieved in a stable manner with University of Wisconsin (UW) solution, and the effect of 3OMG. Without 3OMG, the stable temperature inventors could reach was −3.3±0.01° C., whereas with an isotonic mixture of 3OMG and UW inventors were able to reach −7.6±0.01° C., similar to supercooling obtained by addition of DMSO and glucose (FIG. 44). Whether this is due to freezing point depression or reduction of ice-nucleation is unclear; regardless, these results demonstrate that 3OMG is utilizable for reducing the SZNF preservation temperature. We expect that with superior cooling equipment it will be possible to reach temperatures below ~−15° C., as reported in literature for plasma.

Subzero nonfreezing storage w/3OMG preserves livers in a viable state. In an attempt to test the viability of the proposed sub-zero nonfreezing preservation studies, inventors loaded harvested rat livers with an isotonic equal-part mixture of 300 mM 3OMG and UW solution, and slowly reduced the preservation medium temperature to −5° C. in a cooling bath. The liver was stored at this temperature for 120 hrs, and no freezing was observed. After 120 hrs, the temperature was increased to 4° C. and the liver was fixed in formalin and sent to histology (FIG. 44). We observed that the hepatocytes in 3OMG supplemented case (FIG. 44A) appeared normal, whereas the UW-only case (FIG. 45R) displayed a higher number of degrading or anucleate cells. This result demonstrates that the liver preservation at subzero temperatures for extended periods is achievable without freezing.

SZNF preserves liver microstructure during 5 days storage (FIG. 45). H&E staining: A) −5 0C in 3OMG-supplemented University of Wisconsin medium, B) Conventional UW storage. A single-blinded pathologist's evaluation of the liver preserved at −5 0C was that it had no indication of structural damage after 5 days of storage. Liver architecture was homogeneously well-preserved with uniform cytoplasm and normal-appearing nuclei. Patchy edematous sinusoids were observed in places, suggesting possible hypertonicity of the storage medium. In the conventionally stored liver (B), general degradation of cell structure was observed. Many of the hepatocytes were pale-stained and vacuole-filled. A significant proportion of hepatocytes were pyknotic or anucleate. These results indicate subzero storage is superior to conventional storage. Methods: Male SD rat livers were harvested. The experiment group (SZNF w/3OMG) was perfused for 2 hrs at 4° C. with 3OMG supplemented UW solution (1:1 mixture of UW solution and 300 mM 3OMG dissolved in distilled water). The liver was super-cooled slowly (at 0.3° C./min) to −5° C. in hypothermic bath cooled chamber in 3OMG supplemented solution, and kept there for 5 days. For control group, the liver was flushed with UW solution and transferred to the preservation chamber which is filled with UW solution and kept in ice. At the end of experiment the livers were allowed to rewarm to 4° C. before being fixed in formalin. Tissue slices from the left lateral lobe were taken and stained with H&E.

Motivated by these encouraging results, inventors tested the feasibility of the entire proposed preservation scheme: The livers were loaded with 3OMG, stored for 24 hours at −5° C., and placed in the NELP system. This was an important test, as the endothelial cells in particular are sensitive to cold ischemia, and there was a significant risk that their degradation would lead to destruction of sinusoidal architecture rendering the livers essentially non-transplantable. With this high-viscosity medium, any such microcirculatory damage would be immediately revealed during perfusion, with extensive RBC infiltration and disruption of liver sinusoidal architecture. As it can be observed in FIG. 45, no such damage was observed, and the histology displayed perfect preservation of microstructure.

Proposed preservation protocol (3OMG loading, SZNF storage, rewarming in the NELP system) is feasible. After storage and perfusion in the NELP system with red blood cells, liver microstructure is preserved perfectly (FIG. 46).

These results demonstrate that i) the proposed preservation modality is feasible, as rat livers can be preserved at SZNF temperatures up to 5 days without freezing, and liver microcirculation is not at all affected by the gradation in temperatures.

Figure 47:
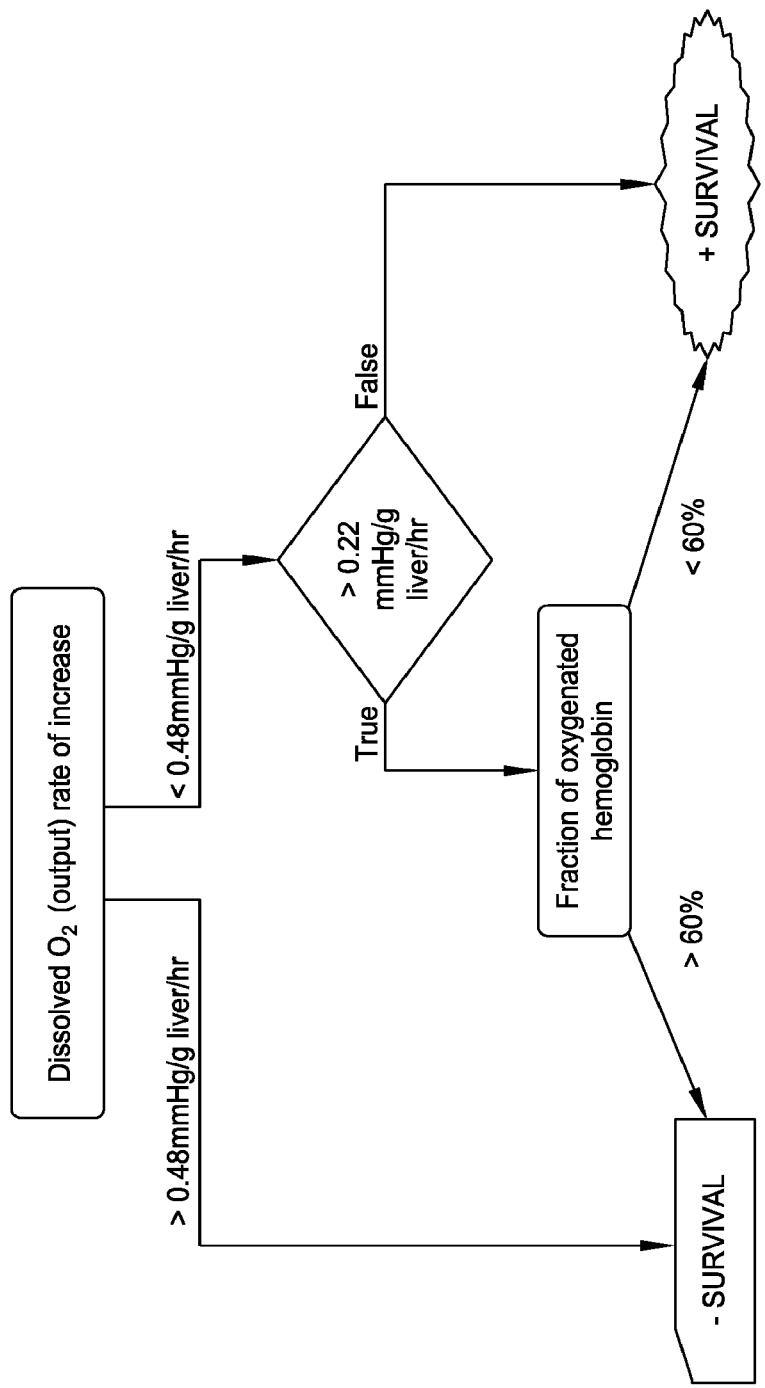
FIG. 47 illustrates a decision tree for recipient survival: survival can be predicted with >91% accuracy.

Graft recipient survival is correlated to oxygen levels. For preserved tissues, it is important to evaluate the viability prior to transplantation, to maximize graft and recipient survival. Therefore, inventors statistically tested the hypothesis that recipient survival is correlated to the metabolic performance of the livers during normothermic perfusion (in this preliminary study, there was no cold or SZNF storage). We have performed a data mining study to identify a model that can predict the recipient survival (monitored 4 weeks) from on-line measurements during the experiment. The conclusion of the study was that recipient survival could be predicted with an estimated accuracy of 91% based on the oxygen uptake of the liver during perfusion (FIG. 47).

Graft viability can be assessed during perfusion. Dissolved oxygen levels can be measured with sensors, continuously and without sample withdrawal. However, analysis of hemoglobin-bound oxygen requires withdrawal of samples for a Blood Gas analyzer. Therefore inventors investigated the possibility of replacing oxygenated hemoglobin with more easily measurable variables. Upon testing various available models, the following linear model, (obtained via M5P pruned tree model, WEKA data mining software), resulting in a cross validated correlation of 0.93 was identified:

$$\text{Avg·oxygenated hemoglobin}(\%) = 5.33 \times \text{liver weight}(gr) + 9.78 \times \text{Avg·}O2\text{Outlet}(\text{mmHg/g liver}) - 41.18$$

The use of the above equation in the decision tree displayed in FIG. 46, instead of the actual oxygenated hemoglobin readings, did not affect the predictions for any of the experiments. An interesting corollary is that the liver weight (measured before perfusion) appears as a secondary factor in determination of survival, with lower weights apparently better for survival rates.

In these preliminary studies, inventors have only utilized blood gas analysis data. In the proposed work, inventors will employ much more detailed metabolic flux analysis methodologies to obtain a snapshot of the liver activity during perfusion, and hence will be in position to develop more detailed, accurate, and reliable standards of tissue viability prior to transplantation.

Decision tree for recipient survival: survival can be predicted with >91% accuracy (FIG. 47). The conclusion is that the graft recipient survival can be predicted with a decision tree, with the use of two measures: dissolved oxygen output rate of change (increase) and average fraction of oxygenated hemoglobin. Both variables are directly related to the total oxygen uptake by the liver during perfusion, as discussed below.

Methods for Example7

Hepatocytes were incubated with 200 mM 3OMG for 60 min and then washed with sugar-free medium for 30 min. Controls were incubated in glucose-free DMEM (no-sugar control), sucrose (non-permeable/non-intracellular control), and D-glucose (permeable but metabolizable control). Following incubation, cells were pelleted by centrifugation for 5 min, supernatant decanted, and resuspended in cold Hypo-Thermosol solution (HTS) with 200 mM 3OMG, 2 DG, sucrose, or D-glucose (1×10⁶ cell/mL). Cell suspensions were transferred to 1 mL cryogenic vials and cooled at −1° C./min to −6° C., seeded to induce the formation of extracellular ice by application of cold forceps to the exterior of the cryovials, and then cooled at −1° C./min to −80° C., and finally transferred to liquid nitrogen (−196° C.) for storage lasting 1 to 7 days. Following storage, samples were rapidly thawed in a 37° C. water bath for 2 min with gentle agitation. The samples were then diluted 1:10 in D-glucose-free DMEM and incubated for 10 min at 37° C. to wash out the loaded sugar compounds. Samples were then centrifuged, supernatant decanted, and resuspended in culture medium. The viability of the cryopreserved cells was determined immediately after thawing using a trypan blue exclusion assay and expressed as percent of unfrozen control. Cells were seeded and cultured in a collagen sandwich configuration for imaging; the actin staining was performed with rhodamine phalloidin as detailed elsewhere.

The system consists of a closed primary circuit where perfusate is continuously recycled through a bubble trap, heater, and membrane oxygenator before entering the liver. Perfusate passes through the portal vein only and exits via the suprahepatic vena cava, bathing the liver in a perfusion chamber. Flow rate through the liver is 1.5 ml/min/g liver wet weight, and portal pressure is maintained between 10 and 15 cm water. The total volume of perfusate is ~50 ml and comprises rat erythrocytes (20% hematocrit) Williams Medium E (Sigma), hydrocortisone (10 mg/L), insulin (2u/L), penicillin (40,000 U/L) streptomycin (40 mg/L), 10% v/v rat plasma, and heparin (1000 U/L). A secondary circuit interfaces with the primary circuit through a hollow fiber dialyzer with 2200 cm2 30 kD nominal M. W. cut-off membrane. The dialysate acts as a medium reservoir and limits the amount of priming volume required. As a cumulative time course experiment, samples of the perfusate and dialysate were taken hourly for immediate blood chemistry measurements using a blood gas analyzer (Bayer), and a Piccolo (Abaxis, Union City, CA) blood chemistry analysis.

Male SD rat livers were harvested and perfused for 2 hrs at 4° C. in 3OMG supplemented UW solution (1:1 mixture of UW solution and 300 mM 3OMG dissolved in distilled water). The liver was supercooled slowly (at 0.3° C./min) to −5° C. in a hypothermic bath cooled chamber, and stored for 24 hrs. The livers were then directly placed in the NELP system described in FIG. 39, and perfused for 3 hours before being fixed in formalin. Tissue slices from the left lateral lobe were taken and stained with H&E.

Livers were harvested from heparinized rats (inbred Lewis strain) and held at 34° C. This temperature is slightly lower than normothermic, which is justified by the fact that core body temperature tends to decrease after death. The use of blood clotting inhibitors is justified in the context of "controlled cardiac death" in a hospital setting where potential donors are often medicated prior to organ retrieval, and at this stage inventors did wish to address mechanisms of liver repair in the absence of the confounding effects of blood clotting. Warm ischemic livers remained at 34° C. for 60 minutes, while combination group went through 45 min warm and 2 hrs of cold ischemia. After ischemia, the livers were perfused for up to 5 hrs in the NELP system and transplanted to syngeneic recipients. Perfusate samples (1 ml) were collected from the inlet of the liver and analyzed using a Piccolo miniature blood chemistry analyzer (Abaxis, Union City, CA). Data are means±SE, N=6.

To determine the post-operative concentrations, 100-200 W of blood was drawn from the tail vein into a heparinized syringe under isofluorane anesthesia on post-operative days 1, 3, 5 and 7 and immediately analyzed using a Piccolo miniature blood chemistry analyzer.

Mixture of UW solution and 300 mM solution to be tested, or 150 mM of solution alone, was placed in the liver storage chamber. A 2 mm diameter thermocouple was passed through the center of the chamber cover and suspended mid-mixture. The chamber was sealed, immersed in a cooling bath, and slowly cooled down (at −0.3° C./min). The temperature at which the mixture froze (the lowest temperature was noted prior to a rapid rise from latent heat release) was noted for >5 trials with each solutions (FIG. 44).

Expected accuracy was evaluated via leave-1-out cross validation. It was observed that a slightly better accuracy was obtained with artificial neural networks, though since the difference is not significantly higher (t-test. $\alpha=0.05$) the simpler method (decision tree) was preferred. It should be noted that for the study above, only directly measured variables (i.e. dissolved $O_2$ & $CO_2$, electrolytes, and free and bound hemoglobin levels, measured in the feed and effluent of the liver) were used. Metabolically it is more reasonable to combine dissolved oxygen and oxygenated hemoglobin measurements at inlet and outlet into a single oxygen uptake rate variable. We have tested this approach and found that a similar accuracy (>90%, not different from the previous results at $\alpha=0.05$) could be obtained from uptake rates alone. However, the use of direct variables is preferred, primarily due to the possibility of using sensors for monitoring the perfused liver status continuously. The data here includes results from 11 survivors and 4 non-survivors.

Example 8

Figure 48:
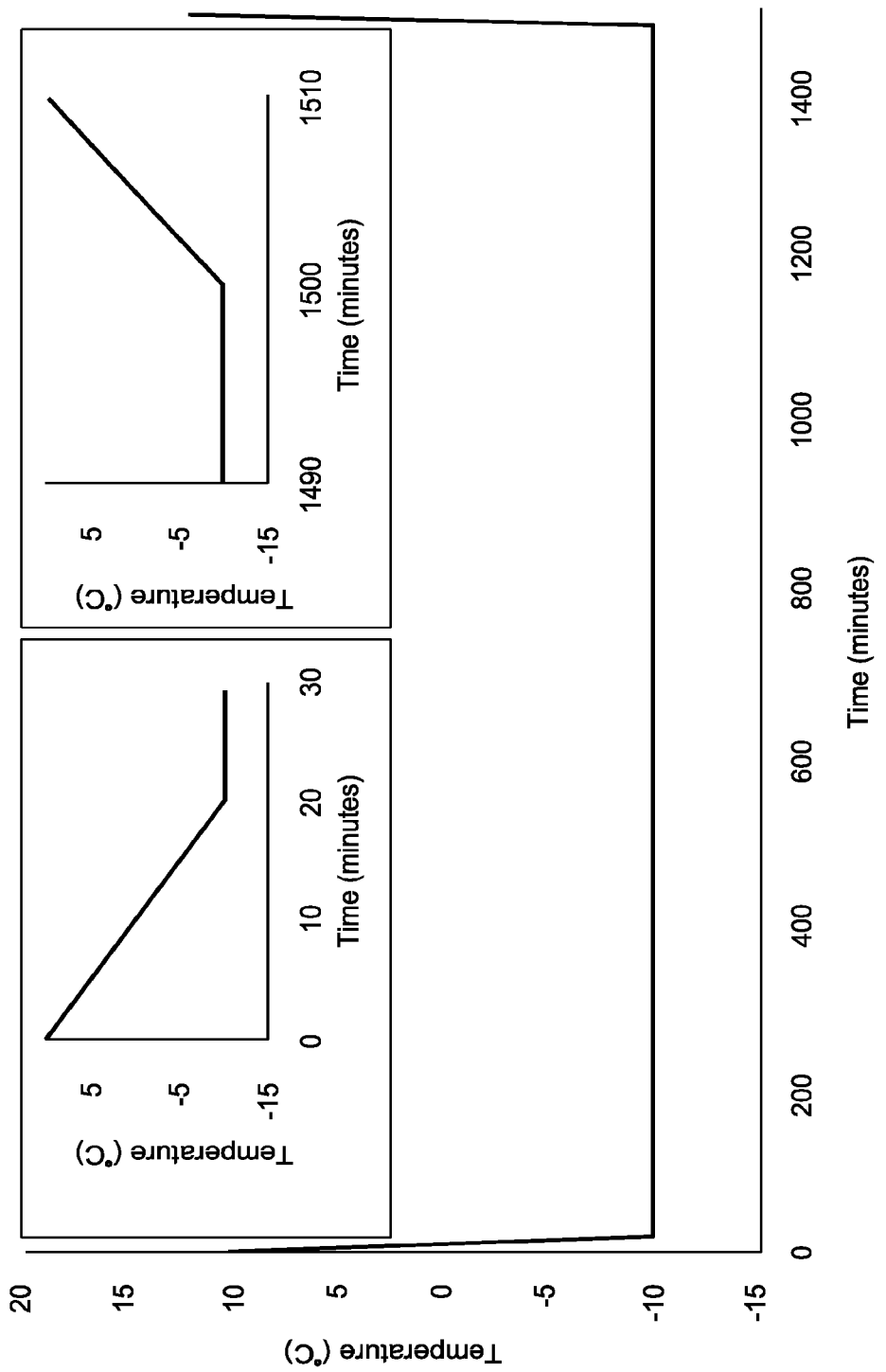
FIG. 48 illustrate the temperature profile for successful 24 hrs preservation at $-10°$ C.

Successful preservation of hepatocytes in vitro at subzero non-freezing (SZNF) temperatures. Establishment of a protocol to reach −10° C. without any freezing. We tested a variety of preservation media and additives for achieving SZNF storage overnight in a controlled rate freezer. We were able to reach −10° C. without any freezing in supplemented University of Wisconsin (UW) and Hypothermosol (HTS) by proper tuning of the rate of temperature reduction. Use of 3OMG enabled reducing temperature down to −15° C. in HTS, however this protocol is currently stable only about 50% of the time at concentrations that do not significantly exceed normal osmolality. A summary of some of the tested solutions and additives is presented in Table 11 below. We have also replicated these results in 6 well tissue culture plates and 15 ml centrifuge tubes. FIG. 48 depicts the temperature profile for successful subzero cooling at −10° C.

TABLE 11

Supercooling in Cryovials at Subzero Temperatures in Selected Media Formulations.

| Solution | −10° C. Success (%) | −15° C. Success (%) | −20° C. Success (%) |
|---|---|---|---|
| HTS | 100 | 0 | 0 |
| UW | 100 | 0 | 0 |
| HTS + 3-OMG (0.3 mM) | 100 | 53.3 | 0 |
| HTS + Trehalose (0.3 mM) | N/A | 6.67 | N/A |
| UW + 3-0MG | 100 | 0 | 0 |

Figure 49:
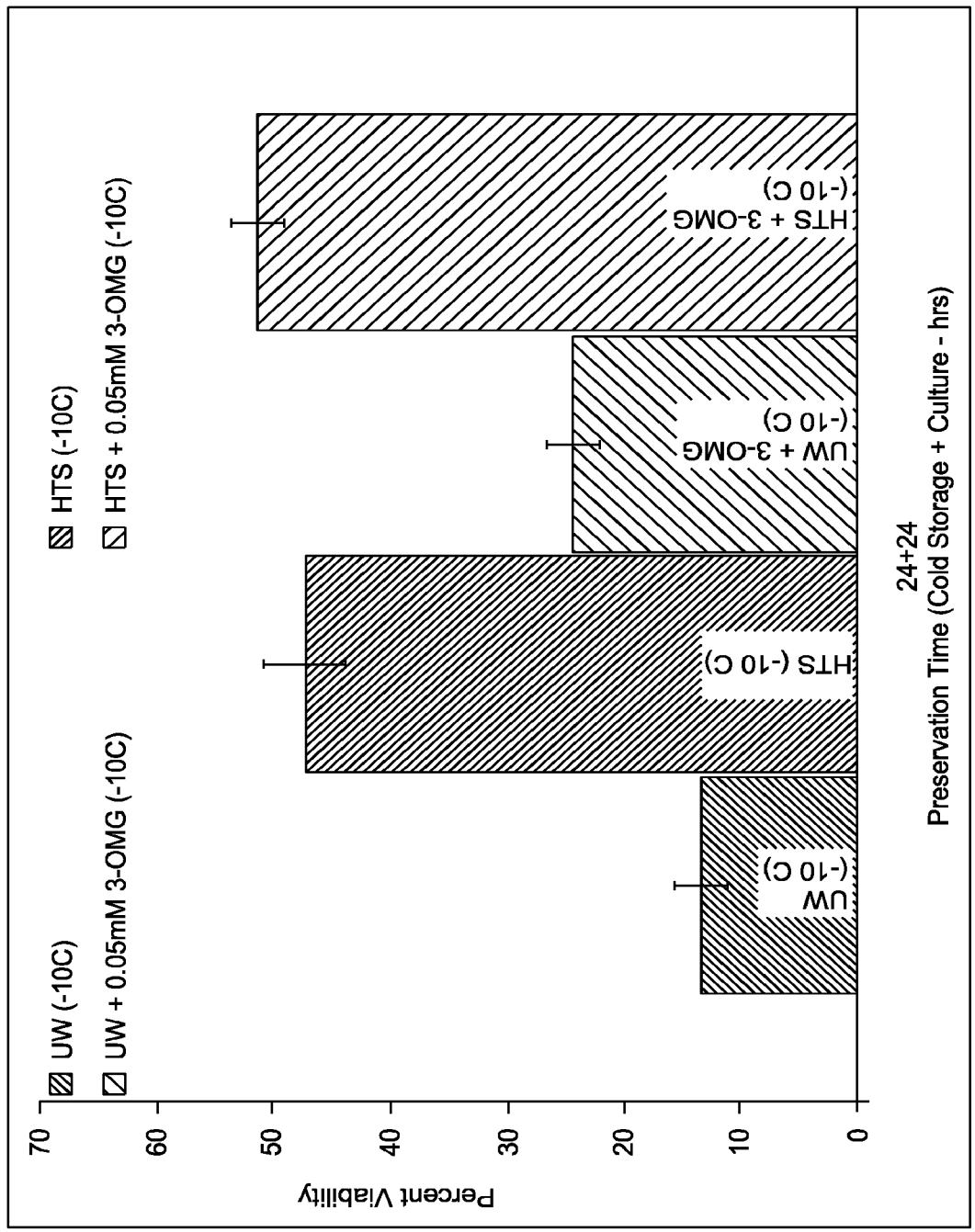
FIG. 49 illustrates the successful preservation of rat hepatocytes in SZNF storage at $-10°$ C. (Left panel) Viability of cells after 24 hrs SZNF storage and 24 hrs of culture; (Right panel) images of randomly selected fields from plate cultures. Note that cells were not seeded in densities to reach full confluency in order to be able to do automated microscopic cell viability counts for this experiment; at normal seeding density, the cells reach full confluency and are indistinguishable from fresh rat hepatocytes.

Successful preservation of rat hepatocytes at −10° C. For the selected media above, inventors tested cell viability after SZNF storage. Cells were preserved in cryovials, 15 ml centrifuge tubes as well as in 6 well plates after collagen coating. FIG. 49 below depicts the viability of hepatocytes cultured on plates after 24 hrs of SZNF storage followed by 24 hrs culture. These results demonstrate that inventors can triple the cell viability post preservation compared to UW control by using HTS+3OMG.

Figure 50:
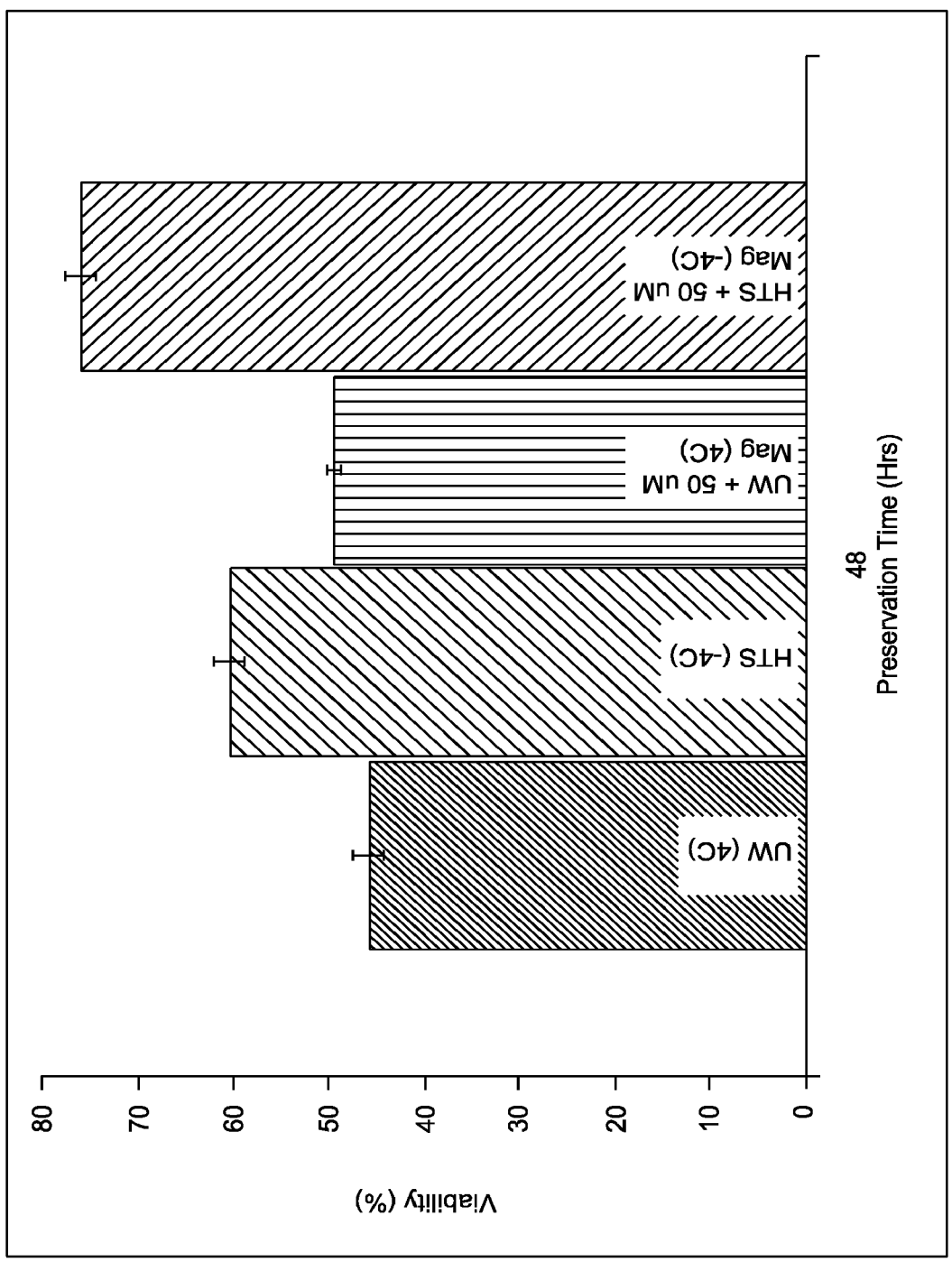
FIG. 50 illustrates that antioxidants increase cell viability with SZNF storage. Viability of cells after 24 hrs SZNF storage.

Metabolic supplements further enhance cell viability in SZNF. Inventors are testing a variety of metabolic supplements to enhance viability during preservation. One of the most successful additives inventors tested is magnolol, a biphenolic compound with multiple properties (including tumor suppression and antioxidative capabilities). As depicted below in FIG. 50, magnolol increases cell viability in SZNF preservation significantly, and the tandem of SZNF storage at −4° C. in HTS and magnolol was able to increase cell viability by 60% compared to UW storage. Note that this study was performed early on where stable preservation temperature in plate culture models was −4° C., testing at −10° C. is currently in progress.

Successful preservation of rat livers at subzero nonfreezing temperatures and transplantation. Results demonstrate that inventors can successfully preserve rat livers at SZNF temperatures (−7° C.) overnight, and that the SZNF preserved livers are comparable to fresh livers in function during perfusion-rewarming. Furthermore, inventors have recently had our first successful transplantation with the proposed scheme, about 1 year ahead of schedule.

Figure 51:
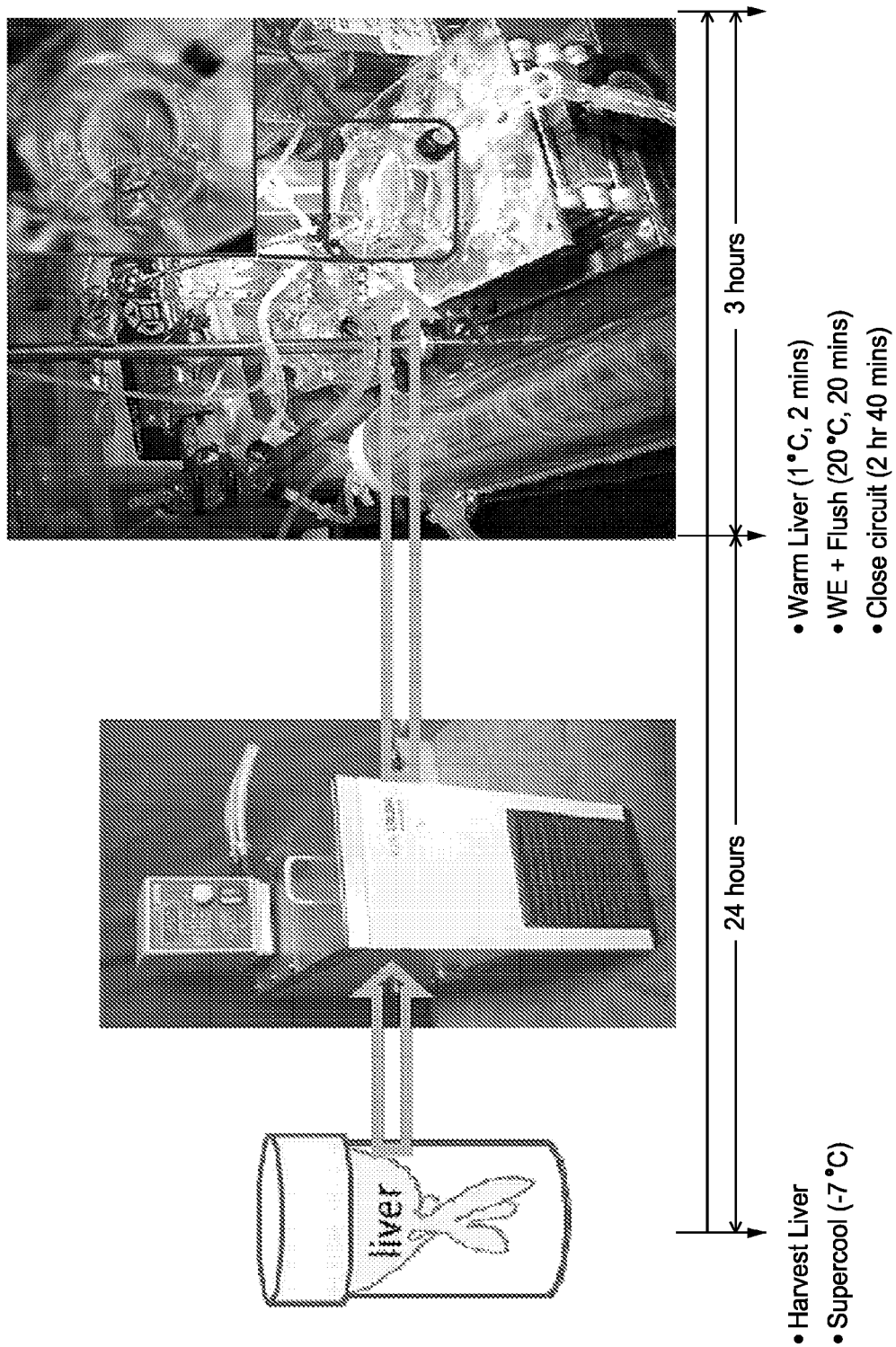
FIG. 51 illustrates the SZNF preservation protocol and system.
Figure 52A:
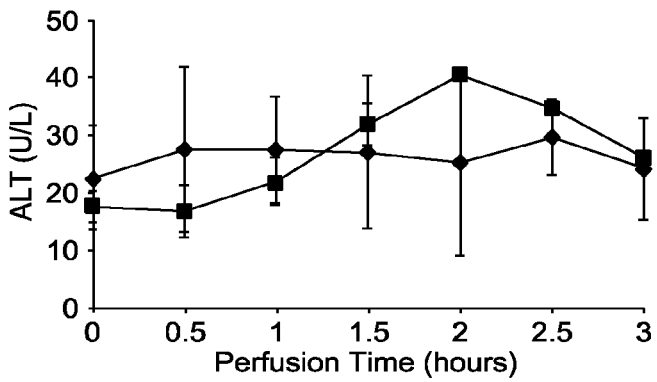
FIG. 52 illustrates that SZNF preserved livers show function similar to fresh livers during perfusion.
Figure 52B:
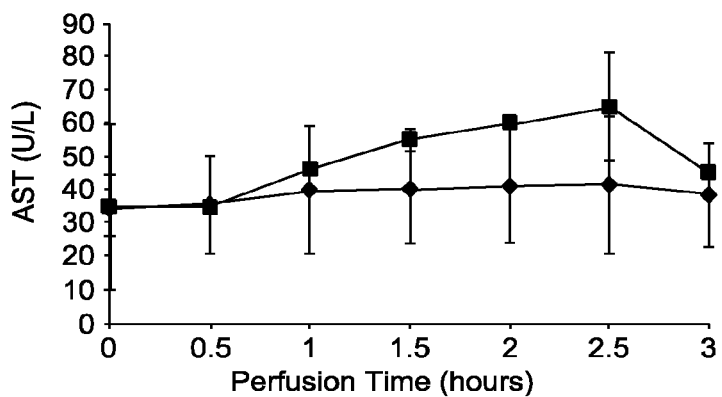
Figure 52C:
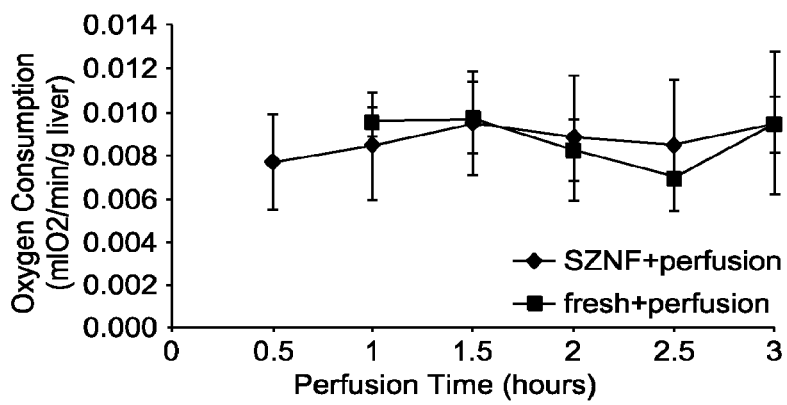
Figure 52D:
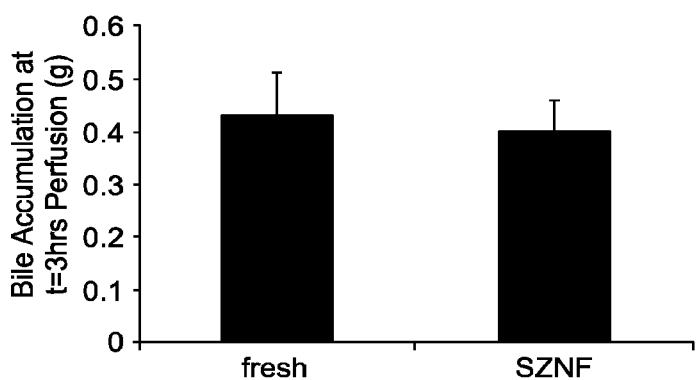

Development of a system & protocol for stable subzero-nonfreezing storage of rat livers at −7° C. This is a highly significant achievement as inventors have gone well beyond the SZNF temperatures reported in literature in whole organ preservation, which is −2° C. FIG. 51 below depicts the SZNFprotocol inventors used, which was based on the cooling and warming protocols that inventors had established in vitro (The chiller used in whole-organ supercooling resulted in occasional freezing, hence inventors had to institute a temporary safety margin of 30%, and perform SZNF preservation at −7° C. instead). FIG. 52 displays the comparisons of the functions of these preserved livers in comparison to perfused fresh livers, which are very similar. Based on this preliminary success, inventors initiated transplantation studies ahead of plan, and achieved our first successful SZNF preserved liver transplant. The recipient rat is still alive and well (currently day 10 post-transplant) as displayed in FIG. 53. To our knowledge, this is the first successful transplantation after storage below 0° C.; existing literature in this area is limited to either evaluation via in vitro perfusion or transplant recipients have perished within 24 hrs.

SZNF preserved livers show function similar to fresh livers during perfusion (FIG. 52). Liver enzyme release (Alanine aminotransferase, ALT and Aspartate aminotransferase, AST) are statistically not different at any time points, indicating no additional injury to the liver cells during SZNF preservation. The function of these livers, as measured via oxygen consumption and bile production (direct indicators of metabolic function of the liver), are also statistically same. These results indicate that SZNF preservation does not cause any discernible injury on livers.

Figure 53:
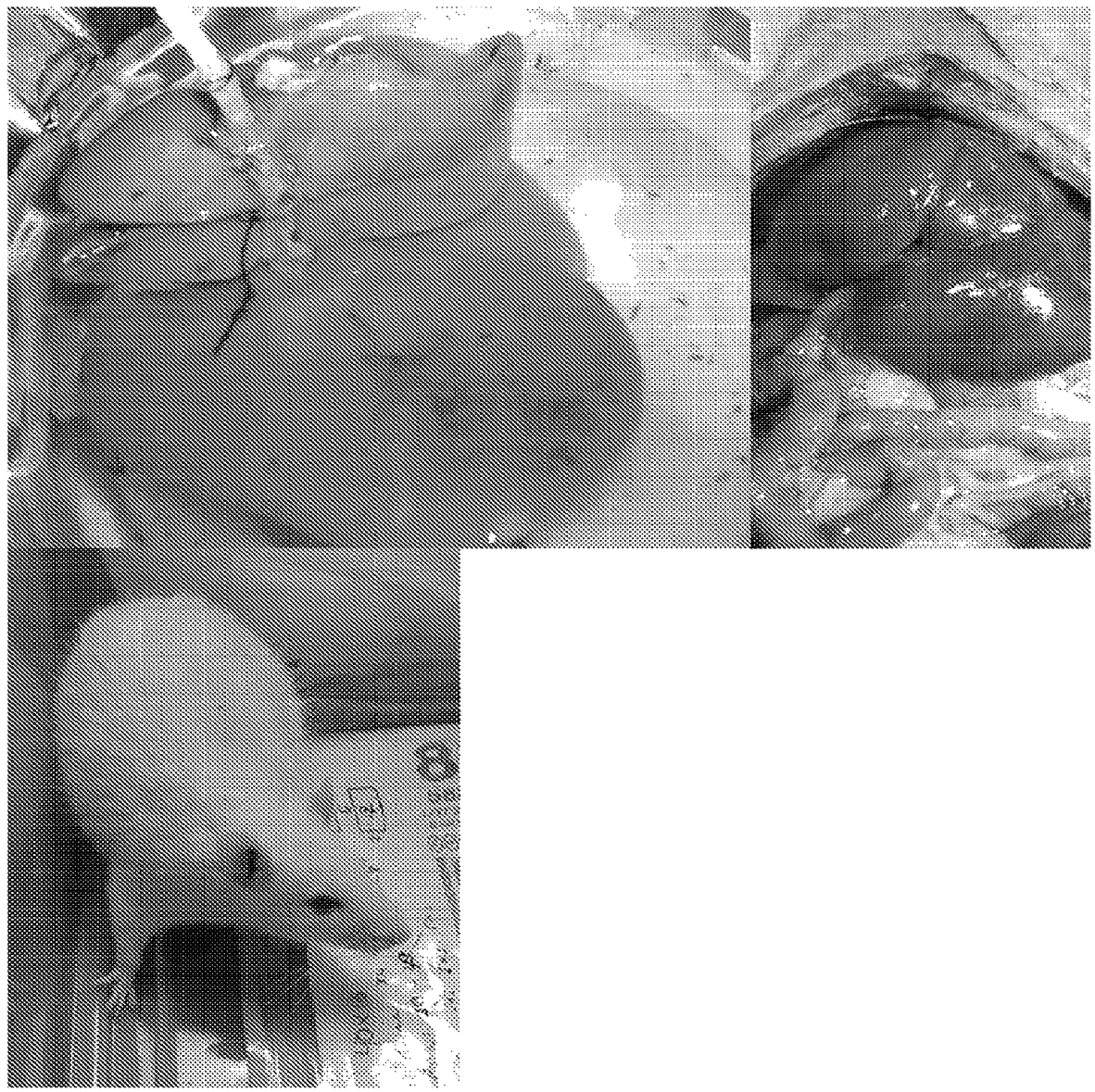
FIG. 53 illustrates the recipient of successful SZNF preserved rat liver. (Left panel): the liver during perfusion-recovery; (middle panel): right after transplantation; (right panel): the recipient, 9 days post-transplant (note the absence of any jaundice and the fully alert posture).

Recipient of successful SZNF preserved rat liver (FIG. 53). (Left panel): the liver during perfusion-recovery; (middle panel): right after transplantation; (right panel): the recipient, 9 days post-transplant (note the absence of any jaundice and the fully alert posture). With the success obtained in evaluation of SZNF preserved livers during machine perfusion, inventors decided to perform a preliminary test by transplantation. The liver was harvested, stored at −7° C. for 24 hrs, and treated by machine perfusion as described in FIG. 4. The recipient rat (FIG. 53)was able to recover from the transplant surgery, although recovery was somewhat slower compared to recipients of fresh livers and the animal showed some signs of pain (slow mobility). However, these clinical signs disappeared entirely after 3 days of surgery, and the animal is currently (day 10 post-txp) healthy and displays normal behavior.

Methods for Example 8

The cells were preserved on collagen coated 6 well plates and cultured at 37° C. for one day prior to preservation. Cells were then preserved 48 hours at −4° C.; viability was determined 1 hr after rewarming SZNF preservation protocol and system (FIG. 51). The liver is harvested, flushed with preservation media and placed in a latex bag in a jar. The jar is placed in a chiller where the temperature is dropped to SZNF temperatures (currently −7° C. for whole rat livers) and stored for 24 hrs. The chiller is then stopped and allowed to reach+1° C. (about 2 minutes). The liver is transferred to the machine perfusion system and perfusion is initiated; an initial 20 min flush with media (where the liver effluent is discarded) allows for washing of preservation media and removal of any cellular debris accumulated during preservation. This is followed by a 2 hr and 40 min closed circuit perfusion where the liver is allowed to recover from preservation, followed by transplantation. After SZNF storage for 24 hrs, livers were rewarmed and perfused in our system.

Example 9

Viability Index

Figure 54:
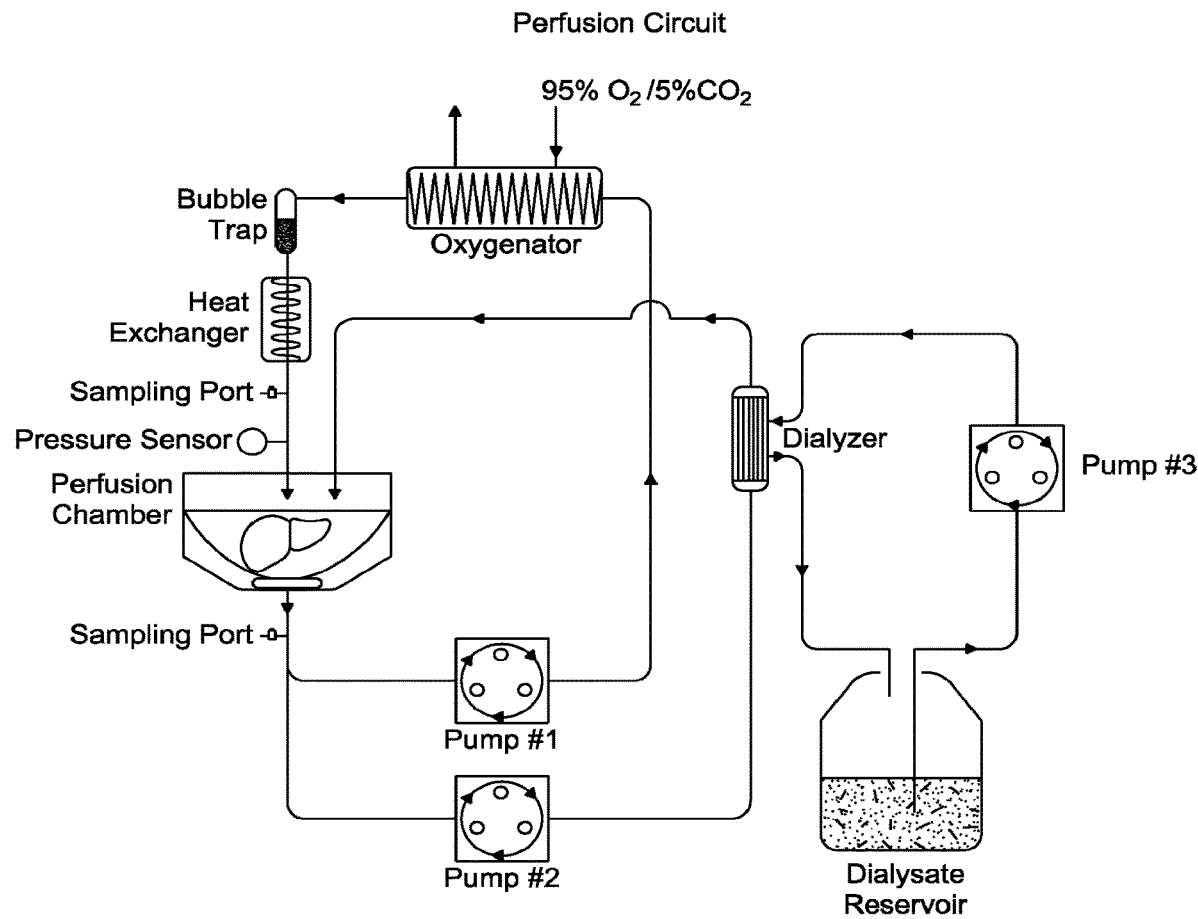
FIG. 54 illustrates the NELP machine perfusion system.

Machine Perfusion is a feasible liver preservation method. Our group has recently developed a Normothermic Extracorporeal Liver Perfusion (NELP) system that incorporates red blood cells and a dialyzer, and operates at a near physiological flow rate (FIG. 54). Studies with this system using normal rat livers show that livers can be perfused for at least 6 h at 37° C. and exhibit stable metabolic function[4]. We successfully transplanted 10 out of 11 perfused livers with recipients surviving >1 month after the procedure. There was also excellent preservation of the liver structure after perfusion.

Cadaveric livers were successfully transplanted to syngeneic recipients after 6 hrs of perfusion in the system in 10 out of 11 cases, with recipients surviving >1 month after the procedure.

Figure 55:
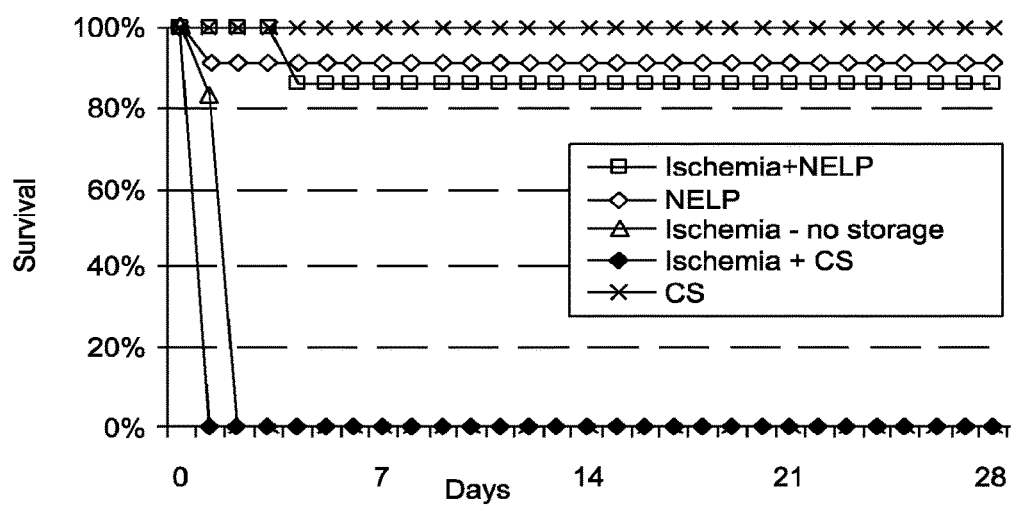
FIG. 55 illustrates the survival of rats transplanted with ischemic livers. CS: Cold Storage, NELP: Normothermic Extracorporeal Liver Perfusion.

Cadaveric rat livers can be resuscitated with machine perfusion. As a model of Donors after Cardiac Death (DCD), rat livers were harvested from rats (inbred Lewis strain) and held at 34° C. for 60 min to induce warm ischemic injury. This temperature is slightly lower than normothermic, which is justified by the fact that the core body temperature tends to decrease after death. Subsequently, the ischemic livers were perfused up to 6 hrs in the perfusion system. After normothermic perfusion, warm ischemic livers were orthotopically transplanted into recipient rats successfully transplanted 10 out of 11 times, with the animals recovering quickly from surgery. The controls did not survive past first day (Cold stored:0/5, warm ischemia directly transplanted 0/6, see FIG. 55); although animals did wake up from surgery, they died within 24 hrs. These studies clearly show the feasibility of ex vivo machine perfusion for the recovery of cadaveric livers.

With no ex vivo preservation, one rat survived past 24 hrs. Both normothermic perfusion studies, with or without ischemia, demonstrated excellent survival, similar to the positive control (healthy livers with cold storage) showing that normothermic perfusion enables rescue of the cadaveric livers.

Multi-way Partial Least Squares (MPLS) can successfully classify success and failure in cadaveric liver transplantation. Partial least squares or projections to latent structures (PLS) is a regression method that is used to connect the information in two blocks of variables, namely the predictor block X and response block Y. PLS provides a way of predicting the y-values from the x-values, a generalization of multiple regression, by correlating X to Y and finding the orthogonal directions that maximize the correlation between X and Y. An algorithm for Nonlinear Iterative Partial Least Squares is provided elsewhere[39].

$$X = TP^T + E$$

$$Y = UQ^T + F \quad (1)$$

$$U = TB + H \quad \text{(B diagonal)}$$

Interrelation gives the predictive formulation for y.

$$Y = TBQ^T + F^* \quad (2)$$

Here T and U are the score matrices; P and Q are the loading matrices and E and F are the residuals for X and Y, respectively. The matrices are denoted by bold capital letters and the vectors are denoted by bold letter in the text.

For dynamic datasets, PLS has been extended to Multi-way-PLS (MPLS) which is equivalent to an ordinary PLS model performed on a 2D matrix constructed by unfolding the three-way data array (Nomikos, P. & Macgregor, J. F. *Monitoring batch process using multiway principal component analysis Aiche Journal* 40, 1361-1375 (1994); Kourti, T., Nomikos, P. & Macgregor, J. F. *Analysis, monitoring and fault-diagnosis of batch processes using multiblock and multiway pls* Journal of Process Control 5, 277-284 (1995); Nomikos, P. & MacGregor, J. F. Multi-way partial least squares in monitoring batch processes. Chemometrics and Intelligent Laboratory Systems 30, 97-108 (1995); Undey, C. & Cinar, A. Statistical monitoring of multistage, multiphase batch processes. Ieee Control Systems Magazine 22, 40-52 (2002).). An (I ×J ×K) data array can be unfolded by preserving the batch direction I and augmenting the J variable measurements taken at each time point k (k=1, ..., K) side by side resulting in an I×JK matrix (Wold, S., Kettaneh, N., Friden, H. & Holmberg, A. Modelling and diagnostics of batch processes and analogous kinetic experiments. *Chemometrics and Intelligent Laboratory Systems* 44, 331-340 (1998)).

Figure 56:
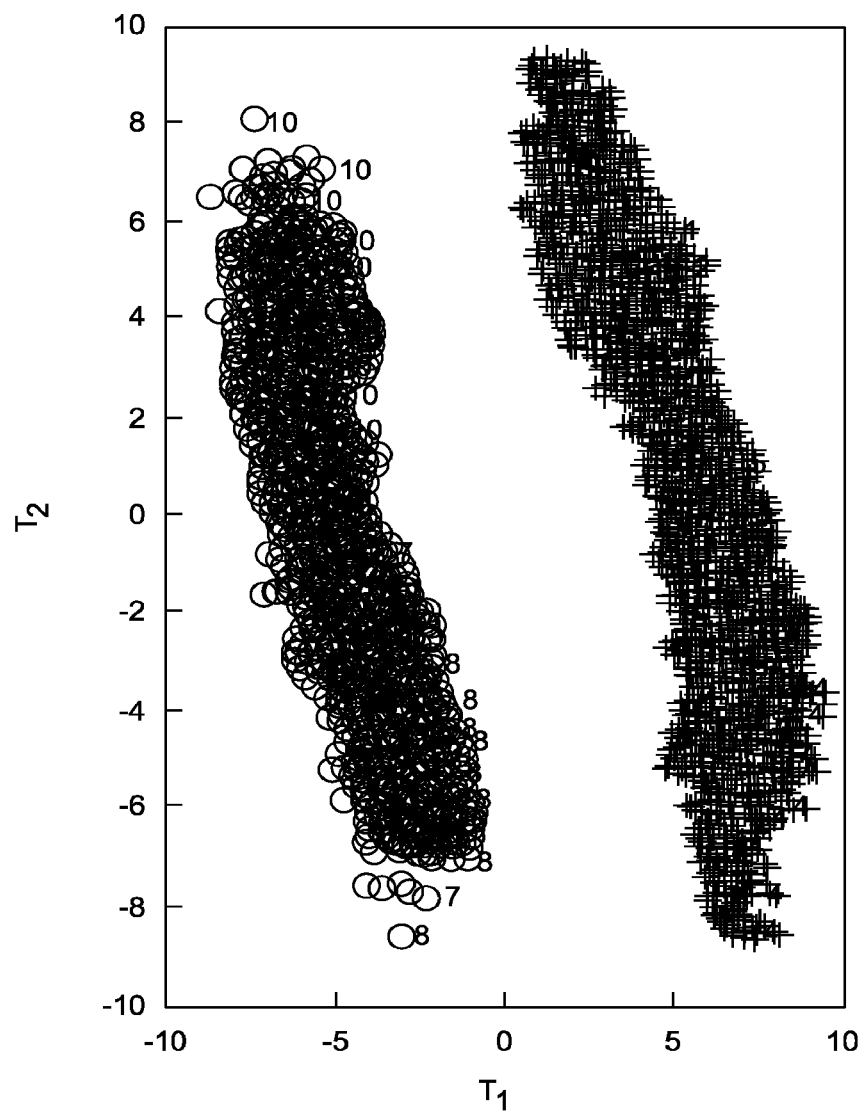
FIG. 56 illustrates MPLS classification survivor and non-survivor livers. Score biplot ($t_1$ vs $t_2$): left (green) nonsurvival group; right (blue) survival group.

In a preliminary study, a Blood Gas Analysis of the Perfusion Media in perfused livers was performed. Measurements include the rate of changes in oxygen uptake, release, and concentration of dissolved oxygen and oxygen carried by the red blood cells during perfusion. The Y response matrix was formed with transplant success after perfusion of cadaveric livers, indicated by 1 and failure by 0. These preliminary results were obtained from livers perfused for up to 12 hours, which resulted in a transplant success of only about 50. Since only 11 total such long-term perfusions were available for this preliminary study, for sensitivity and specificity evaluation of MPLS classifications, case multi-sampling was performed via bootstrapping[44], with 500 runs repeated 3 times. As displayed in Table 12, MPLS model effectively predicted the survival rates for the successful and unsuccessful perfusions with accuracy >95%. FIG. 56 depicts how the first two scores obtained from MPLS clearly can distinguish between the two classes. These results demonstrate that cadaveric livers have distinct profiles during machine perfusion.

TABLE 12

MPLS can accurately classify survivor and non-survivor livers.

|  | Run 1 | Run 2 | Run 3 |
| --- | --- | --- | --- |
| Sensitivity | 0.928 | 0.972 | 0.917 |
| Specificity | 0.967 | 0.980 | 0.970 |

Figure 57:
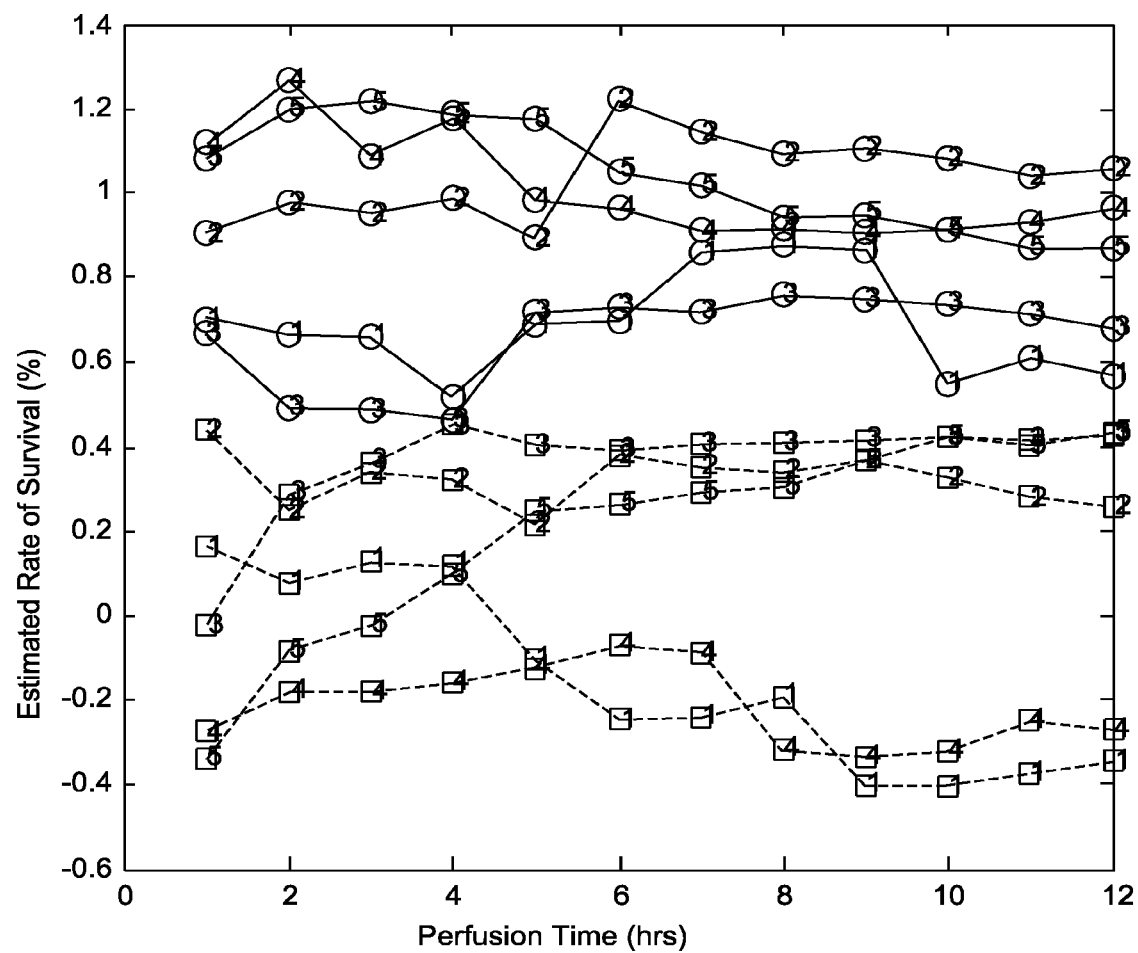
FIG. 57 illustrates that MPLS can predict survival results online during perfusion: Average survival rate predictions using online MPLS during machine perfusion. Y-axis 1: survival, 0: nonsurvival. blue: actual survival, black: actual nonsurvival

Transplant success can be predicted online during perfusion. Further, inventors performed an online MPLS to predict the rate of survival as perfusion progresses. FIG. 57 shows the MPLS-predicted survival rates after transplantation. As before, the Y response matrix is formed with success indicated by 1 and failure by 0. The online MPLS model effectively predicts the survival rates for the successful and unsuccessful perfusions. Noticeably, the "quality" of the unsuccessful livers' perfusions have been worse from the beginning. The model successfully predicts the unsuccessful perfusions since the predictions are <0.5 most of the time. The quality of all other perfusions and the post-transplantation survival rates are predicted within a well-acceptable accuracy (>0.95, see Table 12), especially considering that only oxygen related variables were available for this analysis.

It is worth noting that the MPLS model also provides a measure of variable importance on viability (estimated rate of survival). The main parameters that were different between these two groups and affect the classification were dissolved oxygen and fraction of carboxyhemoglobin, where as overall oxygen content in the perfusion media was not essential in successful classification (results not shown). These results indicate that during the unsuccessful perfusions, rather than insufficient oxygen supply, the livers were not capable of effective oxygen transport within the tissue, and this diminished their recovery during perfusion and chances of survival at the end. The fact that dissolved oxygen rather than oxygen carried by the red blood cells as oxygenated hemoglobin is important indicates that the red blood cells cannot fully penetrate the tissue, a known issue in cadaveric livers due to blood vessel restriction that endures for up to 6 hours until there is sufficient energy (ATP) production to achieve full vasorelaxation (Serracino-Inglott, F., Habib, N. A. & Mathie, R. T. Hepatic ischemia-reperfusion injury. *American Journal of Surgery* 181, 160-166 (2001)).

In these preliminary studies, inventors have utilized blood gas analysis data. Inventors will employ much more detailed metabolic analysis methodologies to obtain detailed snapshots of the liver activity during perfusion, and hence will be in position to develop more detailed, accurate, and reliable standards of organ viability prior to transplantation. Inventors have shown the possibility of developing a quantitative measure of preserved organ viability.

TABLE 13

List of metablits used in the multiway data analysis

| ACAC | 10 | Glutamine | 19 | Phenylalanine |
| --- | --- | --- | --- | --- |
| Alanine | 11 | Glycine | 20 | Proline |
| Albumin | 12 | Histidine | 21 | Serine |
| Ammonia | 13 | Isoleucine | 22 | Threonine |
| Arginine | 14 | Lactate | 23 | Tyrosine |
| Asparagine | 15 | Leucine | 24 | Urea |
| Aspartate | 16 | Lysine | 25 | Valine |

TABLE 13-continued

List of metablits used in the multiway data analysis

| Glucose | 17 | Methionine |
|---------|----|-----------|
| Glutamate | 18 | Ornithine |

Figure 58:
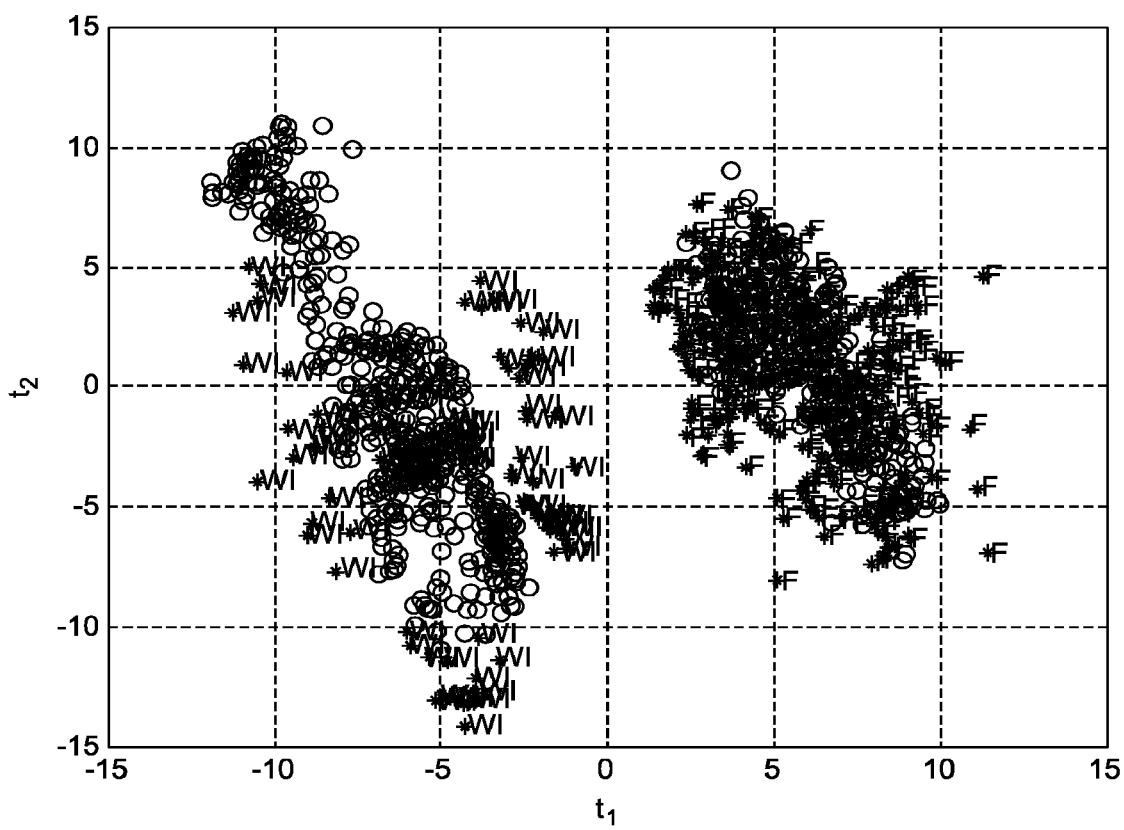
FIG. 58 illustrates that MPLS accurately classifies fresh and cadaveric perfused livers based on metabolite profiles. Warm Ischemic (WI) (left cluster) Fresh: (F) (Right Cluster). Note that classification accuracy is 100%.

Degree of Ischemia Alters Amino Acid Profiles. For the perfused livers in FIG. 55, inventors performed a metabolic analysis of 25 amino acids (see Table 13) to evaluate the impact of ischemia on liver metabolism during perfusion, and performed MPLS analysis on these metabolic profiles. However, note that contrary to FIGS. 3 and 4 above, this is only an analysis of the impact of ischemic injury on liver metabolism of amino acids. All the livers were perfused for 6 hours and transplant success rates are 100% survival for both cadaveric and fresh livers. As displayed below in FIG. 58, MPLS was able to classify fresh and cadaveric livers based on amino acid profiles during perfusion with perfect accuracy, further indicating that the proposed assessment of injury in cadaveric livers is possible via MPLS.

Figure 59:
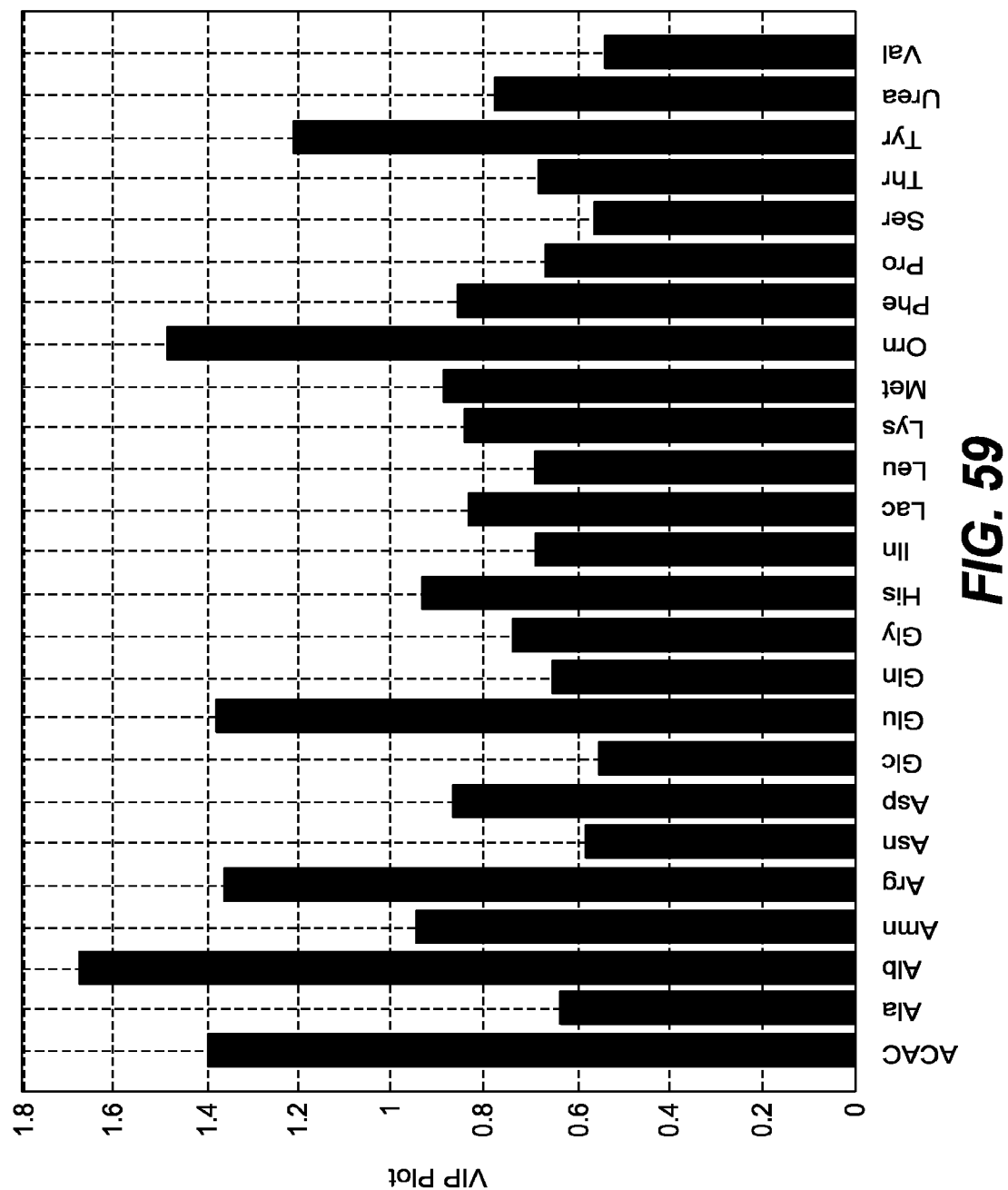
FIG. 59 illustrates that MPLS identifies variables essential in determining the viability of the perfused livers. The most important variables that mark the differentiation of warm ischemic livers from fresh perfused livers have VIP values greater than 1.

MPLS Identifies key variables in determination of liver viability. Finally, FIG. 59 as disclosed hereindisplays the most important variables in determination of class membership for each liver sample. Variable importance in the projection (VIP) was calculated by summing the squared PLS weights over all dimensions. The variables with VIP >1 are effective on the response Y. The most important variables that separate WI livers from fresh livers are albumin, arginine, glutamate, ornithine, tyrosine and acetoacetate. This analysis is key in identification of potential manipulated variables for enhancing perfused organ viability. These variables not only provide a first guess, but further enable formulation of a scientific hypothesis as well. For instance, this preliminary data points out arginine as a key variable; arginine is a Nitric Oxide donor, a necessary biochemical for re-dilatation of the blood vessels after ischemic injury. In combination with the finding above that dissolved oxygen is key in predicting transplant success, along with literature data on ischemic injury (Serracino-Inglott, F., Habib, N.A. & Mathie, R.T. Hepatic ischemia-reperfusion injury. *American Journal of Surgery* 181, 160-166 (2001)) these results provide clear evidence that use of pharmacological interventions inducing dilatation of the blood vessels are expected to enhance organ viability.

Methods for Example 9

The system consists of a primary circuit where the perfusate is continuously recycled (FIG. 54). Perfusion is through the portal vein and the liver is bathed in the perfusate in a perfusion chamber. Flow rate through the liver is 1.5 ml/min/g liver wet weight, and portal pressure was maintained between 10 and 15 cm water. The total volume of perfusate is ~50 ml. Perfusate includes rat red blood cells (25% hematocrit,) Williams Medium E (Sigma), hydrocortisone (10 mg/L), insulin (2u/L), penicillin (40,000 U/L) streptomycin (40 mg/L), 10% v/v rat plasma, and heparin (1000 U/L). A secondary circuit interfaces with the primary circuit through a hollow fiber dialyzer with 2200 cm$^2$ 30 kD nominal M. W. cut-off membrane. The dialysate consists of the same medium as the primary circuit excluding plasma and red blood cells.

In ischemia cases, donor livers were harvested and stored in saline at 34° C. for 1 hr, a model for donors after cardiac death. Livers were perfused or kept in cold storage in University of Wisconsin (UW) solution prior to transplantation.

In order to prevent any bias due to the size of the whole set, multiple MPLS models are built using multi-sampling techniques (Witten, III. & Frank, E. *Data Mining: Practical machine learning tools and techniques*, (Morgan Kaufmann, San Francisco, 2005). A total of 500 models were built for three times with eight randomly selected perfusions and the remaining were projected onto the model. As displayed here, the first two scores separate the two groups into distinct clusters.

Media samples were taken hourly during perfusions and analyzed for twelve variables via a standard Blood Gas analyzer (Tolboom, H., Pouw, R., Uygun, K., Tanimura, Y., Izamis, M.-L., Berthiaume, F. & Yarmush, M. L. A Model for Normothermic Preservation of the Rat Liver. *Tissue Eng* 13, 2143-2151 (2007): measured variables included dissolved $O_2$, dissolved $CO_2$, Hemoglobin concentration, Fractions of Oxygenated, Free and Irreversibly Oxidized hemoglobin (i.e. useless for oxygen carrying) contents in the red blood cells, and oxygen uptake rate. A total number of n=11 cadaveric livers were perfused in the MP system in FIG. 54. After the perfusions, the livers were transplanted; Six recipient animals survived (monitored for >3 months), whereas the remaining five animals died shortly after transplantation. Once an MPLS model was built, the perfusions that were not used in the model building were projected onto the MPLS model and the survival rates and days were predicted. For Sensitivity and Specificity evaluation for MPLS Classifications, case multi-sampling was performed via bootstrapping as before ENREF 44 (Witten, I. H. & Frank, E. *Data Mining: Practical machine learning tools and techniques*, (Morgan Kaufmann, San Francisco, 2005)), with on 500 Runs, repeated 3 times. Since multiple models are built during bootstrapping, each line represents the average predicted survival rates for each perfusion.

Classification of fresh (F) and warm ischemic (WI) liver samples using case resampling cross-validation. During cross-validations some of the liver samples were left out to be used in model testing. These samples were then projected onto the MPLS model and they are denoted as WI and F. All of the test samples for all 100 models were clustered correctly.

REFERENCES

The references cited herein in the Examples and throughout the specification are incorporated herein in their entirety by reference.

The invention claimed is:

1. A method for extending the viable preservation of a harvested organ for transplantation, the method comprising:
contacting at least a portion of the harvested organ with a preservation perfusion solution, wherein the preservation perfusion solution comprises (i) at least 3 of the following: insulin, L-glutamine, hydrocortisone, heparin, penicillin, streptomycin sulfate, and adenosine, and (ii) a PPARγ ligand selected from the group consisting of troglitazone and rosiglitazone, or derivatives thereof, wherein the harvested organ is a liver, pancreas, kidney, spleen, or lung.

2. The method of claim 1, wherein the preservation perfusion solution does not comprise erythrocytes.

3. The method of claim 1, wherein contacting at least a portion of the harvested organ with the preservation perfusion solution comprises immersing, partially or completely, the harvested organ with the preservation perfusion solution.

4. The method of claim 1, wherein contacting at least a portion of the harvested organ with the preservation perfusion solution comprises perfusing the harvested organ with the preservation perfusion solution.

5. The method of claim 1, wherein the harvested organ has ischemic damage.

6. The method of claim 1, wherein the harvested organ is cooled and stored at a predetermined sub-zero temperature without freezing.

7. The method of claim 5, wherein the harvested organ is contacted with a media comprising a supercoolant agent prior to cooling and freezing.

8. The method of claim 7, wherein the supercoolant agent is selected from the group consisting of: 3-O-methyl-glucose (3OMG), hypothermosol, trehalose, polyvinyl alcohol, polyvinylpyrrolidone, DMSO, polygylcerol, K3Glc (Kaempferol 3-O-β-D-glucopyranoside); K7Glc (Kaempferol 7-O-β-D-glucopyranoside), Q7Glc (Quercetin 7-O-β-D-glucopyranoside), Q3Gal (Quercetin 3-O-β-D-galactopyranoside), and polyethylene glycol.

9. The method of claim 8, wherein the supercoolant agent is 3-O-methyl-glucose (3OMG).

10. A method for extending the viable preservation of a harvested organ, the method comprising:
contacting at least a portion of the harvested organ with a first preservation perfusion solution, wherein the first preservation perfusion solution comprises at least 3 of the following: insulin, L-glutamine, hydrocortisone, heparin, penicillin, streptomycin sulfate, and adenosine; and
contacting at least a portion of the harvested organ with a second preservation solution comprising a PPARγ ligand selected from the group consisting of troglitazone and rosiglitazone, or derivatives thereof,
wherein the harvested organ is a liver, pancreas, kidney, spleen, or lung.

* * * * *

SEQUENCE LISTING

<160> NUMBER OF SEQ ID NOS: 2

<210> SEQ ID NO 1
<211> LENGTH: 19
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 1
gcccttcact actgttgac                                                    19

<210> SEQ ID NO 2
<211> LENGTH: 1818
<212> TYPE: DNA
<213> ORGANISM: Homo sapiens

<400> SEQUENCE: 2
ggcgcccgcg cccgccccg cgccgggccc ggctcggccc gacccggctc cgccgcgggc      60
aggcggggcc cagcgcactc ggagcccgag cccgagccgc agccgccgcc tggggcgctt     120
gggtcggcct cgaggacacc ggagaggggc gccacgccgc cgtggccgca gaaatgacca     180
tggttgacac agagatgcca ttctggccca ccaactttgg gatcagctcc gtggatctct     240
ccgtaatgga agaccactcc cactcctttg atatcaagcc cttcactact gttgacttct     300
ccagcatttc tactccacat tacgaagaca ttccattcac aagaacagat ccagtggttg     360
cagattacaa gtatgacctg aaacttcaag agtaccaaag tgcaatcaaa gtggagcctg     420
catctccacc ttattattct gagaagactc agctctacaa taagcctcat gaagagcctt     480
ccaactccct catggcaatt gaatgtcgtg tctgtggaga taaagcttct ggatttcact     540
atggagttca tgcttgtgaa ggatgcaagg gtttcttccg gagaacaatc agattgaagc     600
ttatctatga cagatgtgat cttaactgtc ggatccacaa aaaagtagaa ataaatgtc     660 agtactgtcg gtttcagaaa tgccttgcag tggggatgtc tcataatgcc atcaggtttg     720
ggcggatgcc acaggccgag aaggagaagc tgttggcgga gatctccagt gatatcgacc     780
agctgaatcc agagtccgct gacctccggg ccctggcaaa acatttgtat gactcataca     840
taaagtcctt cccgctgacc aaagcaaagg cgagggcgat cttgacagga aagacaacag     900
acaaatcacc attcgttatc tatgacatga attccttaat gatgggagaa gataaaatca     960
agttcaaaca catcacccc ctgcaggagc agagcaaaga ggtggccatc cgcatctttc    1020
agggctgcca gtttcgctcc gtggaggctg tgcaggagat cacagagtat gccaaaagca    1080
ttcctggttt tgtaaatctt gacttgaacg accaagtaac tctcctcaaa tatggagtcc    1140
acgagatcat ttacacaatg ctggcctcct gatgaataaa gatggggtt ctcatatccg     1200 agggccaagg cttcatgaca agggagtttc taaagagcct gcgaaagcct tttggtgact    1260
ttatggagcc caagtttgag tttgctgtga agttcaatgc actggaatta gatgacagcg    1320
acttggcaat atttattgct gtcattattc tcagtggaga ccgcccaggt ttgctgaatg    1380
tgaagcccat tgaagacatt caagacaacc tgctacaagc cctggagctc cagctgaagc    1440
tgaaccaccc tgagtcctca cagctgtttg ccaagctgct ccagaaaatg acagacctca    1500
gacagattgt cacggaacac gtgcagctac tgcaggtgat caagaagacg agacagacag    1560
tgagtcttca cccgctcctg caggagatct acaaggactt gtactagcag agagtcctga    1620
gccactgcca acatttccct tcttccagtt gcactattct gagggaaaat ctgacaccta    1680 agaaattac tgtgaaaaag cattttaaaa agaaaaggtt ttagaatatg atctatttta    1740
tgcatattgt ttataaagac acatttacaa tttacttttta atattaaaaa ttaccatatt    1800
atgaaattgc tgatagta                                                  1818